(12) United States Patent
Jans et al.

(10) Patent No.: US 8,383,152 B2
(45) Date of Patent: Feb. 26, 2013

(54) PHARMACEUTICAL DOSAGE FORM

(75) Inventors: Eugeen Marie Jozef Jans, Meerhout (BE); Filip René Irena Kiekens, Geel (BE); Jody Firmin Marceline Voorspoels, Reningelst (BE); Anne Faure, Vosselaar (BE); Elisabeth Arkenau-Maric, Köln (DE); Lutz Barnscheid, Mönchengladbach (DE); Johannes Bartholomäus, Aachen (DE); Marc Frevel, Monschau (DE); Eric Galia, Inden (DE); Iris Ziegler, Neusäβ (DE); Andrea Schüssele, Berlin (DE)

(73) Assignee: Gruenenthal GmbH, Anchen (DE)

( * ) Notice: Subject to any disclaimer, the term of this patent is extended or adjusted under 35 U.S.C. 154(b) by 368 days.

(21) Appl. No.: 12/358,415

(22) Filed: Jan. 23, 2009

(65) Prior Publication Data
US 2009/0202634 A1 Aug. 13, 2009

(30) Foreign Application Priority Data

Jan. 25, 2008 (EP) .................................... 08001415
Jan. 25, 2008 (EP) .................................... 08001416
Oct. 17, 2008 (EP) .................................... 08018221

(51) Int. Cl.
*A61K 9/22* (2006.01)
*A61K 9/20* (2006.01)
*A61K 9/28* (2006.01)
*A61K 31/135* (2006.01)

(52) U.S. Cl. ......... 424/468; 424/464; 424/474; 514/654

(58) Field of Classification Search .................. 424/468, 424/464, 474; 514/654
See application file for complete search history.

(56) References Cited

U.S. PATENT DOCUMENTS

| 3,806,603 A | 4/1974 | Gaunt et al. |
| 3,865,108 A | 2/1975 | Hartop |
| 3,966,747 A | 6/1976 | Monkovic et al. |
| 3,980,766 A | 9/1976 | Shaw et al. |
| 4,002,173 A | 1/1977 | Manning et al. |
| 4,014,965 A | 3/1977 | Stube et al. |
| 4,070,494 A | 1/1978 | Hoffmeister et al. |

(Continued)

FOREIGN PATENT DOCUMENTS

| AR | 46994 | 12/2004 |
| AR | 045353 | 10/2005 |

(Continued)

OTHER PUBLICATIONS

El-Egakey, Adel et al, Pharmacerutica Acta Helvetiae, vol. 46, Mar. 19, 1970.

(Continued)

*Primary Examiner* — Aradhana Sasan
(74) *Attorney, Agent, or Firm* — Norris McLaughlin & Marcus, P.A.

(57) ABSTRACT

The invention relates to a pharmaceutical dosage form, preferably with controlled release of a pharmacologically active compound (A) contained therein, the pharmaceutical dosage form very preferably being tamper-resistant and most preferably having a breaking strength $B_1$ of at least 500 N in direction of extension $E_1$ and having a breaking strength $B_2$ of less than 500 N in direction of extension $E_2$.

79 Claims, 21 Drawing Sheets

U.S. PATENT DOCUMENTS

| | | | |
|---|---|---|---|
| 4,070,497 A | 1/1978 | Wismer et al. |
| 4,175,119 A | 11/1979 | Porter |
| 4,200,704 A | 4/1980 | Stanley et al. |
| 4,207,893 A | 6/1980 | Michaels |
| 4,262,017 A | 4/1981 | Kuipers |
| 4,343,789 A | 8/1982 | Kawata et al. |
| 4,353,887 A | 10/1982 | Hess et al. |
| 4,404,183 A | 9/1983 | Kawata et al. |
| 4,427,681 A | 1/1984 | Munshi et al. |
| 4,462,941 A | 7/1984 | Lee et al. |
| 4,603,143 A | 7/1986 | Schmidt |
| 4,612,008 A | 9/1986 | Wong et al. |
| 4,629,621 A | 12/1986 | Snipes |
| 4,667,013 A | 5/1987 | Reichle |
| 4,690,822 A | 9/1987 | Uemura et al. |
| 4,713,243 A | 12/1987 | Schiraldi et al. |
| 4,744,976 A | 5/1988 | Snipes et al. |
| 4,764,378 A | 8/1988 | Keith et al. |
| 4,765,989 A | 8/1988 | Wong et al. |
| 4,774,074 A | 9/1988 | Snipes |
| 4,774,092 A | 9/1988 | Hamilton |
| 4,783,337 A | 11/1988 | Wong et al. |
| 4,806,337 A | 2/1989 | Snipes et al. |
| RE33,093 E | 10/1989 | Schiraldi et al. |
| 4,880,585 A | 11/1989 | Klimesch et al. |
| 4,892,778 A | 1/1990 | Theeuwes et al. |
| 4,892,889 A | 1/1990 | Kirk |
| 4,940,556 A | 7/1990 | MacFarlane et al. |
| 4,957,668 A | 9/1990 | Plackard et al. |
| 4,957,681 A | 9/1990 | Klimesch et al. |
| 4,960,814 A | 10/1990 | Wu et al. |
| 4,992,278 A | 2/1991 | Khanna |
| 4,992,279 A | 2/1991 | Palmer et al. |
| 5,004,601 A | 4/1991 | Snipes |
| 5,051,261 A | 9/1991 | McGinity et al. |
| 5,082,668 A | 1/1992 | Wong et al. |
| 5,139,790 A | 8/1992 | Snipes |
| 5,169,645 A | 12/1992 | Shukla et al. |
| 5,198,226 A | 3/1993 | MacFarlane et al. |
| 5,200,197 A | 4/1993 | Wright et al. |
| 5,211,892 A | 5/1993 | Gueret |
| 5,273,758 A | 12/1993 | Royce |
| 5,350,741 A | 9/1994 | Takada |
| 5,378,462 A | 1/1995 | Boedecker et al. |
| 5,427,798 A | 6/1995 | Ludwig et al. |
| RE34,990 E | 7/1995 | Khanna et al. |
| 5,458,887 A | 10/1995 | Chen et al. |
| 5,460,826 A | 10/1995 | Merrill et al. |
| 5,508,042 A | 4/1996 | Oshlack et al. |
| 5,556,640 A | 9/1996 | Ito et al. |
| 5,562,920 A * | 10/1996 | Demmer et al. ............... 424/464 |
| 5,593,694 A | 1/1997 | Hayashida et al. |
| 5,601,842 A | 2/1997 | Bartholomaeus |
| 5,620,697 A | 4/1997 | Törmälä et al. |
| 5,681,517 A | 10/1997 | Metzger |
| 5,741,519 A | 4/1998 | Rosenberg et al. |
| 5,792,474 A | 8/1998 | Rauchfuss |
| 5,801,201 A | 9/1998 | Gradums et al. |
| 5,811,126 A | 9/1998 | Krishanamurthy |
| 5,849,240 A | 12/1998 | Miller et al. |
| 5,866,164 A | 2/1999 | Kuczynski et al. |
| 5,908,850 A | 6/1999 | Zeitlin et al. |
| 5,916,584 A | 6/1999 | O'Donoghue et al. |
| 5,928,739 A | 7/1999 | Pophusen et al. |
| 5,939,099 A | 8/1999 | Grabowski et al. |
| 5,945,125 A | 8/1999 | Kim |
| 5,948,787 A | 9/1999 | Merill et al. |
| 5,968,925 A | 10/1999 | Knidlberger |
| 6,001,391 A | 12/1999 | Zeidler et al. |
| 6,009,390 A | 12/1999 | Gupta et al. |
| 6,009,690 A | 1/2000 | Rosenberg et al. |
| 6,077,538 A | 6/2000 | Merrill et al. |
| 6,096,339 A | 8/2000 | Ayer et al. |
| 6,117,453 A | 9/2000 | Seth et al. |
| 6,120,802 A | 9/2000 | Breitenbach et al. |
| 6,133,241 A | 10/2000 | Bok et al. |
| 6,228,863 B1 | 5/2001 | Palermo et al. |
| 6,235,825 B1 | 5/2001 | Yoshida et al. |
| 6,238,697 B1 | 5/2001 | Kumar et al. |
| 6,245,357 B1 | 6/2001 | Edgren et al. |
| 6,248,737 B1 | 6/2001 | Buschmann et al. |
| 6,261,599 B1 | 7/2001 | Oshlack |
| 6,290,990 B1 | 9/2001 | Grabowski et al. |
| 6,306,438 B1 | 10/2001 | Oshlack et al. |
| 6,309,668 B1 | 10/2001 | Bastin et al. |
| 6,318,650 B1 | 11/2001 | Breitenbach et al. |
| 6,340,475 B2 | 1/2002 | Shell et al. |
| 6,344,535 B1 | 2/2002 | Timmermann et al. |
| 6,348,469 B1 | 2/2002 | Seth |
| 6,355,656 B1 | 3/2002 | Zeitlin et al. |
| 6,375,957 B1 | 4/2002 | Kaiko et al. |
| 6,375,963 B1 | 4/2002 | Repka et al. |
| 6,399,100 B1 | 6/2002 | Clancy et al. |
| 6,419,954 B1 | 7/2002 | Chu et al. |
| 6,436,441 B1 | 8/2002 | Sako et al. |
| 6,461,644 B1 | 10/2002 | Jackson et al. |
| 6,488,939 B1 | 12/2002 | Zeidler et al. |
| 6,488,962 B1 | 12/2002 | Berner et al. |
| 6,488,963 B1 | 12/2002 | McGinity et al. |
| 6,534,089 B1 | 3/2003 | Ayer et al. |
| 6,547,997 B1 | 4/2003 | Breithenbach et al. |
| 6,562,375 B1 | 5/2003 | Sako et al. |
| 6,569,506 B1 | 5/2003 | Jerdee et al. |
| 6,592,901 B2 | 7/2003 | Durig et al. |
| 6,635,280 B2 | 10/2003 | Shell et al. |
| 6,699,503 B1 | 3/2004 | Sako et al. |
| 6,723,340 B2 | 4/2004 | Gusler et al. |
| 6,723,343 B2 | 4/2004 | Kugelmann |
| 6,733,783 B2 | 5/2004 | Oshlack et al. |
| 6,753,009 B2 | 6/2004 | Luber et al. |
| 6,821,588 B1 | 11/2004 | Hammer |
| 7,074,430 B2 | 7/2006 | Miller et al. |
| 7,129,248 B2 | 10/2006 | Chapman et al. |
| 7,141,250 B2 | 11/2006 | Oshlack et al. |
| 7,157,103 B2 | 1/2007 | Sackler |
| 7,176,251 B1 | 2/2007 | Bastioli et al. |
| 7,201,920 B2 | 4/2007 | Kumar et al. |
| 7,214,385 B2 | 5/2007 | Gruber |
| 7,300,668 B2 | 11/2007 | Pryce Lewis et al. |
| 7,399,488 B2 | 7/2008 | Hirsh et al. |
| 7,674,799 B2 | 3/2010 | Chapman et al. |
| 7,674,800 B2 | 3/2010 | Chapman et al. |
| 7,683,072 B2 | 3/2010 | Chapman et al. |
| 7,776,314 B2 | 8/2010 | Bortholomaus et al. |
| 7,851,482 B2 | 12/2010 | Dung et al. |
| 7,939,543 B2 | 5/2011 | Kupper |
| 8,075,872 B2 | 12/2011 | Arkenau-Maric et al. |
| 8,114,383 B2 | 2/2012 | Bartholomaus et al. |
| 8,192,722 B2 | 6/2012 | Arkenau-Maric et al. |
| 2001/0038852 A1 | 11/2001 | Kolter et al. |
| 2002/0012701 A1 | 1/2002 | Kolter et al. |
| 2002/0015730 A1 | 2/2002 | Hoffmann et al. |
| 2002/0051820 A1 | 5/2002 | Shell et al. |
| 2002/0114838 A1 | 8/2002 | Ayer et al. |
| 2002/0132359 A1 | 9/2002 | Waterman |
| 2002/0176888 A1 | 11/2002 | Bartholomaeus et al. |
| 2002/0187192 A1 | 12/2002 | Joshi et al. |
| 2002/0192277 A1 | 12/2002 | Oshlack et al. |
| 2003/0008409 A1 | 1/2003 | Spearman et al. |
| 2003/0015814 A1 | 1/2003 | Krull et al. |
| 2003/0017532 A1 | 1/2003 | Biswas et al. |
| 2003/0021546 A1 | 1/2003 | Sato |
| 2003/0031546 A1 | 2/2003 | Araki et al. |
| 2003/0044458 A1 | 3/2003 | Wright et al. |
| 2003/0044464 A1 | 3/2003 | Zeigler et al. |
| 2003/0064099 A1 | 4/2003 | Oshlack et al. |
| 2003/0068276 A1 | 4/2003 | Hughes et al. |
| 2003/0068370 A1 | 4/2003 | Sackler |
| 2003/0068371 A1 | 4/2003 | Oshlack et al. |
| 2003/0068392 A1 | 4/2003 | Sackler |
| 2003/0069263 A1 | 4/2003 | Breder et al. |
| 2003/0091630 A1 | 5/2003 | Louie-Helm et al. |
| 2003/0104052 A1 | 6/2003 | Berner et al. |
| 2003/0104053 A1 | 6/2003 | Gusler et al. |
| 2003/0118641 A1 | 6/2003 | Maloney et al. |
| 2003/0124185 A1 | 7/2003 | Oshlack et al. |
| 2003/0125347 A1 | 7/2003 | Anderson et al. |

| | | | | | | |
|---|---|---|---|---|---|---|
| 2003/0133985 | A1 | 7/2003 | Louie-Helm et al. | 2010/0221322 A1 | 9/2010 | Bartholomaus et al. |
| 2003/0152622 | A1 | 8/2003 | Louie-Helm et al. | 2010/0226855 A1 | 9/2010 | Nangia et al. |
| 2003/0158242 | A1 | 8/2003 | Kugelmann | 2010/0249045 A1 | 9/2010 | Babul |
| 2003/0175326 | A1 | 9/2003 | Thombre | 2010/0260833 A1 | 10/2010 | Bartholomaus et al. |
| 2003/0232895 | A1 | 12/2003 | Omidian et al. | 2011/0020451 A1 | 1/2011 | Bartholomaus et al. |
| 2004/0010000 | A1 | 1/2004 | Ayer et al. | 2011/0020454 A1 | 1/2011 | Casado |
| 2004/0011806 | A1 | 1/2004 | Luciano et al. | 2011/0038930 A1 | 2/2011 | Barnscheid et al. |
| 2004/0052731 | A1 | 3/2004 | Hirsh et al. | 2011/0082214 A1 | 4/2011 | Faure et al. |
| 2004/0052844 | A1 | 3/2004 | Hsiao et al. | 2011/0097404 A1 | 4/2011 | Oshlack et al. |
| 2004/0081694 | A1 | 4/2004 | Oshlack | 2011/0159100 A1 | 6/2011 | Andersen et al. |
| 2004/0091528 | A1 | 5/2004 | Rogers et al. | 2011/0187017 A1 | 8/2011 | Haupts |
| 2004/0126428 | A1 | 7/2004 | Hughes et al. | 2012/0034171 A1 | 2/2012 | Arkenau-Maric et al. |
| 2004/0131671 | A1 | 7/2004 | Zhang et al. | 2012/0059065 A1 | 3/2012 | Barnscheid et al. |
| 2004/0156899 | A1 | 8/2004 | Louie-Helm et al. | 2012/0065220 A1 | 3/2012 | Barnscheid et al. |
| 2004/0170567 | A1 | 9/2004 | Sackler | 2012/0107250 A1 | 5/2012 | Bartholom us et al. |
| 2004/0185105 | A1 | 9/2004 | Berner et al. | 2012/0135071 A1 | 5/2012 | Bartholom us et al. |
| 2004/0213848 | A1 | 10/2004 | Li et al. | 2012/0136021 A1 | 5/2012 | Barnscheid et al. |
| 2005/0015730 | A1 | 1/2005 | Gunturi et al. | | | |
| 2005/0031546 | A1* | 2/2005 | Bartholomaus et al. ..... 424/10.1 | FOREIGN PATENT DOCUMENTS | | |
| 2005/0058706 | A1 | 3/2005 | Bartholomaeus et al. | AR | 049562 | 8/2006 |
| 2005/0063214 | A1 | 3/2005 | Takashima | AR | 053304 | 5/2007 |
| 2005/0089475 | A1 | 4/2005 | Gruber | AR | 054222 | 6/2007 |
| 2005/0095291 | A1 | 5/2005 | Oshlack et al. | AR | 054328 | 6/2007 |
| 2005/0106249 | A1 | 5/2005 | Hwang et al. | AU | 2003237944 | 12/2003 |
| 2005/0112067 | A1 | 5/2005 | Kumar et al. | AU | 2003274071 | 5/2004 |
| 2005/0127555 | A1 | 6/2005 | Gusik et al. | AU | 2003278133 | 5/2004 |
| 2005/0152843 | A1 | 7/2005 | Bartholomaeus et al. | AU | 2003279317 | 5/2004 |
| 2005/0186139 | A1 | 8/2005 | Bartholomaeus et al. | AU | 2004264666 | 2/2005 |
| 2005/0191244 | A1 | 9/2005 | Bartholomaeus et al. | AU | 2004264667 | 2/2005 |
| 2005/0192333 | A1 | 9/2005 | Hinze et al. | AU | 2004308653 | 4/2005 |
| 2005/0214223 | A1 | 9/2005 | Bartholomaeus et al. | AU | 2005259476 | 1/2006 |
| 2005/0222188 | A1 | 10/2005 | Chapman et al. | AU | 2005259478 | 1/2006 |
| 2005/0236741 | A1 | 10/2005 | Arkenau et al. | AU | 2006210145 | 8/2006 |
| 2005/0245556 | A1 | 11/2005 | Brogmann et al. | AU | 2009207796 | 7/2009 |
| 2005/0266084 | A1 | 12/2005 | Li et al. | AU | 2009243681 | 11/2009 |
| 2006/0002859 | A1* | 1/2006 | Arkenau et al. ............ 424/10.1 | BR | P10413318 | 10/2006 |
| 2006/0002860 | A1* | 1/2006 | Bartholomaus et al. ..... 424/10.1 | BR | P10413361 A | 10/2006 |
| 2006/0004034 | A1 | 1/2006 | Hinze et al. | BR | P10513300 | 5/2008 |
| 2006/0039864 | A1* | 2/2006 | Bartholomaus et al. ..... 424/10.2 | BR | P10606145 | 2/2009 |
| 2006/0099250 | A1 | 5/2006 | Tian et al. | CA | 722109 A | 11/1965 |
| 2006/0188447 | A1 | 8/2006 | Arkenau-Maric et al. | CA | 2082573 | 5/1993 |
| 2006/0193782 | A1* | 8/2006 | Bartholomaus et al. ..... 424/10.1 | CA | 2317747 | 7/1999 |
| 2006/0193914 | A1* | 8/2006 | Ashworth et al. ............ 424/469 | CA | 2352874 | 6/2000 |
| 2006/0240110 | A1 | 10/2006 | Kiick et al. | CA | 2502965 | 5/2004 |
| 2007/0003616 | A1 | 1/2007 | Arkenau-Maric et al. | CA | 2534925 | 2/2005 |
| 2007/0020188 | A1 | 1/2007 | Sackler | CA | 2534932 | 2/2005 |
| 2007/0020335 | A1 | 1/2007 | Chen et al. | CA | 2551231 | 7/2005 |
| 2007/0048228 | A1* | 3/2007 | Arkenau-Maric et al. ... 424/10.1 | CA | 2572352 | 1/2006 |
| 2007/0065365 | A1 | 3/2007 | Kugelmann et al. | CA | 2572491 | 1/2006 |
| 2007/0092573 | A1 | 4/2007 | Joshi et al. | CA | 2595954 | 7/2006 |
| 2007/0183979 | A1* | 8/2007 | Arkenau-Maric et al. ... 424/10.2 | CA | 2229650 C | 8/2006 |
| 2007/0183980 | A1* | 8/2007 | Arkenau-Maric et al. ... 424/10.3 | CA | 2595979 | 8/2006 |
| 2007/0190142 | A1 | 8/2007 | Breitenbach et al. | CA | 2713128 | 7/2009 |
| 2007/0196396 | A1 | 8/2007 | Pilgaonkar et al. | CA | 2723438 | 11/2009 |
| 2007/0196481 | A1 | 8/2007 | Amidon et al. | CH | 689109 | 10/1998 |
| 2007/0224129 | A1 | 9/2007 | Guimberteau et al. | CL | 20162004 | 5/2005 |
| 2007/0264327 | A1 | 11/2007 | Kumar et al. | CL | 20172004 | 5/2005 |
| 2007/0269505 | A1* | 11/2007 | Flath et al. .................... 424/451 | CL | 200403308 | 9/2005 |
| 2008/0069871 | A1 | 3/2008 | Vaughn et al. | CL | 200500952 | 11/2005 |
| 2008/0081290 | A1 | 4/2008 | Wada et al. | CL | 200501624 | 12/2005 |
| 2008/0234352 | A1 | 9/2008 | Fischer et al. | CL | 200501625 | 6/2006 |
| 2008/0247959 | A1* | 10/2008 | Bartholomaus et al. ..... 424/10.3 | CN | 87102755 A | 10/1987 |
| 2008/0248113 | A1* | 10/2008 | Bartholomaus et al. ...... 424/469 | CN | 1980643 | 4/2005 |
| 2008/0311049 | A1 | 12/2008 | Arkenau-Maric et al. | CN | 101010071 | 6/2005 |
| 2008/0311187 | A1 | 12/2008 | Ashworth et al. | CN | 101022787 | 1/2006 |
| 2008/0311197 | A1 | 12/2008 | Arkenau-Maric et al. | CN | 001863513 | 11/2006 |
| 2008/0311205 | A1 | 12/2008 | Habib et al. | CN | 001863514 | 11/2006 |
| 2008/0312264 | A1 | 12/2008 | Arkenau-Maric et al. | CN | 01917862 | 2/2007 |
| 2008/0317854 | A1 | 12/2008 | Arkenau et al. | CN | 101027044 | 8/2007 |
| 2009/0004267 | A1 | 1/2009 | Arkenau-Maric et al. | CN | 101111232 | 1/2008 |
| 2009/0005408 | A1 | 1/2009 | Arkenau-Maric et al. | CN | 101175482 | 2/2008 |
| 2009/0017121 | A1 | 1/2009 | Berner et al. | DE | 2530563 | 1/1977 |
| 2009/0081290 | A1 | 3/2009 | McKenna et al. | DE | 28 08 505 | 9/1978 |
| 2009/0202634 | A1 | 8/2009 | Jans et al. | DE | 4229085 A1 | 3/1994 |
| 2010/0015223 | A1 | 1/2010 | Cailly-Deufestel et al. | DE | 4309528 | 9/1994 |
| 2010/0092553 | A1 | 4/2010 | Guimberteau et al. | DE | 4446470 A1 | 6/1996 |
| 2010/0098758 | A1 | 4/2010 | Bartholomaus et al. | DE | 69400215 | 10/1996 |
| 2010/0151028 | A1 | 6/2010 | Ashworth et al. | DE | 19522899 C1 | 12/1996 |
| 2010/0203129 | A1 | 8/2010 | Andersen et al. | DE | 19753534 | 6/1999 |

| | | | | | | |
|---|---|---|---|---|---|---|
| DE | 19800689 C1 | 7/1999 | | EP | 1492506 B1 | 1/2005 |
| DE | 19800698 | 7/1999 | | EP | 1658055 | 2/2005 |
| DE | 692 29 881 | 12/1999 | | EP | 1515702 | 3/2005 |
| DE | 19822979 | 12/1999 | | EP | 1527775 A1 | 4/2005 |
| DE | 198 56 147 | 6/2000 | | EP | 1527775 A1 | 5/2005 |
| DE | 19855440 | 6/2000 | | EP | 1558221 A1 | 8/2005 |
| DE | 19940740 | 3/2001 | | EP | 1558257 | 8/2005 |
| DE | 19960494 | 6/2001 | | EP | 1560585 | 8/2005 |
| DE | 10036400 | 6/2002 | | EP | 1658054 | 5/2006 |
| DE | 69429710 | 8/2002 | | EP | 1740161 | 1/2007 |
| DE | 10250083 | 12/2003 | | EP | 1658055 B1 | 3/2007 |
| DE | 10250084 | 5/2004 | | EP | 1765303 | 3/2007 |
| DE | 10250087 | 5/2004 | | EP | 1786403 | 5/2007 |
| DE | 10250088 | 5/2004 | | EP | 1558221 B1 | 6/2007 |
| DE | 10336400 | 3/2005 | | EP | 1658054 B1 | 6/2007 |
| DE | 10 361 596 | 9/2005 | | EP | 1842533 A2 | 10/2007 |
| DE | 10 2004 020 220 | 11/2005 | | EP | 1845955 | 10/2007 |
| DE | 102004019916 | 11/2005 | | EP | 1845956 | 10/2007 |
| DE | 102004020220 | 11/2005 | | EP | 1859789 | 11/2007 |
| DE | 10 2004 032049 | 1/2006 | | EP | 1 897 545 | 3/2008 |
| DE | 10 2004 032051 | 1/2006 | | EP | 2131830 | 12/2009 |
| DE | 10 2004 032103 | 1/2006 | | EP | 2249811 | 11/2010 |
| DE | 10 2005 005446 | 8/2006 | | EP | 2273983 | 1/2011 |
| DE | 10 2005 005449 | 8/2006 | | EP | 2 402 004 A2 | 1/2012 |
| DE | 102007011485 | 9/2008 | | EP | 2402004 A2 | 1/2012 |
| DK | 1658055 | 7/2007 | | ES | 2336571 | 12/2004 |
| DK | 1658054 | 10/2007 | | ES | 2260042 | 11/2006 |
| DK | 1515702 | 1/2009 | | ES | 2285497 | 11/2007 |
| EC | SP066345 | 8/2006 | | ES | 2288621 | 1/2008 |
| EP | 0008131 | 2/1980 | | ES | 2289542 | 2/2008 |
| EP | 0216453 | 2/1980 | | ES | 2315505 | 4/2009 |
| EP | 0043254 A1 | 1/1982 | | GB | 1147210 A | 4/1969 |
| EP | 0177893 | 4/1986 | | GB | 1 567 727 | 5/1980 |
| EP | 0226061 | 6/1987 | | GB | 2 057 878 | 4/1981 |
| EP | 0228417 | 7/1987 | | HR | P20070272 | 6/2007 |
| EP | 0229652 A2 | 7/1987 | | HR | 20070456 | 11/2007 |
| EP | 0232877 | 8/1987 | | JP | 03-501737 A | 4/1991 |
| EP | 0240906 A2 | 10/1987 | | JP | 8-505076 A | 6/1996 |
| EP | 0261616 A2 | 3/1988 | | JP | 2002-275175 | 9/2002 |
| EP | 0270954 | 6/1988 | | JP | 2005534664 | 11/2005 |
| EP | 0277289 | 8/1988 | | KR | 1020060069832 | 6/2006 |
| EP | 0293066 | 11/1988 | | KR | 20070039041 | 4/2007 |
| EP | 0328775 | 8/1989 | | KR | 20070111510 | 11/2007 |
| EP | 0477135 A1 | 3/1992 | | KR | 20100111303 | 10/2010 |
| EP | 0544144 A1 | 6/1993 | | KR | 20110016921 | 2/2011 |
| EP | 0583726 | 2/1994 | | MX | 2007000008 | 3/2007 |
| EP | 0598606 | 5/1994 | | MX | 2007000009 | 3/2007 |
| EP | 0636370 A1 | 2/1995 | | MX | 2007009393 | 8/2007 |
| EP | 0641195 A1 | 3/1995 | | MX | 2010008138 | 8/2010 |
| EP | 0647448 A1 | 4/1995 | | MX | 2010012039 | 11/2010 |
| EP | 0654263 A1 | 5/1995 | | NO | 20061054 | 3/2006 |
| EP | 0661045 | 7/1995 | | NO | 20070578 | 1/2007 |
| EP | 0675710 A1 | 10/1995 | | NO | 20074412 | 11/2007 |
| EP | 0682945 | 11/1995 | | PT | 1699440 | 12/2004 |
| EP | 0693475 | 1/1996 | | PT | 1658054 | 5/2006 |
| EP | 0820693 | 1/1996 | | PT | 1658055 | 7/2007 |
| EP | 0696598 | 2/1996 | | PT | 1515702 | 12/2008 |
| EP | 0756480 A1 | 2/1997 | | RU | 2131244 | 6/1999 |
| EP | 0760654 A1 | 3/1997 | | RU | 2396944 C2 | 7/2004 |
| EP | 0761211 | 3/1997 | | RU | 2354357 | 12/2007 |
| EP | 0780369 | 6/1997 | | RU | 2007103712 | 9/2008 |
| EP | 0785775 A1 | 7/1997 | | RU | 2007103707 | 11/2008 |
| EP | 0809488 A1 | 12/1997 | | RU | 2007132975 | 4/2009 |
| EP | 0820698 | 1/1998 | | SI | 1515702 | 4/2009 |
| EP | 0857062 A2 | 8/1998 | | SI | 1699440 | 11/2009 |
| EP | 0864324 A1 | 9/1998 | | WO | 8000841 | 5/1980 |
| EP | 0864326 A2 | 9/1998 | | WO | 89 05624 | 6/1989 |
| EP | 0980894 | 2/2000 | | WO | 90/03776 | 4/1990 |
| EP | 0988106 A1 | 3/2000 | | WO | 90/03776 A1 | 4/1990 |
| EP | 1014941 A1 | 7/2000 | | WO | 93/06723 | 4/1993 |
| EP | 1070504 | 1/2001 | | WO | 93/10758 | 6/1993 |
| EP | 1127871 | 8/2001 | | WO | 93/11749 | 6/1993 |
| EP | 1138321 | 10/2001 | | WO | 93 23017 | 11/1993 |
| EP | 1138321 A2 | 10/2001 | | WO | 94/06414 | 3/1994 |
| EP | 1166776 | 1/2002 | | WO | 94/08567 | 4/1994 |
| EP | 1250045 | 10/2002 | | WO | 95/17174 A1 | 6/1995 |
| EP | 1251120 | 10/2002 | | WO | 95/20947 | 8/1995 |
| EP | 1293127 | 3/2003 | | WO | 95/22319 | 8/1995 |
| EP | 1293196 A2 | 3/2003 | | WO | 95/30422 | 11/1995 |

| | | |
|---|---|---|
| WO | 96/00066 | 1/1996 |
| WO | 96/03979 A1 | 2/1996 |
| WO | 96/14058 | 5/1996 |
| WO | 97/33566 | 9/1997 |
| WO | 9749384 | 12/1997 |
| WO | 9835655 A3 | 2/1998 |
| WO | 98/20073 | 5/1998 |
| WO | 98/28698 | 7/1998 |
| WO | 98/35655 A2 | 8/1998 |
| WO | 99/12864 A1 | 3/1999 |
| WO | 99/32120 | 7/1999 |
| WO | 99/44591 | 9/1999 |
| WO | 99 48481 | 9/1999 |
| WO | 00/33835 | 6/2000 |
| WO | 00/40205 | 7/2000 |
| WO | 01 08661 | 2/2001 |
| WO | 01/12230 | 2/2001 |
| WO | 01/15667 | 3/2001 |
| WO | 01/52651 | 7/2001 |
| WO | 01 97783 | 12/2001 |
| WO | 02/26061 | 4/2002 |
| WO | 02/26262 | 4/2002 |
| WO | 02/26928 | 4/2002 |
| WO | 0235991 A2 | 5/2002 |
| WO | 02/088217 A1 | 11/2002 |
| WO | 03/006723 | 1/2003 |
| WO | 03/013476 | 2/2003 |
| WO | 03/013479 | 2/2003 |
| WO | 03/015531 | 2/2003 |
| WO | 03/024430 | 3/2003 |
| WO | 2003024426 A1 | 3/2003 |
| WO | 03/026624 A1 | 4/2003 |
| WO | 03 026743 | 4/2003 |
| WO | 03/028698 | 4/2003 |
| WO | 03/028990 A1 | 4/2003 |
| WO | 03/031546 | 4/2003 |
| WO | 03026743 A2 | 4/2003 |
| WO | 03/035029 | 5/2003 |
| WO | 03/035053 | 5/2003 |
| WO | 03/035054 | 5/2003 |
| WO | 03/035177 A2 | 5/2003 |
| WO | 03/053417 | 7/2003 |
| WO | 03/068392 | 8/2003 |
| WO | 03/092648 A1 | 11/2003 |
| WO | 03 094812 | 11/2003 |
| WO | 03/105808 | 12/2003 |
| WO | 2004/004693 A1 | 1/2004 |
| WO | 2004/026262 | 4/2004 |
| WO | 2004/026263 | 4/2004 |
| WO | 2004/037230 | 5/2004 |
| WO | 2004/037259 | 5/2004 |
| WO | 2004/037260 | 5/2004 |
| WO | 2004 043967 | 5/2004 |
| WO | 2004/066910 A2 | 8/2004 |
| WO | 2004/084869 A1 | 10/2004 |
| WO | 2004/093801 A2 | 11/2004 |
| WO | 2004/093819 | 11/2004 |
| WO | 2004 098567 A2 | 11/2004 |
| WO | 2004/100894 A2 | 11/2004 |
| WO | 2005 016313 | 2/2005 |
| WO | 2005 016314 | 2/2005 |
| WO | 2005/032524 A2 | 4/2005 |
| WO | 2005/065646 A2 | 4/2005 |
| WO | 2005/041968 | 5/2005 |
| WO | 2005/053587 A1 | 6/2005 |
| WO | 2005/053656 A1 | 6/2005 |
| WO | 2005/055981 A2 | 6/2005 |
| WO | 2005 063214 | 7/2005 |
| WO | 2005 066183 | 7/2005 |
| WO | 2005 079760 A1 | 9/2005 |
| WO | 2005 105036 A1 | 10/2005 |
| WO | 2005 102286 | 11/2005 |
| WO | 2005102294 | 11/2005 |
| WO | 2005105036 A1 | 11/2005 |
| WO | 2006 002883 | 1/2006 |
| WO | 2006 002884 | 1/2006 |
| WO | 2006 002886 | 1/2006 |
| WO | 2006002884 | 1/2006 |
| WO | 2006058249 A2 | 6/2006 |
| WO | 2006 082097 | 8/2006 |
| WO | 2006 082099 | 8/2006 |
| WO | 2007/005716 A2 | 1/2007 |
| WO | 2007/008752 | 1/2007 |
| WO | WO 2007 005716 A2 * | 1/2007 |
| WO | 2007/048233 | 5/2007 |
| WO | 2007/053698 | 5/2007 |
| WO | 2007/085024 A2 | 7/2007 |
| WO | 2007085024 A2 | 7/2007 |
| WO | 2007085024 A3 | 7/2007 |
| WO | WO 2007 085024 A2 * | 7/2007 |
| WO | 2007 103286 | 9/2007 |
| WO | 2007103105 A2 | 9/2007 |
| WO | 2007 112285 | 10/2007 |
| WO | 2008 023261 A1 | 2/2008 |
| WO | 2008033523 A1 | 3/2008 |
| WO | 2008/086804 A2 | 7/2008 |
| WO | 2008/107149 A2 | 9/2008 |
| WO | 2008107149 | 9/2008 |
| WO | 2008107149 A2 | 9/2008 |
| WO | 2008107149 A3 | 9/2008 |
| WO | 2008/148798 A2 | 12/2008 |
| WO | 2009/092601 A1 | 7/2009 |
| WO | 2009092601 | 7/2009 |
| WO | 2009112273 A2 | 9/2009 |
| WO | 2009/135680 A1 | 11/2009 |
| WO | 2009135680 | 11/2009 |
| WO | 2010057036 A2 | 5/2010 |
| WO | 2010140007 A2 | 12/2010 |
| WO | 2010140007 A9 | 12/2010 |
| WO | 2011009602 | 1/2011 |
| WO | 2011009603 | 1/2011 |
| WO | 2011009604 | 1/2011 |
| WO | 2011095314 A3 | 8/2011 |
| WO | 2012028317 A1 | 3/2012 |
| WO | 2012028318 A1 | 3/2012 |

OTHER PUBLICATIONS

Apicella A., Biomaterials, vol. 14, No. 2, pp. 83-90, 1993.
Bailey F.E., Journal of Applied Polymer Science, vol. 1, Issue No. 1, pp. 56-62, 1959.
Braun, et al. Angel Orthodontist, vol. 65 (5) pp. 373-377, 1995.
Crowley M.M., Biomaterials 23, 2002, pp. 4241-4248.
Coppens, Pharmaceutical Technology, 62-70, Jan. 2005.
Caraballo, Journal of Controlled Release, vol. 69, pp. 345-355, 2000.
Dow Technical Data, POLYOX, Feb. 2003.
Dow Excipients Chem. of Poly. Water Soluble-Resin 2004.
Dejong (Pharmaceutisch Weekblad Scientific Edition 1987, p. 24-28.
Efentakis M., Pharmaceutical Development and Technology, 5 (3), pp. 339-346, 2000.
European Pharmacopoeia, pharmaceutical technical procedures, 1997, 135.
El-Sherbiny, European Polymer Journal, vol. 41, pp. 2584-2591, 2005.
Follonier N., Drug Development and Industrial Pharmacy, 20(8), pp. 1323-1339, 1994.
Follonier N., Journal of Controlled Release 36, pp. 243-250, 1995.
Graham N.B., Poly(Ethylene Glycol) Chemistry: Biotechnical and Biomedical Applications, Chapter 17, 1992.
Griffith, Drug Administration, vol. 19, No. 1, pp. 41-42, 2003.
Hanning C.D., British Journal of Anaesthesia, 61, pp. 221-227, 1988.
Janicki S., Acta Pharm. Technol. 33 (3) 154-155, 1987.
Kim C.-J. J Pharm. Sciences 1995, 84(3).
Kim, Chem. Pharm Bull. 1992, 40(10), 2800-2804.
J.W. McGinity—Letter of Jan. 26, 2009.
Dr. Rick Matos, Ph.D—Letter Jan. 6, 2011.
Levina, Journal of Pharmaceutical Sciences, vol. 89, No. 6, pp. 703-723, Jun. 2000.
Levina, Drug Development and Industrial Pharmacy, vol. 28, No. 5, pp. 495-514, 2002.
Madorsky S.L., Journal of Polymer Science, vol. 84, No. 3, Mar. 1959.
Mank R., Pharmazie 44, H. 11, pp. 773-776, 1989, Abstract only.
Mank R., Pharmazie 45, H. 8, pp. 592-593 1990, Abstract only.

Mesiha M.S., Drug Development and Industrial Pharmacy, 19(8), pp. 943-959, 1993.
Moroni A., Drug Development and Industrial Pharmacy, 21(12) pp. 1411-1428, 1995.
Maggi et al., Biomaterials, 2002, 23, 1113-1119.
Miller, Nursing, pp. 50-52, Feb. 2000.
Mitchell, Special Resource, vol. 35, No. 5, pp. 535-557, 2000.
Ohnishi N., Chem. Pharm. Bull, 35(8), pp. 3511-3515, 1987.
Ozeki T., Journal of Controlled Release 58, pp. 87-95, 1999.
Pharm. Research, 1989, 6(9), 6-98.
Pharm. Research, 1991, 8(10), 8-192.
Prapaitrakul W., J. Pharm. Pharmacol. 43, pp. 377-381, 1991.
Proeschel, J. Dent. Res., vol. 81, No. 7, pp. 464-468, 2002.
Remington's Pharmaceutical Sciences, pp. 1553-1593, Ch. 89, 1980, 16$^{th}$ Edition.
Radko S., Applied ad Theoretical Electrophoresis 5, pp. 79-88, 1995.
Remington's Pharmaceutical Sciences 17th ed., 1418 (1985).
Rippie E.G., Journal of Pharmaceutical Sciences, Vo. 58, No. 4, pp. 428-431, Apr. 1969.
Scheirs J. Polymer, vol. 32, No. 11, 1991.
Shivanand P. Pharmaceutical Research, Oct. 1991, vol. 8, No. 10.
Sprockel O.L., J. Pharma. Pharmacol. 42, pp. 152-157, 1990.
Stringer J.L., Journal of Controlled Release 42, pp. 195-202, 1996.
Third Party Observations, Feb. 2, 2009.
Thoma V.K., Pharm. Ind. 51, Nr. 3, 1989.
US Pharmacopoeia, Chapter 1217, Aug. 1, 2008.
Wikipedia—inert gas data sheet, Dec. 2009.
Yang, Journal of Pharmaceutical Sciences, vol. 85, No. 10, Oct. 1996.
Yarbrough et al, Letters to Nature 322, 347-349 (Jul. 24, 1986) "Extraordinary effects of mortar-and-pestle grinding on microstructure of sintered alumina gel".
Zhang et al., Pharmaceutical Development and Technology, 1999, 4, 241-250.
Fell, et al; "determination of Tablet Strength by the Diametral-Compression Test"; Journal of Pharmaceutical Sciences, vol. 59, No. 5, May 1970; p. 688-691.
Davies, et al; "The determination of the mechanical strength of tablets of different shapes"; European Journal of Pharmaceutics and Biopharmaceutics, 67, (2007) pp. 268-276.
Summers et al; "Influence of Crystal Form on Tensile Strength of Compacts of Pharmaceutical Materials"; Journal of Pharmaceutical Sciences, vol. 66, No. 8, Aug. 1977, pp. 1172-1175.
Lockhart et al; "Packaging of Pharmaceuticals and Healthcare Products"; Blackie Academic & Professional; First Edition 1996.
Manthena et al; "Factors affecting mechanism and kinetics of drug release from matrix-based oral controlled drug delivery systems": Am J. Drug Deliv. 2004 : 2 (1): 43-57.
Bauer et al; "Coated Pharmaceutical Dosage Forms—Fundamentals, Manufacturing Techniques, Biopharmaceutical Aspects, Test Methods and Raw Materials" 1st edition, 1998, Medpharm Scientific Publishers.
Katz et al., Clin. J. Pain, 23(8): 648-660 (2007).
Arnold, "Teen Abuse of Painkiller OxyContin on the Rise," www.npr.org, Dec. 19, 2005.
Baum et al., Public Health Reports, 102(4): 426-429 (1987).
Purdue News, "Purdue Pharma Provides Update on Development of New Abuse-Resistant Pain Medications; FDA Cites Patient Needs As First Priority; New Drug Application Delayed," www.headaches.about.com, Jun. 18, 2002.
Strang, British Med. J., 302: 969 (1991).
Tompkins et al., Psychopharma., 210: 471-480 (2010).
Waters et al., Am. J. Psychiatry, 164(1): pp. 173-174 (2007).
Tablet, www.docstoc.com (2011).
Dachille, F. et al., "High-Pressure Phase Transformation in Laboratory Mechanical Mixers and Mortars", 1960, Nature, 186, pp. 1-2 (abstract).
Remington's Pharmaceutical Sciences, Ch. 90, 1985, 17th Edition.
Wu, et al; "Mathematical modeling and in vitro study of controlled drug release via a highly swellable and dissoluble polymer matrix: polyethylene oxide with high molecular weights"; Journal of Controlled Release 102 (2005) 569-581.
Waltimo et al. A novel bite force recorder and maximal isometric bite force values for healthy young adults. Scand J Dent Res. 1993, vol. 101, pp. 171-175.
Waltimo et al. Maximal bite force and its association with signs and symptoms of crandiomandibular disorders in young Finnish non-patients. Acta Odonol. Scand. 1995, vol. 53, pp. 254-258.
2.9 Methoden der pharmazeutischen Technologie 143-144, 1997.
Pharmazeutische Biologie—Drogen und ihre Inhaltsstoffe-Scharfstoffdrogen, 1982, pp. 82-92.
Tipler et al. Physics for Scientists and Engineers, 6th Edition, pp. 234-235, 2003.
Sfafford, J. Uberzogene feste Formen, 1991, pp. 346-368.
Schroeder J., Granulierung hydrophober Wirkstoffe im Planetwalzenextruder, 2003, vol. 65, No. 4, pp. 367-372, Summary.
Maggi. Therapeutic Potential of Capsaicin-like Molecules. 1Life Sciences, vol. 51, pp. 1777-1781, 1992.
Dachille, F. et al., "High-Pressure Phase Transformation in Laboratory Mechanical Mixers and Mortars", 1960., Nature, 186, pp. 1-2 (abstract).
Bauer, Coated Pharmaceutical Dosage Forms, CRC Press, 1998, pp. 1-10.
Conversion of 18.8 kiloponds to newtons, http://www.unitconversion.org/force/newtons-to-kiloponds-conversion.html on Jul. 5, 2011.
Freed et al. pH control of nucleophilic/electrophilic oxidation. International Journal of Pharmaceutics. 2008, vol. 357, pp. 180-188.
Waterman et al. Stabilization of Pharmaceuticals to Oxidative Degradation. Pharmaceutical Development and Technology. 2002, vol. 7, No. 1, pp. 1-32.
Maggi, L. et al., "High molecular weight polyethylene oxides (PEOs) as an alternative to HPMC in controlled release dosage form", 2000, International Journal of Pharmaceutics, 195 pp. 229-238.
Handbuch der Kunststoff-Extrusionstechnik 1, "Grundlagen" in Chapter 1.2 "Klassifizierung von Extrudern", pp. 3-7. 1989.
Remington's Pharmaceutical Sciences, Ch. 76, 1985, 17th Edition.
Remington's Pharmaceutical Sciences, Ch. 77, 1985, 17th Edition.
Remington's Pharmaceutical Sciences, Ch. 78, 1985, 17th Edition.
Remington's Pharmaceutical Sciences, Ch. 79, 1985, 17th Edition.
Remington's Pharmaceutical Sciences, Ch. 80, 1985, 17th Edition.
Remington's Pharmaceutical Sciences, Ch. 81, 1985, 17th Edition.
Remington's Pharmaceutical Sciences, Ch. 82, 1985, 17th Edition.
Remington's Pharmaceutical Sciences, Ch. 83, 1985, 17th Edition.
Remington's Pharmaceutical Sciences, Ch. 84, 1985, 17th Edition.
Remington's Pharmaceutical Sciences, Ch. 85, 1985, 17th Edition.
Remington's Pharmaceutical Sciences, Ch. 86, 1985, 17th Edition.
Remington's Pharmaceutical Sciences, Ch. 87, 1985, 17th Edition.
Remington's Pharmaceutical Sciences, Ch. 88, 1985, 17th Edition.
Remington's Pharmaceutical Sciences, Ch. 89, 1985, 17th Edition.
Remington's Pharmaceutical Sciences, Ch. 91, 1985, 17th Edition.
Remington's Pharmaceutical Sciences, Ch. 92, 1985, 17th Edition.
Remington's Pharmaceutical Sciences, Ch. 93, 1985, 17th Edition.
Repka MA, Drug Dev Ind Pharm. Oct. 2007;33(10):1043-57. (Abstract).
Herbert A. Lieberman, Pharmaceutical Dosage Forms, Tablets, Second Edition, Revised and Expanded, 1990 (Table of Contents).
O.G. Piringer et al., Plastic Packaging: Interactions with Food and Pharmaceuticals, Wiley-VCH, 2nd ed. (Table of Content), Feb. 13, 2008.
Guidance for Industry—Bioavailability and Bioequivalence—Studies for Orally Administered Drug Products—General Considerations, FDA, BP, Announced in the Federal Register: vol. 68, No. 53/Mar. 19, 2003.
Crowley MM, Drug Dev Ind Pharm. Sep. 2007;33(9):909-26. (Abstract).
D.A. Dean, Pharmaceutical Packaging Technology, Taylor & Francis, 1st ed, Nov. 30, 2000.
Dexheimer, Terahertz Spectroscopy: Principles and Applications (Optical Science and Engineering Series), CRC; 1 edition 2007.
Encyclopedia of Pharmaceutical Technology, Third Edition, vol. 1, edited by James Swarbrick PharmaceuTech, Inc., Pinehurst, North Carolinia, USA (Tabel of Contents), 2006.

Encyclopedia of Pharmaceutical Technology, Third Edition, vol. 2, edited by James Swarbrick PharmaceuTech, Inc., Pinehurst, North Carolinia, USA (Tabel cf Contents), 2006.
Encyclopedia of Pharmaceutical Technology, Third Edition, vol. 3, edited by James Swarbrick PharmaceuTech, Inc., Pinehurst, North Carolinia, USA (Tabel cf Contents), 2006.
Encyclopedia of Pharmaceutical Technology, Third Edition, vol. 4, edited by James Swarbrick PharmaceuTech, Inc., Pinehurst, North Carolinia, USA (Tabel cf Contents), 2006.
Encyclopedia of Pharmaceutical Technology, Third Edition, vol. 5, edited by James Swarbrick PharmaceuTech, Inc., Pinehurst, North Carolinia, USA (Tabel of Contents), 2006.
Encyclopedia of Pharmaceutical Technology, Third Edition, vol. 6, edited by James Swarbrick PharmaceuTech, Inc., Pinehurst, North Carolinia, USA (Tabel of Contents), 2006.
Y.-S. Lee et al., Principles of Terahertz Science and Technology (Lecture Notes in Physics), Springer; 1 edition 2008 (Table of Contents).
R.E. Miles et al., Terahertz Frequency Detection and Identification of Materials and Objects (NATO Science for Peace and Security Series B: Physics and Biophysics), Springer; 1 edition 2007 (Table of Contents).
Guidance for Industry—Statistical Approaches to Establishing Bioequivalence, FDA, BP, Jan. 2001.
Note for Guidance on the Investigation of Bioavailability and Bioequivalence, EMEA, London, Jul. 26, 2001 (CPMP/EWP/QWP/1401/98.
Rowe et al. Handbook of Pharmaceutical Excipients. Sixth Edition. 2009, pp. v-ix, Table of Contents.
Bioavailability and Bioequivalence—Studies for Orally Administered Drug Products—General Considerations, FDA, BP, Announced in the Federal Register: vol. 68, No. 53/Mar. 19, 2003.
Braun, et al. Angel Orthodontist, 6(5) pp. 373-377, 1995.
Brown, "The Dissolution Procedure: Development and Validation" vol. 31(5). Chapter 1092, 2006, 1-15.
Ritschel et al. Die Tablette: Handbuch der Entwicklung, Herstellung and Qualitatssicherung. 2002, Ch 6, pp. 515-519.
European Pharmacopoeia, Third Edition, Council of Europe, Strasbourg, 1997, pp. 127-152.
European Pharmacopoeia, Third Edition Supplement 2000, Council of Europe, Strasbourg, 2000, pp. 85-107.
Hong et al. Dissolution kinetics and physical characterization of three-layered tablet with poly(ethylene oxide) core matrix capped by Carbopol. Int .J. Pharmacol. 2008, vol. 356, pp. 121-129.
Hoepfner et al. Fiedler Encyclopedia of Excipients. 2007, Table of Contents only.
Cawello, "Parameters for Compartment-free Pharmacokinetics—Standardization of Study Design, Data Analysis and Reporting" 1999, pp. XI-XIII (table of contents).
Bauer et al. Lehrbuch der Pharmazeutischen Technologie. 1999. Pages IX-XV, Table of contents.
"Pharmazeutische Biologie-Drogen and ihre Inhaltsstoffe" by Prof. Dr. Hildebert Wagner, 2nd., revised edition, Gustav Fischer Verlag, Stuttgart-N.Y., 1982, pp. 82-92. 0.
Yeh et al., Stability of Morphine in Aqueous Solution III: Kinetics of Morphine Degradation in Aqueous Solution, Wiley Subscription Services, Inc., Journal of Pharmaceutical Sciences, 50(1): 35-42 (1961).
Andre et al., "O-Demethylation of Opiod Derivatives With Methane Sulfonic Add/Methoinine: Application to the Synthesis of Naloxone and Analogues" Synthetic Comm. 22(16), pp. 2313-2327, 1992.
Augustine, R.L., Catalytic Hydrogenation of a, B-Unsaturated Ketones. III The Effect of Quantity and Type of Catalysts,' J.Org Chem. 28(1), pp. 152-155, Abstract 1963.
P. Comish "Avoid the Crush": hazards of medication administration in patients with dysphagia or a feeding tube, CMA Media Inc., CMAJ. 172(7), pp. 871-872, 2005.
"The Dissolution Procedure: Development and Validation", heading "Study Design", "Time Points" US Pharmacopoeia (USP), General Chapter 1092, pp. 1-15, 2006.
European Pharmacopoeia 2.9.40 "Uniformity of Dosage Units", 2006, pp. 3370-3373.
European Pharmacopoeia 5.0, 2.9.8 "Resistance to Crushing of Tablets", 2005, p. 235.
European Search Report, Application No./Patent No. 11006253.6-2112, Dec. 16, 2011.
European Search Report, Application No./Patent No. 11006254.4-2112, Dec. 16, 2011.
European Search Report, Application No./Patent No. 11008131.2-1219, Feb. 24, 2012.
European Search Report, Application No./Patent No. 12001296.8-1219, Jun. 26, 2012.
European Search Report, Application No./Patent No. 11009129.5-2112, Apr. 10, 2012.
European Search Report, Application No./Patent No. 12001301.6-1219, Jun. 26, 2012.
Goodman and Gilman, "The Pharmacological Basis of Therapeutics, Seventh Edition", MacMillan Publishing Company, Table of Contents. 1985.
Griffin, "Classification of Surface-Active Agents by HLB" Journal of the Society of Cosmetic Chemists, Atlas Powder Company, 1949, pp. 311-326.
Griffith et al. "Tablet Crushing and the Law: The Implications for Nursing" Professional Nurse 19(1), pp. 41-42, 2003.
A. James, "The legal and clinical implications of crushing tablet medication", Nurse Times 100(50), 28-33, 2004.
McGinity et al., Hot-Melt Extrusion as a Pharmaceutical Process, American Pharmaceutical Review, vol. 4 (2), pp. 25-36, 2001.
C. W. McGary, Jr. "Degradation of Poly(ethylene Oxide)", Journal of Polymer Science vol. XLVI, 1960, pp. 51-57.
Mitchell, "Oral Dosage Forms That Should Not Be Crushed: 2000 Update" Hospital Pharmacy 35(5), 553-557, 2000.
Munjal et al."Polynneric Systems for Amorphous Delta$^{\wedge}$9—Tetrahydrocannabinol Produced by a Hot-Melt Method. Part II: Effect of Oxidation Mechanisms and Chemical Interactions on Stability" Journal of Pharmaceutical Sciences vol. 95 No. 11, Wiley InterScience, 2006, pp. 2473-2485.
Munsell Color Company, "The Munsell Book of Color: Glossy Collection", X-Rite, Originally published in 1966, pp. 1-7.
Ozeki et al. "Control of Medicine Release From Solid Dispersion Through Poly(ethylene oxide)-Carboxyvinylpolymer Interaction", International Journal of Pharmaceutics, 165, 1998, pp. 239-244.
Ozeki et al. "Controlled Release From Solid Dispersion Composed of Poly(ethylene oxide)—Carbopol Interpolynner Complex With Various Cross-Linking Degrees of Carbopol", Journal of Controlled Release. 63, 2000. Pages 287-295.
Schier et al. "Fatality from Administration of Labetalol and Crushed Extended-Release Nifedipine" The Annals of Pharmacotherapy vol. 37, 1420-1423, Oct. 2003.
Wade and Weller, "Handbook of Pharmaceutical Excipients: 2nd Edition", The American Pharmaceutical Association and the Pharmaceutical Press, Table of Contents pp. v-vi, 1994.
Weiss, U., "Derivatives of Morphine. I 14-Dihydroxydihydromorphinone," J. Am. Chem. Soc. 77, pp. 5891-92, Nov. 20, 1955.
European Search Report from related EP Application No. 12003743.7-1219 mailed Sep. 24, 2012.
European Search Report from related EP Application No. 12002708.1-1219 mailed Sep. 24, 2012.
European Search Report, Application No./Patent No. 12003743.7-1219, Sep. 24, 2012.
Henrist et al. In vitro and in vivo evaluation of starch-based hot stage extruded double matrix systems. Journal of Controlled Release. 2001, vol. 75, pp. 391-400.
McNeill et al. Properties controlling the diffusion and release of water-soluble solutes from poly(ethylene oxide) hydrogels. 4. Extended constant rate release from partly-coated spheres. Journal Biomat. Sci. Polym. Ed. 1996, vol. 7, pp. 953-63.
Pillay et al. A novel approach for constant rate delivery of highly soluble bioactives from a simple monolithic system. Journal of Controlled Release. 2000, vol. 67, pp. 67-78.

* cited by examiner

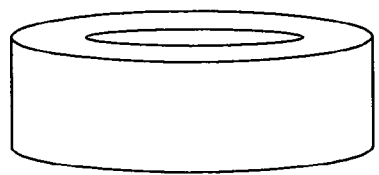
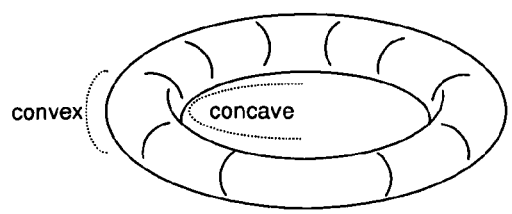
Figure 15A                                    Figure 15B
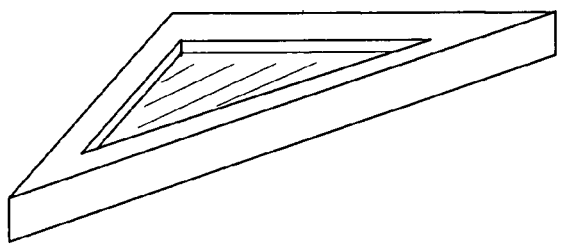
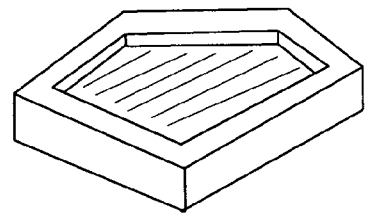
Figure 16A                                    Figure 16B

PHARMACEUTICAL DOSAGE FORM

FIELD OF THE INVENTION

The invention relates to a pharmaceutical dosage form, preferably a tablet for oral administration.

BACKGROUND ART

For many pharmaceutically active compounds it is still preferred to have them orally administered by way of tablets. It is also well known that depending on how a pharmaceutically active ingredient is formulated into a tablet its release pattern can be modified. In this regard, tablets providing a retarded release profile are of primary importance. With retarded release tablets care has to be taken that under no circumstances the pharmaceutically active ingredient will be released completely and instantaneously in an uncontrolled manner ("dose-dumping") since regularly the dosage used for retarded release tablets is much higher than for non-retarded release tablets. This may cause serious adverse effects or even death depending on the active ingredient and potency thereof.

Controlled release (e.g. delayed release, prolonged release, sustained release, and the like) may be based upon various concepts such as coating the pharmaceutical dosage form with a controlled release membrane, embedding the pharmacologically active compound in a matrix, binding the pharmacologically active compound to an ion-exchange resin, forming a complex of the pharmacologically active compound, and the like. In this context it can be referred to, e.g., W. A. Ritschel, Die Tablette, 2. Auflage, Editio Cantor Verlag Aulendorf, 2002.

In WO 01/97783 A1 a controlled-release, in particular a retarded release oral drug dosage form for releasing a drug into at least a portion of a region defined by the stomach and the front gastrointestinal tract is obtained by employing a solid monolithic matrix having a non-circular shape wherein the longitudinal axis has a maximum length of 3.0 cm and the transversal axis achieves a minimum length of 1.2 cm within one hour of immersion in water. Furthermore, it is required that the matrix has a shape which when projected onto a plane is either an oval or a parallelogram.

U.S. Pat. No. 4,353,887 discloses a divisible tablet which exhibits controlled and delayed release of an active substance. This is achieved by use of a coating on a compacted tablet having an oblong shape in which the ratio of length to width to depth is approximately 2.5 to 5:approximately 0.9 to 2:1 and the width constitute at most ⅔ of the length. In addition, one or more relatively deep dividing grooves have to be present which run perpendicular to the length and depth and have a total depth of from approximately ⅓ to approximately ½ of the depth of the tablet.

WO 01/08661 is directed to a controlled release formulation, capable of providing sustained, prolonged, repeat and/or delayed release of oxycodone.

WO 03/094812 relates to abuse-resistant opioid-containing solid dosage pharmaceuticals comprising a sustained release carrier and an analgesically effective amount of an opioid analgesic in combination with an opioid euphoria-inhibiting amount of an isolated nontoxic N-methyl-D-aspartate receptor antagonist which is substantially not released when the dosage form is administered intact.

WO 99/48481 discloses a tablet for the controlled release of an active pharmaceutical ingredient. The tablet comprises a core having a donut-like configuration with a cylindrical hole extending through the center of the core. The core is coated with a hydrophobic, water-insoluble material covering all of the core except that which is defined by the cylindrical hole.

GB-A 2 057 878 discloses a divisible tablet having controlled and delayed release of the active substance, consisting of a compact that is formed by at least one active substance in an adjunct composition that effects a delayed and controlled release of the active substance, the compact being of an oblong shape in which the ratio of length to width to depth is approximately 2.5 to 5:approximately 0.9 to 2:1 and the width constitutes at most ⅔ of the length, and in which one or more relatively deep dividing grooves are present which run perpendicularly to the length and depth and have a total depth of from approximately 113 to approximately '12 of the depth of the tablet, but are at least so deep that one fracture surface area multiplied by the number of possible fragments constitutes a maximum of 15% of the surface area of the undivided tablet, the base and top faces independently of one another are planar or are convexly curved about the longitudinal axis or about parallels to this axis, the side faces are planar, the end faces can be of any shape and edges are optionally bevelled or rounded.

DE-A 198 56 147 discloses a solid, elongate dosage form with a long axis and with a length which is defined by projection of the ends of the dosage form onto the long axis, where a cross-sectional area oriented perpendicular to the long axis has an area which is variable along the long axis and increases from a cross-sectional area which is located between the ends and has a minimal area essentially continuously toward the two ends up to in each case a cross-sectional area with a maximal area, wherein the distance of the maximal cross-sectional area which is located near one end from the maximal cross-sectional area which is located near the other end is, projected on the long axis, more than half the length of the dosage form.

DE 28 08 505 $C_2$ discloses a tablet which dissolves at essentially constant speed and which contains a water soluble component as well as a water insoluble coating. It is required that the side of the tablet has to comprise one or more cavities having a breadth of 0.1 to 1.0 mm, a depth of 0.1 to 0.4 mm and a length of more than 0.1 mm, wherein the side of said cavities is less than ⅙ of the total side of the tablet.

In DE 692 29 881 T2 it is proposed to obtain a tablet having a retarded release profile by use of a water soluble gel as well as of a specific coating having a specific thickness. The coating has to contain either ethylcellulose or acetylcellulose and has to be water insoluble as well as insoluble in gastric liquids.

A tablet having a controlled release profile will according to WO 99/48481 A1 be obtained by use of a doughnut-shaped core material with a cylindrical hole. A hydrophobic, water-insoluble coating is applied to the doughnut-shaped core except for the side of said core which surrounds the cylindrical hole. In such a manner an inherent limitation of compressed monolithic tablets for extended release dosages shall be overcome, namely the increase in diffusion length resistance over time due to the insolubility of the polymer. Apparently, this problem has been solved by insuring that the inner exposed area of the doughnut-shaped configuration is clear of any coating.

In DE 42 39 085 A1 it is described to make use of an oblong tablet only the opposed edges of which are in contact with an underlying side but not the intermediate section. In this manner the tablet is easily divisible by use of one hand only. The two parts forming such an oblong tablet may have the form of spherical sectors.

It is well known that a pharmaceutical formulation or its mode of manufacture, e.g. for an oral dosage form, might undergo modifications during clinical testing, for example with respect to the ingredients used or to the relative amounts of the excipients, or with respect to the reaction conditions and reactants used during manufacture. Frequently, such modifications at least to some extent have an impact on the release profile of pharmaceutically active ingredients. This is particularly unpleasant if for a specific formulation an approved optimized release profile has already been found which can not be reproduced with the modified formulation. In such a case, the clinical tests have either to be interrupted or have to be started from the beginning. Given the huge expenditures necessary to bring a new drug formulation up to and through clinical testing the above scenario has indeed proven to be rather unsatisfactory.

Pharmaceutical dosage forms having an increased breaking strength (resistance to crushing) have been recently reported. Dosage forms of this type may also exhibit a certain degree of controlled release of the pharmacologically active compound contained therein. The major advantage of such pharmaceutical dosage forms is that comminuting, particularly pulverization, by conventional means, such as grinding in a mortar or fracturing by means of a hammer, is impossible or at least substantially impeded.

On the one hand, pharmaceutical dosage forms having an increased breaking strength are useful for avoiding drug abuse of the pharmacologically active compound contained therein. Many pharmaceutical active compounds, in addition to having excellent activity in their appropriate application, also have abuse potential, i.e., they can be used by an abuser to bring about effects other than those intended. Opiates, for example, which are highly active in combating severe to very severe pain, are frequently used by abusers to induce a state of narcosis or euphoria. In order to make abuse possible, the corresponding pharmaceutical dosage forms, such as tablets or capsules are comminuted, for example ground in a mortar, by the abuser, the active compound is extracted from the resultant powder using a preferably aqueous liquid and the resultant solution, optionally after being filtered through cotton wool or cellulose wadding, and is administered parenterally, in particular intravenously. An additional phenomenon of this kind of administration, in comparison with abusive oral administration, is a further accelerated increase in active compound levels giving the abuser the desired effect, namely the "kick" or "rush". This kick is also obtained if the powdered pharmaceutical dosage form is administered nasally, i.e. is sniffed. Since controlled-release pharmaceutical dosage forms containing active compounds with abuse potential do not give rise to the kick desired by the abuser when taken orally even in abusively high quantities, such pharmaceutical dosage forms are also comminuted and extracted in order to be abused. Pharmaceutical dosage forms exhibiting an increased breaking strength, however, may not be powdered by conventional means and thus, cannot be administered nasally thereby avoiding drug abuse. In the context of such tamper resistant dosage forms, it can be referred to, e.g., WO 2005/016313, WO 2005/016314, WO 2005/063214, WO 2005/102286, WO 2006/002883, WO 2006/002884, WO 2006/002886, and WO 2006/082097.

These dosage forms have a breaking strength of at least 500 N in every direction of extension.

On the other hand, pharmaceutical dosage forms having an increased breaking strength are useful for avoiding an (unintentional) overdose of the pharmacologically active compound contained therein, which overdose would otherwise be caused by diminishing the retardant effect due to pulverization. It is known that many patients, particularly older patients frequently have difficulties in taking solid pharmaceutical dosage forms, such as tablets, gelatine capsules, etc. They choke on them and sometimes develop pronounced aversion to such pharmaceutical dosage forms. To counter this problem, various apparatuses have been developed by means of which conventional solid pharmaceutical dosage forms may be comminuted or pulverized ("tablet crushers"). Such apparatuses are used, for example, by the care staff in old people's homes. The pharmaceutical dosage forms are then administered to the people being cared for not as tablets etc. but rather as powder, for example to get round the difficulties involved in swallowing tablets. However, the comminution of pharmaceutical dosage forms with such apparatuses is problematic if the pharmaceutical dosage forms are prolonged-release formulations. As a rule, comminution results in destruction of the inner structure of the pharmaceutical dosage form, which is responsible for the prolonged release, so doing away with the prolonged-release action. Consequently, after administration, frequently all the physiologically active substance originally contained in the pharmaceutical dosage form is released in a relatively short time, whereby a comparatively very high plasma concentration of the substance is abruptly reached within a relatively short time frame. In this way, the originally prolonged-release formulations become immediate release formulations. Depending on the physiological activity of the substance, this may cause considerable side-effects however, and in extreme cases may even lead to the death of the patient. Pharmaceutical dosage forms having an increased breaking strength, however, cannot be comminuted by tablet crushers and thus, have to be swallowed as a whole thereby avoiding any (unintentional) overdose. In this context, it can be further referred to, e.g., WO 2006/082099.

These dosage forms also have a breaking strength of at least 500 N in every direction of extension.

The release profile of controlled-release formulations depends on a variety of factors, such as properties of the pharmaceutical dosage form per se, nature and content of the matrix, nature of the release medium, nature and content of the active compound, nature and content of further pharmaceutical excipients as well as the interrelationship of these factors. When the control of the release profile relies on a polymer matrix in which the active compound is embedded, the release rate depends on the properties of the pharmaceutical dosage form as such, e.g. its geometry, method of manufacture, additives and excipients contained therein, and the like. Further, the release rate depends on the properties of the matrix polymer, such as molecular weight, viscosity, particle properties, interaction with other polymers, chain entanglements, degree of cross-linking, chemical nature of monomer units, interaction of the matrix material with the release medium (e.g., swelling and gelling), and the like. Still further, the release rate depends on the properties of the active compound, e.g., its dose, particle size, particle form and its solubility in the release medium, which in turn is a function of various properties, such as molecular size, molecular weight, ionogenicity, acidity, steric hindrance, arrangement of dipols, hydrophilicity, etc. Furthermore, the release rate depends on the individual interactions of a given matrix material with a given active compound (cf. Ning Wu et al., Journal of Controlled Release 102 (2005) 569-81; V. S. Manthena et al., Am J Drug Deliv. 2004 2(1) 43-57).

The release profile of conventional pharmaceutical dosage forms that do not exhibit an increased breaking strength can usually be adjusted within certain limits, usually by the variation of the content and/or the nature of the pharmaceutical excipients, such as the matrix forming polymer.

In some cases it has also been reported that the release of a drug in the body can be controlled by the surface area to volume ratio of a conventional dosage form which does not exhibit an increased breaking strength. For example, U.S. Pat. No. 5,427,798 discloses film coated tablets containing bupropion hydrochloride and having a surface area to tablet volume of 3:1 to 25:1 cm$^{-1}$ for tablets of 50, 100 and 150 mg drug content. Similarly, U.S. Pat. No. 4,940,556 and U.S. Pat. No. 5,198,226 disclose spheroids containing dihydropyridine calcium channel blockers and having area radius to circumference radius ratios in the range of 0.85 to 1.0.

With respect of pharmaceutical dosage forms exhibiting an increased breaking strength, however, the variation of the content, the nature of the pharmaceutical excipients and/or the surface area to volume ratio also affects the mechanical properties. This is because the increased breaking strength of the pharmaceutical dosage form typically relies on the presence of a particular polymer that is processed by a particular method when manufacturing the pharmaceutical dosage form. It seems that said polymer also serves as a matrix embedding the pharmacologically active compound. In consequence, the polymer matrix that is essential to the breaking strength of the pharmaceutical dosage form simultaneously serves as a controlled release matrix and thus, varying the content, nature and/or spacial distribution of the polymer causes both, a change of the release profile as well as a change of the mechanical properties of the pharmaceutical dosage form.

Particular problems arise when the dose of the pharmacologically active compound and thus, also the total weight of the pharmaceutical dosage form is comparatively high. Depending upon the content and the nature of the pharmacologically active compound and of the pharmaceutical excipients, the retardant effect of the polymer may be so strong that the pharmaceutical dosage form cannot be adapted to a specific dosing regimen, e.g., twice daily, particularly when the increased breaking strength is to be maintained.

On the one hand, a decrease of the content of the retardant polymer for the purpose of accelerating drug release would substantially affect the mechanical properties of the pharmaceutical dosage form and in a worst case scenario, would completely diminish its specific and unique mechanical properties (breaking strength). Further, a decrease of the content of the matrix polymer beyond a certain limit may cause a deterioration or even loss of other desired properties, such as storage stability. A poor storage stability results, e.g., in a change of the release profile over time.

On the other hand, the addition of non-retardant pharmaceutical excipients (auxiliaries) for the purpose of weakening the retardant effect of the retardant polymer would increase the total weight of the dosage form. As highly dosed pharmaceutical dosage forms have comparatively high total weights anyway, a further increase of the total weight is disadvantageous and could deteriorate patient compliance (e.g. swallowability).

Thus, there is a demand for pharmaceutical dosage forms, particularly tamper-resistant pharmaceutical dosage forms, the release profile of which may be varied within certain limits without diminishing the tamper resistance and without deteriorating the compliance of the pharmaceutical dosage form.

It, thus, has been an object of the present invention to provide an oral dosage form which does not exhibit the shortcomings of the dosage forms of the state of the art and which in particular allows for an improved control of the release profile of the active pharmaceutical ingredient incorporated in the oral dosage form. It has been another object of the present invention to be able to regain the original release profile of an elaborated formulation for an oral dosage form, the release pattern of which has experienced changes due to modifications to the composition of said formulation.

This object has been solved by the subject-matter described hereinbelow.

SUMMARY OF THE INVENTION

The present invention relates in a first aspect to a pharmaceutical dosage form, especially an oral dosage form, particularly a tablet, comprising at least one pharmaceutically active ingredient, and having a shape comprising a longitudinal axis and two opposite longitudinal edges, a transversal axis perpendicular to the longitudinal axis and two opposite transversal edges, a front side, an opposite back side and a circumferential rim between said front and back side, wherein the front side and/or the back side comprise a basis area and wherein the front side and/or the back side comprise at least one bulge which extends above said basis area, said at least one bulge being present at and/or adjacent to at least a section of one or both longitudinal edges and/or at and/or adjacent to at least a section of one or both transversal edges and/or between both longitudinal edges and both transversal edges. The front side and/or the back side of the dosage form, in particular the basis area of the front side and/or the basis area of the back side, can further comprise at least one indentation.

The present invention relates in a second aspect to a tamper-resistant pharmaceutical dosage form having a retarded release profile, especially a tamper-resistant oral dosage form having a retarded release profile, particularly a tamper-resistant tablet having a retarded release profile, comprising at least one pharmaceutically active ingredient with potential for abuse, and having a shape comprising a longitudinal axis and two opposite longitudinal edges, a transversal axis perpendicular to the longitudinal axis and two opposite transversal edges, a front side, an opposite back side and a circumferential rim between said front and back side, wherein the front side and/or the back side comprise a basis area and wherein the front side and/or the back side comprise at least one bulge which extends above said basis area, said at least one bulge being present at and/or adjacent to at least a section of one or both longitudinal edges and/or at and/or adjacent to at least a section of one or both transversal edges and/or between both longitudinal edges and both transversal edges. The front side and/or the back side of the dosage form, in particular the basis area of the front side and/or the basis area of the back side, can further comprise at least one indentation.

The present invention relates in a third aspect to a pharmaceutical dosage form with controlled release of a pharmacologically active compound (A) contained therein, the pharmaceutical dosage form having a breaking strength $B_1$ of at least 500 N in direction of extension $E_1$ and having a breaking strength $B_2$ of less than 500 N in direction of extension $E_2$.

The pharmaceutical dosage forms according to the invention preferably exhibit anisotropic mechanical properties (i.e., different mechanical properties in different directions).

With the dosage form of the invention, preferably a tablet, it is possible to have in general a greater control on the release profile of pharmaceutically active ingredients. The release profile can be finely adjusted or tailored in a more accurate, predictable and reliable manner; the release profile can be manipulated or tailored so that a variety of retarded release profiles can be provided for the same formulation. Control of the release profile with the dosage form of the present invention can be achieved for dosage forms designed for immediate release or dosage forms designed for retarded (sustained) release. It is also an advantage that it is no longer necessary to rely on the choice and amount of hydrophilic polymer(s) to modify the dissolution profile of a retarded release formulation which in various circumstances has proven to not even be possible under realistic conditions.

It has also been surprisingly found that by modifying the outer shape of the pharmaceutical dosage form the release profile may be modified without simultaneously diminishing the breaking strength of the pharmaceutical dosage form. In particular, it has been surprisingly found that in spite of a modified outer shape of the pharmaceutical dosage form which causes a certain degree of fragility, the overall tamper resistance of the pharmaceutical dosage form can be maintained.

Furthermore, it has been surprisingly found that by modifying the outer shape of the pharmaceutical dosage form the storage stability, e.g. the storage stability of the release profile, can be increased compared to conventional dosage forms having a comparable release profile before storage.

BRIEF DESCRIPTION OF THE DRAWINGS

FIG. 15 is a schematic view of pharmaceutical dosage forms according to the invention. The pharmaceutical dosage form depicted in FIG. 15A) assumes the shape of a short tube, the pharmaceutical dosage form depicted in FIG. 15B) assumes the shape of a ring.

FIG. 16 is a schematic view of pharmaceutical dosage forms according to the invention. The pharmaceutical dosage form depicted in FIG. 16A) assumes the shape of a triangle with two recesses on opposing sides, the pharmaceutical dosage form depicted in FIG. 16B) assumes the shape of a pentagon with two recesses on opposing sides.

FIG. 17 is a schematic view of the cross-sectional face of the preferred pharmaceutical dosage form depicted in FIG. 10.

FIG. 18 is a schematic view of the pharmaceutical dosage form shown in FIG. 10 and the set-up for measuring the breaking strength in directions of extension $E_1$, $E_2$ and $E_3$, respectively.

DETAILED DESCRIPTION OF THE INVENTION

Figure 1A:
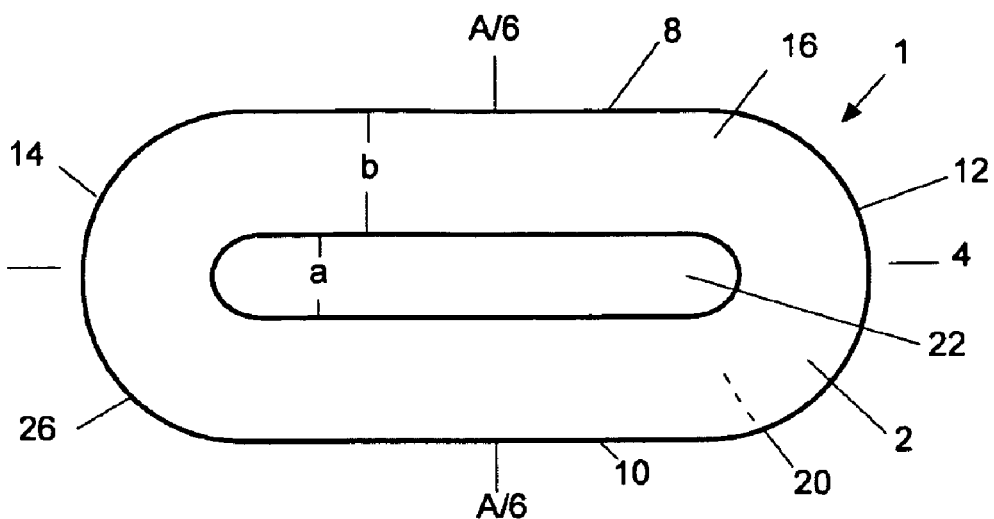
FIG. 1A) is a schematic top view of a tablet of the invention.

Unless expressly stated otherwise, any preferred embodiment of the invention that will be described in connection with a particular aspect of the invention hereinafter shall also apply to the other aspects of the invention. In this regard, embodiments that have been described in terms of key words that are synonymous to or at least partially overlap with similar key words mentioned elsewhere in the specification, such as "pharmaceutically active ingredient" and "pharmacologically active compound (A)", or "pharmaceutical dosage form" and "tablet", shall be understood as being also applicable in terms of said similar key words.

A first aspect of the invention relates to a pharmaceutical dosage form, especially an oral dosage form, particularly a tablet, comprising at least one pharmaceutically active ingredient, and having a shape comprising a longitudinal axis and two opposite longitudinal edges, a transversal axis perpendicular to the longitudinal axis and two opposite transversal edges, a front side, an opposite back side and a circumferential rim between said front and back side, wherein the front side and/or the back side comprise a basis area and wherein the front side and/or the back side comprise at least one bulge which extends above said basis area, said at least one bulge being present at and/or adjacent to at least a section of one or both longitudinal edges and/or at and/or adjacent to at least a section of one or both transversal edges and/or between both longitudinal edges and both transversal edges. The front side and/or the back side of the dosage form, in particular the basis area of the front side and/or the basis area of the back side, can further comprise at least one indentation.

Although it is also possible that the longitudinal axis and the transversal axis of the tablet have essentially the same length, it is preferred that the tablet of the invention has a longitudinal axis being longer than its transversal axis. That is, preferred embodiments of the tablet of the invention exhibit an oblong shape. The longitudinal axis is typically extending through the middle part of the tablet between both opposing longitudinal edges from one transversal edge to the opposite transversal edge, in particular in such a way that its length is maximized. The transversal axis is typically extending from one longitudinal edge to the opposite longitudinal edge, in particular in such a way that its length is maximized. The transversal axis is oriented perpendicular to the longitudinal axis.

The basis area of the front side and/or the back side of the tablet of the invention does not necessarily have to be flat, but can in one embodiment exhibit an irregular or regular three dimensional pattern, which, however, is not extending to any significant degree towards the dimension of a bulge or an indentation.

The average distance between the front basis area and the back basis area of one embodiment of the tablet of the invention usually is smaller than the length of its transversal axis. Those opposite sides of the tablet which have the smallest average distance are usually comprising the front and the back basis areas.

According to another preferred embodiment, a tablet is provided, wherein the front side and the back side each comprise at least one bulge at least along a section at and/or adjacent to both longitudinal edges and/or at least along a section at and/or adjacent to both transversal edges. In this respect it is even more preferred in certain cases that said front side and said back side comprise an at least essentially continuous bulge at and/or adjacent to at least two third of both opposite longitudinal edges and/or at and/or adjacent to at least two third of both opposite transversal edges.

The bulge may have any geometric cross-section, and can, for example, be rounded or can have a rectangular, triangular or square cross-section. The bulges preferably have a width which is less than half the width, more preferably less than one third of the width of the tablet. The length of the bulges can vary to a great extent. It is preferred that the overall length of an individual bulge is at least one half of the length of the longitudinal edge or of the transversal edge, depending on its location. Typically, the overall length of a bulge is much longer than its width, e.g. several times the width of the bulge, such as more than 2, 3, 4, 5 or 6 times of its width, in particular when oriented in the longitudinal direction, or more than 2, 3 or 4 times of its width, in particular when oriented in the transversal direction. A bulge in the meaning of the present invention shall also comprise a series of adjacent bulge portions. These bulge portions, when viewed from above, can, for example, have the circumferential form of a circle, an oval, a rectangle, a square, a triangle or any other polygonal form, or may come close to these forms, or may even have an irregular form.

A bulge which is located at a longitudinal and/or at a transversal edge regularly passes over from the circumferential rim of the tablet without a significant transition zone or transition step, i.e. without a "land". In such an embodiment there is a smooth transition from the rim part to the bulge part so that the outer surfaces of the rim and the bulge form a continuous surface at least over a section. A bulge which is positioned adjacent to a longitudinal or adjacent to a transversal edge is in contrast thereto not directly placed at the circumferential rim of the tablet but is separated from the rim in the plane of the basis area by a portion, in particular a minor portion, which can be attributed to be part of the basis area. Said minor portion is known in the field of tablet technology as "the land". This minor area usually has a width being smaller than the average width of the bulge itself. In a preferred embodiment, the land is in the range from about 0.05 mm to about 0.5 mm, e.g. about 0.1 mm.

In a particularly suitable embodiment, the tablet of the invention is provided with bulges at both longitudinal edges and/or both transversal edges of both the front side and the back side of the tablet, wherein these bulges extend at least over one half, more preferably over two thirds of the length of the longitudinal and/or transversal edges, even more preferably over the whole length of the longitudinal and/or transversal edges. In another preferred embodiment, the bulges continuously circumscribe the basis area of the front side and/or the back side, preferably the front and the back side, at and/or adjacent to the respective longitudinal and transversal edges. Most desirable results in terms of an improved release profile can for example be obtained with tablets of the invention having bulges at both longitudinal edges of both sides of the tablet. The cross-section of these tablets can be described to have or come close to an H-shape. By use of the expression H-shape it shall just be indicated that a tablet body having opposite, in particular rather flat, basis areas is provided with opposing bulges at the longitudinal edges on both sides of the tablet body. For example, in one H-shape embodiment the bulges can protrude above their respective basis areas only to a minor extent compared to the lateral distance between the bulges along opposite longitudinal edges, e.g. up to about 1 or 2 mm.

In one preferred embodiment, a tablet of the invention, in particular its oblong form, comprises at or adjacent to, in particular adjacent to, major portions of both opposite longitudinal edges, in particular at least along two thirds of the longitudinal edges, of the front side at least one bulge. In another preferred embodiment, a tablet of the invention, in particular its oblong form, comprises at least one bulge at or adjacent to, in particular adjacent to, major portions of both opposite longitudinal edges, in particular at least along two thirds of the longitudinal edges, of both the front side and the back side of the tablet. In another preferred embodiment, the tablet of the invention, in particular its oblong form, comprises a circumferential bulge at or adjacent to, in particular adjacent to, the circumferential edge of the front side of said tablet. In another preferred embodiment, the tablet of the invention, in particular its oblong form, comprises a circumferential bulge at or adjacent to, in particular adjacent to, the circumferential edge of both the front side and the back side of said tablet.

According to another suitable embodiment of the tablet of the invention, it is provided that one or both longitudinal edges are essentially straight over at least a major part of their length and/or wherein one or both transversal edges are curved over a major part of their length, in particular curved in the form of an essentially circular arc. It is of course also possible that the longitudinal edges exhibit any other irregular or regular shape, for example, having a wave-like edge portion at least over a section. It is also possible that the transversal edge exhibits the shape of a triangle or any other polygonal shape. In general, both longitudinal and transversal edges form the circumference of the front side and the back side of the tablet.

For most applications it is sufficient that the longitudinal length, that is, the length of the longitudinal axis, of the tablet does not exceed 30 mm.

According to another embodiment, the tablet of the invention preferably has an average thickness over the basis areas of the front and the back side of at least about 1 mm, and in particular of no more than about 6 mm, more in particular ranging from about 1 mm to about 3 mm or more in particular ranging from about 2 mm to about 4 mm.

According to one embodiment of the tablet of the invention, the bulge extends perpendicular from the basis area of the front side and/or from the basis area of the back side in average from about 0.5 mm to about 2 mm, in particular from about 0.5 mm to about 1 mm.

Tablets of the invention preferably have a length in the longitudinal direction in the range of about 5 mm to about 30 mm, in particular in the range of about 15 mm to about 25 mm, more in particular about 17 mm to about 23 mm, even more in particular about 21 mm; a width in the range of about 5 mm to about 15 mm, in particular in the range of about 7 mm to about 12 mm, more in particular about 7 mm to about 10 mm, even more in particular 7 mm, 9 mm or 10 mm; and a thickness over the basis areas in the range of about 1 mm to about 6 mm, in particular in the range of about 1.5 mm to about 4 mm, even more in particular from 2 mm to about 4 mm, even further in particular from about 2.5 mm to about 3.5 mm.

As indicated above, the front side and/or the back side of the tablet of the invention, in particular the basis area of the front side and/or the basis area of the back side, can in one embodiment further comprise at least one indentation. As has been found, this generally allows for a further improvement of the control of the release profile. The indentation in general in one embodiment represents a hollow space which is provided or embedded in the overall surface of the tablet. For example, the front side, the back side, in particular the basis areas of the front side and/or the back side, the rim and/or at least one bulge can be provided with at least one indentation.

Indentations, when viewed from above, can have any irregular or regular shape, for example, the form of a square, rectangle, triangle, oval or circle. In one embodiment the indentations can take the form of a cylinder, a cube, a cuboid or a half-sphere, that is the walls and the opening forming the indentation come close to describing the form of a cylinder, a cube, a cuboid or a half-sphere. When viewed from above, the silhouette shape of the indentations has essentially the same width and length dimensions. It is also possible that when viewed from above, the silhouette shape of an indentation has a longer length dimension than a width dimension, for example, a length dimension which is at least 2, 3 or 4 times the width dimension. Accordingly, when viewed from above, the silhouette shape can be rather elongate, e.g. a rectangle, and can have a regular silhouette form, e.g. straight, wave-like, or zig-zag, or can be rather irregular. In another embodiment an array of indentations can be formed, for example on the front side and/or the back side. For many applications it has been found to be sufficient that when viewed from above, the silhouette-shape of the indentation has a length dimension which is essentially identical to its width dimension as, for example, can be found with a circular, square-like or slightly oval or slightly rectangular shape. Said width dimension of the indentations, which is regularly determined parallel to the transversal axis, usually is less than one half of the transversal length of the tablet, in particular less than one third of the transversal length of the tablet. In one embodiment the width dimension is essentially identical to the depth of the indentation or is no more than 2 or 3 times the depth of the indentation. The length dimension of the indentation, which is regularly determined parallel to the longitudinal axis, usually is no longer than three quarters of the longitudinal length of the tablet, in particular no longer than one half of the longitudinal length of the tablet, and preferably no longer than one third of the longitudinal length of the tablet. A hole in a tablet is not an indentation in the meaning of the present invention. The silhouette shape and the depth of said indentations can vary depending on the desired release profile. Usually care should be taken that the depths of these indentations does not come too close to the thickness of the tablet in order to prevent that upon handling a hole through the tablet will be formed. Preferably the indentations have a depth which does not go beyond half the thickness of the tablets of the invention. For most applications it is frequently already sufficient that the maximum depth of said indentations does not go beyond one third of the thickness of the tablet of the invention. The average thickness of the tablet of the invention in general is determined as the distance between the front and back side of the tablet or preferably between the basis area of the front side and the basis area of the back side.

By using the expressions front side and back side it shall be indicated that the tablet of the invention has two opposite sides which each can be provided with bulges and/or indentations. In consequence, the selection of which is the front side and which is the back side is rather arbitrary. Accordingly, the expressions front side and back side could also be replaced by first side and opposite second side, respectively.

In one embodiment of the invention, there is provided a tablet wherein the front side and/or the back side, in particular the, in particular essentially flat, basis area of the front side and/or the, in particular essentially flat, basis area of the back side, comprise in addition to at least one bulge at least one indentation, in particular between opposite longitudinal and/or transversal bulges.

In one embodiment of the invention it is provided that both the front and the back side comprise at least one indentation.

The indentations on the front side and on the back side of the tablet of the invention can at least once be at least partially off-set or can at least once be positioned in a congruent manner. In one preferred embodiment, all the indentations of the front side and all indentations on the back side are at least partially off-set or are positioned in a congruent manner.

The indentations are regularly positioned in the basis area of the front and/or the back side of the tablet of the invention. It is for example possible to place two or more of such indentations adjacent to each other, e.g. in a row located between the longitudinal edges of the front and/or the back side. The indentations are preferably located between opposite longitudinally extending bulges at or adjacent to the longitudinal edges of the front and/or the back side of the tablet of the invention.

In one preferred embodiment, a tablet of the invention, in particular its oblong form, comprises at or adjacent to, in particular adjacent to, major portions of both longitudinal edges, in particular at least along two thirds of the longitudinal edges of the front side at least one bulge, and, in particular between the bulges along opposite longitudinal edges, at least one indentation.

In another preferred embodiment, a tablet of the invention, in particular its oblong form, comprises at least one bulge at or adjacent to, in particular adjacent to, major portions of both opposite longitudinal edges, in particular at least along two thirds of the longitudinal edges of both the front side and the back side of the tablet as well as at least one indentation on the front side and/or the back side, in particular on the basis area of the front side and/or the basis of the back side, of the tablet, in particular between the bulges which are located along opposite longitudinal edges on the front side and/or the back side, respectively. In another preferred embodiment, the tablet of the invention, in particular its oblong form, comprises a circumferential bulge at or adjacent to, in particular adjacent to, the circumferential edge of the front side and/or back side of said tablet, and at least one indentation on the front side and/or back side, in particular on the basis area circumscribed by the circumferential bulge on the front and/or on the back side. In another preferred embodiment, the tablet of the invention, in particular its oblong form, comprises a circumferential bulge at or adjacent to, in particular adjacent to, the circumferential edge of both the front side and the back side of said tablet and at least one indentation on the front side and the back side, in particular on the basis area circumscribed by the circumferential bulge of the front side and on the basis area circumscribed by the circumferential bulge of the back side.

There are generally no limitations as to the pharmaceutically active ingredient(s) which can be incorporated into the tablet of the invention.

Suitable active ingredients are those which exert a local physiological effect, as well as those which exert a systemic effect, after oral administration. Examples of suitable active ingredients encompass:

analgesic and anti-inflammatory drugs (NSAIDs, fentanyl, indomethacin, ibuprofen, ketoprofen, nabumetone, paracetamol, piroxicam, tramadol, COX-2 inhibitors such as celecoxib and rofecoxib);

anti-arrhythmic drugs (procainamide, quinidine, verapamil); antibacterial and antiprotozoal agents (amoxicillin, ampicillin, benzathine penicillin, benzylpenicillin, cefaclor, cefadroxil, cefprozil, cefuroxime axetil, cephalexin, chloramphenicol, chloroquine, ciprofloxacin, clarithromycin, clavulanic acid, clindamycin, doxyxycline, erythromycin, flucloxacillin sodium, halofantrine, isoniazid, kanamycin sulphate, lincomycin, mefloquine, minocycline, nafcillin sodium, nalidixic acid, neomycin, norfloxacin, ofloxacin, oxacillin, phenoxymethyl-penicillin potassium, pyrimethamine-sulfadoxime, streptomycin, TMC207);

anti-coagulants (warfarin);

antidepressants (amitriptyline, amoxapine, butriptyline, clomipramine, desipramine, dothiepin, doxepin, fluoxetine, reboxetine, amineptine, selegiline, gepirone, imipramine, lithium carbonate, mianserin, milnacipran, nortriptyline, paroxetine, sertraline; 3-[2-[3,4-dihydrobenzofuro[3,2-c]pyridin-2(1H)-yl]ethyl]-2-methyl-4H-pyrido[1,2-a]pyrimidin-4-one);

anti-diabetic drugs (glibenclamide, metformin);

anti-epileptic drugs (carbamazepine, clonazepam, ethosuximide, gabapentin, lamotrigine, levetiracetam, phenobarbitone, phenyloin, primidone, tiagabine, topiramate, valpromide, vigabatrin);

antifungal agents (amphotericin, clotrimazole, econazole, fluconazole, flucytosine, griseofulvin, itraconazole, ketoconazole, miconazole nitrate, nystatin, terbinafine, voriconazole);

antihistamines (astemizole, cinnarizine, cyproheptadine, decarboethoxyloratadine, fexofenadine, flunarizine, levocabastine, loratadine, norastemizole, oxatomide, promethazine, terfenadine);

anti-hypertensive drugs (captopril, enalapril, ketanserin, lisinopril, minoxidil, prazosin, ramipril, reserpine, terazosin);

anti-muscarinic agents (atropine sulphate, hyoscine);

antineoplastic agents and antimetabolites (platinum compounds, such as cisplatin, carboplatin; taxanes, such as paclitaxel, docetaxel; tecans, such as camptothecin, irinotecan, topotecan; vinca alkaloids, such as vinblastine, vindecine, vincristine, vinorelbine; nucleoside derivatives and folic acid antagonists such as 5-fluorouracil, capecitabine, gemcitabine, mercaptopurine, thioguanine, cladribine, methotrexate; alkylating agents, such as the nitrogen mustards, e.g. cyclophosphamide, chlorambucil, chlormethine, iphosphamide, melphalan, or the nitrosoureas, e.g. carmustine, lomustine, or other alkylating agents, e.g. busulphan, dacarbazine, procarbazine, thiotepa; antibiotics, such as daunorubicin, doxorubicin, idarubicin, epirubicin, bleomycin, dactinomycin, mitomycin; HER 2 antibody, such as trastuzumab; podophyllotoxin derivatives, such as etoposide, teniposide; farnesyl transferase inhibitors; anthrachinon derivatives, such as mitoxantron);

anti-migraine drugs (alniditan, naratriptan, sumatriptan);
anti-Parkinsonian drugs (bromocriptine mesylate, levodopa, selegiline);
antipsychotic, hypnotic and sedating agents (alprazolam, buspirone, chlordiazepoxide, chlorpromazine, clozapine, diazepam, flupenthixol, fluphenazine, flurazepam, 9-hydroxyrisperidone, lorazepam, mazapertine, olanzapine, oxazepam, pimozide, pipamperone, piracetam, promazine, risperidone, selfotel, seroquel, sertindole, sulpiride, temazepam, thiothixene, triazolam, trifluperidol, ziprasidone, zolpidem);
anti-stroke agents (lubeluzole, lubeluzole oxide, riluzole, aptiganel, eliprodil, remacemide) antitussive (dextromethorphan, laevodropropizine);
antivirals (acyclovir, ganciclovir, loviride, tivirapine, zidovudine, lamivudine, zidovudine+lamivudine, didanosine, zalcitabine, stavudine, abacavir, lopinavir, amprenavir, nevirapine, efavirenz, delavirdine, indinavir, nelfinavir, ritonavir, saquinavir, adefovir, hydroxyurea, TMC120, TMC125, TMC278);
beta-adrenoceptor blocking agents (atenolol, carvedilol, metoprolol, nebivolol, propanolol) cardiac inotropic agents (aminone, digitoxin, digoxin, milrinone);
corticosteroids (beclomethasone dipropionate, betamethasone, budesonide, dexamethasone, hydrocortisone, methylprednisolone, prednisolone, prednisone, triamcinolone);
disinfectants (chlorhexidine);
diuretics (acetazolamide, frusemide, hydrochlorothiazide, isosorbide);
enzymes;
essential oils (anethole, anise oil, caraway, cardamom, *cassia* oil, cineole, cinnamon oil, clove oil, coriander oil, dementholised mint oil, dill oil, eucalyptus oil, eugenol, ginger, lemon oil, mustard oil, neroli oil, nutmeg oil, orange oil, peppermint, sage, spearmint, terpineol, thyme);
gastro-intestinal agents (cimetidine, cisapride, clebopride, diphenoxylate, domperidone, famotidine, lansoprazole, loperamide, loperamide oxide, mesalazine, metoclopramide, mosapride, nizatidine, norcisapride, olsalazine, omeprazole, pantoprazole, perprazole, prucalopride, rabeprazole, ranitidine, ridogrel, sulphasalazine) haemostatics (aminocaproic acid);
lipid regulating agents (atorvastatin, lovastatin, pravastatin, probucol, simvastatin) local anaesthetics (benzocaine, lignocaine);
opioid analgesics (buprenorphine, codeine, dextromoramide, dihydrocodeine, hydrocodone, oxycodone, morphine);
parasympathomimetics and anti-dementia drugs (ATT-082, eptastigmine, galanthamine, metrifonate, milameline, neostigmine, physostigmine, tacrine, donepezil, rivastigmine, sabcomeline, talsaclidine, xanomeline, memantine, lazabemide);
peptides and proteins (antibodies, becaplermin, cyclosporine, erythropoietin, immunoglobulins, insuline);
sex hormones (oestrogens; conjugated oestrogens, ethinyloestradiol, mestranol, oestradiol, oestriol, oestrone; progestogens; chlormadinone acetate, cyproterone acetate, 17-deacetyl norgestimate, desogestrel, dienogest, dydrogesterone, ethynodiol diacetate, gestodene, 3-keto desogestrel, levonorgestrel, lynestrenol, medroxy-progesterone acetate, megestrol, norethindrone, norethindrone acetate, norethisterone, norethisterone acetate, norethynodrel, norgestimate, norgestrel, norgestrienone, progesterone, quingestanol acetate);
stimulating agents (sildenafil);
vasodilators (amlodipine, buflomedil, amyl nitrite, diltiazem, dipyridamole, glyceryl trinitrate, isosorbide dinitrate, lidoflazine, molsidomine, nicardipine, nifedipine, oxpentifylline, pentaerythritol tetranitrate); their N-oxides, their pharmaceutically acceptable acid or base addition salts and their stereochemically isomeric forms.

Pharmaceutically acceptable acid addition salts comprise the acid addition salt forms which can conveniently be obtained by treating the base form of the active ingredient with appropriate organic and inorganic acids. Active ingredients containing an acidic proton may be converted into their non-toxic metal or amine addition salt forms by treatment with appropriate organic and inorganic bases. The term addition salt also comprises the hydrates and solvent addition forms which the active ingredients are able to form. Examples of such forms are e.g. hydrates, alcoholates and the like. The N-oxide forms of the active ingredients comprise those active ingredients wherein one or several nitrogen atoms are oxidized to the so-called N-oxide.

The active ingredient(s) is (are) present in the dosage form in a therapeutically effective amount. The amount that constitutes a therapeutically effective amount varies according to the ingredients being used, the condition being treated, the severity of said condition, the patient being treated, and whether the dosage form is designed for an immediate or retarded release. The amount of active ingredient(s) used in the present invention preferably ranges from about 0.01% to about 90% (w/w), in particular from about 0.01% to about 50% (w/w), more in particular from about 20% to about 50% (w/w).

Unless explicitly stated otherwise, in the meaning of the present invention the indication "w/w" shall mean weight of the compound specified per total weight of the composition forming the tablet.

In one embodiment, the one or more active ingredients are incorporated in a tablet for immediate release.

In another embodiment, the one or more active ingredients are incorporated in a tablet for retarded release. In this case, the active ingredient(s) of the tablet of the invention is (are) conventionally embedded in conventional formulating aids and/or one or more hydrophilic polymers. These hydrophilic polymers tend to swell upon contact with aqueous fluids following administration, and result in a viscous, drug release regulating gel layer. Preferably the viscosity of these polymers ranges from 150 to 100.000 mPa·s (apparent viscosity of a 2% aqueous solution at 20° C.). Examples of suitable hydrophilic polymers include:
  alkylcelluloses, such as, methylcellulose;
  hydroxyalkylcelluloses, for example, hydroxymethylcellulose, hydroxyethylcellulose, hydroxypropylcellulose and hydroxybutylcellulose;
  hydroxyalkyl alkylcelluloses, such as, hydroxyethyl methylcellulose and hydroxypropyl methylcellulose;
  carboxyalkylcelluloses, such as, carboxymethylcellulose;
  alkali metal salts of carboxyalkylcelluloses, such as, sodium carboxymethylcellulose;
  carboxyalkylalkylcelluloses, such as, carboxymethylethylcellulose;
  carboxyalkylcellulose esters;
  other natural, semi-synthetic, or synthetic polysaccharides, such as, alginic acid, alkali metal and ammonium salts thereof, carrageenans, galactomannans, tragacanth, agar-agar, gummi arabicum, guar gummi, xanthan gummi, starches, pectins, such as sodium carboxymethylamylopectin, chitin derivates such as chitosan, polyfructans, insulin;
  polyacrylic acids and the salts thereof;
  polymethacrylic acids and the salts thereof, methacrylate copolymers;

polyvinylalcohol;

polyvinylpyrrolidone, copolymers of polyvinylpyrrolidone with vinyl acetate;

combinations of polyvinylalcohol and polyvinylpyrrolidone;

polyalkylene oxides such as polyethylene oxide and polypropylene oxide and copolymers of ethylene oxide and propylene oxide.

Preferably the one or more hydrophilic polymers are cellulose derivatives, in particular cellulose ether derivatives, such as for example alkylcelluloses or hydroxyalkylcelluloses or hydroxyalkyl alkylcelluloses, more in particular hydroxyalkylcelluloses or hydroxyalkyl alkylcelluloses.

Most preferred cellulose ether derivatives are hydroxypropyl methylcellulose (HMPC) and hydroxypropyl cellulose (HPC). Different viscosity grades of hydroxypropyl cellulose and hydroxypropyl methylcellulose are commercially available. Hydroxypropyl methylcellulose preferably used in the present invention has a viscosity grade ranging from about 3,500 mPa·s to about 100,000 mPa·s, in particular ranging from about 4,000 mPa·s to about 20,000 mPa·s and most in particular a viscosity grade of about 6,500 mPa·s to about 15,000 mPa·s (apparent viscosity of a 2% aqueous solution at 20° C.), e.g. hypromellose 2208 (DOW, Antwerp, Belgium). Hydroxypropyl cellulose having a viscosity lower than 1,500 mPa·s (apparent viscosity of a 2% aqueous solution at 20° C.) is preferred, in particular hydroxypropyl cellulose having a viscosity in the range from about 150 to about 700 mPa·s, preferably from 200 to 600 mPa·s, e.g. Klucel EF (Hercules, Wilmington, USA).

Preferably, the amount of viscous hydrophilic polymers, in particular HPMC and HPC, in the present formulation ranges from about 0.01 to about 80% (w/w), in particular from about 10 to about 60% (w/w), more in particular between 30 and 60% (w/w).

In addition to the one or more hydrophilic polymers, the retarded release formulation can in one embodiment comprise pregelatinized starch. The amount of pregelatinized starch preferably is in the range from 5 to 80% (w/w), in particular from 5 to 15% (w/w).

In one embodiment, the tablet of the invention comprises at least one pharmaceutically active ingredient, pregelatinized starch, and HPC and/or HPMC, in particular at least one pharmaceutically active ingredient, pregelatinized starch, HPC and HPMC.

The tablets according to the invention are preferably prepared by way of compression using a die and a punch.

The tablets of the invention can optionally be provided, partially or completely, with a conventional tablet coating. The tablets of the present invention are preferably film coated with art-known film coating compositions. The coating is applied to improve the aesthetic impression and/or the taste of the tablets and the ease with which they can be swallowed.

Coating the tablets of the present invention can also serve other purposes, e.g. improving stability and shelf-life. Suitable coating formulations comprise a film forming polymer such as, for example, hydroxypropyl methylcellulose, e.g. hypromellose 2910 (5 mPa·s), a plasticizer such as, for example, a glycol, e.g. propylene glycol or polyethylene glycol, an opacifier, such as, for example, titanium dioxide, and a film smoothener, such as, for example, talc. Suitable coating solvents are water as well as organic solvents. Examples of organic solvents are alcohols, e.g. ethanol or isopropanol, ketones, e.g. acetone, or halogenated hydrocarbons, e.g. methylene chloride. Optionally, the coating can contain a therapeutically effective amount of one or more active ingredients to provide for an immediate release of said active ingredient(s) and thus for an immediate relief of the symptoms treated by said active ingredient(s). Coated tablets of the present invention are prepared by first making the tablet cores in the way as described above and subsequently coating said tablet cores using conventional techniques, such as coating in a coating pan. For example, PEG, e.g. PEG 20.000, or HPMC can be used for the coating.

Beside active ingredient(s) and optional hydrophilic polymers, the tablet of the present invention can also optionally comprise pharmaceutically acceptable formulation agents such as fillers, glidants, binding agents, granulating agents, anti-caking agents, lubricants, flavors, dyes, and preservatives.

The filler may be selected from soluble fillers, for example, sucrose, lactose, trehalose, maltose, mannitol, sorbitol, insulin, and from insoluble fillers, for example, dicalcium or tricalcium phosphate, talc. An interesting filler is lactose, in particular, lactose monohydrate. Different grades of lactose can be used. One type of lactose preferably used in the present invention is lactose monohydrate 200 mesh (DMV, Veghel, the Netherlands). Another lactose monohydrate, lactose monohydrate of the type DCL 11 (DMV, Veghel, the Netherlands), can also preferably be used. The notation DCL refers to "Direct Compression Lactose". The number 11 is a reference number of the manufacturer. This type of lactose is characterised in that 98% (w/w) of the particles, based on the total amount of lactose employed, have a diameter smaller than 250 µm, 30% (w/w) to 60% (w/w) of the particles, based on the total amount of lactose employed, have a diameter of 100 µm, and at maximum 15% (w/w) of the particles, based on the total amount of lactose employed, have a diameter of smaller than 45 µm. The weight percentage of filler ranges between about 6% and about 54% (w/w).

Among the optional formulating agents that further can be comprised in the present formulation there can be mentioned agents such as polyvidone; starch; acacia gum; gelatin; seaweed derivatives, e.g. alginic acid, sodium and calcium alginate; cellulose derivatives, e.g. ethylcellulose, hyoroxypropyl methylcellulose, having useful binding and granulating properties; glidants such as colloidal silica, starch or talc; lubricants such as magnesium stearate and/or palmitate, calcium stearate, stearic acid, polyethylene glycol, liquid paraffin, sodium or magnesium lauryl sulphate; anti-adherents such as talc and corn starch.

The first aspect of the present invention can be more readily understood by reference to FIGS. 1-6.

In FIG. 1A) a tablet 1 is depicted showing its front side 2 from the top. The tablet 1 has a longitudinal axis 4 in the longitudinal direction and a transversal axis 6, perpendicular thereto, in the transversal direction. The two opposing longitudinal edges 8 and 10 and the two opposing transversal edges 12 and 14 are forming the circumference of the front side 2 of the tablet 1. In the depicted embodiment the longitudinal edges 8, 10 are essentially straight whereas the transversal edges 12, 14 are rounded. Tablet 1 of FIG. 1A) has a circumferential bulge 16, 20 on both the upper side 2 and the lower side 18 (FIG. 1B)) having reference sign 20. The bulges 16 and 20 are positioned adjacent to the longitudinal and transversal edges and raise above the basis area 22 of the front side 2, and above the basis area 24 of the back side 18, respectively. In the embodiment shown in FIGS. 1A), 1B) the basis areas 22, 24 have a transversal width "a" which is smaller than the transversal width "b" of the bulges.

Figure 1B:
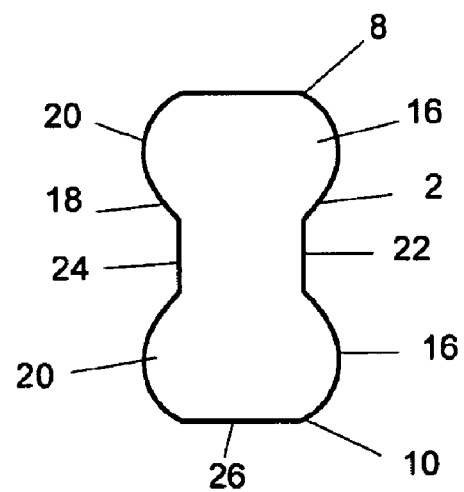
FIG. 1B) is a cross-sectional view along A-A of the tablet of FIG. 1A).
Figure 2A:
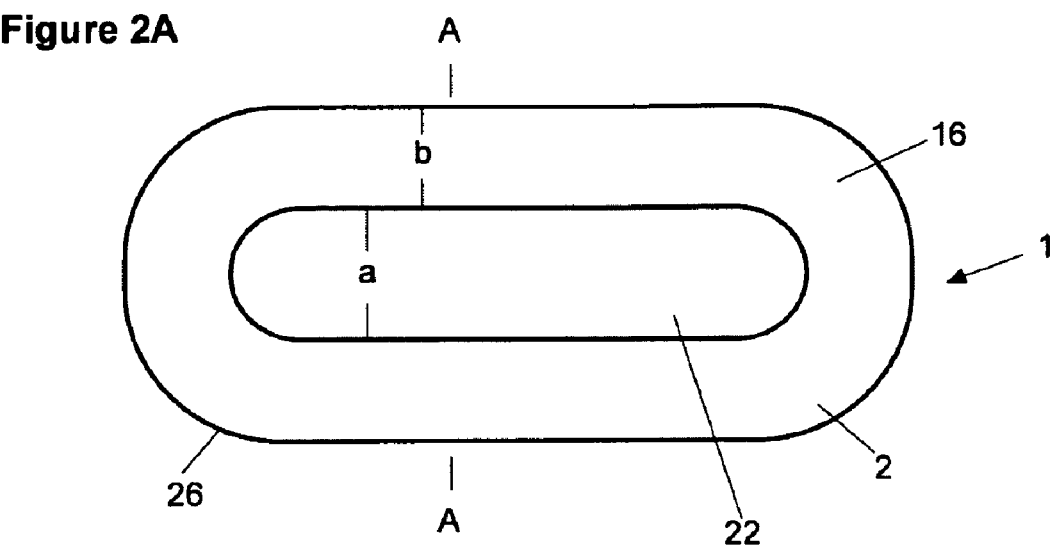
FIG. 2A) is a schematic top view of another embodiment of the tablet of the invention.
Figure 2B:
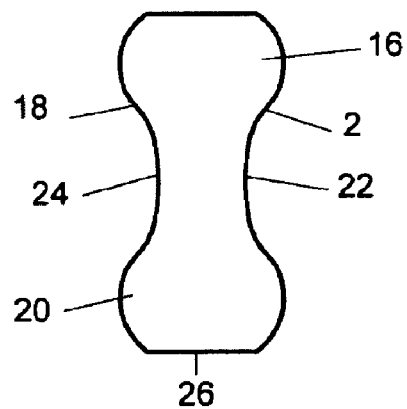
FIG. 2B) is a cross-sectional view along A-A of the tablet of FIG. 2A).

In FIG. 2A) tablet 1 is depicted which is rather similar to the tablet shown in FIG. 1A) with the difference that the lateral width a of the basis area 22 of the front side 2 is larger than the transversal width b of the respective bulges 16, 20 of the front side 2 and the back side 18, respectively. The embodiment of the tablet 1 of FIG. 2A) also differs from that of FIG. 1A) insofar as the basis areas 22, 24 are no longer completely flat as depicted in FIG. 1B) but can be curved inwardly, in particular in a symmetrical manner towards the center, as depicted in FIG. 2B).

Both embodiments as shown in FIGS. 1 and 2 have in common that the circumferential rim 26 which connects the front side 2 and the back side 18 has a rather flat profile as can be derived from FIGS. 1B) and 2B).

Figure 3A:
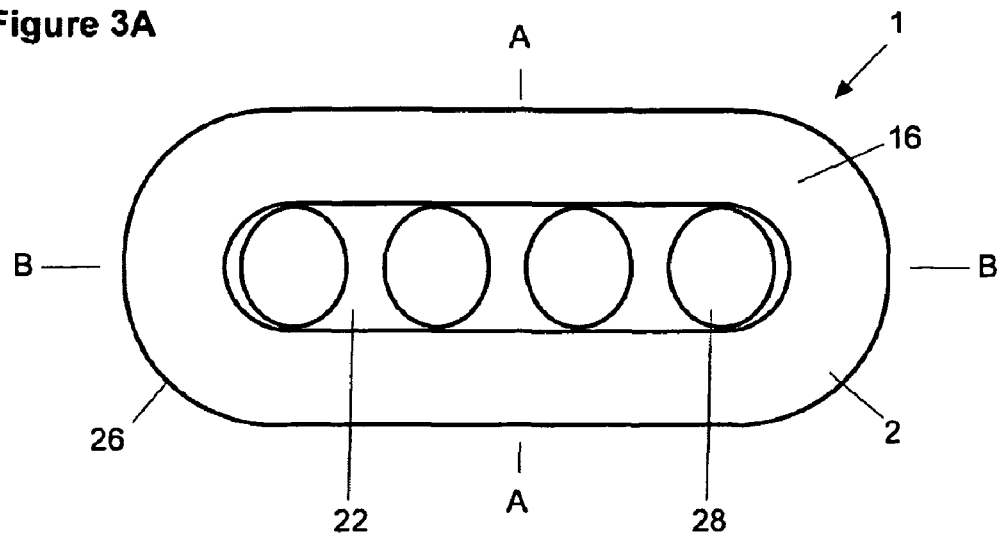
FIG. 3A) is a schematic top view of another embodiment of a tablet of the invention.
Figure 3B:
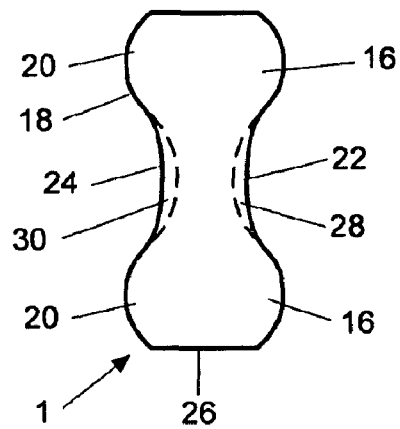
FIG. 3B) is a cross-sectional view along line A-A of the tablet of FIG. 3A).
Figure 3C:
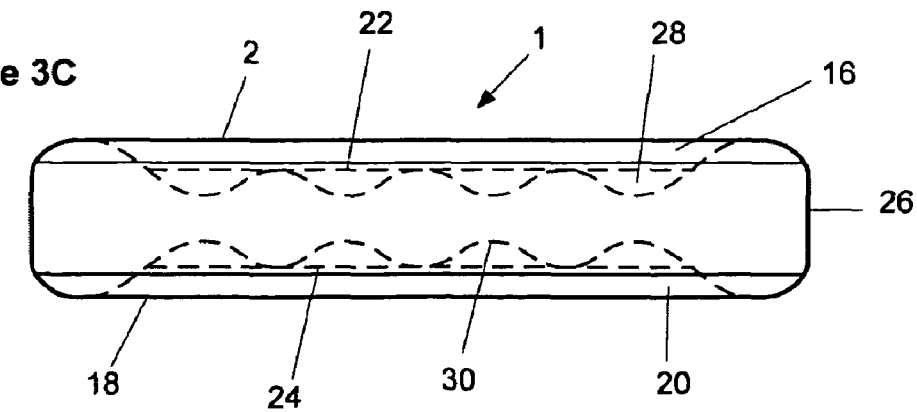
FIG. 3C) is a cross-sectional side view along B-B of the tablet of FIG. 3A).

In FIG. 3A) another embodiment of tablet 1 of the invention is shown which differs from the tablet as depicted in FIG. 2A) insofar as the basis areas 22 and 24 of the front side 2 and the back side 18, respectively, each are provided with four indentations 28. These indentations 28 have an essentially circular shape and are positioned in a row within the basis areas 22 and 24 (s.a. FIG. 3B) and FIG. 3C)). As can be derived from FIGS. 3B) and 3C) the indentations 28 of the front side 2 are placed in a congruent manner with respect to the indentations 30 in the basis area 24 of the back side 18. Again, the rim 26 has a rather flat profile. The indentations 28, 30 have a trough-like, hollow form in the depicted embodiment, that is, from the circumferential rim of the indentations the depth is slightly increasing up to the center of the indentations, which can, for example be derived from FIG. 3B).

Figure 4A:
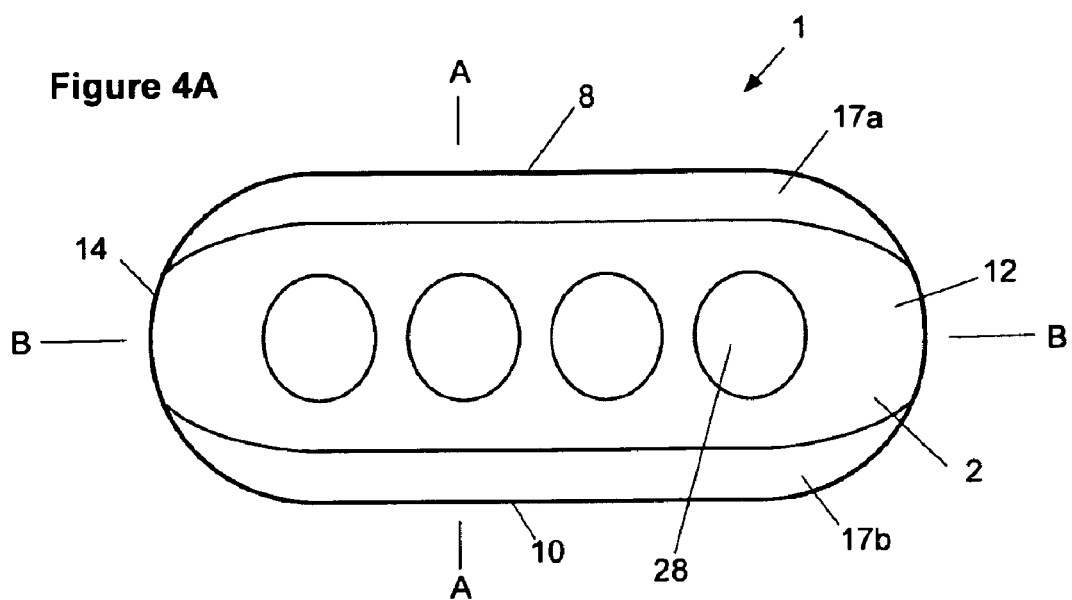
FIG. 4A) is a schematic top view of another embodiment of a tablet of the invention.
Figure 4B:
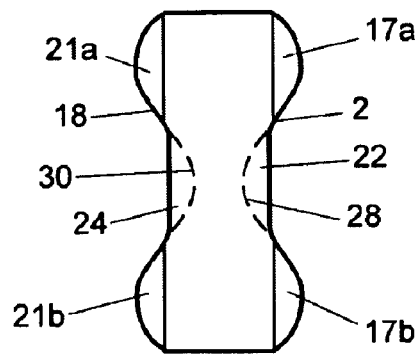
FIG. 4B) is a cross-sectional view along line A-A of the tablet of FIG. 4A).
Figure 4C:
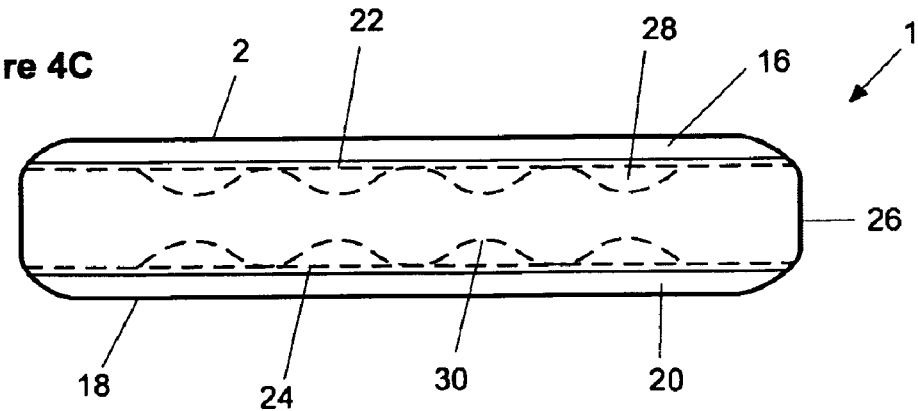
FIG. 4C) is a cross-sectional side view along B-B of the tablet of FIG. 4A).

The embodiment of tablet 1 according to the invention as depicted in FIG. 4A) differs from the embodiment of FIG. 3A) in that the bulges 16 and 20 of the front and back sides 2, 18 are no longer present along the entire circumference of the tablet. In the embodiment of FIG. 4 sections of the opposite transversal edges 12 and 14 of the front side 2 and back side 18 are no longer provided with a bulge section. Accordingly, the bulge 16 of the front side 2 extends only along the longitudinal edges 8 and 10 of the front side as well as over portions of opposing transversal edges 12 and 14 of the front side leaving on both opposing transversal edges of the front and back side significant portions without any bulge. The same applies to the back side in the present case. The individual bulge portions of the front side of the embodiment of FIG. 4 have been assigned reference numbers 17a and 17b for the front side 2 and 21a and 21b for the back side 18. The indentations 28 and 30 of the front and back side are lying within the basis areas 22 and 24, respectively, and are placed in a congruent manner as with the embodiment of FIG. 3 (s.a. FIG. 4C)). Again, the circumferential rim 26 has an essentially flat configuration.

Figure 5A:
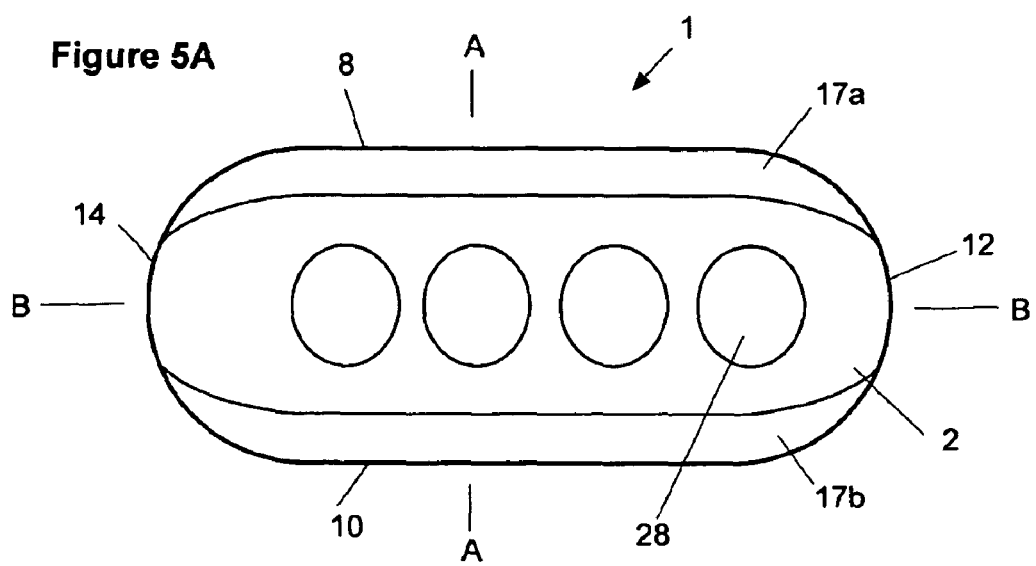
FIG. 5A) is a schematic top view of another embodiment of a tablet of the invention.
Figure 5B:
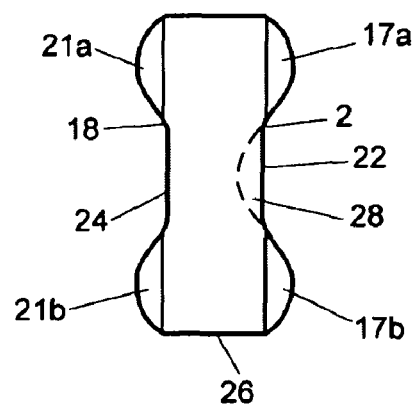
FIG. 5B) is a cross-sectional view along line A-A of the tablet of FIG. 5A).
Figure 5C:
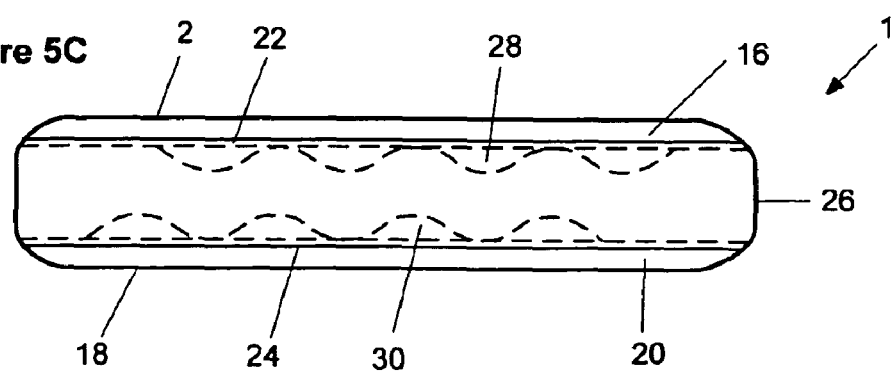
FIG. 5C) is a cross-sectional side view along B-B of the tablet of FIG. 5A).

The embodiment of a tablet 1 of the present invention as depicted in FIG. 5A) differs from the tablet as shown in FIG. 4 only insofar as the indentations 28 of the front side 2 and the indentations 30 of the back side 18 are no longer located in a congruent manner, but are at least partially off-set as can be best derived from FIG. 5C).

Figure 6A:
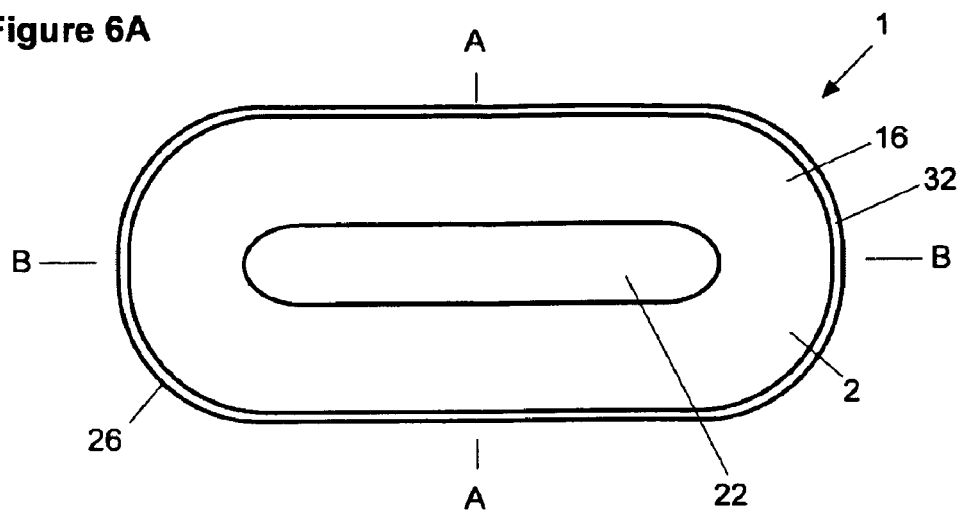
FIG. 6 is a schematic top view of another embodiment of the tablet of the invention.
FIG. 6B) is a cross-sectional view along A-A of the tablet of FIG. 6A).
FIG. 6C) is a cross-sectional side view along B-B of the tablet of FIG. 6A).
Figure 6B:
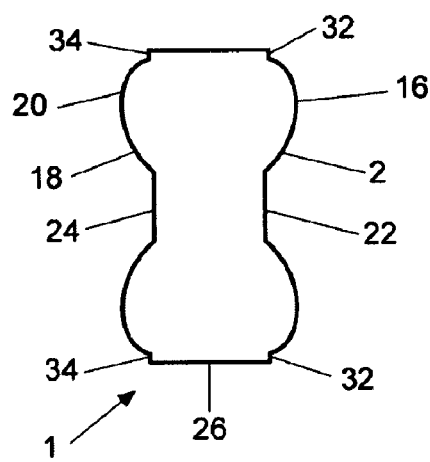
Figure 6C:
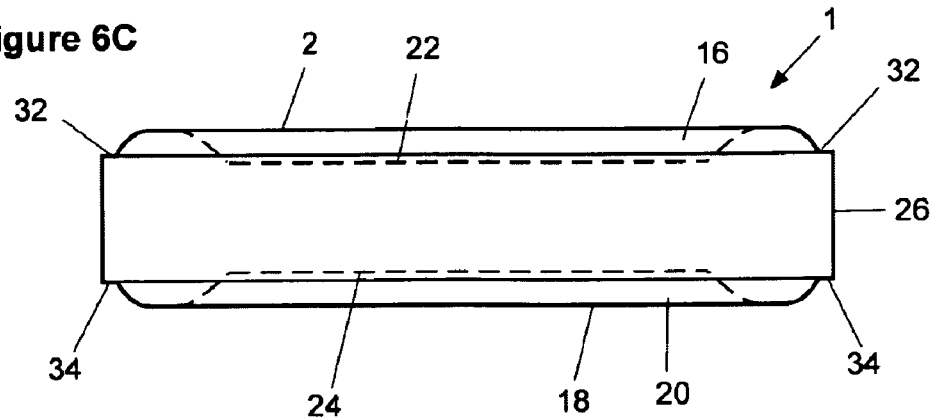

FIG. 6A) shows another embodiment of a tablet 1 of the invention which is rather similar to the embodiment depicted in FIG. 1, for example, as to the circumferential bulge 16 on the front side 2 as well as to the circumferential bulge 20 on the back side 18 (not shown in FIG. 6A, but in FIGS. 6B) and 6C)) and as to its oblong shape and dimensions. Different from the tablet of FIG. 1 the embodiment shown in FIG. 6 makes use of a circumferential land 32 on the front side 2 of a tablet as well as of such a corresponding circumferential land 34 on back side 18 (not shown in FIG. 6A), but in FIGS. 6B) and 6C)). That is, the circumferential bulges 16 and 20 are not extending up to circumferential rim 26, but are located adjacent to, i.e. spaced apart from said rim 26. As can be derived from FIGS. 6B) and 6C) the bulge 16 does not smoothly go over into the rim section 26, but terminates adjacent to the rim section thereby furnishing a small portion which is located at a height somewhat similar to that of the basis area 22 of the front side 2. The same applies to the circumferential land 34 and the bulge 20 on the back side 18. In the embodiment shown in FIGS. 6A) to 6C) the land 32 of the front side 2 is not exactly lying in the plane of the basis area 22, but slightly above. This can be best derived from FIG. 6C). The same applies to the land 34 of the back side 18. For certain tablet formulations it has been found advantageous to make use of, in particular circumferential, land sections, for example, in order to alleviate the die punching cycle in mass production.

A second aspect of the invention relates to a tamper-resistant pharmaceutical dosage form having a retarded release profile, especially a tamper-resistant oral dosage form having a retarded release profile, particularly a tamper-resistant tablet having a retarded release profile, comprising at least one pharmaceutically active ingredient with potential for abuse, and having a shape comprising a longitudinal axis and two opposite longitudinal edges, a transversal axis perpendicular to the longitudinal axis and two opposite transversal edges, a front side, an opposite back side and a circumferential rim between said front and back side, wherein the front side and/or the back side comprise a basis area and wherein the front side and/or the back side comprise at least one bulge which extends above said basis area, said at least one bulge being present at and/or adjacent to at least a section of one or both longitudinal edges and/or at and/or adjacent to at least a section of one or both transversal edges and/or between both longitudinal edges and both transversal edges. The front side and/or the back side of the dosage form, in particular the basis area of the front side and/or the basis area of the back side, can further comprise at least one indentation.

In general, the foregoing teachings relating to the first aspect of the present invention are also applicable to this second aspect of the present invention. However, there are emphasized the following:

A preferred embodiment of the tablet of the present invention is a tablet with a length (longitudinal axis) of about 21 mm; a width (transversal axis) of about 9 mm; a thickness from the top of the bulge on the front side to the top of the opposite bulge on the back side of about 5 mm; a thickness over the basis area of about 3 mm and an extension of the top of the bulge from the basis area of about 1 mm, and in particular having a circumferential bulge on the front and/or on the back side of the tablet, and preferably without any indentations, as for example derivable from FIG. 1A.

Active ingredients with potential for abuse are known to the person skilled in the art and comprise tranquillisers, stimulants, barbiturates, narcotics, opioids or opioid derivatives.

A pharmaceutically active ingredient which is preferably used with the tamper-resistant tablets of the invention is an analgesic compound or a pain-killing compound, such as for example an opioid or an opioid derivative, in particular tapentadol or salts thereof, more in particular tapentadol.

By tamper-resistant it is meant that the active ingredient can not readily be separated from the tablet in a form suitable for abuse because the tablet is such that it can not easily be grinded. This renders extraction of the active ingredient, which could be used for drug-abuse, from the tablet difficult or this renders it very difficult to transform the tablet into a powder for sniffing.

The tablet of the invention can in one embodiment be rendered tamper-resistant by incorporating at least one synthetic or natural polymer which increases the breaking strength of the tablet so that it is much higher than a conventional tablet. In this way, pulverization of the tablet by conventional means, such as for example by a pestle and mortar, is rendered almost impossible, and, hence, the conversion of the active ingredient incorporated in the tablet in a form which is suitable for abuse is complicated.

In one embodiment of the present invention, said at least one synthetic or natural polymer is a polyalkylene oxide such as polyethylene oxide and polypropylene oxide and copolymers of ethylene oxide and propylene oxide.

Preferably, the polyalkylene oxide is polyethylene oxide, in particular polyethylene oxide having a molecular weight above 500,000, preferably above 1,000,000, and more preferably in the range of about 2,000,000 to about 7,000,000. The amount of polyethylene oxide can in one embodiment range from about 20 to about 80% (w/w), in particular from about 20 to 50% (w/w), more in particular from about 30 to about 50% (w/w).

In one embodiment, the tablet of the present invention has a breaking strength of at least 300 N, in particular at least 350N, more in particular at least 400N, even more in particular at least 450 N. The breaking strength of the tablet of the invention can be determined by the method for determining breaking strength of tablets described in the European Pharmacopoeia 1997, page 143, 144, method No. 2.9.8.

Retarded release of an active ingredient from an oral dosage form is known to a person skilled in the art. For a retarded release tablet, it usually is sufficient to administer the tablet once or twice daily. The retarded release profile of the tablet of the present invention can be achieved by embedding the active ingredient in an amount of hydrophilic polymer or of a blend of hydrophilic polymers, optionally also containing conventional formulating agents. These hydrophilic polymers tend to swell upon contact with aqueous fluids following administration, and result in a viscous, drug release regulating gel layer. Preferably the viscosity of these polymers ranges from 150 to 100.000 mPa·s (apparent viscosity of a 2% aqueous solution at 20° C.). Examples of suitable hydrophilic polymers include:
  alkylcelluloses, such as, methylcellulose;
  hydroxyalkylcelluloses, for example, hydroxymethylcellulose, hydroxyethylcellulose, hydroxypropylcellulose and hydroxybutylcellulose;
  hydroxyalkyl alkylcelluloses, such as, hydroxyethyl methylcellulose and hydroxypropyl methylcellulose;
  carboxyalkylcelluloses, such as, carboxymethylcellulose;
  alkali metal salts of carboxyalkylcelluloses, such as, sodium carboxymethylcellulose;
  carboxyalkylalkylcelluloses, such as, carboxymethylethylcellulose;
  carboxyalkylcellulose esters;
  other natural, semi-synthetic, or synthetic polysaccharides, such as, alginic acid, alkali metal and ammonium salts thereof, carrageenans, galactomannans, tragacanth, agar-agar, gummi arabicum, guar gummi, xanthan gummi, starches, pectins, such as sodium carboxymethylamylopectin, chitin derivates such as chitosan, polyfructans, insulin; polyacrylic acids and the salts thereof;
  polymethacrylic acids and the salts thereof, methacrylate copolymers;
  polyvinylalcohol;
  polyvinylpyrrolidone, copolymers of polyvinylpyrrolidone with vinyl acetate;
  combinations of polyvinylalcohol and polyvinylpyrrolidone.

In one embodiment of the invention, the hydrophilic polymer in which the active ingredient is embedded is selected from a cellulose derivative. Preferably, the cellulose derivative is a cellulose ether derivative, more preferably the cellulose ether derivative is HPMC. The amount of cellulose derivative can in one embodiment range from about 1 to about 20% (w/w), in particular from about 10 to about 20% (w/w).

In addition to said synthetic or natural polymer which increases the breaking strength of the tablet, in particular polyalkylene oxide, and to said hydrophilic polymers, the tablet formulation in one embodiment can further comprise a polyalkylene glycol, such as for example PEG 6000. The amount of polyalkylene glycol can for example range from about 1 to about 20% (w/w), in particular from about 1 to about 10% (w/w).

In one embodiment, the tamper-resistant tablet of the invention comprises at least one pharmaceutically active ingredient with potential for abuse, in particular a pain-killing drug, more in particular an opioid or an opioid derivative, e.g. tapentadol; at least one polyalkylene oxide, in particular polyethylene oxide, more in particular polyethylene oxide having a molecular weight in the range of about 2,000,000 to 7,000,000; at least one cellulose ether derivative, in particular hydroxypropyl methylcellulose (HMPC); and at least one polyalkylene glycol, in particular polyethylene glycol, such as PEG 6000. In preferred compositions further components can be present such as anti-oxidants, for example vitamin E. In another embodiment, the tablet comprises pharmaceutically active ingredient with potential for abuse in an amount of at least 5 weight percent; polyethylene oxide in an amount of at least 15 weight percent; cellulose ether derivatives, in particular HPMC, in an amount of at least 5 weight percent; and polyalkylene glycol, in particular polyethylene glycol, in an amount of at least 5 weight percent.

The tamper-resistant tablets of the present invention are preferably prepared by melt-extruding the tablet formulation. The thus obtained melt-extruded strands are preferably cut into monoliths, which are then compressed into tablets.

It has, for example, been found that in particular when the tablet of the invention is produced from melt extruded monolithic masses, very hard compacted tablets are obtained which can no longer be easily grinded or crushed thereby allowing for a very high degree of tamper-resistance. With these very hard tablets an improved control of the drug release profile can be obtained by the tablet of the present invention.

The tablets according to the invention are preferably prepared by way of compression using a die and a punch, preferably from a monolithic mass obtained by melt extrusion. If obtained via melt extrusion, the compressing step is preferably carried out with a monolithic mass exhibiting ambient temperature, that is, a temperature in the range from 20 to 25° C.

The strands obtained by way of extrusion can either be subjected to the compression step as such or can be cut prior to the compression step. It is of course also possible to subject the extruded strands to the compression step or to the cutting step when still warm, that is more or less immediately after the extrusion step. The extrusion is preferably carried out by way of twin-screw extruder.

The aforementioned polymers used for the preparation of the tablet of the invention, that is, the chains of these polymers are preferably predominantly oriented along the direction of the extrusion. In case the monolith resulting from extrusion has a length greater than its width, the compression of said monolith is preferably performed with a compression direction perpendicular to the length.

A third aspect of the invention relates to a pharmaceutical dosage form with controlled release of a pharmacologically active compound (A) contained therein, the pharmaceutical dosage form having a breaking strength $B_1$ of at least 500 N in a direction of extension $E_1$, and having a breaking strength $B_2$ of less than 500 N in a direction of extension $E_2$.

In general, the foregoing teachings relating to the first aspect of the invention and the second aspect of the invention are also applicable to this third aspect of the invention. However, there are emphasized the following:

Direction of extension $E_1$ and direction of extension $E_2$, respectively, can principally be any directions of extension of the pharmaceutical dosage form, i.e., any arbitrarily chosen directions of extension, provided that the corresponding requirement for the breaking strength $B_1$ and $B_2$, respectively, is satisfied.

The "breaking strength" (resistance to crushing) of a pharmaceutical dosage form is known to the skilled person. In this regard it can be referred to, e.g., W. A. Ritschel, Die Tablette, 2. Auflage, Editio Cantor Verlag Aulendorf, 2002; H Liebermann et al., Pharmaceutical dosage forms: Tablets, Vol. 2, Informa Healthcare; 2 edition, 1990; and Encyclopedia of Pharmaceutical Technology, Informa Healthcare; 1 edition.

For the purpose of the specification, the breaking strength is preferably defined as the amount of force that is necessary in order to fracture the pharmaceutical dosage form (=breaking force). Therefore, for the purpose of the specification the dosage form does preferably not exhibit the desired breaking strength when it breaks, i.e., is fractured into at least two independent parts that are separated from one another. In another preferred embodiment, however, the pharmaceutical dosage form is regarded as being broken if the force decreases by 25% (threshold value) of the highest force measured during the measurement (see below).

The dosage forms according to the invention are preferably distinguished from conventional dosage forms in that, due to their breaking strength, they cannot be pulverized by the application of force with conventional means, such as for example a pestle and mortar, a hammer, a mallet or other usual means for pulverization, in particular devices developed for this purpose (tablet crushers). In this regard "pulverization" means crumbling into small particles that would immediately release the pharmacologically active compound (A) in a suitable medium. Avoidance of pulverization virtually rules out oral or parenteral, in particular intravenous or nasal abuse.

Conventional tablets typically have a breaking strength well below 200 N in any direction of extension. The breaking strength of conventional round tablets may be estimated according to the following empirical formula: Breaking Strength [in N]=10×Diameter Of The Tablet [in mm]. Thus, according to said empirical formula, a round tablet having a breaking strength of at least 500 N would require a diameter of at least 50 mm (about 2 inches). Such a tablet, however, could not be swallowed. The above empirical formula does not apply to the pharmaceutical dosage forms of the invention, which are not conventional but rather special.

Further, the actual mean chewing force is about 220 N (cf., e.g., P. A. Proeschel et al., J Dent Res, 2002, 81(7), 464-468, copy attached). This means that conventional tablets having a breaking strength well below 200 N may be crushed upon chewing, whereas the dosage forms according to the invention may not, at least not in direction of extension $E_1$.

Still further, when applying a gravitational acceleration of about 9.81 m/s$^2$, 500 N correspond to a gravitational force of more than 50 kg, i.e. the pharmaceutical dosage forms according to the invention can withstand a weight of more than 50 kg, at least in direction of extension $E_1$.

Methods for measuring the breaking strength of a pharmaceutical dosage form are known to the skilled artisan. Suitable devices are commercially available.

For example, the breaking strength (resistance to crushing) can be measured in accordance with the European Pharmacopoeia 5.0, 2.9.8 or 6.0, 2.09.08 "Resistance to Crushing of Tablets". The test is intended to determine, under defined conditions, the resistance to crushing of tablets, measured by the force needed to disrupt them by crushing. The apparatus consists of 2 jaws facing each other, one of which moves towards the other. The flat surfaces of the jaws are perpendicular to the direction of movement. The crushing surfaces of the jaws are flat and larger than the zone of contact with the tablet. The apparatus is calibrated using a system with a precision of 1 Newton. The tablet is placed between the jaws, taking into account, where applicable, the shape, the breakmark and the inscription; for each measurement the tablet is oriented in the same way with respect to the direction of application of the force (and the direction of extension in which the breaking strength is to be measured). The measurement is carried out on 10 tablets, taking care that all fragments of tablets have been removed before each determination. The result is expressed as the mean, minimum and maximum values of the forces measured, all expressed in Newton.

A similar description of the breaking strength (breaking force) can be found in the US Pharmacopoeia. The breaking strength can alternatively be measured in accordance with the method described therein where it is stated that the breaking strength is the force required to cause a tablet to fail (i.e., break) in a specific plane. The tablets are generally placed between two platens, one of which moves to apply sufficient force to the tablet to cause fracture. For conventional, round (circular cross-section) tablets, loading occurs across their diameter (sometimes referred to as diametral loading), and fracture occurs in the plane. The breaking force of tablets is commonly called hardness in the pharmaceutical literature; however, the use of this term is misleading. In material science, the term hardness refers to the resistance of a surface to penetration or indentation by a small probe. The term crushing strength is also frequently used to describe the resistance of tablets to the application of a compressive load. Although this term describes the true nature of the test more accurately than does hardness, it implies that tablets are actually crushed during the test, which is often not the case.

Alternatively, the breaking strength (resistance to crushing) can be measured in accordance with WO 2006/082099, which can be regarded as a modification of the method described in the European Pharmacopoeia. The apparatus used for the measurement is preferably a "Zwick Z 2.5" materials tester, $F_{max}$=2.5 kN with a maximum draw of 1150 mm, which should be set up with one column and one spindle, a clearance behind of 100 mm and a test speed adjustable between 0.1 and 800 mm/min together with testControl software. Measurement is performed using a pressure piston with screw-in inserts and a cylinder (diameter 10 mm), a force transducer, $F_{max}$. 1 kN, diameter=8 mm, class 0.5 from 10 N, class 1 from 2 N to ISO 7500-1, with manufacturer's test certificate M according to DIN 55350-18 (Zwick gross force $F_{max}$=1.45 kN) (all apparatus from Zwick GmbH & Co. KG, Ulm, Germany) with Order No BTC-FR 2.5 TH. D09 for the tester, Order No BTC-LC 0050N. P01 for the force transducer, Order No BO 70000 S06 for the centering device.

In a preferred embodiment of the invention, the breaking strength is measured by means of a breaking strength tester Sotax®, type HT100 (Allschwil, Switzerland). Preferably, the Auto Alignment™ device of the Sotax® HT100 is not used, just to allow placing the dosage form individually between the jaws in order to measure the breaking strength in specific directions of extension. The Sotax® HT100 can measure the breaking strength according to two different measurement principles: constant speed (where the test jaw is moved at a constant speed adjustable from 5-200 mm/min) or constant force (where the test jaw increases force linearly adjustable from 5-100 N/sec). In principle, both measurement principles are suitable for measuring the breaking strength of the dosage form according to the invention. Preferably, the breaking strength is measured at constant speed, preferably at a constant speed of 120 mm/min.

In a preferred embodiment, the pharmaceutical dosage form is regarded as being broken if it is fractured into at least two separate pieces.

In another preferred embodiment, the pharmaceutical dosage form is regarded as being broken if the force decreases by 25% (threshold value) of the highest force measured during the measurement. For example, if the highest force measured during the measurement is 144 N, the tablet is regarded as being broken when the force decreases below 108 N (=75% of 144 N; decrease by 25%). The value of the breaking strength in the respective direction of extension is then 144 N. In a preferred embodiment, said threshold value is 30%, more preferably 35%, still more preferably 40%, most preferably 45% and in particular 50%. Under these circumstances, a dosage form may have to be regarded as being broken although it has not been fractured into at least two separate pieces. For example, a dosage form that has been torn in the middle but that has not been fragmented, may have to be regarded as being broken in accordance with this definition of the breaking strength. Thus, in accordance with this definition, failure of the breaking strength test at a particular force may be due to fracture of the dosage form or any other deformation that causes the force to drop below the above threshold value, e.g. rupture, cracking, dunting, cleaving, fissure, and the like.

Figure 18A:
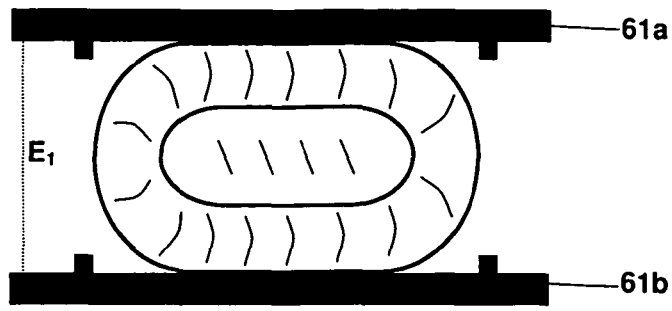
FIG. 18A) shows how the pharmaceutical dosage form should be placed between the two plain jaws (61a) and (61b) of the measuring device in order to measure the breaking strength in direction of extension $E_1$.
Figure 18B:
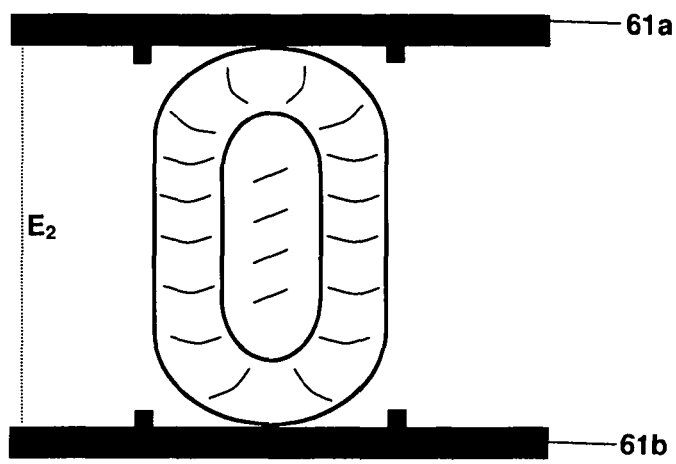
FIG. 18B) shows how the pharmaceutical dosage form should be placed between the two plain jaws (61a) and (61b) of the measuring device in order to measure the breaking strength in direction of extension $E_2$.
Figure 18C:
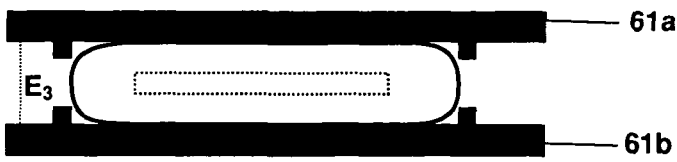
FIG. 18C) shows how the pharmaceutical dosage form should be placed between the two plain jaws (61a) and (61b) of the measuring device in order to measure the breaking strength in direction of extension $E_3$.

FIG. 18 schematically illustrates the measurement of the breaking strength of the dosage form depicted in FIG. 10, in particular the adjustment device for the dosage form used for this purpose before and during the measurement, in three different directions of extension a) to c). This measurement set-up is applicable to the various methods for measuring the breaking strength of the dosage form, including the above method according to the European Pharmacopeia, the variation thereof (according to Zwick) and the preferred method using the Sotax® HT100. To this end, the dosage form is held between the plain jaw (61*a*) and the plain jaw (61*b*) of the force application apparatus (not shown) with the assistance of two 2-part clamping devices, which are in each case firmly attached (not shown) to the jaws once the spacing necessary for accommodating and centering the tablet to be measured has been established. The spacing may be established by moving the 2-part clamping devices horizontally outwards or inwards in each case on the jaw on which they are mounted. The measurement of the breaking strength in different directions of extensions is illustrated in FIG. 18A) to FIG. 18C). FIG. 18A) illustrates the arrangement for measuring the breaking strength in direction of extension $E_1$ that is perpendicular to the main direction of extension $E_2$ of the dosage form. FIG. 18B) illustrates the arrangement for measuring the breaking strength in the main direction of extension $E_2$ of the dosage form. This arrangement is the standard arrangement when measuring the breaking strength of conventional oblong tablets. The Auto Alignment™ device of the Sotax® HT100 serves the purpose of aligning the tablet shapes automatically in order to ensure reproducible results in this direction of extension. According to the present invention, however, the breaking strength of the dosage form needs to be measured in different directions of extension and the main direction of extension may be among said different directions of extension, but does not have to necessarily. FIG. 18C) illustrates the arrangement for measuring the breaking strength in direction of extension $E_3$ that is perpendicular to the main direction of extension $E_2$ of the dosage form as well as perpendicular to direction of extension $E_1$.

In a preferred embodiment, the breaking strength tester, preferably the Sotax® HT100, is equipped with two plain jaws (cf. FIG. 18).

Figure 19A:
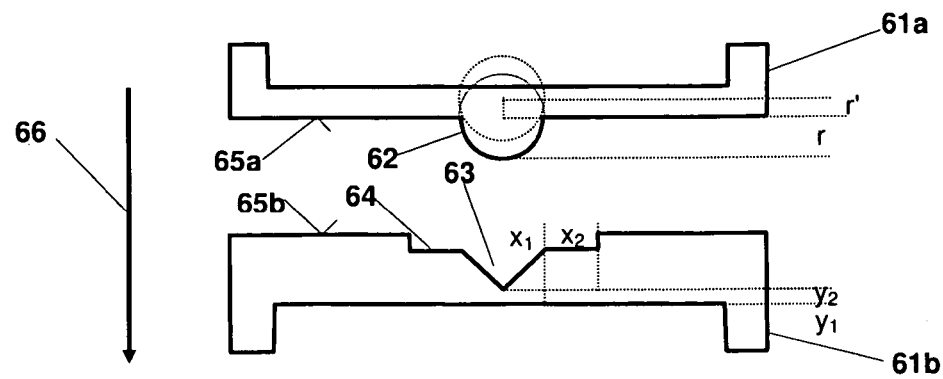
FIG. 19 is a preferred embodiment of the measuring system that is used in order to measure the breaking strength of the pharmaceutical dosage form according to the invention. The two jaws (61a) and (61b) of this measuring system are not plain, but contain an embossment (62) and a cavity (63, 64), respectively.
Figure 19B:
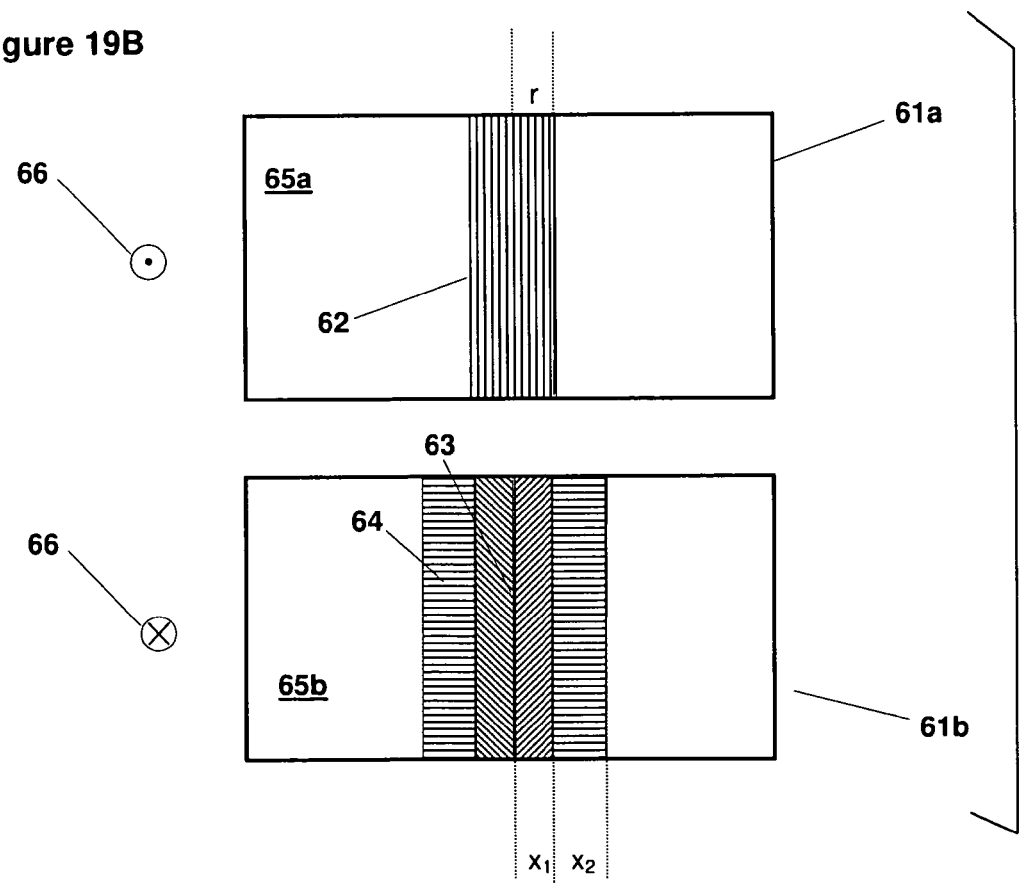
Figure 20A:
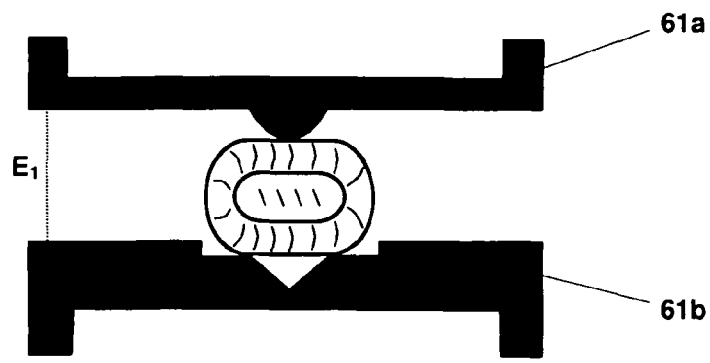
FIG. 20A) shows how the pharmaceutical dosage form shown in FIG. 10 should be placed between the two jaws (61a) and (61b) of the measuring device shown in FIG. 19 in order to measure the breaking strength in direction of extension $E_1$.
Figure 20B:
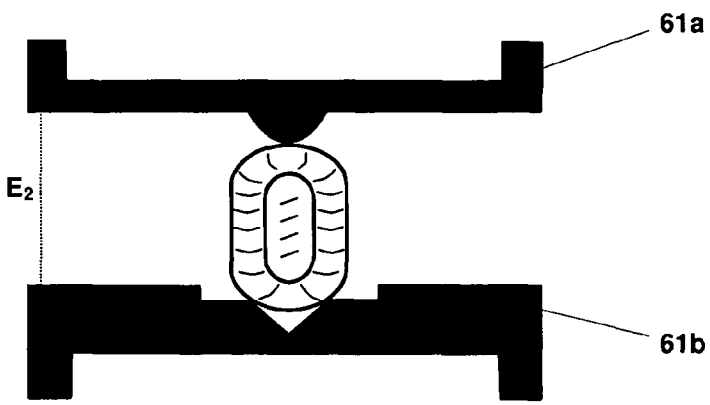
FIG. 20B) shows how the pharmaceutical dosage form should be placed between the two jaws (61a) and (61b) of the measuring device in order to measure the breaking strength in direction of extension $E_2$.

In another preferred embodiment, the breaking strength tester, preferably the Sotax® HT100, is equipped with two jaws that are not plain (cf. FIGS. 19, 20). Preferably, one jaw contains an embossment and the other jaw contains an indentation. Embossment and indentation can be congruent with one another (like positive and negative), but do not have to.

Preferably, the embossment serves as an arbor, spike or mandrel and can be round of angular (e.g., triangular, rectangular, etc.). In a preferred embodiment, the embossment assumes the shape of a hemisphere. In another preferred embodiment, the embossment assumes the shape of a cone. In yet another preferred embodiment, the embossment assumes the shape of a trigonal or rectangular pyramid. Most preferably, the embossment assumes the shape of a half cylinder, preferably having a radius of curvature of 2.5 mm. In a preferred embodiment, the centre of said half cylinder lies within the surface of the main area of extension of the jaw. In another preferred embodiment, the centre lies about 0.5 mm away from said surface, just in the inside of the jaw.

Preferably, the indentation serves as a recess for the embossment. In a preferred embodiment, the indentation assumes the shape of a hollow hemisphere. In another preferred embodiment, the indentation assumes the shape of a hollow cone. In yet another preferred embodiment, the indentation assumes the shape of a hollow trigonal or rectangular pyramid. Most preferably, the indentation assumes the shape of a chamfering, kerf or notch with an angle of preferably 90°.

FIG. 19A) shows a schematic view of jaw (61*a*) containing embossment (62) and jaw (61*b*) containing indentation (63/64). The embossment (62) assumes the shape of a half cylinder that is characterized by radius r. Preferably, r=2.5 mm. The center of the circular cross-section of the half cylinder may lie within the surface main area of extension of the jaw so that the entire half cylinder forms the embossment (62). Alternatively, the center of the circular cross-section of the half cylinder may lie within the body of the jaw, e.g. at a distance r' from the surface of the main area of extension, so that the only a part of the half cylinder forms the embossment (62). Preferably, r'=0 or 0.5 mm. The indentation is located in a rectangular recess (64) having a side length of 2 $x_1$+2 $x_2$ and a height of $y_2$. In the centre of said rectangular recess (64) is located a chamfering, kerf or notch (63) having a side length of 2 $x_1$ and a height/depth of $y_1$. In a preferred embodiment, $x_1$=3 mm, $x_2$=6 mm, $y_1$=3 mm and $y_2$=2 mm. In another preferred embodiment, $x_1$=4 mm, $x_2$=7 mm, $y_1$=4 mm and $y_2$=2 mm. Preferably, the chamfering, kerf or notch (63) assumes an angle of 90°. FIG. 19B) shows a schematic view of jaws (61*a*) and (61*b*) on faces (65*a*) and (65*b*), respectively.

FIG. 20 shows in analogy to FIG. 18 how the dosage form depicted in FIG. 10 should be placed between the two jaws having embossment and indentation, respectively, in order to measure the breaking strength in directions of extension $E_1$, $E_2$ and $E_3$. The skilled person recognizes that during the measurement, i.e. the movement of the jaws towards one another, it may become necessary to additionally clamp the dosage form, e.g. by means of suitable guiding shafts or leading tracks (not shown), in order to avoid that the dosage form is tilted or evades to the side.

In general, a measuring set-up with jaws equipped with embossment and indentation (cf. FIG. 20) realizes harsher measuring conditions than a measuring set-up with plain jaws (cf. FIG. 18). Thus, it may happen that a given dosage form which passes the measurement in accordance with FIG. 18 fails when being measured in the same direction of extension in accordance with FIG. 20.

As far as tablet orientation during the measurement of the breaking force is concerned, the US Pharmacopoeia (USP) states that in general, tablets are tested either across the diameter or parallel to the longest axis. Scored tablets have two orientation possibilities. When they are oriented with their scores perpendicular to the platen faces, the likelihood that tensile failure will occur along the scored line increases. This provides information about the strength of the matrix at the weakest point in the structure. When scored tablets are oriented with their scores parallel to the platen faces, more general information about the strength of the matrix is derived. Capsule-shaped tablets or scored tablets may best be broken in a three-point flexure test. A fitting, which is either installed on the platens or substituted for the platens, supports the tablet at its ends and permits the breaking load to be applied to the opposite face at the unsupported midpoint of the tablet. The fittings are often available from the same source that supplies the hardness tester. FIG. 20 is in accordance with this description in the USP.

The pharmaceutical dosage form according to the invention preferably has a breaking strength $B_1$ of at least 500 N in direction of extension $E_1$. Preferably, direction of extension $E_1$ is perpendicular to the main direction of extension of the dosage form. Preferably, the breaking strength in direction of extension $E_1$ is at least 500 N regardless of whether the measuring device is equipped with plain jaws or with two jaws one of which containing an embossment and the other containing an indentation, as described above.

Further, the pharmaceutical dosage form according to the invention preferably has a breaking strength $B_2$ of less than 500 N in direction of extension $E_2$. Preferably, direction of extension $E_2$ is the main direction of extension of the dosage form. Preferably, the breaking strength in direction of extension $E_2$ is less than 500 N when being measured with two plain jaws. However, it is not required (but possible) that the breaking strength in direction of extension $E_2$ is less than 500 N when being measured with two jaws one of which containing an embossment and the other containing an indentation, as described above.

In a preferred embodiment according to the invention, the breaking strength $B_1$ of the pharmaceutical dosage form in direction of extension $E_1$ is measured in accordance with FIG. 20A), i.e. orthogonal to the main direction of extension and by means of embossment and indentation. The breaking strength $B_2$ in direction of extension $E_2$, however, is preferably measured in accordance with FIG. 18B), i.e. along the main direction of extension and by means of plain jaws.

The pharmaceutical dosage form according to the invention preferably exhibits mechanical strength over a wide temperature range, in addition to the breaking strength (resistance to crushing) optionally also sufficient hardness, impact resistance, impact elasticity, tensile strength and/or modulus of elasticity, optionally also at low temperatures (e.g. below −24° C., below −40° C. or in liquid nitrogen), for it to be virtually impossible to pulverize by spontaneous chewing, grinding in a mortar, pounding, etc. Thus, preferably, in direction of extension $E_1$ the comparatively high breaking strength of the pharmaceutical dosage form according to the invention is maintained even at low or very low temperatures, e.g., when the pharmaceutical dosage form is initially chilled to increase its brittleness, for example to temperatures below −25° C., below −40° C. or even in liquid nitrogen.

The pharmaceutical dosage form according to the invention is preferably characterized by a certain degree of breaking strength. This does not mean that the pharmaceutical dosage form must also exhibit a certain degree of hardness. Hardness and breaking strength are different physical properties. Therefore, the tamper resistance of the pharmaceutical dosage form does not necessarily depend on the hardness of the pharmaceutical dosage form. For instance, due to its breaking strength, impact strength, elasticity modulus and tensile strength, respectively, the pharmaceutical dosage form can preferably be deformed when exerting an external force, for example using a hammer, but cannot be pulverized, i.e., crumbled into a high number of fragments. In other words, the pharmaceutical dosage form according to the invention is characterized by a certain degree of breaking strength, but not necessarily also by a certain degree of form stability.

Therefore, in the meaning of the specification, a pharmaceutical dosage form that is deformed when being exposed to a force in a particular direction of extension but that does not break is to be regarded as having the desired breaking strength in said direction of extension.

Due to the anisotropic mechanical properties in directions of extension $E_1$ and $E_2$, the application of force with conventional means, e.g. the application of 400 N, may cause disruption of the dosage form to a certain and limited degree, but may not cause pulverization thereof. For example, when the breaking strength in direction of extension $E_2$ is below 400 N, the dosage form is disrupted into pieces by applying 400 N in direction of extension $E_2$. Preferably, however, said pieces may not be disrupted any further by applying 400 N or more.

It has been surprisingly found that the outer shape of the pharmaceutical dosage forms may be varied within wide limits without diminishing their breaking strength. Although a variation of the outer shape of the pharmaceutical dosage forms may cause a decrease of the breaking strength in a certain direction of extension, it has been found that specific forms and shapes establish a certain degree of fragility at predetermined sites of fracture (weakening points) without completely diminishing the overall breaking strength of the remainder of the pharmaceutical dosage forms (fragments).

The degree of weakening can be controlled and when exerting a force on the pharmaceutical dosage forms, said weakening points can serve as predetermined sites of fracture, provided that the amount of force is sufficiently high.

The degree of fragility may be adjusted to values that are still well above the typical breaking strength of conventional pharmaceutical dosage forms, e.g. well above 100 N or 200 N. In particular, it has been surprisingly found that pharmaceutical dosage forms can be designed which can be fractured into large pieces, e.g. into halves or thirds, by conventional means (e.g. tablet crushers), but not any further. In consequence, the resultant fragments (subunits) in turn exhibit a breaking strength which is far above the breaking strength at the predetermined site of fracture, e.g. well above 500 N, preferably in any direction of extension.

Figure 7A:
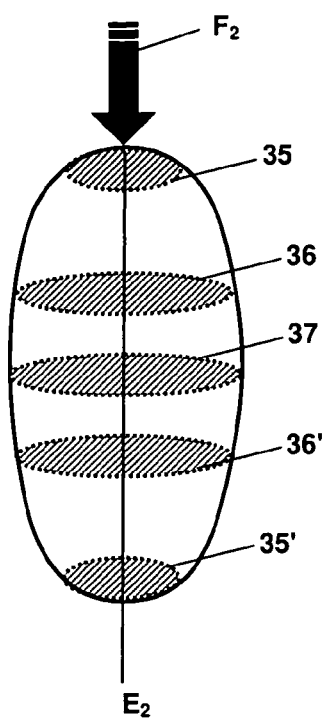
FIG. 7A) is a schematic view of a conventional oblong tablet.

FIG. 7A) is a schematic view of a conventional oblong tablet. Cross-sectional areas (35) and (35') are smaller than cross-sectional areas (36) and (36') which in turn are smaller than cross-sectional area (37). When exerting external force ($F_2$) in direction of extension ($E_2$), the implied pressure is not constant but varies with varying cross-sectional areas. For example, the pressure implied at the section having cross-sectional area (37) is lower than the pressure at the section having cross-sectional areas (35) and (35'), respectively, because cross-sectional area (37) is larger than cross-sectional areas (35) and (35').

Figure 7B:
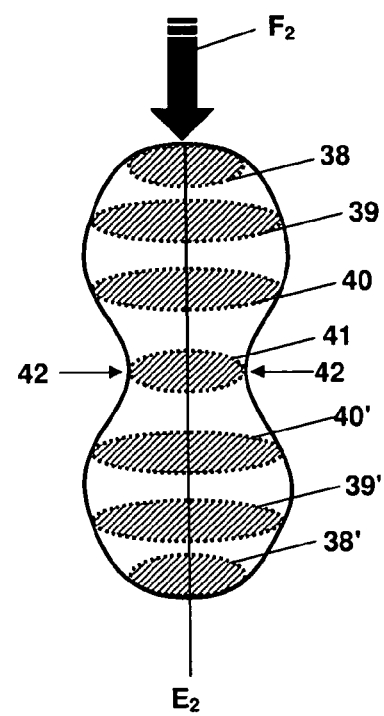
FIG. 7B) is a schematic view of an embodiment of a pharmaceutical dosage form according to the invention having an increased ratio of surface to volume and surface to weight, respectively, achieved by a taper right in the middle of the pharmaceutical dosage form.

FIG. 7B) is a schematic view of an embodiment of a pharmaceutical dosage form according to the invention. An increased surface to volume ratio and surface to weight ratio, respectively, is achieved by taper T right in the middle of the pharmaceutical dosage form. Under these circumstances, when exerting external force ($F_2$) in direction of extension ($E_2$), the implied pressure at the section having cross-sectional area (42) is higher than the pressure at the section having cross-sectional areas (38) and (38'), respectively, because cross-sectional area (42) is smaller than cross-sectional areas (38) and (38'). The pharmaceutical dosage form depicted in FIG. 7B) exhibits a breaking strength in direction of extension ($E_2$) that is substantially lower than the breaking strength of the pharmaceutical dosage form depicted in FIG. 7A) in direction of extension ($E_2$).

In FIGS. 7A) and 7B), direction of extension ($E_2$) is the principal direction of extension of the pharmaceutical dosage forms (main direction of extension, major direction of extension).

The predetermined sites of fracture (weakening points) can improve the patient compliance, as patients having problems in swallowing large pharmaceutical dosage forms can fracture the pharmaceutical dosage forms along the predetermined sites of fracture (weakening points) prior to swallowing. Those patients can limitedly fracture the pharmaceutical dosage form into fragments of a size they can swallow. However, as the resultant fragments in turn cannot be comminuted any further, at least not by conventional means, the pharmaceutical dosage forms are still tamper resistant, i.e. efficiently avoid drug abuse and (unintentional) drug overdose, respectively. In other words, the pharmaceutical dosage forms according to the invention realize both, a very high mechanical resistance in order to avoid misuse as well as a certain degree of a mechanical weakness in order to improve patient compliance.

In a preferred embodiment, the pharmaceutical dosage form according to the invention provides fragments when exerting a force higher than $B_2$ in direction of extension $E_2$, preferably under the standard conditions for measuring the breaking strength set forth above, said fragments in turn having a breaking strength of preferably at least 500 N, at least 550 N or at least 600 N; more preferably at least 650 N, at least 700 N or at least 750 N; still more preferably at least 800 N, at least 850 N or at least 900 N; yet more preferably at least 950 N, at least 1000 N or at least 1100 N; and in particular at least 1200 N, at least 1300 N, at least 1400 N or at least 1500 N; preferably in any (each and every) of their directions of extension.

Preferably, the dosage form provides at most 10, more preferably at most 8, still more preferably at most 6, yet more preferably at most 5, most preferably at most 4 and in particular at most 3 fragments when exerting a force that is higher than $B_2$ in direction of extension $E_2$.

Preferably the volume of each fragment is at least 5%, more preferably at least 10%, still more preferably at least 15%, yet more preferably at least 20%, most preferably at least 25% and in particular at least 30% of the volume of the pharmaceutical dosage form.

It has been surprisingly found that the release profile of the pharmaceutical dosage form may be varied within certain limits by varying the outer shape of the pharmaceutical dosage form without diminishing its tamper resistance. Therefore, particularly at a high drug load, the pharmaceutical dosage forms according to the invention allow to realize release profiles that may not be achieved with conventional pharmaceutical dosage forms having an increased breaking strength (e.g. oblong tablets).

Typically, the pharmaceutical dosage form according to the invention assumes the form of a tablet. The pharmaceutical dosage form is preferably not in film form.

The pharmaceutical dosage form according to the invention may assume various shapes. Preferably, from top view, the shape of the pharmaceutical dosage form can be substantially hexagonal, elliptic, cyclic, oblong, rectangular, squared, triangular, and the like. Preferably, from side view, the shape of the pharmaceutical dosage form can be substantially flat-convex, biconvex, flat with facet, flat without facet, cyclic, and the like.

Figure 13A:
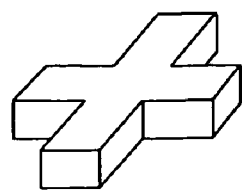
FIG. 13 is a schematic view of pharmaceutical dosage forms according to the invention. The pharmaceutical dosage form depicted in FIG. 13A) assumes the shape of a cross, the pharmaceutical dosage form depicted in FIG. 13B) assumes the shape of a star.
Figure 13B:
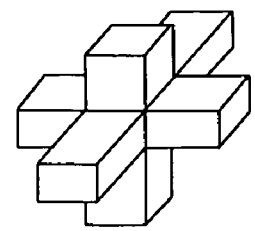
Figure 14A:
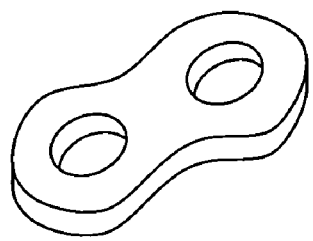
FIG. 14 is a schematic view of various pharmaceutical dosage forms according to the invention. The pharmaceutical dosage form depicted in FIG. 14A) assumes the shape of an eight, the pharmaceutical dosage form depicted in FIG. 14B) assumes the shape of a flattened peanut, the pharmaceutical dosage form depicted in FIG. 14C) assumes the shape of a parallel double cylinder, the pharmaceutical dosage form depicted in FIG. 14D) assumes the shape of a parallel double tube, the pharmaceutical dosage form depicted in FIG. 14E) assumes the shape of a square with a round hole in the middle, and the pharmaceutical dosage form depicted in FIG. 14F) assumes the shape of a wavy or corrugated item.
Figure 14B:
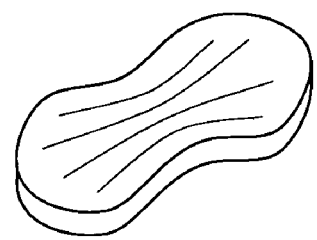
Figure 14C:
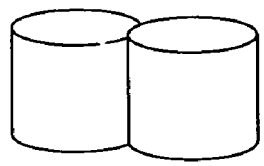
Figure 14D:
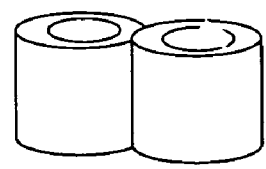
Figure 14E:
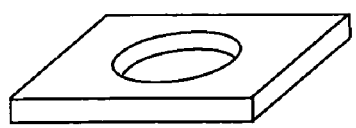
Figure 14F:

For example, the pharmaceutical dosage form according to the invention may assume simple geometries, such as spherical, planar, cubic, hexagonal and cylindrical, or complex geometries, such as convex, hollow cylindrical, doughnut-shaped, hemispheric, cruciform, astral (cf. FIGS. 13, 14 and 15).

Particularly preferred shapes of the dosage form according to the invention have already been described in connection with the first and second aspects of the invention above.

In a particularly preferred embodiment, the pharmaceutical dosage form according to the invention can be described as a body having a recess or cavity on at least one side, preferably two recesses or two cavities on two sides, preferably on opposing sides. Alternatively, said cavities and recesses, respectively, may be regarded as bulges, indentations, troughs, hollows, depressions, synclines, deepenings, and the like. Examples of such embodiments are depicted in FIGS. 8-10, 16A) and 16B).

The pharmaceutical dosage form is preferably adapted for oral administration, i.e., should be capable of being swallowed. Thus, obscure geometrical forms which are obviously harmful cannot be regarded as pharmaceutical dosage forms according to the invention.

According to a preferred embodiment, the pharmaceutical dosage form is characterized by a specific aspect ratio. For the purpose of the specification, the aspect ratio is defined as the ratio of the main direction of extension of the dosage form to the maximum extension of the pharmaceutical dosage form orthogonal to said main direction of extension, e.g. maximum length to maximum height (and maximum length to maximum width, respectively). Preferably, said aspect ratio is within the range of 2.4±1.31, more preferably 2.4±1.0:1, still more preferably 2.4±0.8:1, yet more preferably 2.4±0.6:1, most preferably 2.4±0.4:1 and in particular 2.4±0.2:1.

According to a preferred embodiment, the pharmaceutical dosage form is characterized by a specific length to height to width ratio, where length>height≧width. For the purpose of the specification, in this embodiment the length corresponds to the main direction of extension of the dosage form, the height corresponds to the maximum extension of the pharmaceutical dosage form orthogonal to the length, and the width corresponds to the maximum extension orthogonal to the length and orthogonal to the width (Cartesian space). Preferably, the length to height to width ratio is within the range of 4.7±2.0:2.0±1.0:1, more preferably 4.7±1.6:2.0±0.8:1, still more preferably 4.7±1.2:2.0±0.6:1, yet more preferably 4.7±0.8:2.0±0.4:1, most preferably 4.7±0.6:2.0±0.31, and in particular 4.7±0.4:2.0±0.2:1.

Preferably, a portion of the surface of the pharmaceutical dosage form is convex, i.e. curved out or bulged outward, and another portion of its surface is concave, i.e. curved in or hollowed inward. For the purpose of the specification, the radius of curvature is not critical.

Preferably, the overall surface of the pharmaceutical dosage form can be divided into concave portions, convex portions and planar portions. Typically, the sum of the concave portions, convex portions and planar portions corresponds to the overall surface of the dosage form. However, at least theoretically, a given portion can be convex and concave simultaneously (saddle). Under these circumstances, the sum of the concave portions, convex portions and planar portions exceeds the overall surface of the dosage form.

In a preferred embodiment, the convex portion of the surface of the dosage form is at most 95%, more preferably at most 90% or at most 85%, still more preferably at most 80% or at most 75%, yet more preferably at most 70% or at most 65%, most preferably at most 60% or at most 55% and on particular at most 50% or at most 45%, based on the sum of concave portions, convex portions and planar portions.

In another preferred embodiment, the concave portion of the surface of the dosage form is at least 5%, more preferably at least 10% or at least 15%, still more preferably at least 20% or at least 25%, yet more preferably at least 30% or at least 35%, most preferably at least 40% or at least 45% and in particular at least 50% or at least 55%, based on the sum of concave portions, convex portions and planar portions.

Figure 17A:
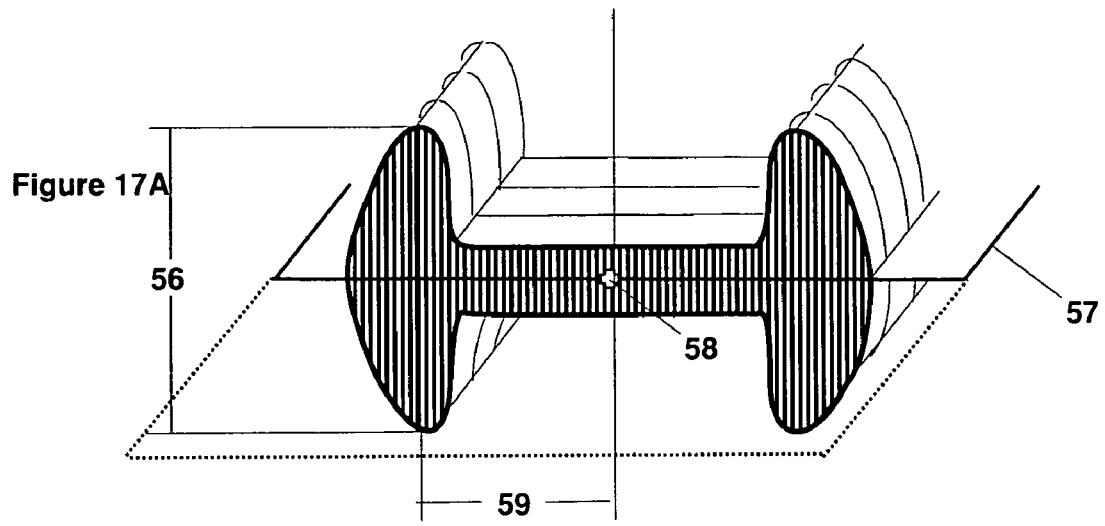
In FIG. 17A) the maximum extension (56) of the dosage form orthogonal to the main area of extension (57) of the dosage form is spaced from the centre of mass (58) of the dosage form parallel to said main area of extension (57).

In a preferred embodiment of the pharmaceutical dosage form according to the invention, the maximum extension of the dosage form orthogonal to the main area of extension of the dosage form is spaced from the centre of mass of the dosage form parallel to said main area of extension. For the purpose of the specification, the main area of extension of the dosage form is preferably the largest plain area that can be placed along a cut of the body of the dosage form. This embodiment is further illustrated in FIG. 17A) which shows a schematic view of the cross-sectional face of the preferred pharmaceutical dosage form depicted in FIG. 10. The maximum extension (56) of the dosage form orthogonal to the main area of extension (57) of the dosage form is spaced from the centre of mass (58) of the dosage form parallel to said main area of extension (57).

Preferably, the closest distance (59) from the maximum extension of the dosage form orthogonal to the main area of extension of the dosage form to the centre of mass of the dosage form is at least 0.5 mm, more preferably at least 1.0 mm, still more preferably at least 1.5 mm, yet more preferably at least 2.0 mm, most preferably at least 2.5 mm and in particular at least 3.0 mm.

Preferably, the pharmaceutical dosage form according to the invention has a shape so that when exerting an increasing amount of force in direction of extension $E_2$, the dosage form is firstly deformed and, when the amount of force reaches the breaking strength $B_2$, deformation causes tractive forces that lead to disruption of the dosage form.

Figure 17B:
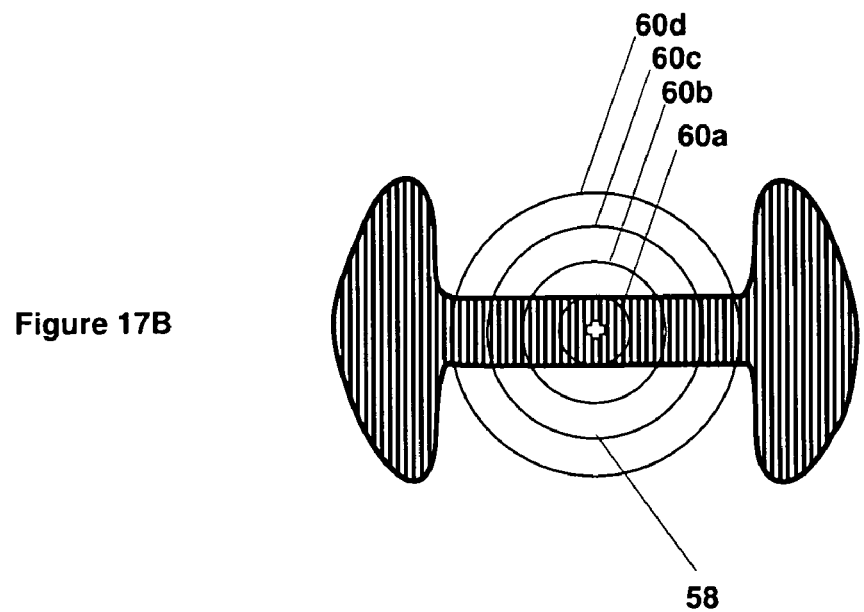
In FIG. 17B) the centre of mass (58) is surrounded by concentric rings (60a) to (60d) indicating increasing distances from the centre of mass.

In a preferred embodiment, the cross sectional area of the pharmaceutical dosage form that is orthogonal to the main direction of extension and that contains the centre of mass of the dosage form has a shape so that at least 50%, more preferably at least 60% and in particular at least 75% of its area is spaced at least 0.2 mm, at least 0.3 mm, at least 0.4 mm or at least 0.5 mm, more preferably at least 0.6 mm, at least 0.7 mm, at least 0.8 mm or at least 0.9 mm, still more preferably at least 1.0 mm, at least 1.1 mm, at least 1.2 mm or at least 1.3 mm, yet more preferably at least 1.4 mm, at least 1.5 mm, at least 1.6 mm or at least 1.7 mm, most preferably at least 1.8 mm, at least 1.9 mm, at least 2.0 mm or at least 2.1 mm and in particular at least 2.2 mm, at least 2.3 mm, at least 2.4 mm or at least 2.5 mm from the centre of mass. Preferably, said cross sectional area contains the centre of mass as well as direction of extension $E_1$, or the centre of mass as well as direction of extension $E_2$. This embodiment is further illustrated in FIG. 17B) in which the centre of mass (58) is surrounded by concentric rings (60a) to (60d) indicating increasing distances from the centre of mass (58). The portions of the cross sectional area which do not overlap with any of the concentric rings are spaced from the centre of mass by more than the radius of ring (60d).

In a preferred embodiment of the pharmaceutical dosage form according to the invention, the closest distance of each and every geometrical point within the dosage form to the surface of the dosage form is at most 10 mm, at most 9 mm, at most 8 mm or at most 7.5 mm; more preferably at most 7.0 mm, at most 6.5 mm or at most 6.0 mm; still more preferably at most 5.8 mm, at most 5.6 mm, at most 5.4 mm, at most 5.2 mm or at most 5.0 mm; yet more preferably at most 4.8 mm, at most 4.6 mm, at most 4.4 mm, at most 4.2 mm or at most 4.0 mm; yet more preferably at most 3.8 mm, at most 3.6 mm, at most 3.4 mm, at most 3.2 mm or at most 3.0 mm; most preferably at most 2.8 mm, at most 2.6 mm, at most 2.4 mm, at most 2.2 mm or at most 2.0 mm; and in particular at most 1.8 mm, at most 1.6 mm, at most 1.4 mm, at most 1.2 mm or at most 1.0 mm.

Preferably, the pharmaceutical dosage form according to the invention is not radial symmetric about its main direction of extension (principal direction of extension), preferably the pharmaceutical dosage form is not radial symmetric at all.

In a preferred embodiment, the symmetry of the pharmaceutical dosage form is selected from the group consisting of $C_i$, $C_s$, $C_1$, $C_2$, $C_3$, $C_4$, $C_5$, $C_6$, $C_7$, $C_8$, $C_\infty$, $C_{2h}$, $C_{3h}$, $C_{4h}$, $C_{5h}$, $C_{6h}$, $C_{7h}$, $C_{8h}$, $C_{\infty h}$, $C_2V$, $C_{3V}$, $C_{4V}$, $C_{5V}$, $C_{6V}$, $C_{7V}$, $C_{8V}$, $C_{\infty V}$, $C_{3i}$, $D_2$, $D_3$, $D_4$, $D_5$, $D_6$, $D_7$, $D_8$, $D_\infty$, $D_{2h}$, $D_{3h}$, $D_{4h}$, $D_{5h}$, $D_{6h}$, $D_{7h}$, $D_{8h}$, $D_{\infty h}$, $D_{2d}$, $D_{3d}$, $D_{4d}$, $D_{5d}$, $D_{6d}$, $D_{7d}$, $D_{8d}$, $D_{\infty d}$, $S_2$, $S_4$, $S_6$, $S_8$, $T$, $T_h$, $T_d$, $O$, $O_h$ and $I_h$ according to Schoenflies notation. $D_{2h}$ and $D_{4h}$ are particularly preferred.

In a preferred embodiment, the centre of mass of the pharmaceutical dosage form lies within the main area of extension of the dosage form. Preferably, the pharmaceutical dosage form is symmetric about its main area of extension.

The pharmaceutical dosage form according to the invention preferably has a breaking strength $B_1$ of at least 500 N in at least one of its directions of extension, namely $E_1$, preferably, however, in more than one of its directions of extension, more preferably in a plurality of directions of extension.

In direction of extension $E_1$ the pharmaceutical dosage form according to the invention preferably has a breaking strength $B_1$ of at least 500 N, preferably of at least 510 N, at least 520 N, at least 530 N, at least 540 N or at least 550 N; more preferably at least 560 N, at least 570 N, at least 580 N, at least 590 N or at least 600 N; still more preferably at least 620 N, at least 640 N, at least 660 N, at least 680 N or at least 700 N; yet more preferably at least 720 N, at least 740 N, at least 760 N, at least 780 N or at least 800 N; most preferably at least 850 N, at least 900 N, at least 950 N, at least 1000 N or at least 1050 N; and in particular at least 1100 N, at least 1200 N, at least 1300 N, at least 1400 N, at least 1500 N, at least 1600 N, at least 1700 N, at least 1800 N, at least 1900 N or at least 2000 N.

$E_1$ may be any direction of extension of the pharmaceutical dosage form, i.e. any straight line connecting any first point on the surface of the pharmaceutical dosage form with any second point on the surface of the pharmaceutical dosage form. Preferably, said straight line lies completely within the body of the pharmaceutical dosage form, i.e., preferably does not "leave" the pharmaceutical dosage form somewhere and "reenters" the pharmaceutical dosage form elsewhere. Preferably, the distance between said first point and said second point of direction of extension $E_1$ is at least 50%, more preferably at least 75% of the main direction of extension of the pharmaceutical dosage form. The latter is defined as the maximal distance between two points on the surface of the pharmaceutical dosage form (principal direction of extension), regardless of whether it completely lies within the body of the dosage form or not. Preferably, the main direction of extension of the dosage form goes through the centre of mass of the dosage form.

In a preferred embodiment, the main direction of extension of the pharmaceutical dosage form according to the invention is not longer than 32 mm, more preferably not longer than 30 mm, still more preferably not longer than 28 mm, yet more preferably not longer than 26 mm, most preferably not longer than 24 mm, and in particular not longer than 22 mm.

In a preferred embodiment, the pharmaceutical dosage form according to the invention is deformed in the breaking strength tester when the measurement of the breaking strength is conducted. Deformation means typically compression, although bending, turning and other modes of deformation are also possible. When exerting a force of 100 N in direction of extension $E_1$, the dosage form is preferably deformed by at least 0.1 mm but does not break. When exerting a force of 200 N in direction of extension $E_1$, the dosage form is preferably deformed by at least 0.2 mm, more preferably at least 0.3 mm, but does not break. When exerting a force of 300 N in direction of extension $E_1$, the dosage form is preferably deformed by at least 0.5 mm, more preferably at least 0.7 mm, but does not break. When exerting a force of 400 N in direction of extension $E_1$, the dosage form is preferably deformed by at least 1.0 mm, more preferably at least 1.2 mm, but does not break. When exerting a force of 500 N in direction of extension $E_1$, the dosage form is preferably deformed by at least 1.5 mm, more preferably at least 2.0 mm, but does not break. When exerting a force of 1000 N in direction of extension $E_1$, the dosage form is preferably deformed by at least 3.0 mm, more preferably at least 4.0 mm, but does not break.

For theoretical reasons, every pharmaceutical dosage form comprises an unlimited number of directions of extension.

Figure 8A:
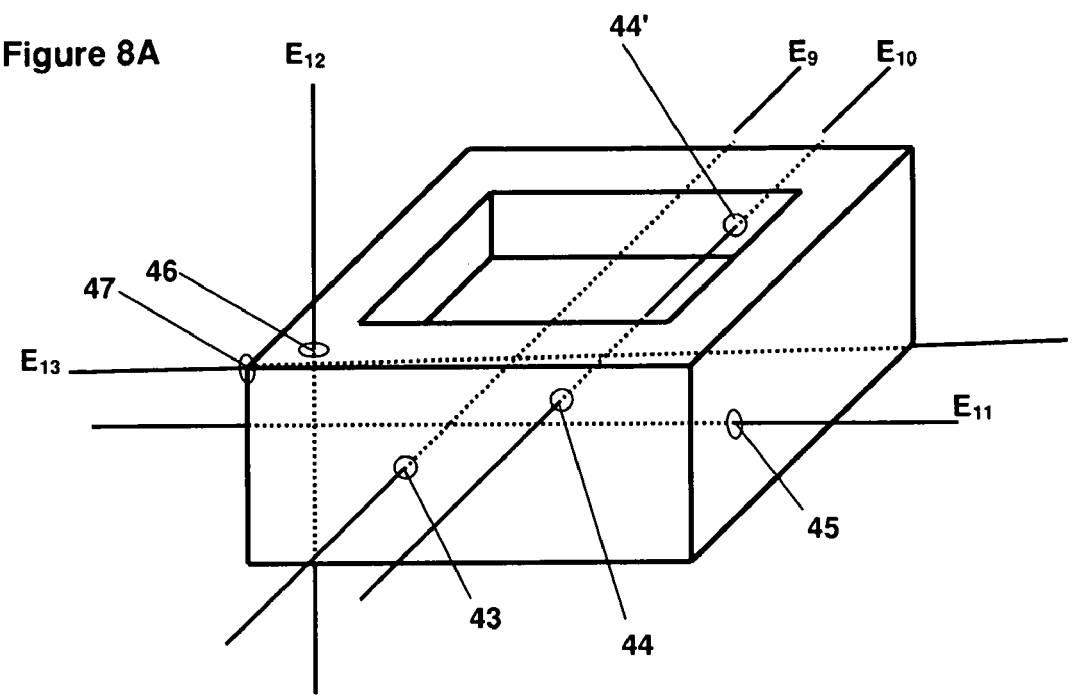
FIG. 8A) is a schematic view of a preferred pharmaceutical dosage form according to the invention having two recesses on opposing sides ("inner courtyards").

Some typical directions of extension of a preferred pharmaceutical dosage form according to the invention are illustrated in FIG. 8. FIG. 8A) shows different directions of extension. Directions of extension $E_9$ and $E_{10}$ are parallel to one another, directions of extension $E_{10}$, $E_{11}$ and $E_{12}$ (and $E_9$, respectively) are orthogonal to one another. Directions of extension $E_9$, $E_{10}$, $E_{11}$ and $E_{12}$ enter the body of the pharmaceutical dosage form at sites (43), (44), (45) and (46), respectively. Direction of extension $E_9$ lies completely within the body of the pharmaceutical dosage form; it enters the body of the pharmaceutical dosage form at site (43 and leaves the body of the pharmaceutical dosage form at its rear side (not shown). Direction of extension $E_{10}$, however, enters the body of the pharmaceutical dosage form at site (44), transiently leaves the body of the pharmaceutical dosage form at the rear side of the upper front edge (not shown) and re-enters the body of the pharmaceutical dosage form at site (44'), before it finally leaves the body of the pharmaceutical dosage form at its rear side (not shown). Direction of extension $E_{13}$ enters the body of the pharmaceutical dosage form at corner (47) and leaves the pharmaceutical dosage form at the diagonally opposite corner. The dotted line of direction of extension $E_{13}$ represents the maximal distance between two points on the surface of the pharmaceutical dosage form, i.e., direction of extension $E_{13}$ is the main direction of extension of the pharmaceutical dosage form. In total, the pharmaceutical dosage form depicted in FIG. 8A) has four of such main directions of extension.

Figure 8B:
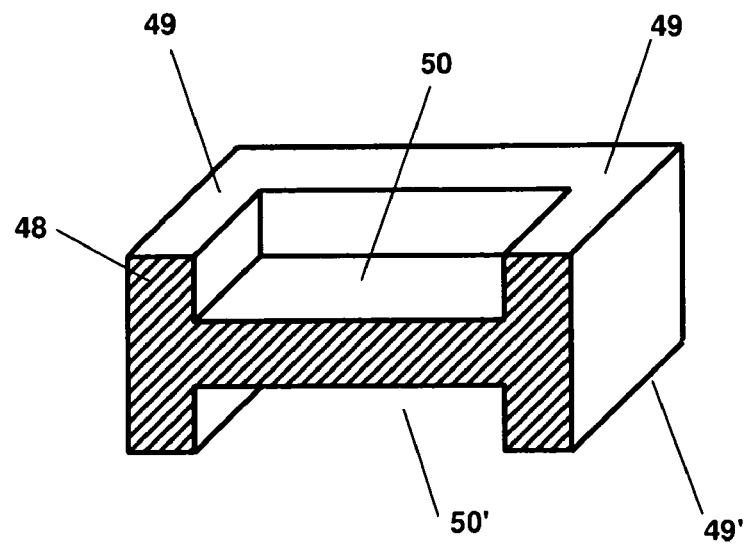
FIG. 8B) is a schematic view of the cross-section of the pharmaceutical dosage form depicted in FIG. 8A) showing that the face of the cross-section assumes the shape of a H.

FIG. 8B) shows a cross-sectional view of the pharmaceutical dosage form according to FIG. 8A). The cross-sectional face (48, hatched) assumes the shape of an H. The pharmaceutical dosage form assumes a rectangular shape with two recesses (50, 50') on opposing sides. In other words, the pharmaceutical dosage form has the size of a comparatively flat rectangle with an edge (49) circumventing the upper side and an edge (49') circumventing the opposite side. Pharmaceutical dosage forms of this type may be manufactured by a tabletting tool that is equipped with a so-called H-plunger.

Figure 9A:
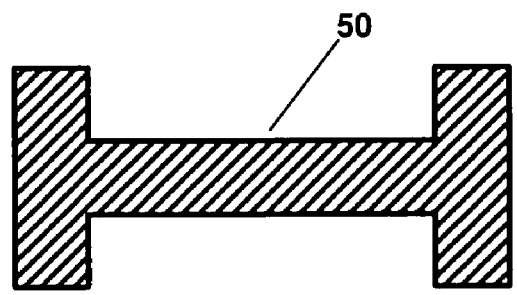
FIG. 9A) is a schematic view of the cross-sectional face of the pharmaceutical dosage form depicted in FIG. 8A).
Figure 9B:
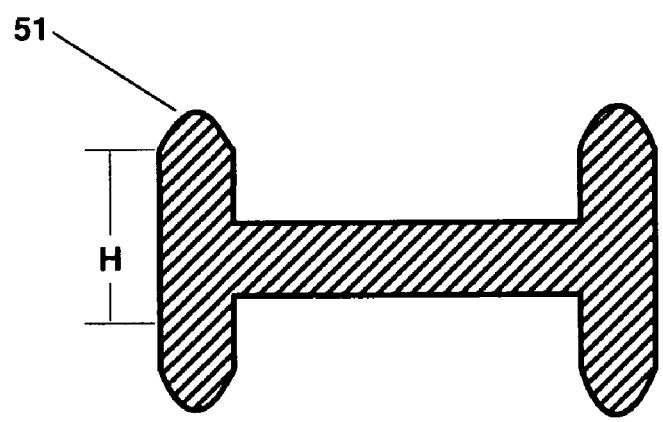
FIG. 9B) is a schematic view of the cross-sectional face of a pharmaceutical dosage form according to the invention that is similar to the cross-sectional face of the pharmaceutical dosage form depicted in FIG. 9A).
Figure 9C:
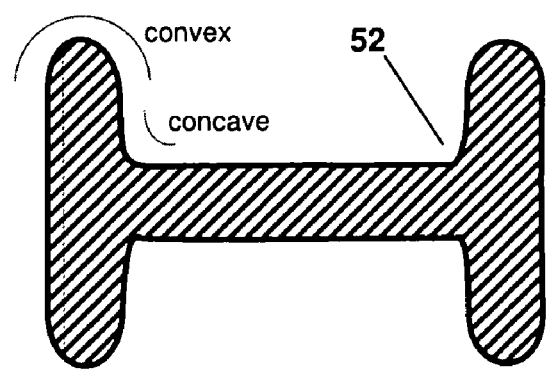
FIG. 9C) is a schematic view of the cross-sectional face of a pharmaceutical dosage form according to the invention that is similar to the cross-sectional face of pharmaceutical dosage forms depicted in FIGS. 9A) and 9B).

FIG. 9A) is a schematic view of the cross-sectional face (48) of the pharmaceutical dosage form depicted in FIG. 8A). FIG. 9B) is a schematic view of the cross-sectional face of a pharmaceutical dosage form according to the invention that is similar to the cross-sectional face of the pharmaceutical dosage form depicted in FIG. 9A). The rim (49) of the cross-sectional face, however, is rounded (51) thereby forming a convex surface area. FIG. 9C is a schematic view of the cross-sectional face of a pharmaceutical dosage form according to the invention that is similar to the cross-sectional face of pharmaceutical dosage forms depicted in FIGS. 9A) and 9B). The edge at the bottom of the recess is rounded (52) thereby forming a concave surface area.

Figure 10A:
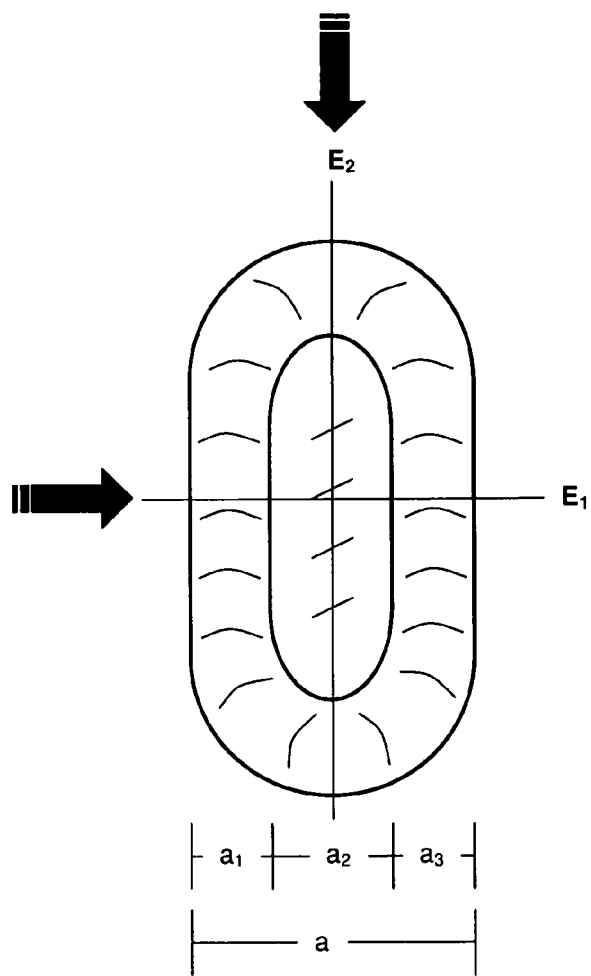
FIG. 10A) is a top view, FIG. 10B) is a side view.
Figure 10B:
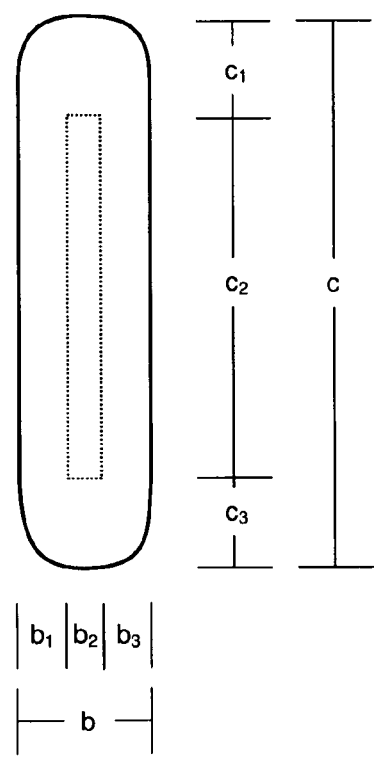
FIG. 10 is a schematic view of a particularly preferred pharmaceutical dosage form according to the invention.

FIG. 10 is a schematic view of a particularly preferred pharmaceutical dosage form according to the invention. FIG. 10A) is a top view which is identical from both opposing sides and FIG. 10B) is a side-view which is also identical from both opposing sides.

In the Cartesian space, the principal dimensions of the pharmaceutical dosage form schematically illustrated in FIG. 10 can be defined as a, b and c, where $a=a_1=a_2+a_3$, $b=b_1+b_2+b_3$ and $c=c_1+c_2+c_3$. Preferred relative dimensions D1 to D6 of the pharmaceutical dosage form depicted in FIG. 10 can be defined in relative relations of a, b and c; $a_1$, $a_2$ and $a_3$; $b_1$, $b_2$ and $b_3$; and $c_1$, $c_2$ and $C_3$, respectively:

$D1: c>a \geq b; c>a>b;$ $D2: c>1.5a; c>2a; c>2.5a; c>3a;$ $D3: a_2>a_1 \cong a_3; a_2>1.1a_1 \cong 1.1a_3; a_2>1.2a_1 \cong 1.2a_3;$
$a_2>1.3a_1 \cong 1.3a_3;$ $D4: b_2 \geq b_1 \cong b_3; b_2 \geq 1.1b_1 \cong 1.1b_3; b_2 \geq 1.2b_1 \cong 1.2b_3;$
$b_2 \geq 1.3b_1 \cong 1.3b_3;$ $D5: b_2 \leq b_1 \cong b_3; b_2 \leq 0.9b_1 \cong 0.9b_3; b_2 < 0.8b_1 \cong 0.8b_3;$
$b_2 \leq 0.7b_1 \cong 0.7b_3;$ and/or $D6: c_2>c_1 \cong c_3; c_2>1.1c_1 \cong 1.1c_3; c_2>1.2c_1 \cong 1.2c_3;$
$c_2>1.3c_1 \cong 1.3c_3.$ Preferred embodiments D7 to D18 regarding the absolute dimensions of the pharmaceutical dosage form depicted in FIG. 10 are displayed in the table here below:

| [mm] | D7 | D8 | D9 | D10 |
|---|---|---|---|---|
| a | 8.6 ± 4.3 | 8.6 ± 2.1 | 8.6 ± 1.0 | 9.0 ± 4.5 |
| b | 4.9 ± 2.5 | 4.9 ± 1.3 | 4.9 ± 0.7 | 4.3 ± 2.1 |
| c | 21.9 ± 11.0 | 21.9 ± 5.5 | 21.9 ± 2.7 | 20.4 ± 10.2 |

| [mm] | D11 | D12 | D13 | D14 |
|---|---|---|---|---|
| a | 9.0 ± 2.2 | 9.0 ± 1.1 | 9.0 ± 4.3 | 9.0 ± 2.1 |
| b | 4.3 ± 1.0 | 4.3 ± 0.6 | 4.1 ± 2.5 | 4.1 ± 1.3 |
| c | 20.4 ± 5.1 | 20.4 ± 2.5 | 20.5 ± 11.0 | 20.5 ± 5.5 |

-continued

| [mm] | D15 | D16 | D17 | D18 |
|---|---|---|---|---|
| a | 9.0 ± 1.0 | 9.1 ± 4.5 | 9.1 ± 2.2 | 9.1 ± 1.1 |
| b | 4.1 ± 0.7 | 4.5 ± 2.1 | 4.5 ± 1.0 | 4.5 ± 0.6 |
| c | 20.5 ± 2.7 | 20.5 ± 10.2 | 20.5 ± 5.1 | 20.5 ± 2.5 |

Preferred embodiments D19 to D30 regarding the absolute dimensions of the pharmaceutical dosage form depicted in FIG. 10 are displayed in the table here below:

| [mm] | | D19 | D20 | D21 | D22 |
|---|---|---|---|---|---|
| a | | 8.6 ± 4.3 | 8.6 ± 2.1 | 8.6 ± 1.0 | 9.0 ± 4.5 |
| | $a_1$ | 3.3 ± 1.6 | 3.3 ± 0.8 | 3.3 ± 0.4 | 3.5 ± 1.8 |
| | $a_2$ | 2.1 ± 1.0 | 2.1 ± 0.5 | 2.1 ± 0.3 | 2.1 ± 1.1 |
| | $a_3$ | 3.3 ± 1.6 | 3.3 ± 0.8 | 3.3 ± 0.4 | 3.5 ± 1.8 |
| b | | 4.9 ± 2.5 | 4.9 ± 1.3 | 4.9 ± 0.7 | 4.3 ± 2.1 |
| | $b_1$ | 0.9 ± 0.5 | 0.9 ± 0.3 | 0.9 ± 0.2 | 0.9 ± 0.4 |
| | $b_2$ | 3.1 ± 1.5 | 3.1 ± 0.7 | 3.1 ± 0.4 | 2.6 ± 1.3 |
| | $b_3$ | 0.9 ± 0.5 | 0.9 ± 0.3 | 0.9 ± 0.2 | 0.9 ± 0.4 |
| c | | 21.9 ± 11.0 | 21.9 ± 5.5 | 21.9 ± 2.7 | 20.4 ± 10.2 |
| | $c_1$ | 3.2 ± 1.6 | 3.2 ± 0.8 | 3.2 ± 0.4 | 3.3 ± 1.7 |
| | $c_2$ | 15.6 ± 7.8 | 15.6 ± 3.9 | 15.6 ± 2.0 | 13.8 ± 6.9 |
| | $c_3$ | 3.2 ± 1.6 | 3.2 ± 0.8 | 3.2 ± 0.4 | 3.3 ± 1.7 |

| [mm] | | D23 | D24 | D25 | D26 |
|---|---|---|---|---|---|
| a | | 9.0 ± 2.2 | 9.0 ± 1.1 | 9.0 ± 4.3 | 9.0 ± 2.1 |
| | $a_1$ | 3.5 ± 0.9 | 3.5 ± 0.5 | 3.2 ± 1.6 | 3.2 ± 0.8 |
| | $a_2$ | 2.1 ± 0.6 | 2.1 ± 0.3 | 2.6 ± 1.0 | 2.6 ± 0.5 |
| | $a_3$ | 3.5 ± 0.9 | 3.5 ± 0.5 | 3.2 ± 1.6 | 3.2 ± 0.8 |
| b | | 4.3 ± 1.0 | 4.3 ± 0.6 | 4.1 ± 2.5 | 4.1 ± 1.3 |
| | $b_1$ | 0.9 ± 0.2 | 0.9 ± 0.1 | 1.0 ± 0.5 | 1.0 ± 0.3 |
| | $b_2$ | 2.6 ± 0.6 | 2.6 ± 0.3 | 2.1 ± 1.5 | 2.1 ± 0.7 |
| | $b_3$ | 0.9 ± 0.2 | 0.9 ± 0.1 | 1.0 ± 0.5 | 1.0 ± 0.3 |
| c | | 20.4 ± 5.1 | 20.4 ± 2.5 | 20.5 ± 11.0 | 20.5 ± 5.5 |
| | $c_1$ | 3.3 ± 0.9 | 3.3 ± 0.4 | 3.3 ± 1.6 | 3.3 ± 0.8 |
| | $c_2$ | 13.8 ± 3.5 | 13.8 ± 1.7 | 13.9 ± 7.8 | 13.9 ± 3.9 |
| | $c_3$ | 3.3 ± 0.9 | 3.3 ± 0.4 | 3.3 ± 1.6 | 3.3 ± 0.8 |

| [mm] | | D27 | D28 | D29 | D30 |
|---|---|---|---|---|---|
| a | | 9.0 ± 1.0 | 9.1 ± 4.5 | 9.1 ± 2.2 | 9.1 ± 1.1 |
| | $a_1$ | 3.2 ± 0.4 | 3.2 ± 1.8 | 3.2 ± 0.9 | 3.2 ± 0.5 |
| | $a_2$ | 2.6 ± 0.3 | 2.7 ± 1.1 | 2.7 ± 0.6 | 2.7 ± 0.3 |
| | $a_3$ | 3.2 ± 0.4 | 3.2 ± 1.8 | 3.2 ± 0.9 | 3.2 ± 0.5 |
| b | | 4.1 ± 0.7 | 4.5 ± 2.1 | 4.5 ± 1.0 | 4.5 ± 0.6 |
| | $b_1$ | 1.0 ± 0.2 | 1.0 ± 0.4 | 1.0 ± 0.2 | 1.0 ± 0.1 |
| | $b_2$ | 2.1 ± 0.4 | 2.5 ± 1.3 | 2.5 ± 0.6 | 2.5 ± 0.3 |
| | $b_3$ | 1.0 ± 0.2 | 1.0 ± 0.4 | 1.0 ± 0.2 | 1.0 ± 0.1 |
| c | | 20.5 ± 2.7 | 20.5 ± 10.2 | 20.5 ± 5.1 | 20.5 ± 2.5 |
| | $c_1$ | 3.3 ± 0.4 | 3.3 ± 1.7 | 3.3 ± 0.9 | 3.3 ± 0.4 |
| | $c_2$ | 13.9 ± 2.0 | 13.9 ± 6.9 | 13.9 ± 3.5 | 13.9 ± 1.7 |
| | $c_3$ | 3.3 ± 0.4 | 3.3 ± 1.7 | 3.3 ± 0.9 | 3.3 ± 0.4 |

The pharmaceutical dosage form according to the invention preferably has a breaking strength $B_2$ in a second direction of extension $E_2$, wherein $B_2 < 500$ N.

Direction of extension $E_1$ differs from direction of extension $E_2$. $E_2$ may be any direction of extension of the pharmaceutical dosage form, i.e. any straight line connecting any first point on the surface of the pharmaceutical dosage form with any second point on the surface of the pharmaceutical dosage form. Preferably, said straight line lies completely within the body of the pharmaceutical dosage form, i.e., preferably does not "leave" the pharmaceutical dosage form somewhere and "re-enters" the pharmaceutical dosage form elsewhere. Preferably, the distance between said first point and said second point is at least 50%, more preferably at least 75% of the main direction of extension of the pharmaceutical dosage form, the latter being defined as the maximal distance between two points on the surface of the pharmaceutical dosage form.

Preferably, $E_1$ and $E_2$ assume an angle with one another of from 10 to 170°, more preferably 20 to 160°, still more preferably 30 to 150°, yet more preferably 40 to 140°, most preferably 50 to 130°, and in particular 60 to 120°. In a particularly preferred embodiment, $E_1$ is orthogonal to $E_2$.

Preferably, $E_2$ is the main direction (principal direction) of extension of the pharmaceutical dosage form, i.e., $B_2$ can preferably be measured by placing the pharmaceutical dosage form between the jaws of the measuring device so that the two jaws have the maximum distance from one another but are each in contact the pharmaceutical dosage form.

In a preferred embodiment, $E_1$ and $E_2$, which both are preferably orthogonal to each another, lie within the main area of extension of the dosage form, which main area of extension preferably also contains the centre of mass of the dosage form.

In a preferred embodiment, $B_2$ is below 490 N, below 480 N, below 460 N, below 440 N, or below 420 N; more preferably below 400 N, below 380 N, below 360 N, below 340 N, or below 320 N; still more preferably below 300 N, below 280 N, below 260 N, below 240 N or below 220 N.

In another preferred embodiment, $B_2$ is at least 200 N, at least 220 N, at least 240 N, at least 260 N, or at least 280 N; more preferably at least 300 N, at least 320 N, at least 340 N, at least 360 N, or at least 380 N; still more preferably at least 420 N, at least 440 N, at least 460 N, or at least 480 N.

Preferably, the ratio of $B_1$ to $B_2$ is within the range of from 100:1 to 1.1:1, more preferably 75:1 to 1.2:1, still more preferably 50:1 to 1.3:1, yet more preferably 25:1 to 1.4:1, most preferably 10:1 to 1.5:1 and in particular 5:1 to 1.6:1.

Preferably, the difference $B_1 - B_2$ is at least 10 N, at least 20 N, at least 30 N, at least 40 N or at least 50 N, more preferably at least 60 N, at least 70 N, at least 80 N or at least 90 N, still more preferably at least 100 N, at least 125 N, at least 150 N, at least 175 N or at least 200 N, most preferably at least 250 N, at least 300 N, at least 350 N, at least 400 or at least 450 N, and in particular at least 500 N, at least 600 N, at least 750 or at least 1000 N.

In a preferred embodiment of the pharmaceutical dosage form according to the invention, $B_1$ and $B_2$ satisfy one of the following conditions C 1 to C 72:

| C | $B_2$ | $B_1$ |
|---|---|---|
| 1 | 100 N < $B_2$ < 500 N | 500 N < $B_1$ |
| 2 | 100 N < $B_2$ < 500 N | 600 N < $B_1$ |
| 3 | 100 N < $B_2$ < 500 N | 700 N < $B_1$ |
| 4 | 100 N < $B_2$ < 500 N | 800 N < $B_1$ |
| 5 | 100 N < $B_2$ < 500 N | 900 N < $B_1$ |
| 6 | 100 N < $B_2$ < 500 N | 1000 N < $B_1$ |
| 7 | 100 N < $B_2$ < 500 N | 1500 N < $B_1$ |
| 8 | 100 N < $B_2$ < 500 N | 2000 N < $B_1$ |
| 9 | 200 N < $B_2$ < 500 N | 500 N < $B_1$ |
| 10 | 200 N < $B_2$ < 500 N | 600 N < $B_1$ |
| 11 | 200 N < $B_2$ < 500 N | 700 N < $B_1$ |
| 12 | 200 N < $B_2$ < 500 N | 800 N < $B_1$ |
| 13 | 200 N < $B_2$ < 500 N | 900 N < $B_1$ |
| 14 | 200 N < $B_2$ < 500 N | 1000 N < $B_1$ |
| 15 | 200 N < $B_2$ < 500 N | 1500 N < $B_1$ |
| 16 | 200 N < $B_2$ < 500 N | 2000 N < $B_1$ |
| 17 | 300 N < $B_2$ < 500 N | 500 N < $B_1$ |
| 18 | 300 N < $B_2$ < 500 N | 600 N < $B_1$ |
| 19 | 300 N < $B_2$ < 500 N | 700 N < $B_1$ |
| 20 | 300 N < $B_2$ < 500 N | 800 N < $B_1$ |
| 21 | 300 N < $B_2$ < 500 N | 900 N < $B_1$ |
| 22 | 300 N < $B_2$ < 500 N | 1000 N < $B_1$ |
| 23 | 300 N < $B_2$ < 500 N | 1500 N < $B_1$ |
| 24 | 300 N < $B_2$ < 500 N | 2000 N < $B_1$ |
| 25 | 400 N < $B_2$ < 500 N | 500 N < $B_1$ |

| C | $B_2$ | $B_1$ |
|---|---|---|
| 26 | 400 N < $B_2$ < 500 N | 600 N < $B_1$ |
| 27 | 400 N < $B_2$ < 500 N | 700 N < $B_1$ |
| 28 | 400 N < $B_2$ < 500 N | 800 N < $B_1$ |
| 29 | 400 N < $B_2$ < 500 N | 900 N < $B_1$ |
| 30 | 400 N < $B_2$ < 500 N | 1000 N < $B_1$ |
| 31 | 400 N < $B_2$ < 500 N | 1500 N < $B_1$ |
| 32 | 400 N < $B_2$ < 500 N | 2000 N < $B_1$ |
| 33 | 100 N < $B_2$ < 400 N | 500 N < $B_1$ |
| 34 | 100 N < $B_2$ < 400 N | 600 N < $B_1$ |
| 35 | 100 N < $B_2$ < 400 N | 700 N < $B_1$ |
| 36 | 100 N < $B_2$ < 400 N | 800 N < $B_1$ |
| 37 | 100 N < $B_2$ < 400 N | 900 N < $B_1$ |
| 38 | 100 N < $B_2$ < 400 N | 1000 N < $B_1$ |
| 39 | 100 N < $B_2$ < 400 N | 1500 N < $B_1$ |
| 40 | 100 N < $B_2$ < 400 N | 2000 N < $B_1$ |
| 41 | 200 N < $B_2$ < 400 N | 500 N < $B_1$ |
| 42 | 200 N < $B_2$ < 400 N | 600 N < $B_1$ |
| 43 | 200 N < $B_2$ < 400 N | 700 N < $B_1$ |
| 44 | 200 N < $B_2$ < 400 N | 800 N < $B_1$ |
| 45 | 200 N < $B_2$ < 400 N | 900 N < $B_1$ |
| 46 | 200 N < $B_2$ < 400 N | 1000 N < $B_1$ |
| 47 | 200 N < $B_2$ < 400 N | 1500 N < $B_1$ |
| 48 | 200 N < $B_2$ < 400 N | 2000 N < $B_1$ |
| 49 | 300 N < $B_2$ < 400 N | 500 N < $B_1$ |
| 50 | 300 N < $B_2$ < 400 N | 600 N < $B_1$ |
| 51 | 300 N < $B_2$ < 400 N | 700 N < $B_1$ |
| 52 | 300 N < $B_2$ < 400 N | 800 N < $B_1$ |
| 53 | 300 N < $B_2$ < 400 N | 900 N < $B_1$ |
| 54 | 300 N < $B_2$ < 400 N | 1000 N < $B_1$ |
| 55 | 300 N < $B_2$ < 400 N | 1500 N < $B_1$ |
| 56 | 300 N < $B_2$ < 400 N | 2000 N < $B_1$ |
| 57 | 100 N < $B_2$ < 300 N | 500 N < $B_1$ |
| 58 | 100 N < $B_2$ < 300 N | 600 N < $B_1$ |
| 59 | 100 N < $B_2$ < 300 N | 700 N < $B_1$ |
| 60 | 100 N < $B_2$ < 300 N | 800 N < $B_1$ |
| 61 | 100 N < $B_2$ < 300 N | 900 N < $B_1$ |
| 62 | 100 N < $B_2$ < 300 N | 1000 N < $B_1$ |
| 63 | 100 N < $B_2$ < 300 N | 1500 N < $B_1$ |
| 64 | 100 N < $B_2$ < 300 N | 2000 N < $B_1$ |
| 65 | 200 N < $B_2$ < 300 N | 500 N < $B_1$ |
| 66 | 200 N < $B_2$ < 300 N | 600 N < $B_1$ |
| 67 | 200 N < $B_2$ < 300 N | 700 N < $B_1$ |
| 68 | 200 N < $B_2$ < 300 N | 800 N < $B_1$ |
| 69 | 200 N < $B_2$ < 300 N | 900 N < $B_1$ |
| 70 | 200 N < $B_2$ < 300 N | 1000 N < $B_1$ |
| 71 | 200 N < $B_2$ < 300 N | 1500 N < $B_1$ |
| 72 | 200 N < $B_2$ < 300 N | 2000 N < $B_1$ |

Further preferred embodiments C 73 to C 96 are summarized in the table here below:

| C | $B_2$ | $B_1$ |
|---|---|---|
| 73 | 320 N < $B_2$ < 420 N | 500 N < $B_1$ |
| 74 | 320 N < $B_2$ < 420 N | 600 N < $B_1$ |
| 75 | 320 N < $B_2$ < 420 N | 700 N < $B_1$ |
| 76 | 320 N < $B_2$ < 420 N | 800 N < $B_1$ |
| 77 | 320 N < $B_2$ < 420 N | 900 N < $B_1$ |
| 78 | 320 N < $B_2$ < 420 N | 1000 N < $B_1$ |
| 79 | 320 N < $B_2$ < 420 N | 1500 N < $B_1$ |
| 80 | 320 N < $B_2$ < 420 N | 2000 N < $B_1$ |
| 81 | 330 N < $B_2$ < 420 N | 500 N < $B_1$ |
| 82 | 330 N < $B_2$ < 420 N | 600 N < $B_1$ |
| 83 | 330 N < $B_2$ < 420 N | 700 N < $B_1$ |
| 84 | 330 N < $B_2$ < 420 N | 800 N < $B_1$ |
| 85 | 330 N < $B_2$ < 420 N | 900 N < $B_1$ |
| 86 | 330 N < $B_2$ < 420 N | 1000 N < $B_1$ |
| 87 | 330 N < $B_2$ < 420 N | 1500 N < $B_1$ |
| 88 | 330 N < $B_2$ < 420 N | 2000 N < $B_1$ |
| 89 | 340 N < $B_2$ < 420 N | 500 N < $B_1$ |
| 90 | 340 N < $B_2$ < 420 N | 600 N < $B_1$ |
| 91 | 340 N < $B_2$ < 420 N | 700 N < $B_1$ |
| 92 | 340 N < $B_2$ < 420 N | 800 N < $B_1$ |
| 93 | 340 N < $B_2$ < 420 N | 900 N < $B_1$ |
| 94 | 340 N < $B_2$ < 420 N | 1000 N < $B_1$ |
| 95 | 340 N < $B_2$ < 420 N | 1500 N < $B_1$ |
| 96 | 340 N < $B_2$ < 420 N | 2000 N < $B_1$ |

Due to the property $B_2 < B_1$, the pharmaceutical dosage form according to the invention preferably has anisotropic mechanical properties, i.e., is mechanically weakened with respect of at least one of its directions of extension ($E_2$) compared to its mechanical strength with respect of at least another of its directions of extension ($E_1$). In a preferred embodiment, the quality of the mechanical weakening is such that the pharmaceutical dosage form may be fractured once by exerting a sufficient amount of force in direction of extension $E_2$, but the thus obtained fragments are substantially break resistant in any (each and every) of their directions of extension, i.e., may not be fractured any further by exerting the same amount of force in any (each and every) of their directions of extension. Preferably, said amount of force is 400 N, 500 N, 600 N, 700 N, 800 N, 900 N, 1000 N, 1100 N, 1200 N, 1300 N, 1400 N, or 1500 N. In consequence, according to this embodiment the pharmaceutical dosage form may be fractured once by exerting a sufficient amount of force in direction of extension $E_2$, but may not be fractured any further unless the exerted force is increased. Preferably, the number of fragments that are obtained when the pharmaceutical dosage form is fractured once is limited, preferably only two, three, four, five or six fragments, preferably of substantially identical or different size and/or weight, are obtained.

In a preferred embodiment, the surface S [$mm^2$] to weight W [mg] ratio S/W of the pharmaceutical dosage form according to the invention is at least 0.50 $mm^2$/mg. Preferably, S/W is at least 0.51, at least 0.52, at least 0.53, at least 0.54 or at least 0.55; more preferably at least 0.56, at least 0.57, at least 0.58, at least 0.59 or at least 0.60; still more preferably at least 0.61, at least 0.62, at least 0.63, at least 0.64 or at least 0.65; yet more preferably at least 0.66, at least 0.67, at least 0.68, at least 0.69 or at least 0.70; most preferably at least 0.705, at least 0.710, at least 0.715, at least 0.720, at least 0.725, at least 0.730, at least 0.735, at least 0.740, at least 0.745 or at least 0.750; and in particular at least 0.755, at least 0.760, at least 0.765, at least 0.770, at least 0.775, at least 0.780, at least 0.785, at least 0.790, at least 0.795 or at least 0.80 $mm^2$/mg.

In a preferred embodiment, the pharmaceutical dosage form according to the invention has a total surface S defined by the formula $$S \geq A \cdot W^{2/3},$$

wherein A is at least 4.5, i.e. $S \geq 4.5 \cdot W^{2/3}$.

For example, when the pharmaceutical dosage form according to the invention has a total weight of 623 mg, its total surface S is preferably at least 328 $mm^2$ ($4.5 \cdot 623^{2/3}$) and when the pharmaceutical dosage form according to the invention has a total weight of 983 mg, its total surface S is preferably at least 445 $mm^2$ ($4.5 \cdot 983^{2/3}$).

Methods for measuring the total surface of a pharmaceutical dosage form are known to the skilled artisan. For example, the total surface may be calculated from the three dimensional extension of the pharmaceutical dosage form based on simple geometrical considerations (cf., e.g., Eudragit® Application Guidelines, 10th edition, July 2007, Röhm GmbH, Darmstadt).

Figure 11:
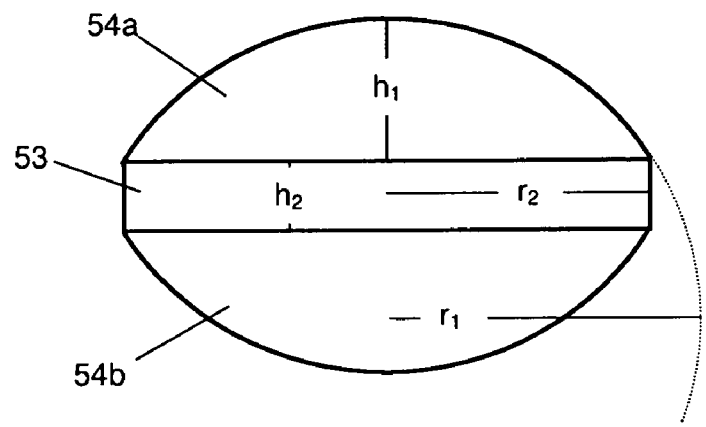
FIG. 11 is a schematic view of a conventional pharmaceutical dosage form comprising a cylindrical central element (53) and two spherical caps (54a) and (54b).

For example, the geometry of the conventional tablet that is depicted in FIG. 11 may be described by a cylindrical element (53) that is located between two spherical caps (54a) and (54*b*). The volumes V(53), V(54*a*) and V(54*b*) as well as the surfaces S(53), S(54*a*) and S(54*b*) can be calculated according to the following formulas:

$$V(53) = \pi r_2^2 h_2 \qquad V(54a) = V(54b) = \frac{1}{6}\pi h_1(3r_2^2 + h_1^2)$$

$$V_t = V(53) + V(54a) + V(54b) \qquad S(53) = 2\pi r_2 h_2$$

$$S(54a) = S(54b) = 2\pi r_1 h_1 \qquad S_t = S(53) + S(54a) + S(56)$$

Figure 12:
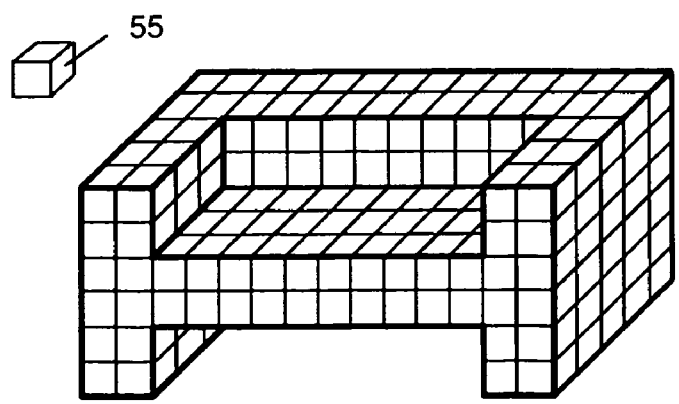
FIG. 12 is a schematic view of a cross-section of a preferred pharmaceutical dosage form divided into voxels (55) of identical volume and surface to roughly estimate the overall surface of the dosage form.

In approximation, the pharmaceutical dosage form may also be mentally divided into a plurality of identical cubic volume elements of suitable size (voxels) and the total surface may be determined by counting the squared area elements (pixels) being located at the surface. This approximation is further illustrated in FIG. 12 where the pharmaceutical dosage form according to FIG. 8B) is divided into a plurality of voxels (55).

Preferably, when measuring the total surface of the pharmaceutical dosage form, the micro-fine structure of the pharmacologically active compound (A) and of all other constituents of the dosage form including polymers and pharmaceutical excipients, e.g. their porosity, is not taken into account. For the purpose of the specification, the term "surface" of the pharmaceutical dosage form preferably refers to the macroscopic surface (outer dimensions, silhouette). In other words, for the purpose of determining the surface of the pharmaceutical dosage form, the surface structure is preferably considered perfectly smooth.

In a preferred embodiment of the pharmaceutical dosage form according to the invention, A is 4.6, 4.7, 4.8, 4.9, 5.0, 5.1, 5.2, 5.3, 5.4, 5.5, 5.6, 5.7, 5.8, 5.9 or 6.0; more preferably 6.05, 6.1, 6.15, 6.2, 6.25, 6.3, 6.35, 6.4, 6.45, 6.5, 6.55, 6.6, 6.65, 6.7, 6.75, 6.8, 6.85, 6.9, 6.95, 7.0, 7.05, 7.1, 7.15, 7.2, 7.25, 7.3, 7.35, 7.4, 7.45 or 7.5.

In another preferred embodiment of the pharmaceutical dosage form according to the invention, A is 7.6, 7.7, 7.8, 7.9, 8.0, 8.1, 8.2, 8.3, 8.4, 8.5, 8.6, 8.7, 8.8, 8.9 or 9.0; more preferably 9.1, 9.2, 9.3, 9.4, 9.5, 9.6, 9.7, 9.8, 9.9, 10.0, 10.1, 10.2, 10.3, 10.4 or 10.5; most preferably 10.6, 10.7, 10.8, 10.9, 11.0, 11.1, 11.2, 11.3, 11.4, 11.5, 11.6, 11.7, 11.8, 11.9 or 12.0; and in particular 12.1, 12.2, 12.3, 12.4, 12.5, 12.6, 12.7, 12.8, 12.9, 13.0, 13.1, 13.2, 13.3, 13.4 or 13.5.

In a preferred embodiment, the total surface S of the pharmaceutical dosage form according to the invention satisfies the following requirement $$B \cdot W^{2/3} \geq S \geq A \cdot W^{2/3}$$

where

A and W are defined as above and

B is at most 20, more preferably at most 19, still more preferably at most 18, yet more preferably at most 17, most preferably at most 16 and in particular at most 15.

In a preferred embodiment, the total surface S of the pharmaceutical dosage form according to the invention is at least 50 mm$^2$, at least 75 mm$^2$, at least 100 mm$^2$, at least 125 mm$^2$, at least 150 mm$^2$, at least 175 mm$^2$ or at least 200 mm$^2$; more preferably at least 225 mm$^2$, at least 250 mm$^2$, at least 275 mm$^2$, at least 300 mm$^2$, at least 325 mm$^2$, at least 350 mm$^2$, at least 375 mm$^2$ or at least 400 mm$^2$; still more preferably at least 425 mm$^2$, at least 450 mm$^2$, at least 475 mm$^2$, at least 500 mm$^2$, at least 525 mm$^2$; at least 550 mm$^2$, at least 575 mm$^2$ or at least 600 mm$^2$; yet more preferably at least 625 mm$^2$, at least 650 mm$^2$, at least 675 mm$^2$, at least 700 mm$^2$, at least 725 mm$^2$, at least 750 mm$^2$, at least 775 mm$^2$ or at least 800 mm$^2$; most preferably at least 825 mm$^2$, at least 850 mm$^2$, at least 875 mm$^2$, at least 900 mm$^2$, at least 925 mm$^2$, at least 950 mm$^2$, at least 975 mm$^2$ or at least 1000 mm$^2$; and in particular at least 1025 mm$^2$, at least 1050 mm$^2$, at least 1075 mm$^2$, at least 1100 mm$^2$, at least 1125 mm$^2$, at least 1150 mm$^2$, at least 1175 mm$^2$ or at least 1200 mm$^2$.

In a preferred embodiment, the total surface S of the pharmaceutical dosage form according to the invention is at most 1500 mm$^2$, more preferably at most 1400 mm$^2$, still more preferably at most 1300 mm$^2$, yet more preferably at most 1200 mm$^2$, most preferably at most 1100 mm$^2$, and in particular at most 1000 mm$^2$.

In a preferred embodiment the pharmaceutical dosage form according to the invention is manufactured, particularly shaped, by means of a so-called H-plunger. The silhouette of a dosage form obtainable by means of such a H-plunger is schematically illustrated in FIG. 10. H-plungers of suitable size and shape are commercially available. Typically, the volume and the surface of the dosage forms that are obtainable by a given H-plunger can be calculated with a formula usually provided by the manufacturer of the H-plunger.

For example, Notter GmbH, Germany offers a H-plunger forming a volume of 94.3+171.6 h [mm$^3$] and a surface of 382+52.3 h [mm$^2$], where h is the height of the dosage form (corresponding to distance b$_2$ in FIG. 10). Therefore, for example, when shaping 650 mg of a compacted composition having an overall density of 1.000 mg/mm$^3$ with such H-plunger, a dosage form is obtained having a height of h=(650−94.3)/171.6=3.24 mm. Thus, said dosage form has a surface of 382+52.3·3.24=551 mm$^2$. When A=4.5, the requirement of 551 mm$^2 \geq 4.5 \cdot 650^{2/3}$ (=337.6 mm$^2$) is satisfied. When A is about 7.3, the requirement of 551 mm$^2 \geq 7.3 \cdot 650^{2/3}$ (=547 mm$^2$) is still satisfied, but when A is 7.4, the requirement 551 mm$^2 \geq 7.4 \cdot 650^{2/3}$ (=555 mm$^2$) is not satisfied.

In a preferred embodiment, the pharmaceutical dosage form according to the invention has a total weight W of at least 50 mg, at least 75 mg, at least 100 mg, at least 125 mg or at least 150 mg; more preferably at least 175 mg, at least 200 mg, at least 225 mg, at least 250 mg or at least 275 mg; still more preferably at least 300 mg, at least 325 mg, at least 350 mg, at least 375 mg or at least 400 mg; yet more preferably at least 425 mg, at least 450 mg, at least 475 mg, at least 500 mg or at least 525 mg; most preferably at least 550 mg, at least 575 mg, at least 600 mg, at least 625 mg or at least 650 mg; and in particular at least 675 mg, at least 700 mg, at least 725 mg, at least 750 mg or at least 775 mg. Preferably, the total weight of the pharmaceutical dosage form according to the invention is within the range from 0.01 g to 1.5 g, more preferably 0.05 g to 1.2 g, still more preferably 0.1 g to 1.0 g, most preferably 0.2 g to 0.9 g and in particular 0.25 g to 0.8 g.

Once the breaking strength of the pharmaceutical dosage form has been measured in a particular direction of extension, its tensile strength in said direction of extension may be calculated taking into account the outer shape of the dosage form. For example, the tensile strength of conventional tablets can be calculated according to the following equation: TS=2×P/π×D×t, where TS is the tensile strength (N·cm$^{-2}$, MPa), P is the breaking strength of the tablet (N), D is the tablet diameter (cm), and t is the tablet thickness (cm). The skilled person knows how to modify the above formula when modifying the outer shape of the dosage form. In this regard it can be referred to, e.g., J. T. Fell et al., J Pharm Sci. 1970, 59, 688-691; M. P. Summers et al., J Pharm Sci., 1977, 66, 1172-1175; and P. N. Davies et al., Eur J Pharm Biopharm. 2007, 67(1), 268-76.

Preferably, the pharmaceutical dosage form according to the invention has a tensile strength of at least 2.5 N/cm$^2$, at least 3.0 N/cm², at least 3.5 N/cm², at least 4.0 N/cm², at least 4.5 N/cm², at least 5.0 N/cm², at least 6.0 N/cm², at least 7.5 N/cm², at least 10.0 N/cm², at least 12.5 N/cm² or at least 15.0 N/cm²; more preferably at least 17.5 N/cm², at least 20.0 N/cm², at least 22.5 N/cm² or at least 25.0 N/cm²; still more preferably at least 27.5 N/cm², at least 30.0 N/cm², at least 32.5 N/cm² or at least 35.0 N/cm²; yet more preferably at least 37.5 N/cm², at least 40.0 N/cm², at least 42.5 N/cm² or at least 45.0 N/cm²; most preferably at least 47.5 N/cm², at least 50.0 N/cm², at least 52.5 N/cm² or at least 55.0 N/cm²; and in particular at least 57.5 N/cm², at least 60.0 N/cm², at least 62.5 N/cm² or at least 65.0 N/cm²; preferably at least in direction of extension $E_1$.

The pharmaceutical dosage forms according to the invention preferably exhibit high impact strength.

For example, the falling impact strength of the pharmaceutical dosage forms is preferably about 0%. The falling impact strength is a breakage ratio obtained when a tablet is allowed to fall from the height of 50 cm onto a stainless steel plate and defined by: {(broken tablets)/(tested tablets)} 100(%).

Preferably, the impact strength of the pharmaceutical dosage form according to the invention is sufficiently high so that it cannot be comminuted by means of a hammer. Preferably, when applying five manual hammer strokes by means of a hammer having a weight of 500 g, the pharmaceutical dosage form cannot be comminuted. In a preferred embodiment, the pharmaceutical dosage form does not only exhibit this impact strength at ambient temperature, but also below +4° C. (refrigerator), more preferably below −33° C. (deep freezer), most preferably below −77° C. (dry ice) and in particular below −190° C. (liquid nitrogen).

Preferably, the pharmaceutical dosage form according to the invention exhibits a cutting resistance of at least 75 N, more preferably at least 100 N, still more preferably at least 125 N, yet more preferably at least 140 N, most preferably at least 150 N and in particular at least 160 N, in at least one direction of extension, preferably in direction of extension $E_1$. Preferably, the cutting test is performed according to DIN EN ISO 604, preferably at a testing speed of 30 mm/min and by means of a universal glass cleaning blade having a thickness of 0.30 mm.

The friability of the pharmaceutical dosage form according to the invention can be measured, e.g., by means of a Pharmatest PTF-E apparatus (Hainburg, Germany) following, e.g., the European Pharmacopeia (Ph. Eur.) specifications. Preferably, the friability of the pharmaceutical dosage form according to the invention is at most 0.50%, more preferably at most 0.40%, still more preferably at most 0.30%, yet more preferably at most 0.20%, most preferably at most 0.10% and in particular at most 0.05%.

In a preferred embodiment the pharmaceutical dosage form according to the invention has an overall density of at least 0.80 or at least 0.85 g/cm³, more preferably at least 0.90 or at least 0.95 g/cm³, still more preferably at least 1.00, at least 1.05 or at least 1.10 g/cm³, most preferably in the range from 0.80 to 1.35 g/cm³, and in particular in the range from 0.95 to 1.25 g/cm³.

In a preferred embodiment, the pharmaceutical dosage form according to the invention has an overall density within the range of 1.00±0.30 g/cm³, more preferably 1.00±0.25 g/cm³, still more preferably 1.00±0.20 g/cm³, yet more preferably 1.00±0.15 g/cm³, most preferably 1.00±0.10 g/cm³, and in particular 1.00±0.05 g/cm³. In another preferred embodiment, the pharmaceutical dosage form according to the invention has an overall density within the range of 1.10±0.30 g/cm³, more preferably 1.10±0.25 g/cm³, still more preferably 1.10±0.20 g/cm³, yet more preferably 1.10±0.15 g/cm³, most preferably 1.10±0.10 g/cm³, and in particular 1.10±0.05 g/cm³. In still another preferred embodiment, the pharmaceutical dosage form according to the invention has an overall density within the range of 1.20±0.30 g/cm³, more preferably 1.20±0.25 g/cm³, still more preferably 1.20±0.20 g/cm³, yet more preferably 1.20±0.15 g/cm³, most preferably 1.20±0.10 g/cm³, and in particular 1.20±0.05 g/cm³. Preferably, the overall density of the pharmaceutical dosage form according to the invention is 1.00±0.02 g/cm³, 1.02±0.02 g/cm³, 1.04±0.02 g/cm³, 1.06±0.02 g/cm³, 1.08±0.02 g/cm³, 1.10±0.02 g/cm³, 1.12±0.02 g/cm³, 1.14±0.02 g/cm³, 1.16±0.02 g/cm³, 1.18±0.02 g/cm³, 1.20±0.02 g/cm³, 1.22±0.02 g/cm³, 1.24±0.02 g/cm³, 1.26±0.02 g/cm³, 1.28±0.02 g/cm³, 1.30±0.02 g/cm³, 1.32±0.02 g/cm³, 1.34±0.02 g/cm³, 1.36±0.02 g/cm³, 1.38±0.02 g/cm³, or 1.40±0.02 g/cm³.

Preferably, the pharmaceutical dosage form according to the invention is characterized by a comparatively homogeneous distribution of density. Preferably, the densities of two segments of the pharmaceutical dosage form having a volume of 1.0 mm³ each, deviate from one another by not more than ±10%, more preferably not more than more than ±7.5%, still more preferably not more than ±5.0%, most preferably not more than ±2.5%, and in particular not more than ±1.0%. When the pharmaceutical dosage form is film coated, said two segments of the pharmaceutical dosage form having a volume of 1.0 mm³ each are preferably segments of the core, i.e. do not contain any coating material.

In a preferred embodiment, the pharmaceutical dosage form according to the invention is thermoformed, preferably by extrusion, although also other methods of thermoforming may be used in order to manufacture the dosage form according to the invention such as press-molding at elevated temperature.

The pharmaceutical dosage form according to the invention contains a pharmacologically active compound (A), for the purpose of the specification also referred to as "component (A)".

Preferred pharmacologically active compounds (A) have already been mentioned as pharmaceutically active ingredients and pharmaceutically active ingredients with potential for abuse in connection with the first and second aspects of the invention.

In a preferred embodiment, under ambient conditions, the solubility of component (A) in pure water is at least 1.0 g/L, more preferably at least 5.0 g/L, still more preferably at least 10 g/L, yet more preferably at least 25 g/L, most preferably at least 50 g/L and in particular at least 100 g/L.

In another preferred embodiment, under ambient conditions, the solubility of component (A) in pure water is at most 1.0 g/L, more preferably at most 0.5 g/L, still more preferably at most 0.1 g/L, yet more preferably at most 0.05 g/L, most preferably at most 0.01 g/L and in particular at most 0.005 g/L.

In a preferred embodiment, the pharmaceutical dosage form according to the invention contains a pharmaceutically effective amount of a pharmacologically active compound (A), which justifies use of the pharmaceutical dosage form as a pharmaceutical preparation and is the cause of the activity thereof. Pharmacologically active compounds (A) which may in principle be considered in the pharmaceutical dosage form according to the invention are any known pharmaceutical substances, wherein these substances may be present in the pharmaceutical dosage form according to the invention as such, in the form the derivatives thereof, in particular esters or ethers, or in each case in the form of corresponding physiologically acceptable compounds, in particular in the form of the corresponding salts or solvates thereof, as racemates or in a form enriched in one or more stereoisomers (enantiomers or diastereomers).

The pharmaceutical dosage form according to the invention is suitable for the administration of a number of pharmacologically active compounds (A) in a single pharmaceutical dosage form. Preferably, the pharmaceutical dosage form contains only one particular pharmacologically active compound (A).

The amount of the pharmacologically active compound (A), based on the total amount of the pharmaceutical dosage form, is preferably within the range from 0.01 to 95 wt.-%, more preferably from 0.5 to 80 wt.-%, still more preferably 1.0 to 70 wt.-%, most preferably 5.0 to 60 wt.-% and in particular 10 to 50 wt.-%. In a preferred embodiment it is more than 20 wt.-%.

In a preferred embodiment the pharmaceutical dosage form according to the invention contains a psychotropically acting substance as the pharmacologically active compound (A).

The person skilled in the art knows which substances have a psychotropic action. Substances which influence psychological processes commonly have a psychotropic action, i.e. they act specifically on psychological functions. Substances with a psychotropic action may thus influence mood, either raising or lowering it. For the purpose of the description, substances with a psychotropic action include in particular opioids, stimulants, tranquillisers (e.g. barbiturates and benzodiazepines) and other narcotics. Substances with a psychotropic action preferably comprise substances which, in particular when improperly administered (in particular with the intention of abuse), cause an accelerated increase in active compound levels relative to proper oral administration, giving the abuser the desired effect, namely the "kick" or "rush". This kick is also obtained if the powdered pharmaceutical dosage form is administered nasally, i.e. is sniffed. Substances with a psychotropic action are preferably substances which (in the appropriate dose and pharmaceutical dosage form and when administered appropriately) influence human mental activity and/or sensory perception in such a way that they are fundamentally suited to abuse.

In particular, the pharmaceutical dosage form according to the invention preferably contains a psychotropically acting substance selected from the group consisting of opioids [A07DA, N01AH, N02A, R05DA, R05FA,]; barbiturates [N01AF, N01AG, N03AA]; benzodiazepine derivatives [N03AE]; agents for treating opiate dependency [N07BC]; anxiolytics [N05B]; hypnotics and sedatives [N05C]; psychostimulants, agents for treating attention-deficit/hyperactivity disorder (ADHD) and nootropics [N06B]; antiemetics [A04A]; antiobesity preparations excluding diet products [A08A]; centrally acting muscle relaxants [M03B]; and antidotes [V03AB]. The abbreviations stated in square brackets here correspond to the ATC Index ("Gelbe Liste"), as used by the WHO for classifying pharmaceutical substances (preferred version: 2007 or 2008).

The pharmaceutical dosage form according to the invention preferably contains a psychotropically acting substance selected from the group consisting of opioids, vanilloid receptor modulators, serotonin/norepinephrine/dopamine modulators, GABA modulators, NMDA antagonists, ion channel blockers/modulators, cannabionoids, and other NSAIDS.

The following opiates, opioids, tranquillisers or other narcotics are substances with a psychotropic action, i.e. have a potential of abuse, and hence are preferably contained in the pharmaceutical dosage form according to the invention: alfentanil, allobarbital, allylprodine, alphaprodine, alprazolam, amfepramone, amphetamine, amphetaminil, amobarbital, anileridine, apocodeine, axomadol, barbital, bemidone, benzylmorphine, bezitramide, bromazepam, brotizolam, buprenorphine, butobarbital, butorphanol, camazepam, carfentanil, cathine/D-norpseudoephedrine, chlordiazepoxide, clobazam clofedanol, clonazepam, clonitazene, clorazepate, clotiazepam, cloxazolam, cocaine, codeine, cyclobarbital, cyclorphan, cyprenorphine, delorazepam, desomorphine, dextromoramide, dextropropoxyphene, dezocine, diampromide, diamorphone, diazepam, dihydrocodeine, dihydromorphine, dihydromorphone, dimenoxadol, dimephetamol, dimethylthiambutene, dioxaphetylbutyrate, dipipanone, dronabinol, eptazocine, estazolam, ethoheptazine, ethylmethylthiambutene, ethyl loflazepate, ethylmorphine, etonitazene, etorphine, fencamfamine, fenethylline, fenpipramide, fenproporex, fentanyl, fludiazepam, flunitrazepam, flurazepam, halazepam, haloxazolam, heroin, hydrocodone, hydromorphone, hydroxypethidine, isomethadone, hydroxymethylmorphinan, ketazolam, ketobemidone, levacetylmethadol (LAAM), levomethadone, levorphanol, levophenacylmorphane, levoxemacin, lisdexamfetamine dimesylate, lofentanil, loprazolam, lorazepam, lormetazepam, mazindol, medazepam, mefenorex, meperidine, meprobamate, metapon, meptazinol, metazocine, methylmorphine, metamphetamine, methadone, methaqualone, 3-methylfentanyl, 4-methylfentanyl, methylphenidate, methylphenobarbital, methyprylon, metopon, midazolam, modafinil, morphine, myrophine, nabilone, nalbuphene, nalorphine, narceine, nicomorphine, nimetazepam, nitrazepam, nordazepam, norlevorphanol, normethadone, normorphine, norpipanone, opium, oxazepam, oxazolam, oxycodone, oxymorphone, *Papaver somniferum*, papaveretum, pernoline, pentazocine, pentobarbital, pethidine, phenadoxone, phenomorphane, phenazocine, phenoperidine, piminodine, pholcodeine, phenmetrazine, phenobarbital, phentermine, pinazepam, pipradrol, piritramide, prazepam, profadol, proheptazine, promedol, properidine, propoxyphene, remifentanil, secbutabarbital, secobarbital, sufentanil, tapentadol, temazepam, tetrazepam, tilidine (cis and trans), tramadol, triazolam, vinylbital, N-(1-methyl-2-piperidinoethyl)-N-(2-pyridyl)propionamide, (1R,2R)-3-(3-dimethylamino-1-ethyl-2-methyl-propyl)phenol, (1R,2R,4S)-2-(dimethylamino)methyl-4-(p-fluorobenzyloxy)-1-(m-methoxyphenyl)cyclohexanol, (1R,2R)-3-(2-dimethylaminomethyl-cyclohexyl)phenol, (1S,2S)-3-(3-dimethylamino-1-ethyl-2-methyl-propyl)phenol, (2R,3R)-1-dimethylamino-3(3-methoxyphenyl)-2-methyl-pentan-3-ol, (1RS,3RS,6RS)-6-dimethylaminomethyl-1-(3-methoxyphenyl)-cyclohexane-1,3-diol, preferably as racemate, 3-(2-dimethylaminomethyl-1-hydroxy-cyclohexyl)phenyl 2-(4-isobutyl-phenyl)propionate, 3-(2-dimethylaminomethyl-1-hydroxy-cyclohexyl)phenyl 2-(6-methoxy-naphthalen-2-yl)propionate, 3-(2-dimethylaminomethyl-cyclohex-1-enyl)-phenyl 2-(4-isobutyl-phenyl)propionate, 3-(2-dimethylaminomethyl-cyclohex-1-enyl)-phenyl 2-(6-methoxy-naphthalen-2-yl)propionate, (RR-SS)-2-acetoxy-4-trifluoromethyl-benzoic acid 3-(2-dimethylaminomethyl-1-hydroxy-cyclohexyl)-phenyl ester, (RR-SS)-2-hydroxy-4-trifluoromethyl-benzoic acid 3-(2-dimethylaminomethyl-1-hydroxy-cyclohexyl)-phenyl ester, (RR-SS)-4-chloro-2-hydroxy-benzoic acid 3-(2-dimethylaminomethyl-1-hydroxy-cyclohexyl)-phenyl ester, (RR-SS)-2-hydroxy-4-methyl-benzoic acid 3-(2-dimethylaminomethyl-1-hydroxy-cyclohexyl)-phenyl ester, (RR-SS)-2-hydroxy-4-methoxy-benzoic acid 3-(2-dimethylaminomethyl-1-hydroxy-cyclohexyl)-phenyl ester, (RR-SS)-2-hydroxy-5-nitrobenzoic acid 3-(2-dimethyl-aminomethyl-1-hydroxy-cyclohexyl)-phenyl ester, (RR-SS)-2',4'-difluoro-3-hydroxy-biphenyl-4-carboxylic acid 3-(2-dimethylaminomethyl-1-hydroxy-cyclohexyl)-phenyl ester, and corresponding stereoisomeric compounds, in each case the corresponding derivatives thereof, physiologically acceptable enantiomers, stereoisomers, diastereomers and racemates and the physiologically acceptable derivatives thereof, e.g. ethers, esters or amides, and in each case the physiologically acceptable compounds thereof, in particular the salts thereof and solvates, e.g. hydrochlorides.

In a preferred embodiment the pharmaceutical dosage form according to the invention contains an opioid selected from the group consisting of DPI-125, M6G (CE-04-410), ADL-5859, CR-665, NRP290 and sebacoyl dinalbuphine ester.

In a preferred embodiment the pharmaceutical dosage form according to the invention contains one pharmacologically active compound (A) or more pharmacologically active compounds (A) selected from the group consisting of oxymorphone, hydromorphone and morphine.

In another preferred embodiment, the pharmacologically active compound (A) is selected from the group consisting of tapentadol, faxeladol and axomadol.

For the purposes of the description, the pharmacokinetic parameters, which may be determined from the blood plasma concentrations of the pharmacologically active compound (A), are defined as follows:

| | |
|---|---|
| $C_{max}$ | maximum measured plasma concentration of the active ingredient after single administration (=average peak plasma level) |
| $t_{max}$ | interval of time from administration of the active ingredient until $C_{max}$ is reached |
| $t_{1/2}$ | half-life |
| $AUC_{0-\infty}$ | total area under the curve |

The above parameters are in each case stated as mean values of the individual values for all investigated patients/test subjects.

A person skilled in the art knows how the pharmacokinetic parameters of the active ingredient may be calculated from the measured concentrations of the active ingredient in the blood plasma. In this connection, reference may be made, for example, to Willi Cawello (ed.) *Parameters for Compartment-free Pharmacokinetics*, Shaker Verlag Aachen (1999).

In a preferred embodiment, after preferably oral administration of the dosage form according to the invention, in vivo the average peak plasma level ($C_{max}$) is on average reached after $t_{max}$ 4.0±2.5 h, more preferably after $t_{max}$ 4.0±2.0 h, still more preferably after $t_{max}$ 4.0±1.5 h, most preferably after $t_{max}$ 4.0±1.0 h and in particular after $t_{max}$ 4.0±0.5 h. In another preferred embodiment, after preferably oral administration of the dosage form according to the invention, in vivo the average peak plasma level ($C_{max}$) is on average reached after $t_{max}$ 5.0±2.5 h, more preferably after $t_{max}$ 5.0±2.0 h, still more preferably after $t_{max}$ 5.0±1.5 h, most preferably after $t_{max}$ 5.0±1.0 h and in particular after $t_{max}$ 5.0±0.5 h. In still another preferred embodiment, after preferably oral administration of the dosage form according to the invention, in vivo the average peak plasma level ($C_{max}$) is on average reached after $t_{max}$ 6.0±2.5 h, more preferably after $t_{max}$ 6.0±2.0 h, still more preferably after $t_{max}$ 6.0±1.5 h, most preferably after $t_{max}$ 6.0±1.0 h and in particular after $t_{max}$ 6.0±0.5 h.

In a preferred embodiment, the average value for $t_{1/2}$ after preferably oral administration of the dosage form according to the invention in vivo is 4.3±2.5 h, more preferably 4.3±2.0 h, still more preferably 4.3±1.5 h, most preferably 4.3±1.0 h, and in particular 4.3±0.5 h. In another preferred embodiment, the average value for $t_{1/2}$ after preferably oral administration of the dosage form according to the invention in vivo is preferably 5.3±2.5 h, more preferably 5.3±2.0 h, still more preferably 5.3±1.5 h, most preferably 5.3±1.0 h, and in particular 5.3±0.5 h. In still another preferred embodiment, the average value for $t_{1/2}$ after preferably oral administration of the dosage form according to the invention in vivo is preferably 6.3±2.5 h, more preferably 6.3±2.0 h, still more preferably 6.3±1.5 h, most preferably 6.3±1.0 h, and in particular 6.3±0.5 h.

In a preferred embodiment, the pharmacologically active compound (A) is tapentadol or a physiologically acceptable salt thereof, and after preferably oral administration of the dosage form according to the invention, in vivo the average value for the total area under the curve $AUC_{0-\infty}$ is 825±600 ng·h/mL, more preferably 825±500 ng·h/mL, still more preferably 825±400 ng·h/mL, yet more preferably 825±300 ng·h/mL, most preferably 825±200 ng·h/mL, and in particular 825±100 ng·h/mL. In another preferred embodiment, the pharmacologically active compound (A) is tapentadol or a physiologically acceptable salt thereof, and after preferably oral administration of the dosage form according to the invention, in vivo the average value for the total area under the curve $AUC_{0-\infty}$ is 1100±600 ng·h/mL, more preferably 1100±500 ng·h/mL, still more preferably 1100±400 ng·h/mL, yet more preferably 1100±300 ng·h/mL, most preferably 1100±200 ng·h/mL, and in particular 1100±100 ng·h/mL.

In a preferred embodiment, the pharmacologically active compound (A) is tapentadol or a physiologically acceptable salt thereof, and after preferably oral administration of the dosage form according to the invention, in vivo the average value of $C_{max}$ is 63±40 ng/mL, more preferably 63±30 ng/mL, still more preferably 63±20 ng/mL, yet more preferably 63±15 ng/mL, most preferably 63±10 ng/mL and in particular 63±5 ng/mL. In another preferred embodiment, the pharmacologically active compound (A) is tapentadol or a physiologically acceptable salt thereof, and after preferably oral administration of the dosage form according to the invention, in vivo the average value of $C_{max}$ is 89±40 ng/mL, more preferably 89±30 ng/mL, still more preferably 89±20 ng/mL, yet more preferably 89±15 ng/mL, most preferably 89±10 ng/mL and in particular 89±5 ng/mL.

In a particularly preferred embodiment the pharmacologically active compound (A) is tapentadol or a physiologically acceptable salt thereof and the pharmaceutical dosage form according to the invention is bioequivalent to a formulation that contains tapentadol or a physiologically acceptable salt thereof in a dosage of 200 mg and 250 mg, respectively, and is characterized by the following pharmacokinetic data:

| Parameter | dosage 200 mg | dosage 250 mg |
|---|---|---|
| $AUC_{0-\infty}$ | 825 ng · h/mL | 1096 ng · h/mL |
| $C_{max}$ | 62.5 ng/mL | 89.3 ng/mL |
| $t_{max}$ | 5.00 h | 5.00 h |
| $t_{1/2}$ | 5.2 h | 5.4 h |

The skilled person is aware what requirement have to be satisfied in order to achieve bioequivalence. In this regard it can be referred e.g. to "*Note for Guidance on the Investigation of Bioavailability and Bioequivalence*", EMEA, London, 26 Jul. 2001 (CPMP/EWP/QWP/1401/98); "*Guidance for Industry—Bioavailability and Bioequivalence—Studies* for Orally Administered Drug Products—General Considerations", FDA, BP, Announced in the Federal Register: Volume 68, Number 53/Mar. 19, 2003; and "Guidance for Industry—Statistical Approaches to Establishing Bioequivalence", FDA, BP, January 2001.

In general, two medicinal products are bioequivalent if they are pharmaceutically equivalent or pharmaceutical alternatives and if their bioavailabilities after administration in the same molar dose are similar to such degree that their effects, with respect to both efficacy and safety, will be essentially the same. Preferably, statistical data should be analyzed using ANOVA based on a 90% confidence interval. For example, as regards AUC-ratio, the 90% confidence interval for this measure of relative bioavailability should lie within an acceptance interval of 0.80-1.25, and as regards Cmax-ratio, the 90% confidence interval for this measure of relative bioavailability should lie within an acceptance interval of 0.80-1.25.

In a preferred embodiment the pharmaceutical dosage form according to the invention contains one pharmacologically active compound (A) or more pharmacologically active compounds (A) selected from the group consisting of 11-(3-dimethylamino-3-phenyl-pentamethylen)-6-fluor-1,3,4,9-tetrahydropyrano[3,4-b]indole, in particular its hemicitrate; 1,1-[3-dimethylamino-3-(2-thienyl)pentamethylen]-1,3,4,9-tetrahydropyrano[3,4-b]indole, in particular its citrate; and 1,1-[3-dimethylamino-3-(2-thienyl)pentamethylen]-1,3,4,9-tetrahydropyrano[3,4-b]-6-fluoro-indole, in particular its hemicitrate. These compounds are known, for example, from WO 2004/043967 or WO 2005/066183. The corresponding descriptions are hereby introduced as a reference and are deemed to be part of the disclosure.

In a preferred embodiment, the pharmaceutical dosage form according to the invention contains no substances which irritate the nasal passages and/or pharynx, i.e. substances which, when administered via the nasal passages and/or pharynx, bring about a physical reaction which is either so unpleasant for the patient that he/she does not wish to or cannot continue administration, for example burning, or physiologically counteracts taking of the corresponding active compound, for example due to increased nasal secretion or sneezing. Further examples of substances which irritate the nasal passages and/or pharynx are those which cause burning, itching, an urge to sneeze, increased formation of secretions or a combination of at least two of these stimuli. Corresponding substances and the quantities thereof which are conventionally to be used are known to the person skilled in the art. Some of the substances which irritate the nasal passages and/or pharynx are accordingly based on one or more constituents or one or more plant parts of a hot substance drug. Corresponding hot substance drugs are known per se to the person skilled in the art and are described, for example, in "Pharmazeutische Biologie—Drogen und ihre Inhaltsstoffe" by Prof. Dr. Hildebert Wagner, 2nd., revised edition, Gustav Fischer Verlag, Stuttgart-New York, 1982, pages 82 et seq. The corresponding description is hereby introduced as a reference and is deemed to be part of the disclosure.

The pharmaceutical dosage form according to the invention furthermore preferably contains no antagonists for the pharmacologically active compound (A), preferably no antagonists against psychotropic substances, in particular no antagonists against opioids. Antagonists suitable for a given pharmacologically active compound (A) are known to the person skilled in the art and may be present as such or in the form of corresponding derivatives, in particular esters or ethers, or in each case in the form of corresponding physiologically acceptable compounds, in particular in the form of the salts or solvates thereof. The pharmaceutical dosage form according to the invention preferably contains no antagonists selected from among the group comprising naloxone, naltrexone, nalmefene, nalide, nalmexone, nalorphine or naluphine, in each case optionally in the form of a corresponding physiologically acceptable compound, in particular in the form of a base, a salt or solvate; and no neuroleptics, for example a compound selected from among the group comprising haloperidol, promethacine, fluphenazine, perphenazine, levomepromazine, thioridazine, perazine, chlorpromazine, chlorprothixine, zuclopenthixol, flupentixol, prothipendyl, zotepine, benperidol, pipamperone, melperone and bromperidol.

The pharmaceutical dosage form according to the invention furthermore preferably contains no emetic. Emetics are known to the person skilled in the art and may be present as such or in the form of corresponding derivatives, in particular esters or ethers, or in each case in the form of corresponding physiologically acceptable compounds, in particular in the form of the salts or solvates thereof. The pharmaceutical dosage form according to the invention preferably contains no emetic based on one or more constituents of ipecacuanha (ipecac) root, for example based on the constituent emetine, as are, for example, described in "Pharmazeutische Biologie—Drogen und ihre Inhaltsstoffe" by Prof. Dr. Hildebert Wagner, 2nd, revised edition, Gustav Fischer Verlag, Stuttgart, N.Y., 1982. The corresponding literature description is hereby introduced as a reference and is deemed to be part of the disclosure. The pharmaceutical dosage form according to the invention preferably also contains no apomorphine as an emetic.

Finally, the pharmaceutical dosage form according to the invention preferably also contains no bitter substance. Bitter substances and the quantities effective for use may be found in US-2003/0064099 A1, the corresponding disclosure of which should be deemed to be the disclosure of the present application and is hereby introduced as a reference. Examples of bitter substances are aromatic oils, such as peppermint oil, eucalyptus oil, bitter almond oil, menthol, fruit aroma substances, aroma substances from lemons, oranges, limes, grapefruit or mixtures thereof, and/or denatonium benzoate.

The pharmaceutical dosage form according to the invention accordingly preferably contains neither substances which irritate the nasal passages and/or pharynx, nor antagonists for the pharmacologically active compound (A), nor emetics, nor bitter substances.

In a preferred embodiment the pharmaceutical dosage form according to the invention contains a non-psychotropically acting substance as the pharmacologically active compound (A).

Particularly preferably the pharmaceutical dosage form according to the invention contains a pharmacologically active compound (A) or two or more such compounds selected from the group consisting of agents for the treatment and prevention of diseases of the alimentary system and metabolism [A]; in particular stomatological preparations [A01], agents for the treatment and prevention of acid-related disorders [A02], agents for the treatment and prevention of functional gastrointestinal tract disorders [A03], serotonin $5HT_3$ antagonists [A04 a)A], antihistamine preparations [A04a)B], agents for bile and liver therapy [A05], laxatives [A06], intestinal antiinfectives [A07A], intestinal adsorbents [A07B], electrolytes with carbohydrates [A07C], intestinal antiinflammatory agents [A07E], microbial antidiarrhoeals [A07F], digestives including enzymes [A09], drugs used in diabetes [A10], vitamins

[A1], minerals [A12], anabolic agents for systemic applications [A14] and appetite stimulants [A15];

agents for the treatment and prevention of diseases of the blood and the blood forming organs [B]; in particular antithrombotic agents [B01], antihaemorrhagics [B02], antianaemic preparations [B03] and other haematological agents [B06];

agents for the treatment and prevention of diseases of the cardiovascular system [α]; in particular agents for cardiac therapy [C01], antihypertensives [C02], diuretics [C03], peripheral vasodilators [C04], vasoprotectives [C05], antihypotensives [C06A], β-adrenoceptor antagonists [C07], calcium channel blockers [C08], agents acting on the renin-angiotensin system [C09] and lipid reducing agents [C10];

dermatologicals [D]; in particular antifungals for systemic use [D01B], antipsoriatics for systemic use [D05B], antiacne preparations for systemic use [D10B];

agents for the treatment and prevention of diseases of the genitourinary system and sex hormones [G]; in particular gynecological antiinfectives and antiseptics [G01], oxytocics [G02A], sympathomimetic labour repressants [G02CA], prolactin inhibitors [G02CB], hormonal contraceptives for systemic use [G03] and urologicals [G04];

systemic hormone preparations excluding sex hormones and insulins [H]; in particular pituitary and hypothalamic hormones and analogue [H01], corticosteroids for systemic use [H02], thyroid preparations [H03], pancreatic hormones [H04], and agents for regulating calcium homeostatis [H05];

antiinfectives for systemic use [J]; in particular antibiotics for systemic use [J01], antimycotics for systemic use [J02], antimycobacterials [J04], antivirals for systemic use [J05], immune sera and immunoglobulins [J06], and vaccines [J07]);

antineoplastic and immunomodulating agents [L] (in particular antineoplastistic agents [L01], agents for endocrine therapy [L02], immunostimulants [L03] and immunosuppressive agents [L04];

agents for the treatment and prevention of diseases of the musculo-skeletal system [M]; in particular antiinflammatory and antirheumatic agents [M01], peripherally acting muscle relaxants [M03A], directly acting muscle relaxants [M03C], antigout preparations [M04] and agents for the treatment of bone diseases [M05];

agents for the treatment and prevention of diseases of the nervous system [N]; in particular salicylic acid the derivatives thereof [N02 b)A], pyrazolones [N02 b)B], anilides [N02 b)E], ergot alkaloids [N02CA], corticosteroid derivatives [N02CB], selective serotonin-5HT, agonists [N02CC], hydantoin derivatives [N03 a)B], oxazolidine derivatives [N03 a)C], succinimide derivatives [N03 a)D], carboxamide derivatives [N03 a)F], fatty acid derivatives [N03 a)G], antiparkinson drugs [N04]), antipsychotics [N05A], antidepressants [N06A], antidementia drugs [N06D], parasympathomimetics [N07A] and antivertigo preparations [N07C];

antiparasitic products, insecticides and repellents [P]; in particular antiprotozoals [P01], anthelmintics [P02] and ectoparasiticides, including scabicides, insecticides and repellents [P03];

agents for the treatment and prevention of diseases of the respiratory system [R]; in particular nasal preparations [R01], throat preparations [R02], drugs for obstructive airways diseases [R03], expectorants, excluding combinations with cough suppressants [R05C] and antihistamines for systemic use [R06];

agents for the treatment and prevention of diseases of the sensory organs [S]; in particular otologicals [S02]; and general diet products [V06] and therapeutic radiopharmaceuticals [V10], wherein the abbreviations stated in square brackets here correspond to the ATC Index, as used by the WHO for classifying pharmaceutical substances (preferred version: 2007 or 2008).

The pharmaceutical dosage form according to the invention preferably contains one, two or more pharmacologically active compounds (A) selected from the group consisting of 4-aminomethylbenzoic acid, abacavir, abamectin, abciximab, abibendan, abrin, acamprosat, acarbose, acebutolol, aceclidine, aceclofenac, acediasulfone, acemetacin, acenocoumarol, acetazolamide, acetoacetic acid, acetyldigoxin, acetylandromedol, acetylcysteine, β-acetyldigoxin, acetylhistamine, acetylsalicylic acid, acetylthiocholine, aciclovir, acipimox, acitretin, aclarubicin, aconitine, acriflavinium chloride, acrivastine, actinoquinol, acylaminopenicillin, adalimumab, adapalene, adefovir, adefovir dipivoxil, adenosine, adenosine phosphate, adenosine triphosphate, adipiodone, adrenalin, aescin, agalsidase alfa, agalsidase beta, agaricic acid, ajmaline, alanine, albendazole, alcuronium, aldesleukin, aldosterone, alemtuzumab, alendronic acid, alfacalcidol, alfuzosin, algeldrate F, alitretinoin, alizapride, allantoin F, allopurinol, allyl isorhodanate, almasilate F, almotriptan, α-acetyldigoxin, alprenolol, alprostadil, alteplase, aluminium glycinate F, aluminium hydroxide F, aluminium phosphate F, aluminium triformate, amantadine, ambazone, ambroxol, ambutonium bromide, formic acid, amicacin, amidephrine, amidotrizoic acid, amifostine, amikacin, amiloride, aminoacetic acid, aminoglutethimide, aminophylline, aminoquinuride, amiodarone, amisulpride, amitriptyline, amitryptiline, amlodipine, amorolfine, amoxicillin, amphotericin B, ampicillin, amprenavir, amylmetacresol, amyl nitrite, anagrelide, anakinra, anastrozole, ancrod, anistreplase, antazoline, antithrombin III, apomorphine, apraclonidine, aprepitant, aprindine, aprotinin, arcitumomab, arginine, aripiprazole, arsenic trioxide, artemether, articaine, ascorbic acid, asparagine, L-asparaginase, aspartic acid, atazanavir, atenolol, atomoxetine, atorvastatin, atosiban, atovaquone, atracurium, atracurium besylate, atropine, auranofin, azapropazone, azathioprine, azelaic acid, azelastine, azidothymidine, azithromycin, aziocillin, aztreonam, N2 alanyl levoglutamide, p-aminosalicylic acid, bacampicillin, bacitracin, baclofen, balsalazide, bambuterol, bamethan, bamipine, barbexaclone, barium sulfate F, barnidipine, basiliximab, batroxobin, becaplermin, beclomethasone, bendamustine, befunolol, bemiparin, benactyzine, benazepril, bencyclane, bendazac, bendroflumethiazide, benproperine, benserazide, benzaseride, benzathine, benzatropine, benzbromarone, benzocaine, benzoyl peroxide, benzyclane, benzydamine, benzylpenicillin, benzylphenyl glycolate, betacarotene, betahistidine, betahistine, betamethasone, bethanechol, betaxolol, bethanechol chloride, betiatide, bevacizumab, bexarotene, bezafibrate, bibenzonium bromide, bicalutamide, bicisate, bifonazole, bimatoprost, biperiden, bisoprolol, bivalirudin, bleomycin, blood clotting factor VII, VIII, IX, X, XIII, bornapine, bornaprine, bortezomib, bosentan, botulinum toxin type B, brimonidine, brinzolamide, brivudin, bromhexine, bromocriptine, bromperidol, brompheniramine, brotizolam, budesonide, budipine, bufexamac, buflomedil, bumetanide, bunazosin, buphenine, bupivacaine, bupranolol, bupropion, buserelin, buspirone, busulfan, butalamine, butanilicaine, butenafine, butethamate, butinoline, butizide, butylscopolaminium, 5-chlorcarvacrol, C1 esterase inhibitor, cabergoline, cadexomer iodine, cafedrine, calcipotriol, calcitonin, calcitriol, camylofine, candesartan cilexetil, canrenoic acid, capecitabine, capreomycin, capsaicin, captopril, carazolol, carbaldrate F, carbamazepine, carbasalate calcium, carbenoxolone, carbidopa, carbimazole, carbinoxamine, carboplatin, carglumic acid, carmustine, caroverine, carteolol, carvedilol, caspofungin, cefaclor, cefadroxil, cefalexin, cefaloridine, cefamandole, cefazolin, cefdinir, cefepime, cefetamet-pivotil, cefixime, cefodizime, cefoperazone, cefotaxime, cefotiam, cefoxitin, cefpirome, cefpodoxime, cefpodoxime-proxetil, cefprozil, ceftazidime, ceftibuten, ceftizoxime, ceftriaxone, cefuroxime, celecoxib, celiprolol, certoparin, cetirizine, cetrimide, cetrimonium bromide, cetrorelix, cetuximab, cetylpyridinium, chenodeoxycholic acid, quinidine, quinine, quinine iron citrate F, quinine tannate F, chlorambucil, chloramphenicol, chlorobutynol, chlorhexidine, chlormidazole, chlorobutanol, chloroquine, chloroxylenol, chlorphenamine, chlorphenesin, chlorphenoxamine, chlorpromazine, chlorprotheaxine, chlorprothixine, chlortalidone, chlortetracycline, chlorzoxazone, choline, chondroitin sulfate, choriogonadotropin alfa, chorionic gonadotropin, chrysarobin, chymotrypsin, ciclesonide, cicletanine, ciclopirox, ciclosporin, cidofovir, cilastatin, cilazapril, cimetidine, cinacalcet, cinchocaine, cinnarizine, cinolazepam, ciprofloxacin, cisapride, cisatracurium besylate, cisplatin, citalopram, citicoline, cladribine, clarithromycin, clavulanic acid, clemastine, clenbuterol, clindamycin, clioquinol, clobetasol, clobetasone, clobutinol, clocortolone, clodronic acid, Clofibrate, clomifene, clomipramine, clonazepam, clonidine, clopamide, clopidogrel, clostebol acetate, *clostridium botulinum*, clotrimazole, cloxiquine, clozapine, cocarboxylase, colchicine, colecalciferol, colesevelam, colestipol, colestyramine, colfosceril palmitate, colistin, zinc eyewash F, corticorelin, corticotrophin, cortisone, cresol, croconazole, cromoglicic acid, crotamiton, cryofluorane, coumarin, cyanamide, cyanocobalamin, cyclizine, cyclobutyrol, cyclopentolate, cyclophosphamide, cycloserine, cyproheptadine, cyproterone, cysteine, cytarabine, cytarabine, 2,4-dichlorobenzyl alcohol, 2-diethylaminoethanol, dacarbazine, daclizumab, dactinomycin, dalfopristin, dalteparin, danaparoid, danazol, dantrolene, dapiprazole, dapsone, darbepoetin alfa, darifenacin, Daunorubicin, deanol, deanolace, decarbazine, dectaflur F, deferiprone, deferoxamine, delapril, demeclocycline, denaverine, depreotide, dequalinium, desflurane, desipramine, desirudin, deslanoside, desloratadine, desmeninol, desmopressin, desogestrel, desoximetasone, deoxyribonuclease, detajmium, dexamethasone, dexchlorpheniramine, dexibuprofen, dexketoprofen, dexrazoxane, dextran, dextromethorphan, diacerein, diacetyl morphine, dibenzepin, diboterminalfa, diclofenac, diclofenamide, didanosine, dienestrol, dienogest, diethylstilbestrol, difloxacin, diflucortolone, diflunisal, digitoxin, digoxin, dihydralazine, dihydroergocornine, dihydroergocristine, dihydroergocryptine, dihydroergotamine, dihydroergotoxine, dihydrotachysterol, diisopropylamine, dipotassium clorazepate, diltiazem, dimenhydrinate, dimepranol, dimercaprol, dimethyl sulfoxide, dimethindene, disodium selenite, dinoprost, dinoprostone, diosmin, diphenhydramine, diphenoxylate, diphenylpyraline, dipivefrine, diprophylline, dipyridamole, disopyramide, dinitrogen monoxide, distigmine, disulfuram, dithranol, dixyrazine, D-norpseudoephedrine, dobesilate calcium, dobutamine, docetaxel, dofetilide, dolasetron, domperidone, donepezil, dopamine, dopexamine, dornase alfa, dorzolamide, dosulepin, doxapram, doxazosin, doxepin, doxorubicin, doxycycline, doxylamine, drofenine, droperidol, drospirenone, drotrecogin alfa, duloxetine, dutasteride, dydrogesterone, N,N'-dihydroxymethyl urea, ebastine, econazole, ecothiopate iodide, efalizumab, efavirenz, eflornithine, iron(III) ammonium citrate F, superparamagnetic iron oxide, elcatonin, eletriptan, emedastine, emepronium, emepronium carrageenate, emetine, emtricitabine, enalapril, enalaprilat, enflurane, enfuvirtide, enoxacin, enoxaparin, entacapone, ephedrine, ephedrine racephedrine, epinastine, epinephrine, epirubicin, eplerenone, epoetin alfa, epoetin beta, epoetin delta, epoprostenol, eprazinone, eprosartan, eptacog alfa, eptifibatide, eptotermin alfa, erdosteine, ergocalciferol, ergometrine, ergotamine, ertapenem, erythromycin, escitalopram, esmolol, esomeprazole, estradiol, estramustine, estriol, estrone, etacrynic acid, etamivan, etanercept, ethacridine, ethambutol, ethaverine, ethinylestradiol, ethisterone, ethosuximide, etidronic acid, etilefrine, etodolac, etofenamate, etofibrate, etofylline, etomidate, etonogestrel, etoposide, etoricoxib, everolimus, exametazime, exemestane, ezetimibe, 3-fluorotyrosine, famciclovir, famotidine, felbamate, felbinac, felodipine, fenbufene, fendiline, fenofibrate, fenoterol, fenticonazole, fexofenadine, fibrinogen, fibrinolysin, filgrastim, finasteride, flavoxate, flecamide, flucloxacillin, fluconazole, fludarabine, fludeoxyglucose [$^{18}$F], fludrocortisone, flufenamic acid, flumazenil, flumetasone, flunarizine, flunisolide, fluocinolone acetonide, fluocinonide, fluocortolone, fluophenozine, fluorescein dilaurate, fluorescein sodium, fluorometholone, fluorouracil, fluorophosphoric acid, fluorosilane, fluoxetil, fluoxetine, flupentixol, fluphenazine, flupirtine, fluprednidene, flurbiprofen, flutamide, fluticasone, flutrimazole, fluvastatin, fluvoxamine, folic acid, follitropin alfa, follitropin beta, folic acid, fomepizole, fomivirsen, fondaparinux, formestane, formoterol, fosamprenavir, foscarnet, fosfestrol, fosfomycin, fosinopril, fosphenytoin, fotemustine, framycetin, framycetin, frovatriptan, fulvestrant, furosemide, fusafungine, fusidic acid, fytic acid, gabapentin, gadobenic acid, gadobutrol, gadodiamide, gadopentetic acid, gadoteridol, gadoteric acid, gadoteric acid-meglumine, gadoxetic acid, galantamine, gallopamil, ganciclovir, ganirelix, gatifloxacin, gemcitabine, gemfibrozil, gentamicin, gepefrine, gestodene, glatiramer, glibenclamide, glibornuride, gliclazide, glimepiride, glipizide, gliquidone, glisoxepide, glucagon, glutamine, glutamic acid, glycopyrronium, glycopyrronium bromide, glycyrrhetinic acid, gonadorelin, goserelin, gramicidin, granisetron, grepafloxacin, griseofulvin, g-strophanthin, guajacol, guanethidine, guanfacine, $^{13}$C urea, 4-hydroxybutyric acid, halcinonide, halofantrine, halometasone, haloperidol, halothane, haem, haematoporphyrin, heparin, hepatitis B vaccine, heptaminol, hexobarbital, hexobendine, hexoprenaline, histamine, histidine, homatropine, homofenazine, human albumin, hyaluronidase, hydralazine, hydrastinine, hydroquinone, hydrochlorothiazide, hydrocortisone, hydrotalcite F, hydroxocobalamin, hydroxycarbamide, hydroxychloroquine, hydroxycine, hydroxylamine, hydroxyprogesterone, hydroxyzine, hymecromone, ibandronic acid, ibopamine, ibritumomab tiuxetan, ibuprofen, ibutilide, idarubicin, ifosfamide, iloprost, imatinib, imatinib mesylate, imidapril, imiglucerase, imipenem, imipramine, imiquimod, immunocyanin, indanazoline, indapamide, indinavir, indium chloride [$^{111}$In], indobufen, indometacin, indoramin, infliximab, inosine, insulin, insulin aspart, insulin detemir, insulin glargine, insulin glulisine, insulin lispro, interferon alfa, interferon alfa-2 b), interferon alfacon-1, interferon beta, interferon beta-1 a), interferon beta-1 b), interferon gamma, iobitridol, iodine, iodamide, iodixanol, ioflupane [$^{123}$I], iohexyl, iomeprol, iopamidol, iopentol, iopromide, iosarcol, iotrolan, iotroxic acid, ioversol, ioxaglic acid, ioxitalamic acid, ipatropium, irbesartan, irinotecan, irinotecan, isepamicin, isoaminile, isoconazole, isoflurane, isoleucine, isoniazid, isonicotinic acid, isoprenaline, isosorbide, isospaglumic acid, isotretinoin, isoxsuprine, isradipine, itraconazole, josamycin, potassium permanganate, kallidinogenase, kanamycin, kawain, kebuzone, ketamine, ketoconazole, ketoprofen, ketorolac, ketotifen, collagenase, creosote, labetalol, lacidipine, lactitol, lamivudine, lamotrigine, lanreotide, lansoprazole, laronidase, latanoprost, leflunomide, lenograstim, lepirudin, lercanidipine, letrozole, leucine, leuprorelin, levallorphan, levamisole, levetiracetam, levobunolol, levobupivacaine, levocabastine, levocetirizine, levodopa, levofloxacin, levofolinate calcium, levomepromazine, levomethadyl, levonorgestrel, levopropylhexedrine, levosimendan, levothyroxine, lidocaine, lincomycin, lindane, linezolid, liothyronine, lisinopril, lisuride, lobeline, lodoxamide, lofepramine, lomefloxacin, lomustine, lonazolac, loperamide, lopinavir, loratadine, lorazepam oxide, lornoxicam, losartan, loteprednole, lovastatin, lumefantrine, lutropin alfa, lymecycline, lynestrenol, lypressin, lysine, magaldrate F, magnesium pidolate, magnesium L-aspartate, mangafodipir, manidipine, maprotiline, mebendazole, mebeverine, meclofenoxate, mecloxamine, meclozine, medrogestone, medroxyprogesterone, mefenamic acid, mefloquine, megestrol, melagatrane, melitracen, melperol, melperone, melphalan, memantine, menadione, mepacrine, mepartricin, mephenyloin, mepindolol, mepivacaine, mepyramine, mequinol, mercaptamine, mercaptopurine, meropenem, mesalazine, mesna, mesterolone, mesuximide, metaclazepam, metamizole, metamphetamine, metenolone, metenolone acetate, metformin, methanthelinium, methazolamide, methenamine, methionine, methohexital, methotrexate, 5-methoxypsoralen, 8-methoxypsoralen, methyl 5-aminolevulinate, methylbenactyzium bromide, methyldopa, methylergometrine, methylprednisolone, methylrosanilinium, methyltestosterone, methylthionium chloride, methysergide, metildigoxin, metipranolol, metoclopramide, metoprolol, methixene, metronidazole, mexiletine, mezlocillin, mianserine, miconazole, midodrine, mifepristone, miglitol, miglustat, milnacipran, milrinone, miltefosine, minocycline, minoxidil, mirtazapine, misoprostol, mitobronitol, mitomycin, mitotane, mitoxantrone, mivacurium chloride, mivacuronium, mizolastine, moclobemide, moexipril, molgramostim, molsidomine, mometasone, monochloroacetic acid, montelukast, moroctocog alfa, moxaverine, moxifloxacin, moxonidine, mupirocin, mycophenolate mofetil, nadifloxacin, nadrolon decanonate, nadroparin calcium, naftidrofuryl, naftifine, nalbuphine, nalide, nalmefene, nalmexone, naloxone, naltrexone, naluphine, naphazoline, 2-naphthol, naproxen, naratriptan, naratriptan, nateglinide, sodium aurothiomalate, sodium phenylbutyrate, sodium fluoride, sodium hyaluronate, sodium iodide [$^{131}$I], sodium molybdate [$^{99}$Mo], sodium phenylbutyrate, n-butyl-p-aminobenzoate, N-butylscopolaminium bromide, nebivolol, nedocromil, nefazodone, nefopam, nelfinavir, neomycin, neostigmine, neostigmine methylsulfate, netilmicin, nevirapine, n-heptyl-2-phenyl glycinate, nicardipine, nicergoline, nicethamide, niclosamine, nicoboxil, nicorandil, nicotine, nicotine aldehyde, nicotinamide, nicotine resinate, nicotinic acid, nicotinic acid ester, nicotinyl alcohol, nifedipine, niflumic acid, nifuratel, nilvadipine, nimesulide, nimodipine, nimorazole, nimustine, nisoldipine, nitisinone, nitrendipine, nitric oxide, nitrofurantoin, nitroglycerine, nizatidine, N-methylephe-drine, nonacog alfa, nonivamide, noradrenalin, norelgestromin, norepinephrine, norethisterone, norfenefrine, norfloxacin, norgestimate, norgestrel, nortriptyline, noscapine, nystatin, obidoxime chloride, octafluoropropane, octocog alfa, octodrine, octreotide, odansetron, ofloxacin, olaflur F, olanzapine, olmesartan medoxomil, olopatadine, olsalazine, omeprazole, omoconazole, ondansetron, opipramol, oral cholera vaccine, orciprenaline, orlistat, ornipressin, orphenadrine, oseltamivir, osteogenic protein-1: BMP-7, oxaprozin, oxatomide, oxcarbazepine, oxedrine tartrate, oxetacaine, oxiconazole, oxilofrine, oxitropium, 2-oxo-3-methylbutyric acid, 2-oxo-3-methylvaleric acid, 2-oxo-3-phenylpropionic acid, 2-oxo-4-methylvaleric acid, oxprenolol, oxybuprocaine, oxybuprocaine, oxybutynin, oxybutynin, oxyfedrine, oxymetazoline, oxytetracycline, oxytocin, paclitaxel, palinavir, palivizumab, palonosetrone, pamidronic acid, pancuronium, pantoprazole, papaverine, paracetamol, paraldehyde, parecoxib, paricalcitol, parnaparin, paromomycin, paroxetine, pefloxacin, pegfilgrastim, peginterferon alfa, pegvisomant, pemetrexed, penbutolol, penciclovir, penfluridol, penicillamine, benperidol, pentaerithrityl tetranitrate, pentamidine, pentetrazol, pentetreotide, pentosan polysulfate sodium, pentoxifylline, pentoxyverine, perazine, perchloric acid, perflenapent, perflisopent, perflutren, pergolide, perindopril, perphenazine, phenacetin, phenamazid, phenazone, phenazopyridine, pheniramine, phenol, phenolphthalein, phenoxybenzamine, phenoxymethylpenicillin, phenprocoumon, phentolamine, phenylalanine, phenylbutazone, phenylephrine, phenylpropanolamine, phenyltoloxamine, phenyloin, phloroglucinol, pholedrine, phthalylsulfathiazole, physostigmine, phytomenadione, phytosterol, picric acid, pilocarpine, pimecrolimus, pimozide, pinaverium bromide, pindolol, pioglitazone, pipamperone, pipazetate, pipecuronium bromide, pipemidic acid, pipenzolate, piperacillin, piprinhydrinate, piracetam, pirarubicin, pirbuterol, pirenzepine, piritramide, piroxicam, pivmecillinam, pizotifen, podophyllotoxin, polidocanol, polycarbophil, polyestradiol phosphate, polymyxin B, polymyxin-B, polystyrenesulfonic acid, porfimer, prajmaline, prajmalium bitartrate, pramipexole, pranoprofen, prasterone, pravastatin, prazepam, prazosin, prednicarbate, prednisolone, prednisone, pregabalin, proglumetacin, pridinol, prilocalne, primaquine, primidone, prithipendyl, procaine, procainamide, procarbazil, procarbazine, procyclidin, progesterone, proglumetacin, proglumide, proguanil, proline, promethazine, propacetamol, propafenon, propanolol, propicillin, propiverine, propofol, propranolol, propylthiouracil, propyphenazone, protamine, protamine sulfate, protein C, prothipendyl, prothrombin, protionamide, protirelin, proxymetacaine, proxyphylline, pseudoephedrine, Pulmonal, pyrantel, pyrazinamide, pyridostigmine, pyridostigmine bromide, pyridoxine, 3-pyridylmethanol, pyrimethamine, pyrithione zinc, pyritinol, pyrogallol, pyrvinium, pyrvinium embonate, mercury amide chloride, quetiapine, quinagolide, quinapril, quinupristin, rabeprazole, racephedrine, racecadotrile, raloxifene, raltitrexed, ramipril, ranitidine, rasagiline, rasburicase, raubasine, reboxetine, repaglinide, reproterol, reserpine, resorcinol, reteplase, retinol, reviparin, ribavirin, riboflavin, rifabutin, rifampicin, rifamycin, rifaximin, rilmenidine, riluzole, rimexolone, risedronic acid, risperidone, ritonavir, rituximab, rivastigmine, rizatriptan, rocuronium bromide, rofecoxib, ropinirole, ropivacaine, ropivacaine, rosiglitazone, red mercuric sulfide F, roxatidine, roxithromycin, salbutamol, salicylic acid, salmeterol, nitric acid, nitrous acid, salverine, samarium [$^{153}$Sm] lexidronam, saquinavir, sulfur hexafluoride, scopolamine, selegiline, selenium sulfide, serine, sermorelin, sertaconazole, sertindole, sertraline, sevelamer, sevoflurane, sibutramine, silver chloride F, sildenafil, silibinin, simvastatin, sirolimus, formaldehyde solution, solifenacine, somatostatin, somatropin, sotalol, spaglumic acid, sparteine, spectinomycin, spiramycin, spirapril, spironolactone, stavudine, streptodornase, streptokinase, streptomycin, strontium ranelate, strontium chloride, strychnine, sucralfate F, sulbactam, sulesomab, sulfacetamide, sulfadiazine, sulfadimethoxine, sulfaguanidine, sulfamerazine, sulfamethoxazole, sulfamethoxydiazine, sulfametrole, sulfanilamide, sulfasalazine, sulfathiazole, sulfisomidine, sulindac, sulodexide, sulfur hexafluoride, sulpiride, sulprostone, sultamicillin, sultiame, sumatriptan, suxamethonium, tacalcitol, tacrolimus, tadalafil, tamoxifen, tamsulosin, tasonermin, taurolidine, tazarotene, tazobactam, tegafur, teicoplanin, telithromycin, telmisartan, temoporfin, temozolomide, tenecteplase, teniposide, tenofovir, tenofovir disoproxil, tenoxicam, terazosin, terbinafine, terbutaline, terfenadine, teriparatide, terizidone, terlipressin, testosterone, testosterone propionate, testosterone undecanoate, tetracaine, tetracosactide, tetracycline, tetrafluoroborate-1+, tetrofosmin, tetryzoline, thallium chloride [$^{201}$Tl], theobromine, theodrenaline, theodrenaline, theophylline, thiamazole, thiamine, thiethylperazine, thiocolchicoside, thiopental, thioridazine, thiotepa, threonine, thrombin, thrombokinase, thymol, thyrotropin alfa, tiagabine, tianeptine, tiapride, tibolone, ticlopidine, tiludronic acid, timolol, tinzaparin, tioconazole, tioguanine, tiotropium bromide, tirilazad, tirofiban, tisopurine, tizamidine, tizanidine, tobramycin, tocamide, tolazoline, tolbutamide, tolcapone, tolfenamic acid, tolmetin, tolperisone, tolterodine, topiramate, topotecan, torasemide, toremifene, tramazoline, trandolapril, tranexamic acid, tranylcypromine, trapidil, trastuzumab, travoprost, trazodone, tretinoin, triamcinolone, triamcinolone acetonide, triamterene, trichloroacetic acid, triethylperazine, trifluoperazine, triflupromazine, trihexyphenidyl, trimebutine, trimecaine, trimegestone, trimetazidine, trimethoprim, trimipramine, tripelennamine, triprolidine, triptorelin, tritoqualine, trofosfamide, tromantadine, trometamol, tropicamide, tropisetron, trospium, tryptophan, tubocurarine chloride, tulobuterol, tyloxapol, tyrosine, tyrothricin, unoprostone, urapid, urapidil, urokinase, ursodeoxycholic acid, valaciclovir, valdecoxib, valganciclovir, valine, valproic acid, valsartan, vancomycin, vardenafil, vecuronium, vecuronium bromide, venlafaxine, verapamil, verteporfin, vigabatrin, viloxazine, vinblastine, vincamine, vincristine, vindesine, vinorelbine, vinpocetine, viquidil, voriconazole, votumumab, hydrogen peroxide, xantinol nicotinate, ximelagatrane, xipamide, xylometazoline, yohimbine, yttrium $^{90}$Y chloride, zalcitabine, zaleplon, zanamivir, zidovudine, zinc acetate dihydrate, zinc chloride, zinc citrate, zinc sulfate, ziprasidone, zofenopril, zoledronic acid, zolmitriptan, zolpidem, zolpidem tartrate, zonisamide, zopiclone, zotepine, zucklopantexol, and zuclopenthixol.

The above-stated compounds are predominantly stated by their international nonproprietary name (INN) and are known to the person skilled in the art. Further details may be found, for example, by referring to International Nonproprietary Names (INN) for Pharmaceutical Substances, World Health Organization (WHO).

In a preferred embodiment, the pharmaceutical dosage form is monolithic.

The pharmaceutical dosage form according to the invention is characterized by a comparatively homogeneous distribution of the pharmacologically active compound (A). Preferably, the content of the pharmacologically active compound (A) in two segments of the pharmaceutical dosage form having a volume of 1.0 mm$^3$ each, deviates from one another by not more than ±10%, more preferably not more than more than ±7.5%, still more preferably not more than ±5.0%, most preferably not more than ±2.5%, and in particular not more than ±1.0%. When the pharmaceutical dosage form is film coated, said two segments of the pharmaceutical dosage form having a volume of 1.0 mm$^3$ each are preferably segments of the core, i.e. do not contain any coating material.

Preferably, all components of the pharmaceutical dosage form according to the invention have a comparatively homogeneous distribution within the pharmaceutical dosage form. Preferably, the content of each component in two segments of the pharmaceutical dosage form having a volume of 1.0 mm$^3$ each, deviates from one another by not more than ±10%, more preferably not more than more than ±7.5%, still more preferably not more than ±5.0%, most preferably not more than ±2.5%, and in particular not more than ±1.0%. When the pharmaceutical dosage form is film coated, said two segments of the pharmaceutical dosage form having a volume of 1.0 mm$^3$ each are preferably segments of the core, i.e. do not contain any coating material.

Preferably, the pharmaceutical dosage form according to the invention is adapted for oral administration. It is also possible, however, to administer the pharmaceutical dosage form via different routes and thus, the pharmaceutical dosage form may alternatively be adapted for buccal, lingual, rectal or vaginal administration. Implants are also possible.

In a preferred embodiment, the pharmaceutical dosage form according to the invention is adapted for administration once daily. In another preferred embodiment, the pharmaceutical dosage form according to the invention is adapted for administration twice daily. In still another preferred embodiment, the pharmaceutical dosage form according to the invention is adapted for administration thrice daily.

For the purpose of the specification, "twice daily" means equal time intervals, i.e., every 12 hours, or different time intervals, e.g., 8 and 16 hours or 10 and 14 hours, between the individual administrations.

For the purpose of the specification, "thrice daily" means equal time intervals, i.e., every 8 hours, or different time intervals, e.g., 6, 6 and 12 hours; or 7, 7 and 10 hours, between the individual administrations.

Preferably, the pharmaceutical dosage form according to the invention effects an at least partially delayed release of the pharmacologically active compounds (A).

Delayed release is understood according to the invention preferably to mean a release profile in which the pharmacologically active compound (A) is released over a relatively long period with reduced intake frequency with the purpose of extended therapeutic action. This is achieved in particular with peroral administration. The expression "at least partially delayed release" covers according to the invention any pharmaceutical dosage forms which ensure modified release of the pharmacologically active compounds (A) contained therein. The pharmaceutical dosage forms preferably comprise coated or uncoated pharmaceutical dosage forms, which are produced with specific auxiliary substances, by particular processes or by a combination of the two possible options in order purposefully to change the release rate or location of release.

In the case of the pharmaceutical dosage forms according to the invention, the release time profile may be modified e.g. as follows: extended release, repeat action release, prolonged release and sustained release.

For the purpose of the specification "extended release" preferably means a product in which the release of active compound is delayed for a finite lag time, after which release is unhindered. For the purpose of the specification "repeat action release" preferably means a product in which a first portion of active compound is released initially, followed by at least one further portion of active compound being released subsequently. For the purpose of the specification "prolonged release" preferably means a product in which the rate of release of active compound from the formulation after administration has been reduced, in order to maintain therapeutic activity, to reduce toxic effects, or for some other therapeutic purpose. For the purpose of the specification "sustained release" preferably means a way of formulating a medicine so that it is released into the body steadily, over a long period of time, thus reducing the dosing frequency. For further details, reference may be made, for example, to K. H. Bauer, Lehrbuch der Pharmazeutischen Technologie, 6th edition, WVG Stuttgart, 1999; and European Pharmacopoeia.

The pharmaceutical dosage form according to the invention may comprise one or more pharmacologically active compounds (A) at least in part in a further delayed-release form, wherein delayed release may be achieved with the assistance of conventional materials and processes known to the person skilled in the art, for example by embedding the substance in a delayed-release matrix or by applying one or more delayed-release coatings. Substance release must, however, be controlled such that addition of delayed-release materials does not impair the necessary breaking strength. Controlled release from the pharmaceutical dosage form according to the invention is preferably achieved by embedding the substance in a matrix. Component (C) may serve as such a matrix. The auxiliary substances acting as matrix materials control release. Matrix materials may, for example, be hydrophilic, gel-forming materials, from which release proceeds mainly by diffusion, or hydrophobic materials, from which release proceeds mainly by diffusion from the pores in the matrix.

Preferably, the release profile is substantially matrix controlled, preferably by embedding component (A) in a matrix comprising component (C) and optionally, further matrix materials. Preferably, the release profile is not osmotically driven. Preferably, release kinetics is not zero order.

Preferably, under physiological conditions the pharmaceutical dosage form according to the invention has released after 30 minutes 0.1 to 75%, after 240 minutes 0.5 to 95%, after 480 minutes 1.0 to 100% and after 720 minutes 2.5 to 100% of the pharmacologically active compound (A). Further preferred release profiles $R_1$ to $R_5$ are summarized in the table here below [all data in wt.-% of released pharmacologically active compound (A)]:

| time | $R_1$ | $R_2$ | $R_3$ | $R_4$ | $R_5$ |
|---|---|---|---|---|---|
| 60 min | 0-30 | 0-50 | 0-50 | 15-25 | 20-50 |
| 120 min | 0-40 | 0-75 | 0-75 | 25-40 | 40-75 |
| 240 min | 3-55 | 3-95 | 10-95 | 40-70 | 60-95 |
| 480 min | 10-65 | 10-100 | 35-100 | 60-90 | 80-100 |
| 720 min | 20-75 | 20-100 | 55-100 | 70-100 | 90-100 |
| 960 min | 30-88 | 30-100 | 70-100 | >80 | |
| 1440 min | 50-100 | 50-100 | >90 | | |
| 2160 min | >80 | >80 | | | |

Preferably, under in vitro conditions the pharmaceutical dosage form has released after 0.5 h 1.0 to 35 wt.-%, after 1 h 5.0 to 45 wt.-%, after 2 h 10 to 60 wt.-%, after 4 h at least 15 wt.-%, after 6 h at least 20 wt.-%, after 8 h at least 25 wt.-% and after 12 h at least 30 wt.-% of the pharmacologically active compound (A) that was originally contained in the pharmaceutical dosage form.

Suitable in vitro conditions are known to the skilled artisan. In this regard it can be referred to, e.g., the European Pharmacopoeia and to the experimental section. Preferably, the release profile is measured under the following conditions: Paddle apparatus equipped with sinker, 50 rpm, 37±5° C., 900 mL simulated intestinal fluid pH 6.8 (phosphate buffer). In a preferred embodiment, to rotational speed of the paddle is increased to 100 rpm.

Preferred release profiles $R_6$ to $R_{11}$ of the pharmacologically active compound (A) contained in the pharmaceutical dosage form are summarized in the following table:

| [wt.-%] | $R_6$ | $R_7$ | $R_8$ | $R_9$ | $R_{10}$ | $R_{11}$ |
|---|---|---|---|---|---|---|
| after 30 min | 16.3 ± 7.5 | 16.3 ± 5.0 | 16.3 ± 2.5 | 15.8 ± 7.5 | 15.8 ± 5.0 | 15.8 ± 2.5 |
| after 60 min | 27.5 ± 7.5 | 25.0 ± 5.0 | 25.0 ± 2.5 | 24.3 ± 7.5 | 24.3 ± 5.0 | 24.3 ± 2.5 |
| after 90 min | 32.1 ± 7.5 | 32.1 ± 5.0 | 32.1 ± 2.5 | 31.2 ± 7.5 | 31.2 ± 5.0 | 31.2 ± 2.5 |
| after 120 min | 38.2 ± 7.5 | 38.2 ± 5.0 | 38.2 ± 2.5 | 37.4 ± 7.5 | 37.4 ± 5.0 | 37.4 ± 2.5 |
| after 150 min | 43.4 ± 7.5 | 43.4 ± 5.0 | 43.4 ± 2.5 | 42.7 ± 7.5 | 42.7 ± 5.0 | 42.7 ± 2.5 |
| after 180 min | 48.2 ± 7.5 | 48.2 ± 5.0 | 48.2 ± 2.5 | 47.6 ± 7.5 | 47.6 ± 5.0 | 47.6 ± 2.5 |
| after 210 min | 52.7 ± 7.5 | 52.7 ± 5.0 | 52.7 ± 2.5 | 52.2 ± 7.5 | 52.2 ± 5.0 | 52.2 ± 2.5 |
| after 240 min | 56.8 ± 7.5 | 56.8 ± 5.0 | 56.8 ± 2.5 | 56.5 ± 7.5 | 56.5 ± 5.0 | 56.5 ± 2.5 |
| after 270 min | 60.7 ± 7.5 | 60.7 ± 5.0 | 60.7 ± 2.5 | 60.4 ± 7.5 | 60.4 ± 5.0 | 60.4 ± 2.5 |
| after 300 min | 64.5 ± 7.5 | 64.5 ± 5.0 | 64.5 ± 2.5 | 64.2 ± 7.5 | 64.2 ± 5.0 | 64.2 ± 2.5 |
| after 330 min | 67.9 ± 7.5 | 67.9 ± 5.0 | 67.9 ± 2.5 | 67.7 ± 7.5 | 67.7 ± 5.0 | 67.7 ± 2.5 |
| after 360 min | 71.1 ± 7.5 | 71.1 ± 5.0 | 71.1 ± 2.5 | 71.0 ± 7.5 | 71.0 ± 5.0 | 71.0 ± 2.5 |
| after 390 min | 74.2 ± 7.5 | 74.2 ± 5.0 | 74.2 ± 2.5 | 74.0 ± 7.5 | 74.0 ± 5.0 | 74.0 ± 2.5 |
| after 420 min | 77.0 ± 7.5 | 77.0 ± 5.0 | 77.0 ± 2.5 | 76.9 ± 7.5 | 76.9 ± 5.0 | 76.9 ± 2.5 |
| after 450 min | 79.5 ± 7.5 | 79.5 ± 5.0 | 79.5 ± 2.5 | 79.5 ± 7.5 | 79.5 ± 5.0 | 79.5 ± 2.5 |
| after 480 min | 81.9 ± 7.5 | 81.9 ± 5.0 | 81.9 ± 2.5 | 82.0 ± 7.5 | 82.0 ± 5.0 | 82.0 ± 2.5 |
| after 510 min | 84.2 ± 7.5 | 84.2 ± 5.0 | 84.2 ± 2.5 | 84.2 ± 7.5 | 84.2 ± 5.0 | 84.2 ± 2.5 |
| after 540 min | 86.3 ± 7.5 | 86.3 ± 5.0 | 86.3 ± 2.5 | 86.3 ± 7.5 | 86.3 ± 5.0 | 86.3 ± 2.5 |
| after 570 min | 88.3 ± 7.5 | 88.3 ± 5.0 | 88.3 ± 2.5 | 88.1 ± 7.5 | 88.1 ± 5.0 | 88.1 ± 2.5 |
| after 600 min | 90.1 ± 7.5 | 90.1 ± 5.0 | 90.1 ± 2.5 | 89.8 ± 7.5 | 89.8 ± 5.0 | 89.8 ± 2.5 |

-continued

| [wt.-%] | $R_6$ | $R_7$ | $R_8$ | $R_9$ | $R_{10}$ | $R_{11}$ |
|---|---|---|---|---|---|---|
| after 630 min | 91.9 ± 7.5 | 91.9 ± 5.0 | 91.9 ± 2.5 | 91.4 ± 7.5 | 91.4 ± 5.0 | 91.4 ± 2.5 |
| after 660 min | 93.3 ± 7.5 | 93.3 ± 5.0 | 93.3 ± 2.5 | 92.7 ± 7.5 | 92.7 ± 5.0 | 92.7 ± 2.5 |
| after 690 min | 94.3 ± 7.5 | 94.3 ± 5.0 | 94.3 ± 2.5 | 94.0 ± 7.5 | 94.0 ± 5.0 | 94.0 ± 2.5 |
| after 720 min | 95.8 ± 7.5 | 95.8 ± 5.0 | 95.8 ± 2.5 | 95.1 ± 7.5 | 95.1 ± 5.0 | 95.1 ± 2.5 |

Preferably, the release properties of the pharmaceutical dosage form according to the invention are substantially independent from the pH value of the release medium, i.e. preferably the release profile in artificial intestinal juice substantially corresponds to the release profile in artificial gastric juice. Preferably, at any given time point the release profiles deviate from one another by not more than 20%, more preferably not more than 15%, still more preferably not more than 10%, yet more preferably not more than 7.5%, most preferably not more than 5.0% and in particular not more than 2.5%.

Figure 22:
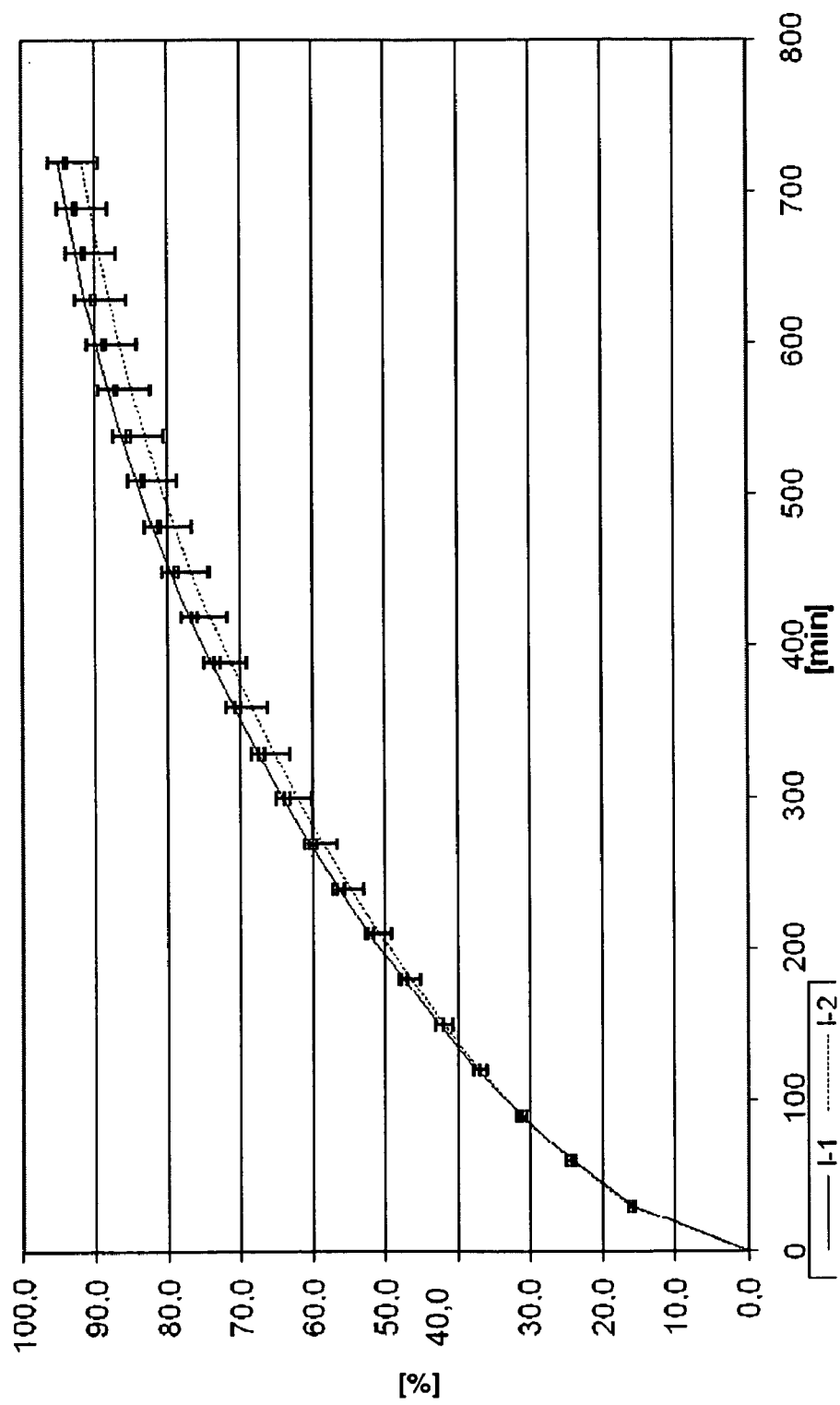
FIG. 22 shows the release profile of the tablet according to inventive example I-1 (H-shape) and of the tablet according to inventive example I-2 (H-shape).

Preferably, the pharmaceutical dosage form according to the invention exhibits a uniform release profile. Preferably, the release profile of the pharmacologically active compound (A) is interindividually uniform (i.e. when comparing pharmaceutical dosage forms obtained from the same process) (c.f. FIG. 22) and/or uniform within a single pharmaceutical dosage form (i.e. when comparing segments of the same pharmaceutical dosage form). Preferably, when comparing two probes each having a mass of preferably 500 mg, the total amount of the released active compound for any given time point of the measurement does not deviate by more than 20%, more preferably not more than 15%, still more preferably not more than 10%, yet more preferably not more than 7.5%, most preferably not more than 5.0% and in particular not more than 2.5%.

Preferably, the entire outer surface of the dosage form, preferably tablet, according to the invention is permeable for water and for component (A), i.e., preferably the water penetration characteristics of the surface are identical everywhere. This means that preferably, the dosage form, preferably tablet, is not partially coated with a material having a barrier effect which would impede the penetration of water at the location of the surface where it is applied.

Preferably, the release profile of the pharmaceutical dosage form according to the present invention is stable upon storage, preferably upon storage at elevated temperature, e.g. 37° C., for 3 months in sealed containers. In this regard "stable" means that when comparing the initial release profile with the release profile after storage, at any given time point the release profiles deviate from one another by not more than 20%, more preferably not more than 15%, still more preferably not more than 10%, yet more preferably not more than 7.5%, most preferably not more than 5.0% and in particular not more than 2.5% (cf. FIG. 24).

It has been surprisingly found that by modifying the outer shape of the pharmaceutical dosage form the storage stability, e.g. the storage stability of the release profile, can be increased compared to conventional dosage forms having a comparable release profile before storage.

Preferably, the pharmaceutical dosage form according to the invention contains at least one polymer (C), for the purpose of the specification also referred to as "component (C)". Preferably, the pharmaceutical dosage form contains at least one synthetic, semi-synthetic or natural polymer (C), which contributes considerably to the elevated breaking strength (resistance to crushing) of the pharmaceutical dosage form.

For the purpose of the specification a "semi-synthetic" product has been produced by chemical manipulation of naturally occurring substances.

Preferably, the mechanical properties of the pharmaceutical dosage form according to the invention, particularly its breaking strength, substantially rely on the presence of polymer (C), although its mere presence does not suffice in order to achieve said properties. The advantageous properties of the pharmaceutical dosage form according to the invention, in particular also its mechanical properties, may not automatically be achieved by simply processing the pharmacologically active compound (A), polymer (C), and optionally further excipients by means of conventional methods for the preparation of pharmaceutical dosage forms. In fact, usually suitable apparatuses must be selected for the preparation and critical processing parameters must be adjusted, particularly pressure/force, temperature and time. Thus, even if conventional apparatuses are used, the process protocols usually must be adapted in order to meet the required criteria.

Preferably, polymer (C) is water-soluble. Preferably, polymer (C) is substantially unbranched.

Polymer (C) may comprise a single type of polymer having a particular average molecular weight, or a mixture (blend) of different polymers, such as two, three, four or five polymers, e.g., polymers of the same chemical nature but different average molecular weight, polymers of different chemical nature but same average molecular weight, or polymers of different chemical nature as well as different molecular weight.

Individual or combinations of polymers may be selected from the group comprising polyalkylene oxide, preferably polymethylene oxide, polyethylene oxide, polypropylene oxide; polyethylene, polypropylene, polyvinyl chloride, polycarbonate, polystyrene, polyvinylpyrrolidone, poly(alk) acrylate, poly(hydroxy fatty acids), such as for example poly (3-hydroxybutyrate-co-3-hydroxyvalerate) (Biopol®), poly (hydroxyvaleric acid); polycaprolactone, polyvinyl alcohol, polyesteramide, polyethylene succinate, polylactone, polyglycolide, polyurethane, polyamide, polylactide, polyacetal (for example polysaccharides optionally with modified side chains), polylactide/glycolide, polylactone, polyglycolide, polyorthoester, polyanhydride, block polymers of polyethylene glycol and polybutylene terephthalate (Polyactive®), polyanhydride (Polifeprosan), copolymers thereof, block-copolymers thereof, and mixtures of at least two of the stated polymers, or other polymers with the above characteristics.

Preferably, polymer (C) comprises a polyalkylene oxide, more preferably a polyethylene oxide, a polypropylene oxide, an ethylene oxide-propylene oxide copolymerisate, which may be e.g. a random copolymer, alternating copolymer or block copolymer, or a mixture of any of the foregoing.

Particularly preferred are high molecular weight polymers with a preferably weight average molecular weight ($M_w$) or viscosity average molecular weight ($M_\eta$) of at least of at least $0.1 \cdot 10^6$ g/mol, of at least $0.2 \cdot 10^6$ g/mol, of at least $0.5 \cdot 10^6$ g/mol, of at least $1.0 \cdot 10^6$ g/mol, of at least $2.5 \cdot 10^6$ g/mol, of at least $5.0 \cdot 10^6$ g/mol, of at least $7.5 \cdot 10^6$ g/mol or of at least $10 \cdot 10^6$ g/mol, preferably $1.0 \cdot 10^6$ g/mol to $15 \cdot 10^6$ g/mol. Suitable methods for determining $M_w$ or $M_\eta$ are known to the person skilled in the art. Preferably, $M_\eta$ is determined using rheological measurements and $M_w$ is determined using gel permeation chromatography (GPC) on suitable phases.

Preferably, the molecular weight dispersity $M_w/M_n$ of polymer (C) is within the range of 2.5±2.0, more preferably 2.5±1.5, still more preferably 2.5±1.0, yet more preferably 2.5±0.8, most preferably 2.5±0.6, and in particular 2.5±0.4.

The polymers preferably have a viscosity at 25° C. of 4,500 to 17,600 cP, measured in a 5 wt.-% aqueous solution using a model RVF Brookfield viscosimeter (spindle no. 2/rotational speed 2 rpm), of 400 to 4,000 cP, measured on a 2 wt.-% aqueous solution using the stated viscosimeter (spindle no. 1 or 3/rotational speed 10 rpm) or of 1,650 to 10,000 cP, measured on a 1 wt.-% aqueous solution using the stated viscosimeter (spindle no. 2/rotational speed 2 rpm).

Most preferred are thermoplastic polyalkylene oxides having a weight average molecular weight ($M_w$) or a viscosity average molecular weight ($M_\eta$) of at least $0.2 \cdot 10^6$ g/mol, more preferably at least $0.3 \cdot 10^6$ g/mol, still more preferably at least $0.4 \cdot 10^6$ g/mol, yet more preferably at least $0.5 \cdot 10^6$ g/mol, most preferably at least $1.0 \cdot 10^6$ g/mol and in particular within the range of $1.0 \cdot 10^6$ to $15 \cdot 10^6$ g/mol are preferred, e.g. polyethylene oxides, polypropylene oxides or the (block-)copolymers thereof.

In a preferred embodiment according to the invention the polymer (C) comprises
a polyalkylene oxide having a weight average molecular weight ($M_w$) or viscosity average molecular weight ($M_\eta$) of at least $0.2 \cdot 10^6$ g/mol
in combination with
at least one further polymer, preferably but not necessarily also having a weight average molecular weight ($M_w$) or viscosity average molecular weight ($M_\eta$) of at least $0.2 \cdot 10^6$ g/mol, selected from the group consisting of polyethylene, polypropylene, polyvinyl chloride, polycarbonate, polystyrene, polyacrylate, poly(hydroxy fatty acids), polycaprolactone, polyvinyl alcohol, polyesteramide, polyethylene succinate, polylactone, polyglycolide, polyurethane, polyvinylpyrrolidone, polyamide, polylactide, polylactide/glycolide, polylactone, polyglycolide, polyorthoester, polyanhydride, block polymers of polyethylene glycol and polybutylene terephthalate, polyanhydride, polyacetal, cellulose esters, cellulose ethers and copolymers thereof. Cellulose esters and cellulose ethers are particularly preferred, e.g. methylcellulose, ethylcellulose, hydroxymethylcellulose, hydroxypropylmethylcellulose, carboxymethylcellulose, and the like.

In a preferred embodiment, said further polymer is neither a polyalkylene oxide nor a polyalkylene glycol. Nonetheless, the pharmaceutical dosage form may contain polyalkylene glycol, e.g. as plasticizer, but then, the pharmaceutical dosage form preferably is a ternary mixture of polymers: component (C)+further polymer+plasticizer.

In a particularly preferred embodiment, said further polymer is a hydrophilic cellulose ester or cellulose ether, preferably hydroxypropylmethylcellulose, preferably having an average viscosity of 100,000±50,000 mPas, more preferably 100,000±20,000 mPas.

Preferably, the content of said further polymer amounts to 0.5 to 25 wt.-%, more preferably 1.0 to 20 wt.-%, still more preferably 2.0 to 17.5 wt.-%, yet more preferably 3.0 to 15 wt.-% and most preferably 4.0 to 12.5 wt.-% and in particular 5.0 to 10 wt.-%, based on the total weight of the polyalkylene oxide.

In a preferred embodiment the relative weight ratio of said polyalkylene oxide and said further polymer is within the range of from 20:1 to 1:20, more preferably 10:1 to 1:10, still more preferably 7:1 to 1:5, yet more preferably 5:1 to 1:1, most preferably 4:1 to 1, 5:1 and in particular 3:1 to 2:1.

Preferably, the content of said further polymer amounts to 0.5 to 25 wt.-%, more preferably 1.0 to 20 wt.-%, still more preferably 2.0 to 22.5 wt.-%, yet more preferably 3.0 to 20 wt.-% and most preferably 4.0 to 17.5 wt.-% and in particular 5.0 to 15 wt.-%, based on the total weight of the pharmaceutical dosage form.

It is not intended to be bound by any theory, but it is believed that the further polymer may serve as a supplementary matrix material that guarantees a minimal retardant effect on the release of the pharmacologically active compound (A) even if the molecular chains of the polyalkylene oxide have been partially damaged in the course of the manufacture of the pharmaceutical dosage form, e.g. by extrusion, thereby decreasing the average molecular weight. Furthermore, it seems that the further polymer contributes to the storage stability of the dosage form, particularly with respect to its release profile.

Physiologically acceptable, hydrophobic materials which are known to the person skilled in the art may be used as supplementary matrix materials. Polymers, particularly preferably cellulose ethers, cellulose esters and/or acrylic resins are preferably used as hydrophilic matrix materials. Ethylcellulose, hydroxypropylmethylcellulose, hydroxypropylcellulose, hydroxymethylcellulose, poly(meth)acrylic acid and/or the derivatives thereof, such as the salts, amides or esters thereof are very particularly preferably used as matrix materials. Matrix materials prepared from hydrophobic materials, such as hydrophobic polymers, waxes, fats, long-chain fatty acids, fatty alcohols or corresponding esters or ethers or mixtures thereof are also preferred. Mono- or diglycerides of C12-C30 fatty acids and/or C12-C30 fatty alcohols and/or waxes or mixtures thereof are particularly preferably used as hydrophobic materials. It is also possible to use mixtures of the above-stated hydrophilic and hydrophobic materials as matrix materials.

Preferably, the overall content of polymer (C) is preferably at least 5 wt.-%, at least 10 wt.-%, at least 15 wt.-% or at least 20 wt.-%, more preferably at least 30 wt.-%, still more preferably at least 40 wt.-%, most preferably at least 50 wt.-% and in particular at least 60 wt.-%, of the total weight of the pharmaceutical dosage form. In a preferred embodiment the content of the polymer (C) is within the range of from about 20 to about 49 wt.-% of the total weight of the pharmaceutical dosage form.

In a preferred embodiment, the overall content of polymer (C) is within the range of 25±20 wt.-%, more preferably 25±15 wt.-%, most preferably 25±10 wt.-%, and in particular 25±5 wt.-%. In another preferred embodiment, the overall content of polymer (C) is within the range of 35±20 wt.-%, more preferably 35±15 wt.-%, most preferably 35±10 wt.-%, and in particular 35±5 wt.-%. In still another preferred embodiment, the overall content of polymer (C) is within the range of 45±20 wt.-%, more preferably 45±15 wt.-%, most preferably 45±10 wt.-%, and in particular 45±5 wt.-%. In yet another preferred embodiment, the overall content of polymer (C) is within the range of 55±20 wt.-%, more preferably 55±15 wt.-%, most preferably 55±10 wt.-%, and in particular 55±5 wt.-%. In a further preferred embodiment, the overall content of polymer (C) is within the range of 65±20 wt.-%, more preferably 65±15 wt.-%, most preferably 65±10 wt.-%, and in particular 65±5 wt.-%. In still a further a preferred embodiment, the overall content of polymer (C) is within the range of 75±20 wt.-%, more preferably 75±15 wt.-%, most preferably 75±10 wt.-%, and in particular 75±5 wt.-%.

In a preferred embodiment, polymer (C) is homogeneously distributed in the pharmaceutical dosage form according to the invention. Preferably, polymer (C) forms a matrix in which the pharmacologically active compound (A) is embedded. In a particularly preferred embodiment, the pharmacologically active compound (A) and polymer (C) are intimately homogeneously distributed in the pharmaceutical dosage form so that the pharmaceutical dosage form does not contain any segments where either pharmacologically active compound (A) is present in the absence of polymer (C) or where polymer (C) is present in the absence of pharmacologically active compound (A).

When the pharmaceutical dosage form is film coated, the polymer (C) is preferably homogeneously distributed in the core of the pharmaceutical dosage form, i.e. the film coating preferably does not contain polymer (C). Nonetheless, the film coating as such may of course contain one or more polymers, which however, preferably differ from the polymer (C) contained in the core.

Preferably, the pharmaceutical dosage form according to the invention contains a coating, preferably a film-coating. Suitable coating materials are known to the skilled person. Suitable coating materials are commercially available, e.g. under the trademarks Opadry® and Eudragit®.

Examples of suitable materials include cellulose esters and cellulose ethers, such as methylcellulose (MC), hydroxypropylmethylcellulose (HPMC), hydroxypropylcellulose (HPC), hydroxyethylcellulose (HEC), sodium carboxymethylcellulose (Na—CMC), ethylcellulose (EC), cellulose acetate phthalate (CAP), hydroxypropylmethylcellulose phthalate (HPMCP); poly(meth)acrylates, such as aminoalkylmethacrylate copolymers, ethylacrylate methylmethacrylate copolymers, methacrylic acid methylmethacrylate copolymers, methacrylic acid methylmethacrylate copolymers; vinyl polymers, such as polyvinylpyrrolidone, polyvinylacetatephthalate, polyvinyl alcohol, polyvinylacetate; and natural film formers, such as shellack.

In a particularly preferred embodiment, the coating is water-soluble. Preferably, the coating is based on polyvinyl alcohol, such as polyvinyl alcohol-part. hydrolyzed, and may additionally contain polyethylene glycol, such as macrogol 3350, and/or pigments.

The coating of the pharmaceutical dosage form can increase its storage stability.

The coating can be resistant to gastric juices and dissolve as a function of the pH value of the release environment. By means of this coating, it is possible to ensure that the pharmaceutical dosage form according to the invention passes through the stomach undissolved and the active compound is only released in the intestines. The coating which is resistant to gastric juices preferably dissolves at a pH value of between 5 and 7.5. Corresponding materials and methods for the delayed release of active compounds and for the application of coatings which are resistant to gastric juices are known to the person skilled in the art, for example from "Coated Pharmaceutical dosage forms—Fundamentals, Manufacturing Techniques, Biopharmaceutical Aspects, Test Methods and Raw Materials" by Kurt H. Bauer, K. Lehmann, Hermann P. Osterwald, Rothgang, Gerhart, 1st edition, 1998, Medpharm Scientific Publishers.

It has been surprisingly found that the pharmaceutical dosage forms can be easily film coated, although the outer shape of the pharmaceutical dosage forms may deviate from conventional shapes of dosage forms. For example, when the pharmaceutical dosage forms according to the invention are shaped by means of an H-plunger, a skilled person would expect that substantial stapling or stacking and pair formation occurs when spraying the coating material on the dosage form in suitable devices. Such stacking and agglomeration of the dosage form would deteriorate the coating performance and hence, the film quality. However, it has been surprisingly found that even pharmaceutical dosage forms having irregular shapes may be smoothly coated.

In a particularly preferred embodiment,
- the pharmaceutical dosage form is thermoformed, preferably by extrusion; and/or
- a portion of the surface of the pharmaceutical dosage form is convex, another portion of its surface is concave; and/or
- the pharmacologically active compound (A) is a psychotropically acting substance, preferably an analgesic, more preferably a drug selected from the group consisting of opioids, stimulants, tranquillisers (e.g. barbiturates and benzodiazepines) and other narcotics; and/or
- the content of the pharmacologically active compound (A) is at least 0.5 wt.-%, based on the total weight of the dosage form; and/or
- polymer (C) is an polyalkylene oxide having a weight average molecular weight of at least 200,000 g/mol, preferably at least 500,000 g/mol, more preferably within the range of from 1,000,000 to 10,000,000 g/mol; and/or
- the content of the polyalkylene oxide is at least 15 wt.-%, based on the total weight of the dosage form; and/or
- the opioid is embedded in the polyalkylene oxide, i.e., in a matrix formed by the polyalkylene oxide; and/or
- the pharmaceutical dosage form contains a plasticizer, preferably polyethylene glycol; and/or
- the content of said plasticizer is at least 5 wt.-%, based on the total weight of the dosage form; and/or
- besides polymer (C), the pharmaceutical dosage form contains a further polymer selected from the group consisting of cellulose ethers, cellulose esters and acrylates, preferably HPMC; and/or
- the content of said further polymer is at least 1 wt.-%, based on the total weight of the dosage form; and/or
- the pharmaceutical dosage form contains an antioxidant, preferably α-tocopherol; and/or
- the content of said antioxidant is at least 0.05 wt.-%, based on the total weight of the dosage form; and/or
- the pharmaceutical dosage form is adapted for oral administration once daily or twice daily; and/or
- the pharmaceutical dosage form contains a coating, preferably a film-coating.

Besides the pharmacologically active compound (A) and polymer (C) the pharmaceutical dosage form according to the invention may contain further constituents, such as conventional pharmaceutical excipients.

In a preferred embodiment, the pharmaceutical dosage form contains at least one natural, semi-synthetic or synthetic wax (D), for the purpose of the specification also referred to as "component (D)". Preferred waxes are those with a softening point of at least 50° C., more preferably of at least 55° C., still more preferably of at least 60° C., most preferably of at least 65° C. and in particular at least 70° C.

Carnauba wax and beeswax are particularly preferred. Carnauba wax is very particularly preferred. Carnauba wax is a natural wax which is obtained from the leaves of the carnauba palm and has a softening point of at least 80° C. When the wax component is additionally contained, its content is sufficiently high so that the desired mechanical properties of the pharmaceutical dosage form are achieved.

Auxiliary substances (B), further purpose of the specification also referred to as "component (B)", which may be contained in the pharmaceutical dosage form according to the invention are those known auxiliary substances which are conventional for the formulation of solid pharmaceutical dosage forms.

Examples of auxiliary substances (B) are plasticizers, (further) matrix materials, antioxidants and the like.

Suitable plasticizers include triacetin and polyethylene glycol, preferably a low molecular weight polyethylene glycol (e.g. macrogol 6000).

Matrix materials are auxiliary substances which influence active compound release, preferably hydrophobic or hydrophilic, preferably hydrophilic polymers, very particularly preferably hydroxypropylmethylcellulose, and/or antioxidants. Polymers, particularly preferably cellulose ethers, cellulose esters and/or acrylic resins are preferably contained as hydrophilic matrix materials. Ethylcellulose, hydroxypropylmethylcellulose, hydroxypropylcellulose, hydroxymethylcellulose, poly(meth)acrylic acid and/or the derivatives thereof, such as the copolymers, salts, amides or esters thereof are very particularly preferably contained as matrix materials.

Suitable antioxidants are ascorbic acid, butylhydroxyanisole (BHA), butylhydroxytoluene (BHT), salts of ascorbic acid, monothioglycerol, phosphorous acid, vitamin C, vitamin E and the derivatives thereof, coniferyl benzoate, nordihydroguajaretic acid, *gallus* acid esters, sodium bisulfite, particularly preferably butylhydroxytoluene or butylhydroxyanisole and α-tocopherol. The antioxidant is preferably used in quantities of 0.01 to 10 wt.-%, preferably of 0.03 to 5 wt.-%, relative to the total weight of the pharmaceutical dosage form.

Preferred compositions $X_1$ to $X_4$ of the pharmaceutical dosage form according to the invention are summarized in the table here below:

| wt.-% | $X_1$ | $X_2$ | $X_3$ | $X_4$ |
| --- | --- | --- | --- | --- |
| component (A) | 26.5 ± 25 | 26.5 ± 20 | 26.5 ± 15 | 26.5 ± 13 |
| polyalkylene oxide (e.g. PEO) | 46.5 ± 25 | 46.5 ± 17 | 46.5 ± 12 | 46.5 ± 10 |
| cellulose ester or ether (e.g. HPMC) | 14 ± 7 | 14 ± 5 | 14 ± 2.5 | 14 ± 0.5 |
| plasticizer (e.g. PEG) | 12.5 ± 10 | 12.5 ± 7 | 12.5 ± 5 | 12.5 ± 3 |
| antioxidant (e.g. α-tocopherol) | 0.125 ± 0.12 | 0.125 ± 0.1 | 0.125 ± 0.05 | 0.125 ± 0.03 |

The pharmaceutical dosage form according to the invention may be produced by different processes, which are explained in greater detail below; the present invention also relates to pharmaceutical dosage forms that are obtainable by any of the processes described here below:

In general, the process for the production of the pharmaceutical dosage form according to the invention preferably comprises the following steps:

(a) mixing of components (A), (C), optionally (B) and/or (D);

(b) optionally pre-forming the mixture obtained from step (a), preferably by applying heat and/or force to the mixture obtained from step (a), the quantity of heat supplied preferably not being sufficient to heat component (C) up to its softening point;

(c) hardening the mixture by applying heat and force, it being possible to supply the heat during and/or before the application of force and the quantity of heat supplied being sufficient to heat component (C) at least up to its softening point;

(d) optionally singulating the hardened mixture;

(e) optionally shaping the pharmaceutical dosage form; and (f) optionally providing a film coating.

Heat may be supplied directly or with the assistance of ultrasound. Force may be applied and/or the pharmaceutical dosage form may be shaped for example by direct tabletting or with the assistance of a suitable extruder, particularly by means of a screw extruder equipped with two screws (twin-screw-extruder) or by means of a planetary gear extruder.

The shaping of the pharmaceutical dosage form according to the invention is of particular importance. The final shape of the pharmaceutical dosage form may either be provided during the hardening of the mixture by applying heat and force (step (c)) or in a subsequent step (step (e)). In both cases, the mixture of all components is preferably in the plastified state, i.e. preferably, shaping is performed at a temperature at least above the softening point of component (C).

Shaping can be performed, e.g., by means of a tabletting press comprising die and plunger of appropriate shape. Preferably, the plunger is a H-plunger so that the cross section of the pharmaceutical dosage form assumes the form of a H.

The following process variants are particularly preferred:
Process Variant 1

In this embodiment, the pharmaceutical dosage form according to the invention is preferably produced without using an extruder by preferably mixing components (A), (C), optionally (B) and/or (D) and, optionally after granulation, shaping the resultant mixture by application of force to yield the pharmaceutical dosage form with preceding and/or simultaneous exposure to heat.

This heating and application of force for the production of the pharmaceutical dosage form proceeds without using an extruder.

Components (A), (C), optionally (B) and/or (D) are mixed in a mixer known to the person skilled in the art. The mixer may, for example, be a roll mixer, shaking mixer, shear mixer or compulsory mixer.

The resultant mixture is preferably directly shaped into the pharmaceutical dosage form according to the invention by application of force with preceding and/or simultaneous exposure to heat. The mixture may, for example, be formed into tablets by direct tabletting.

In direct tabletting with preceding exposure to heat, the material to be pressed is heated immediately prior to tabletting at least to the softening temperature of component (C), preferably to its melting temperature, and then pressed. In the case of direct tabletting with simultaneous application of heat, the mixture to be press-formed is heated at least to the softening point of polymeric component (C) with the assistance of the tabletting tool, i.e. the bottom punch, top punch and the die, and is so press-formed.

This method may also be regarded as a sintering method and the dosage form thus obtained may be regarded as a sintered dosage form. In this regard, sintering means the solidification of crystalline, granular or powdered material by growing together of the crystallites when heated appropriately. The growing together can take place, e.g., by diffusion (solid/solid-reaction). The sintered structure can be analyzed by methods known in the art, e.g., by (electron)microscopy. As the dosage form contains several components, the sintering method is preferably a so-called "fusion sintering" where one of the components involved melts, wets and coats the higher-melting components. When cooling down, the melted component (re)solidifies. In a preferred embodiment, component (C) is the component that melts while the other components do not melt under the given conditions. Nonetheless, the other components may—but do not have to—at least partially dissolve in the melted component (C).

By such process using a tabletting tool with bottom punch, top punch and die, e.g. a powder mixture of all components may be compressed at a temperature of e.g. 80° C., the pressure caused by a force of e.g. 2 kN or 4 kN being maintained for e.g. 15 seconds.

The resultant mixture of components (A), (C), optionally (B) and/or (D) may also first be granulated and then, with preceding and/or simultaneous exposure to heat, be shaped into the pharmaceutical dosage form according to the invention by application of force.

Granulation may be performed in known granulators by wet granulation or melt granulation.

Each of the above-mentioned process steps, in particular the heating steps and simultaneous or subsequent application of force for production of the pharmaceutical dosage form according to the invention proceeds without using an extruder.

Process Variant 2

In this process variant, the pharmaceutical dosage form according to the invention is produced by thermoforming with the assistance of an extruder, preferably without there being any observable consequent discoloration of the extrudate.

In order to investigate the extent of discoloration due to this thermoforming, the colour of the mixture of starting components of which the pharmaceutical dosage form consists is first determined without addition of a color-imparting component, such as for example a coloring pigment or an intrinsically colored component (for example α-tocopherol). This composition is then thermoformed according to the invention, wherein all process steps, including cooling of the extrudate, are performed under an inert gas atmosphere. By way of comparison, the same composition is produced by the same process, but without an inert gas atmosphere. The color of the pharmaceutical dosage form produced according to the invention from the starting composition and of the pharmaceutical dosage form produced by way of comparison is determined. The determination is performed with the assistance of "Munsell Book of Color" from Munsell Color Company Baltimore, Md., USA, 1966 edition. If the color of the pharmaceutical dosage form thermoformed according to the invention has a color with identification no. N 9.5, but at most a color with the identification no. 5Y 9/1, thermoforming is classed as being "without discoloration". If the pharmaceutical dosage form has a color with the identification no. 5Y 9/2 or greater, as determined according to the Munsell Book of Color, the thermoforming is classed as being "with discoloration".

Surprisingly, the pharmaceutical dosage forms according to the invention exhibit no discoloration classed in accordance with the above classification, if the entire production process is performed under an inert gas atmosphere, preferably under a nitrogen atmosphere with the assistance of an extruder for thermoforming.

This variant according to the invention for the production of pharmaceutical dosage forms according to the invention is characterized in that z) components (A), (C), optionally (B) and/or (D) are mixed, y) the resultant mixture is heated in the extruder at least up to the softening point of component (C) and extruded through the outlet orifice of the extruder by application of force, x) the still plastic extrudate is singulated and formed into the pharmaceutical dosage form or w) the cooled and optionally reheated singulated extrudate is formed into the pharmaceutical dosage form, wherein process steps y) and x) and optionally process steps z) and w) are performed under an inert gas atmosphere, preferably a nitrogen atmosphere.

Mixing of the components according to process step z) may also proceed in the extruder.

Components (A), (C), optionally (B) and/or (D) may also be mixed in a mixer known to the person skilled in the art. The mixer may, for example, be a roll mixer, shaking mixer, shear mixer or compulsory mixer.

Before blending with the remaining components, component (C) and/or (D) is preferably provided according to the invention with an antioxidant. This may proceed by mixing the two components, (C) and the antioxidant, preferably by dissolving or suspending the antioxidant in a highly volatile solvent and homogeneously mixing this solution or suspension with component (C) and the optionally present component (D) and removing the solvent by drying, preferably under an inert gas atmosphere.

The, preferably molten, mixture which has been heated in the extruder at least up to the softening point of component (C) is extruded from the extruder through a die with at least one bore.

The process according to the invention requires the use of suitable extruders, preferably screw extruders. Screw extruders which are equipped with two screws (twin-screw-extruders) are particularly preferred.

The extrusion is preferably performed so that the expansion of the strand due to extrusion is not more than 50%, i.e. that when using a die with a bore having a diameter of e.g. 6 mm, the extruded strand should have a diameter of not more than 9 mm. More preferably, the expansion of the strand is not more than 40%, still more preferably not more than 35%, most preferably not more than 30% and in particular not more than 25%. It has been surprisingly found that if the extruded material in the extruder is exposed to a mechanical stress exceeding a certain limit, a significant expansion of the strand occurs thereby resulting in undesirable irregularities of the properties of the extruded strand, particularly its mechanical properties.

Preferably, extrusion is performed in the absence of water, i.e., no water is added. However, traces of water (e.g., caused by atmospheric humidity) may be present.

The extruder preferably comprises at least two temperature zones, with heating of the mixture at least up to the softening point of component (C) proceeding in the first zone, which is downstream from a feed zone and optionally mixing zone. The throughput of the mixture is preferably from 2.0 kg to 8.0 kg/hour.

After heating at least up to the softening point of component (C), the molten mixture is conveyed with the assistance of the screws, further homogenised, compressed or compacted such that, immediately before emerging from the extruder die, it exhibits a minimum pressure of 5 bar, preferably of at least 7.5 bar, more preferably at least 10 bar, still more preferably at least 12.5 bar, yet more preferably at least 15 bar, most preferably at least 17.5 bar and in particular at least 20 bar, and is extruded through the die as an extruded strand or strands, depending on the number of bores which the die comprises.

In a preferred embodiment, the die head pressure is within the range of from 25 to 85 bar. The die head pressure can be adjusted inter alia by die geometry, temperature profile and extrusion speed.

The die geometry or the geometry of the bores is freely selectable. The die or the bores may accordingly exhibit a round, oblong or oval cross-section, wherein the round cross-section preferably has a diameter of 0.1 mm to 15 mm and the oblong cross-section preferably has a maximum lengthwise extension of 21 mm and a crosswise extension of 10 mm. Preferably, the die or the bores have a round cross-section. The casing of the extruder used according to the invention may be heated or cooled. The corresponding temperature control, i.e. heating or cooling, is so arranged that the mixture to be extruded exhibits at least an average temperature (product temperature) corresponding to the softening temperature of component (C) and does not rise above a temperature at which the pharmacologically active compound (A) to be processed may be damaged. Preferably, the temperature of the mixture to be extruded is adjusted to below 180° C., preferably below 150° C., but at least to the softening temperature of component (C). Typical extrusion temperatures are 120° C. and 130° C.

In a preferred embodiment, the extruder torque is within the range of from 25 to 55 N/m. Extruder torque can be adjusted inter alia by die geometry, temperature profile and extrusion speed.

After extrusion of the molten mixture and optional cooling of the extruded strand or extruded strands, the extrudates are preferably singulated. This singulation may preferably be performed by cutting up the extrudates by means of revolving or rotating knives, water jet cutters, wires, blades or with the assistance of laser cutters.

An inert gas atmosphere is not necessary for intermediate or final storage of the optionally singulated extrudate or the final shape of the pharmaceutical dosage form according to the invention.

The singulated extrudate may be pelletized with conventional methods or be press-formed into tablets in order to impart the final shape to the pharmaceutical dosage form. It is, however, also possible not to singulate the extruded strands and, with the assistance of contrarotating calendar rolls comprising opposing recesses in their outer sleeve, to form them into the final shape, preferably a tablet, and to singulate these by conventional methods.

Should the optionally singulated extrudate not immediately be formed into the final shape, but instead cooled for storage, after the period of storage an inert gas atmosphere, preferably a nitrogen atmosphere, should be provided and must be maintained during heating of the stored extrudate up until plasticization and definitive shaping to yield the pharmaceutical dosage form.

The application of force in the extruder onto the at least plasticized mixture is adjusted by controlling the rotational speed of the conveying device in the extruder and the geometry thereof and by dimensioning the outlet orifice in such a manner that the pressure necessary for extruding the plasticized mixture is built up in the extruder, preferably immediately prior to extrusion. The extrusion parameters which, for each particular composition, are necessary to give rise to a pharmaceutical dosage form with a resistance to crushing of at least 400 N, preferably of at least 500 N, may be established by simple preliminary testing.

For example, extrusion may be performed by means of a twin-screw-extruder type Micro 27 GL 40 D (Leistritz, Nürnberg, Germany), screw diameter 27 mm. Screws having eccentric ends may be used. A heatable die with a round bore having a diameter of 8 mm may be used. The entire extrusion process should be performed under nitrogen atmosphere. The extrusion parameters may be adjusted e.g. to the following values: rotational speed of the screws: 100 Upm; delivery rate: 4 kg/h; product temperature: 125° C.; and jacket temperature: 120° C.

Process Variant 3

In this process variant for the production of the pharmaceutical dosage form according to the invention energy is applied to a mixture of the components by means of ultrasonication.

First of all a homogeneous mixture of at least component (A) and component (C) (=binder) is produced. Further auxiliary substances, such as for example fillers, plasticizers, slip agents or dyes, may also be incorporated into this mixture. A low molecular weight polyethylene glycol is preferably used as plasticizer.

Mixing may be performed with the assistance of conventional mixers. Examples of suitable mixers are roll mixers, which are also known as tumbler, drum or rotary mixers, container mixers, barrel mixers (drum hoop mixers or tumbling mixers) or shaking mixers, shear mixers, compulsory mixers, plough bar mixers, planetary kneader-mixers, Z kneaders, sigma kneaders, fluid mixers or high-intensity mixers.

Selection of the suitable mixer is determined inter alia by the flowability and cohesiveness of the material to be mixed.

The mixture is then subjected to shaping. The mixture is preferably shaped during or after ultrasonication, preferably by compaction.

It is particularly preferred during ultrasonication that there is direct contact between the mixture and the sonotrode of the ultrasound device.

A frequency of 1 kHz to 2 MHz, preferably of 15 to 40 kHz, should be maintained during ultrasonication. Ultrasonication should be performed until softening of the polymer (C) is achieved. This is preferably achieved within a few seconds, particularly preferably within 0.1 to 5 seconds, preferably 0.5 to 3 seconds.

Ultrasonication and the application of force ensure uniform energy transfer, so bringing about rapid and homogeneous sintering of the mixture. In this manner, pharmaceutical dosage forms are obtained which have a resistance to crushing of at least 400 N, preferably of at least 500 N, and thus cannot be pulverized.

Before shaping is performed, the mixture may be granulated after the mixing operation, after which the resultant granules are shaped into the pharmaceutical dosage form with ultrasonication and application of force.

Granulation may be performed in machinery and apparatus known to the person skilled in the art.

If granulation is performed as wet granulation, water or aqueous solutions, such as for example ethanol/water or isopropanol/water, may be used as the granulation liquid.

The mixture or the granules produced therefrom may also be subjected to melt extrusion for further shaping, wherein the mixture is converted into a melt by ultrasonication and exposure to force and then extruded through a dies. The strands or strand obtained in this manner may be singulated to the desired length using known apparatus. The formed articles singulated in this manner may optionally furthermore be converted into the final shape with ultrasonication and application of force.

Final shaping to yield the pharmaceutical dosage form preferably proceeds with application of force in appropriate moulds.

The above-described formed articles may also be produced with a calendering process by initially plasticising the mixture or the granules produced therefrom by means of ultrasonication and application of force and performing extrusion through an appropriate die. These extrudates are then shaped into the final shape between two contrarotating shaping rolls, preferably with application of force.

As already mentioned, shaping to yield the final shape of the pharmaceutical dosage form by using a mixture comprising pharmacologically active compound (A) and polymer (C) proceeds preferably in powder form by direct compression with application of force, wherein ultrasonication of this mixture is provided before or during the application of force. The force is at most the force which is conventionally used for shaping pharmaceutical dosage forms, such as tablets, or for press-forming granules into the corresponding final shape.

The tablets produced according to the invention may also be multilayer tablets.

In multilayer tablets, at least the layer which contains pharmacologically active compound (A) should be ultrasonicated and exposed to force.

The corresponding necessary application of force may also be applied to the mixture with the assistance of extruder rolls or calender rolls. Shaping of the pharmaceutical dosage forms preferably proceeds by direct press-forming of a pulverulent mixture of the components of the pharmaceutical dosage form or corresponding granules formed therefrom, wherein ultrasonication preferably proceeds during or before shaping. Such exposure continues until the polymer (C) has softened, which is conventionally achieved in less than 1 second to at most 5 seconds.

A suitable press is e.g. a Branson WPS, 94-003-A, pneumatical (Branson Ultraschall, Dietzenbach, Germany) having a plain press surface. A suitable generator (2000 W) is e.g. a Branson PG-220A, 94-001-A analogue (Branson Ultraschall) with a sonotrode having a diameter of 12 mm. A die having a diameter of 12 mm may be used, the bottom of the die being formed by a bottom punch having a plain press-surface and a diameter of 12 mm. Suitable parameters for plastification are frequency: 20 kHz; amplitude: 50%; force: 250 N. The effect of ultrasound and force by means of the sonotrode may be maintained for e.g. 0.5 seconds, and preferably both effects take place simultaneously.

Process Variant 4

In this process variant for the production of the pharmaceutical dosage form according to the invention, components (A), (C), optionally (B), such as antioxidants, plasticizers and/or delayed-release auxiliary substances, and optionally component (D), are processed with the assistance of a planetary-gear extruder to yield the pharmaceutical dosage form according to the invention.

Planetary-gear extruders are known and described inter alia in detail in Handbuch der Kunststoff-Extrusionstechnik I (1989) "Grundlagen" in Chapter 1.2 "Klassifizierung von Extrudern", pages 4 to 6. The corresponding description is hereby introduced as a reference and is deemed to be part of the disclosure.

The mixture is conveyed into the feed zone of the planetary-gear extruder. By heating at least to the softening point of component (C), the mixture is melted and the molten mixture is conveyed into the area of the central spindle, i.e. the extrusion zone, by the interaction of the central spindle 3 and the planetary spindles 4, further homogenized, compressed or compacted and extruded through the die 8 as an extruded strand or extruded strands, depending on how many bores the die comprises. The die geometry or the geometry of the bores is freely selectable. Thus, the die or the bores may exhibit a round, oblong or oval cross-section, wherein the round cross-section preferably has a diameter of 0.1 mm to 15 mm and the oblong cross-section preferably has a maximum lengthwise extension of 21 mm and a crosswise extension of 10 mm. The extrusion die may also take the form of a slot die. Preferably, the die or the bores have a round, oval or oblong cross-section. Both the casing 6 of the planetary-gear extruder used according to the invention and the central spindle may be heated or cooled. The corresponding temperature control, i.e. heating or cooling, is so arranged that the mixture to be extruded exhibits an average temperature corresponding to the softening temperature of component (C) and does not rise above a temperature at which component (A) to be processed may be damaged. Preferably, the temperature of the mixture to be extruded is adjusted to below 180° C., preferably below 150° C., but at least to the softening temperature of component (C).

After extrusion of the molten mixture and optional cooling of the extruded strand or extruded strands, the extrudates are singulated. This singulation may preferably be performed by cutting up the extrudates by means of revolving or rotating knives, water jet cutters, wires, blades or with the assistance of laser cutters.

Optionally after further cooling of the singulated extrudates, which are preferably present in the form of disks, they are optionally re-shaped into the final shape of the pharmaceutical dosage form, wherein they may be exposed to heat again if necessary.

This shaping for example into tablets may proceed in that the plastic extrudate is shaped with press-forming with the assistance of two contrarotating rolls preferably with mutually opposing recesses for plastification in the roll sleeve, the construction of which recesses determines the tablet shape.

However, it is also possible to form the tablets from the singulated extrudates in each case with the assistance of an optionally heated die and at least one shaping punch. To this end, the cylindrical granules obtained after singulation of the extruded strand may preferably be used. Apart from being press-formed into tablets, these granules or other multiparticulate shapes obtained, such as pellets or spheroids, may also be packaged into capsules in order to be used as a pharmaceutical dosage form produced according to the invention.

In a further preferred embodiment, the extruded strands extruded through a plurality of bores in the extrusion die may, after cooling thereof, optionally be brought together by interlacing or wrapping in the manner of rope production to yield a thicker strand than the individual extruded strands. This strand may optionally be further processed by solvent attack with a suitable solvent or by heating to the softening point of the polymer (C) and optionally removing the solvent in accordance with the above-stated singulation and shaping of an individual strand.

If necessary, the planetary-gear extruder used may comprise not only an extrusion zone but also at least one further zone, so that the mixture to be extruded may optionally also be degassed.

The process according to the invention may be performed discontinuously or continuously, preferably continuously.

A suitable extruder, for example, is a planetary gear extruder type BCG 10 (LBB Bohle, Ennigerloh, Germany) having four planetary spindles and an extrusion die with bores having a diameter of 8 mm. A gravimetrical dosing of 3.0 kg/h is suitable. The extrusion may be performed, for example, at a rotational speed of 28.6 rmp and a product temperature of about 88° C.

Process Variant 5

This variant for the production of the pharmaceutical dosage form according to the invention is performed by processing at least the components (A), (C), optionally (B), such as antioxidants, plasticizers and/or delayed-release auxiliary substances, and optionally component (D), with addition of a solvent for component (C), i.e. for the polymer or polymers (C), to yield the pharmaceutical dosage form.

To this end, components (A), (C), optionally (B) and/or (D) are mixed and, after addition of the solvent and optionally after granulation, the resultant formulation mixture is shaped to yield the pharmaceutical dosage form.

Components (A), (C), optionally (B) and/or (D) are mixed in a mixer known to the person skilled in the art. The mixer may, for example, be a roll mixer, shaking mixer, shear mixer or compulsory mixer.

The solvent for the polymer (C) is added at least in such quantities that the formulation mixture is uniformly moistened.

Solvents which are suitable for the polymer (C) are preferably aqueous solvents, such as water, mixtures of water and aliphatic alcohols, preferably $C_1$ to $C_6$ alcohols, esters, ethers, hydrocarbons, particularly preferably distilled water, short-chain alcohols, such as methanol, ethanol, isopropanol, butanol or aqueous alcohol solutions.

The solvent is preferably added with stirring. The uniformly moistened composition is then dried. Drying preferably proceeds with exposure to heat at temperatures at which it is possible to rule out any discoloration of the composition. This temperature may be established by simple preliminary testing.

Before or after drying, the composition may be divided into sub-portions which preferably in each case correspond to the mass of a unit of the pharmaceutical dosage form. The corresponding dried portions are then shaped to yield the pharmaceutical dosage form.

This is preferably achieved by using tablet presses.

The formulation mixture may also be moistened in such a manner that, before addition of the solvent, the formulation mixture is divided, preferably in moulds, into sub-portions, is dispersed in a liquid dispersant with stirring and then the solvent is added. Component (C) is not soluble in the dispersant, which must be miscible with the solvent.

Suitable dispersants are preferably hydrophilic solvents, such as aliphatic alcohols, ketones, esters. Short-chain alcohols are preferably used.

Alternatively, the formulation mixture may also be moistened in such a manner that the solvent is incorporated into the formulation mixture as a foam. Such a foam of the solvent is preferably produced with the assistance of a high-speed mixer, preferably with the addition of conventional foam stabilizers. Suitable stabilizers are, for example, hydrophilic polymers such as for example hydroxypropylmethylcellulose.

The foam is also preferably incorporated into the formulation mixture with stirring, a granulated composition so preferably being obtained.

Before or after being divided into sub-portions, which preferably correspond to the mass of a unit of the pharmaceutical dosage form, the granulated composition is dried and then shaped into the pharmaceutical dosage form.

Drying and shaping may preferably proceed as described above. The process according to the invention may also be performed in such a manner that solvent is added to the formulation mixture in such a quantity that a shapeable paste is obtained.

Before or after being dried, which may proceed as explained above, such a paste may be divided into sub-portions and the dried portions, after further division in each case into a portion corresponding to the mass of a unit of the pharmaceutical dosage form, are shaped or converted to yield the pharmaceutical dosage form.

It is here possible to form the sub-portions in the form of strands, which may be produced with the assistance of a screen or a strand former. The dried strands are preferably singulated and shaped to yield the pharmaceutical dosage form. This shaping preferably proceeds with the assistance of a tablet press, using shaping rollers or shaping belts equipped with rollers.

It is also possible to convert the paste into a planar structure and to stamp the pharmaceutical dosage form out of it once it has dried.

The paste is advantageously processed with an extruder, wherein, depending on the configuration of the extrusion, strands or planar structures articles are produced, which are singulated by chopping, cutting or stamping. The singulated sub-portions may be shaped, formed or stamped as described above to yield the pharmaceutical dosage form. Corresponding apparatuses are known to the person skilled in the art.

The process according to the invention may here be performed continuously or discontinuously.

It is also possible to add solvent to the formulation mixture in such a quantity that at least the polymer component (C) is dissolved. Such a solution or dispersion/suspension is preferably converted into a planar structure, an extruder with a flat die preferably being used or the solution being cast onto a planar support.

As stated above, after drying, the pharmaceutical dosage forms may be obtained from the planar structures by stamping or calendering. It is also possible, as stated above, to convert the solution into strands and to singulate these, preferably after they have been dried, and shape them to yield the pharmaceutical dosage form.

Alternatively, the solution may also be divided into portions such that, after drying, they each correspond to the mass of a unit of the pharmaceutical dosage form, with moulds which already correspond to the shape of the unit of the pharmaceutical dosage form preferably being used for this purpose.

If the solution is divided into any desired portions, the portions may, after drying, optionally be combined again and be shaped to form the pharmaceutical dosage form, being for example packaged in a capsule or press-formed to form a tablet.

The formulation mixtures combined with solvent are preferably processed at temperatures of 20° C. to 40° C., wherein, apart from during drying to remove the solvent and the optionally present dispersant, no higher temperatures are used. The drying temperature must be selected below the decomposition temperature of the components. After shaping to yield the pharmaceutical dosage form, further drying corresponding to the above-described drying may optionally be performed.

Combinations of individual process steps of the above process variants are also possible in order to produce the pharmaceutical dosage form according to the invention.

Process variants 2 and 4 as described above involve the extrusion of a composition comprising components (A), (C), optionally (B) and/or (D). Preferably, extrusion is performed by means of twin-screw-extruders or planetary-gear-extruders, twin-screw extruders being particularly preferred.

The process for the preparation of the pharmaceutical dosage form according to the invention is preferably performed continuously. Preferably, the process involves the extrusion of a homogeneous mixture of components (A), (C), optionally (B) and/or (D). It is particularly advantageous if the obtained intermediate, e.g. the strand obtained by extrusion, exhibits uniform properties. Particularly desirable are uniform density, uniform distribution of the active compound, uniform mechanical properties, uniform porosity, uniform appearance of the surface, etc. Only under these circumstances the uniformity of the pharmacological properties, such as the stability of the release profile, may be ensured and the amount of rejects can be kept low.

Preferably, the process according to the present invention may be performed with less than 25% rejects, more preferably less than 20%, most preferably less than 15% and in particular less than 10% rejects, wherein the criteria for rejection are the FDA standards regarding the intervariability of the content of component (A), its release profile and/or the density of the pharmaceutical dosage form when comparing two pharmaceutical dosage forms, preferably taken from the same batch.

It has been surprisingly found that the above properties may be obtained by means of twin-screw-extruders and planetary-gear-extruders, twin-screw-extruders being particularly preferred.

Further, it has been surprisingly found that extrudates exhibiting an advantageous morphology are obtainable by means of planetary-gear-extruders and twin-screw-extruders. It has been found that under suitable conditions the extrudate is surrounded by a shell which may be denoted as "extrusion skin". Said extrusion skin can be regarded as a collar-like or tubular structure forming a circumferential section of the extrudate about its longitudinal extrusion axis so that the outer surface of said collar-like or tubular structure forms the closed shell of the extrudate. Usually, only the front faces of the extrudate are not covered by said extrusion skin.

The extrusion skin surrounds the core of the extrudate in a collar-like or tubular arrangement and preferably is connected therewith in a seamless manner. The extrusion skin differs from said core in its morphology. Usually, the extrusion skin is visible with the naked eye in the cross-section of the extrudate, optionally by means of a microscope, since due to the different morphology of the material forming the extrusion skin and the material forming the core, the optical properties differ as well. It seems that during extrusion the material forming the extrusion skin is exposed to mechanical and thermal conditions differing from the conditions the core of the extrudate is exposed to. In consequence, a heterogeneous morphology of the extruded strand is obtained, which e.g. assumes radial symmetry when an extrusion die having circular shape is used. The material forming the extrusion skin and the material forming the core are usually distinguished by their morphology, preferably, however, not by their composition, particularly not by the relative content of components (A), (C), optionally (B) and/or (D).

Usually the extrusion skin covers the entire shell of the extrudate like a one-piece collar, independently of what geometry has been chosen for the extrusion die. Therefore, the extrudate may assume circular, elliptic or other cross-sections.

The extrusion skin is preferably characterized by a unitary thickness. Preferably, the thickness of the extrusion skin is within the range from 0.1 to 4.0 mm, more preferably 0.15 to 3.5 mm, still more preferably 0.2 to 3.0 mm, most preferably 0.2 to 2.5 mm and in particular 0.2 to 2.0 mm. In a preferred embodiment the thickness of the extrusion skin in the sum over both opposing sides amounts to 0.5 to 50%, more preferably 1.0 to 40%, still more preferably 1.5 to 35%, most preferably 2.0 to 30% and in particular 2.5 to 25% of the diameter of the extrudate.

When the pharmaceutical dosage forms according to the invention are prepared by means of extrusion processes which lead to intermediates having an extrusion skin as described above, the pharmaceutical dosage forms obtained therefrom are preferably also characterized by a particular morphology.

In a preferred embodiment those regions, which have formed the extrusion skin in the extruded intermediate, are still visible with the naked eye, optionally by means of a microscope, in the cross-section of the pharmaceutical dosage form. This is because usually by further processing the extrudate, particularly by singulating and/or shaping, the different nature and thereby also the different optical properties of the material forming the extrusion skin and the material forming the core are maintained. In the following, that domain of the pharmaceutical dosage forms which has emerged from the extrusion skin in the course of further processing the extruded intermediate, will be denoted as "skin domain".

Preferably, the pharmaceutical dosage form according to the invention comprises a skin domain and a core located therein. Preferably, the skin domain is connected with the core in a seamless manner. Preferably the skin domain as well as the core have substantially the same chemical composition, i.e. substantially the same relative content of components (A), (C), optionally (B) and/or (D). The material forming the skin domain has a morphology differing from the material forming the core. Usually, this different morphology is also expressed in terms of different optical properties, so that the skin domain and the core are visible with the naked eye in the cross-section of the pharmaceutical dosage form.

In case that the pharmaceutical dosage form has been coated, e.g. by a film coating, the skin domain is located between the film coating and the core.

Since the pharmaceutical dosage form according to the invention may be obtained in different ways from the extrudate containing the extrusion skin (intermediate), the skin domain may take different arrangements and extensions within the pharmaceutical dosage form according to the invention. All arrangements have in common, however, that the skin domain partially covers the surface of the core, but usually not its entire surface. Preferably, two opposing surfaces of the core are not, or at least not fully covered by the skin domain. In other words, preferably the skin domain has two openings/blanks on opposing sides.

The thickness of the skin domain may be uniform. It is also possible, however, that in the course of the processing, i.e. due to the subsequent shaping (e.g. press-forming) of the extrudate, various sections of the extrusion skin are expanded or compressed differently thereby leading to a variation of the thickness of the skin domain within the pharmaceutical dosage form.

Preferably the thickness of the skin domain is within the range from 0.1 to 4.0 mm, more preferably 0.15 to 3.5 mm, still more preferably 0.2 to 3.0 mm, most preferably 0.2 to 2.5 mm and in particular 0.2 to 2.0 mm.

The process according to the invention preferably involves the extrusion of a mixture of components (A), (C), optionally (B) and/or (D), preferably by means of a planetary-gear-extruder or a twin-screw-extruder. After extrusion the extrudate is preferably singulated, shaped and optionally coated in order to obtain the final pharmaceutical dosage form.

In a preferred embodiment of the process according to the invention, shaping is performed in the plasticized state of the mixture of components (A), (C), optionally (B) and/or (D). It has been surprisingly found that the extrusion of certain polymers (C), particular of high molecular weight polyethylene oxides, yields intermediates exhibiting some kind of memory effect: when the singulated extrudates are shaped at ambient temperature, e.g. by press-forming, pharmaceutical dosage forms are obtained which tend to regain their original outer form upon storage under stressed storage conditions, i.e. they return to the form they had prior to shaping.

The shape of the pharmaceutical dosage form upon storage at stressed conditions, e.g. at 40° C./75% RH, may also be unstable for other reasons.

Said memory effect significantly deteriorates the storage stability of the pharmaceutical dosage form, as by regaining its outer form several properties of the pharmaceutical dosage form are changed. The same applies to any changes of the outer form due to other reasons.

It has been found that, for example, depending on the extrusion conditions a significant expansion of the strand may occur thereby resulting in an increase of the volume of the extrudate, i.e. a decrease of its density. Said expansion may be compensated by subsequently press-forming the singulated extrudate at a sufficient pressure, since under these conditions the expansion of the material may be reversed.

However, if press-forming has been performed at ambient temperature, the memory effect of the compressed extrudate will cause it to swell and to expand upon storage, thereby significantly increasing the volume of the pharmaceutical dosage form.

It has been surprisingly found that such memory effect may be suppressed if shaping of the singulated extrudate is performed at increased temperature, i.e. in the plasticized state of the mixture of components (A), (C), optionally (B) and/or (D). Preferably, shaping is performed at a pressure of at least 1 kN, more preferably within the range from 2 kN to 50 kN, e.g. by means of a tablet press. Preferably, shaping is performed at a temperature which preferably is about 40° C., more preferably about 30° C. and in particular about 25° C. below the melting range of the mixture of components (A), (C), optionally (B) and/or (D). The melting range of a given mixture may be determined by conventional methods, preferably by DSC (e.g. with a DSC model 2920 (TA Instruments, New Castle) and ultrahigh pure nitrogen as purge gas at a flow rate of 150 ml/min; approximate sample weight of 10-20 mg, sealed in nonhermetic aluminium pans; temperature ramp speed 10° C./min).

In a preferred embodiment the outer shape of the pharmaceutical dosage form according to the invention does not substantially change when being stored for at least 12 h, preferably for at least 24 h, at 40° C. and 75% RH, preferably in an open container.

In a preferred embodiment the volume of the pharmaceutical dosage form according to the invention increases by not more than 20% or 17.5%, more preferably not more than 15% or 12.5%, still more preferably not more than 10% or 7.5%, most preferably not more than 6.0%, 5.0% or 4.0% and in particular not more than 3.0%, 2.0% or 1.0% when being stored for at least 12 h, preferably for at least 24 h, at a temperature of 20° C. below the melting range of the mixture of components (A), (C), optionally (B) and/or (D), optionally at a temperature of 40° C. and 75% RH.

A further aspect of the invention relates to a packaging containing the pharmaceutical dosage form according to the invention and an oxygen scavenger. Suitable packages include blister packages and bottles, such as glass bottles or bottles made from thermoplastic polymers.

Oxygen scavengers and the application thereof in pharmaceutical packaging are known to the skilled artisan. In a preferred embodiment, the oxygen scavenger is selected from the group consisting of metal-catalyzed oxidizable organic polymers and anti-oxidants. It has been surprisingly found that the storage stability of the pharmaceutical dosage form can be increased when keeping the oxygen content of the atmosphere within the packaging low. Methods for packaging pharmaceutical dosage forms and the application of suitable oxygen scavengers are known to the skilled artisan. In this regard it can be referred to e.g. D. A. Dean, Pharmaceutical Packaging Technology, Taylor & Francis, 1st ed.; F. A. Paine et al., Packaging Pharmaceutical and Healthcare Products, Springer, 1st ed.; and O. G. Piringer et al., Plastic Packaging: Interactions with Food and Pharmaceuticals, Wiley-VCH, 2nd ed.

The pharmaceutical dosage form according to the invention is suitable to avoid various misuses, particularly accidental misuse (e.g. unintentional);

recreational misuse; and experienced drug misuse.

A further aspect of the invention relates to the use of an opioid for the manufacture of the pharmaceutical dosage form as described above for the treatment of pain.

A further aspect of the invention relates to the use of a pharmaceutical dosage form as described above for avoiding or hindering the abuse of the pharmacologically active compound (A) contained therein.

A further aspect of the invention relates to the use of a pharmaceutical dosage form as described above for avoiding or hindering the unintentional overdose of the pharmacologically active compound (A) contained therein.

In this regard, the invention also relates to the use of a pharmacologically active compound (A) as described above and/or a synthetic or natural polymer (C) as described above for the manufacture of the pharmaceutical dosage form according to the invention for the prophylaxis and/or the treatment of a disorder, thereby preventing an overdose of the pharmacologically active compound (A), particularly due to comminution of the pharmaceutical dosage form by mechanical action.

Further, the invention relates to a method for the prophylaxis and/or the treatment of a disorder comprising the administration of the pharmaceutical dosage form according to the invention, thereby preventing an overdose of the pharmacologically active compound (A), particularly due to comminution of the pharmaceutical dosage form by mechanical action. Preferably, the mechanical action is selected from the group consisting of chewing, grinding in a mortar, pounding, and using apparatuses for pulverizing conventional pharmaceutical dosage forms.

The invention is explained below with reference to examples. These explanations are given merely by way of example and do not limit the general concept and scope of the invention.

Example 1

Formulation Examples

A. Formulation Examples for Retarded Release Formulations

| | |
|---|---|
| Active ingredient(s) | 0.01-50% (w/w) |
| Viscous hydrophilic polymer(s) | 0.01-80% (w/w) |
| Pregelatinized starch | 5-80% (w/w) |
| Pharmaceutically acceptable formulating agents | ad 100% (w/w). |
| Active ingredient(s) | 0.01-50% (w/w) |
| Viscous hydrophilic polymer(s) comprising hydroxypropyl cellulose | 0.01-80% (w/w) |
| Pregelatinized starch | 5-80% (w/w) |
| Pharmaceutically acceptable formulating agents | ad 100% (w/w). |
| Active ingredient(s) | 0.01-50% (w/w) |
| Viscous hydrophilic polymer(s) | 0.01-80% (w/w) |
| Pregelatinized starch | 5-15% (w/w) |
| Pharmaceutically acceptable formulating agents | ad 100% (w/w). |
| Active ingredient(s) | 0.01-50% (w/w) |
| Viscous hydrophilic polymer(s) comprising hydroxypropyl cellulose | 0.01-80% (w/w) |
| Pregelatinized starch | 5-15% (w/w) |
| Pharmaceutically acceptable formulating agents | ad 100% (w/w). |
| Active ingredient(s) | 0.01-50% (w/w) |
| Viscous hydrophilic polymer(s) | 0.01-80% (w/w) |
| Pregelatinized starch | 5% (w/w) |
| Pharmaceutically acceptable formulating agents | ad 100% (w/w). |
| Active ingredient(s) | 0.01-50% (w/w) |
| Viscous hydrophilic polymer(s) comprising hydroxypropyl cellulose | 0.01-80% (w/w) |
| Pregelatinized starch | 5% (w/w) |
| Pharmaceutically acceptable formulating agents | ad 100% (w/w). |
| Active ingredient(s) | 0.01-50% (w/w) |
| Hydroxypropyl cellulose | 25-62% (w/w) |
| Hydroxypropyl methylcellulose | 0-16% (w/w) |
| Pregelatinized starch | 5-15% (w/w) |
| Pharmaceutically acceptable formulating agents | ad 100% (w/w). |

The above formulations can generally be prepared according to the following process:

(1.a) one or more active ingredients, pregelatinized starch, one or more viscous hydrophilic polymers and optionally some or all of the pharmaceutically acceptable formulating agents are mixed;

(1.b) the powder mixture prepared under (1.a) is run through a compactor, thus yielding plates;

(1.c) the resulting plates are broken down and sieved, thus yielding granules;

(1.d) the resulting granules are optionally mixed with all or the remainder of the pharmaceutically acceptable formulating agents, preferably until homogeneous.

In case the active ingredient(s) is a sparingly water soluble, slightly water soluble, very slightly water soluble, practically water insoluble or water insoluble drug or a drug with a pH dependent solubility, in particular an alkaline drug, the active ingredient(s) can in one embodiment be incorporated in the controlled release formulation as an intimate mixture with a cyclodextrin or derivatives thereof or another water soluble polymer, as described hereinabove. In said case, the preparation of the present controlled release formulation comprises an additional first step, namely (2.a) one or more active ingredients and the water soluble polymer are intimately mixed;

(2.b) the intimate mixture prepared under (2.a) is mixed with pregelatinized starch, one or more viscous hydrophilic polymers and optionally some or all of the pharmaceutically acceptable formulating agents;

(2.c) the powder mixture prepared under (2.b) is run through a compactor, thus yielding plates;

(2.d) the resulting plates are broken down and sieved, thus yielding granules;

(2.e) the resulting granules are optionally mixed with all or the remainder of the pharmaceutically acceptable formulating agents, preferably until homogeneous.

The formulation obtained by the processes as described hereinabove in one embodiment can then be compressed in a tablet according to the invention by tabletting in a tabletting machine with punches and dies adapted for the tablet of the invention the final blend resulting from the above described processes, i.e. the blend resulting under (1.d) or (2.e).

A compactor as mentioned in step (1.b) or (2.c) of the above described processes is an apparatus wherein the powdery mixture is run between two rollers exerting pressure on the powdery mixture. In this way the mixture is compacted and sheets or plates are formed. Compactors are commercially available, for instance, from the company Gerteis (Jona, Swiss), e.g. a Polygran 3W compactor.

The above general route of preparation of the controlled release formulation may be modified by a person skilled in the art by for instance adding certain ingredients at other stages than indicated above.

As an alternative to the above described route of preparation involving a compaction step, the above described mixture can also be tabletted using direct compression. When using the technique of direct compression, dies or matrices in the form of the desired tablets of the invention are filled with a powdery mixture having the tablet composition and then are punched with punches adapted for the desired tablet. The advantage of this way of tabletting is that it usually requires less steps. Apparatuses for direct compression tabletting are known to the skilled parson. These apparatuses require forced feeding systems whenever the Theological properties of the mixture are not appropriate to fill the dies or matrices without forced feeding.

Example of a Retarded Release Formulation According to the Invention

| | |
|---|---|
| Cisapride-(L)-tartrate | 52.92 mg |
| Lactose monohydrate 200 mesh | 149.43 mg |
| Hydroxypropyl methylcellulose 2208 | 74.1 mg |
| Hydroxypropyl cellulose | 228.00 mg |
| Drum dried waxy maize starch | 28.5 mg |
| Magnesium stearate | 2.85 mg |
| Colloidal anhydrous silica | 5.7 mg |
| Talc | 28.5 mg |

Preparation of the Above Powder Mixture

Cisapride-(L)-tartrate, hydroxypropyl methylcellulose, hydroxypropyl cellulose, drum dried waxy maize starch, the lactose filler, are mixed in a planetary mixer, and than compacted using a dry compactor. The compact is broken down, sieved and mixed in a planetary mixer with colloidal anhydrous silica. Magnesium stearate is added and mixed.

The above mixture can then be compressed into a tablet according to the invention.

B. Formulation Examples for Immediate Release Formulations

A mixture of 100 g of active ingredient(s), 570 g lactose and 200 g starch is mixed well and thereafter humidified with a solution of 5 g sodium dodecyl sulfate and 10 g polyvinylpyrrolidone (Kollidon-K 90®) in about 200 ml of water. The wet powder mixture is sieved, dried and sieved again. Then there are added 100 g microcrystalline cellulose (Avicel®) and 15 g hydrogenated vegetable oil (Sterotex®). The whole is mixed well.

The above mixture can then be compressed into tablets according to the invention, giving 10.000 tablets, each comprising 10 mg of the active ingredient.

Example 2

Pharmaceutical dosage forms were manufactured from the following compositions:

|  | I-1 (#1) | I-2 (#2) | C-1 |
| --- | --- | --- | --- |
| tapentadol HCl | 291.20 | 291.20 | 291.20 |
| PEO Mw 7 Mio g/mol | 245.00 | 245.00 |  |
| PEO Mw 5 Mio g/mol |  |  | 247.70 |
| polyethylene glycole 6000 | 65.10 | 65.10 | 65.00 |
| HPMC 100,000 mPas | 98.00 | 98.00 | 45.50 |
| α-tocopherole | 0.70 | 0.70 | 0.65 |
| SUM | 700.00 | 700.00 | 650.00 |
| tablet format | 9 × 21 H0 | 9 × 21 H0 | 9 × 21 oblong |

291.20 mg tapentadol HCl correspond to 250 mg tapentadol free base.

General Procedure

The polyethylene oxide was melted at 90° C. and the total amount of α-tocopherol was dissolved therein. Then, tapentadol and hydroxypropyl methyl cellulose (HPMC) were mixed in a fast mixer for 5 min at a temperature of 70° C. The melt of polyethylene oxide and α-tocopherole was added to the mixture dropwise within 10 minutes. The thus obtained granulate was sieved on a taper sieving machine and then mixed in a free fall mixer for 15 min. The powder mixture was dosed gravimetrically to an extruder. Extrusion was performed by means of a twin screw extruder of type Micro 27 GL 40 D (Leistritz, Nürnberg, Germany) that was equipped with a heatable round die having a diameter of 8 mm.

The following extrusion conditions were adjusted:
Number of revolutions of screws: 100 Upm
Throughput: 4 kg/h
Product temperature: 120° C.
Shell temperature: 100° C.

The hot extrudate was cooled on a conveyor belt and the cooled extrusion strand was comminuted to cut pieces weighing 700 mg each. The cut pieces were shaped by means of an excenter press. The tablets of inventive examples I-1 and I-2 were shaped by means of an H-plunger (9*21 H0, type 21×9 WR 1.9 with "inner courtyard", Notter, Ölbronn-Dürrn, Germany) and the tablets of comparative example C-1 were shaped by means of a conventional oblong plunger.

The tablets of inventive examples I-1 and I-2 had the following dimensions (base height H according to FIG. 9B); width, height and length a, b and c according to FIG. 10) (average values n=10):

|  |  |  |
| --- | --- | --- |
| a |  | 9.06 |
|  | $a_1$ | 3.17 |
|  | $a_2$ | 2.72 |
|  | $a_3$ | 3.17 |
| b |  | 4.52 |
|  | $b_1$ | 0.99 |
|  | $b_2$ | 2.54 |
|  | $b_3$ | 0.99 |
| c |  | 20.49 |
|  | $c_1$ | 3.26 |
|  | $c_2$ | 13.97 |
|  | $c_3$ | 3.26 |
| H |  | 3.17 |

The manufacturer of the H0-plunger provides the following formula for the surface and the volume of the shaped tablets as a function of the base height (H):
volume = 94.3 + 171.6 × H [mm³] = 638.3 mm³
surface = 382 + 52.3 × H [mm²] = 547.8 mm²

In comparison, the surface of the pharmaceutical dosage form according to comparative example C-1 was estimated to be about 459 mm² (estimation in accordance with Eudragit® Application Guidelines, 10th edition, July 2007, Röhm GmbH, Darmstadt, page 25).

The correlation of the pharmaceutical dosage forms according to inventive examples I-1 and I-2 and according to comparative example C-1 with the requirement $S \geq A \cdot W^{2/3}$ are summarized in the following table:

|  | I-1/I-2 | C-1 |
| --- | --- | --- |
| weight W | 700 mg | 650 mg |
| surface S | 548 mm² | 459 mm² |
| S/W | 0.783 | 0.706 |
| A [for $S = A \cdot W^{2/3}$] | 6.95 | 6.12 |

Example 3

The dissolution profile of the tablets was investigated under the following conditions: Paddle apparatus equipped with sinker, 50 rpm, 37±5° C., 900 mL simulated intestinal fluid pH 6.8 (phosphate buffer).

The results are displayed in FIGS. 21 to 24.

Figure 21:
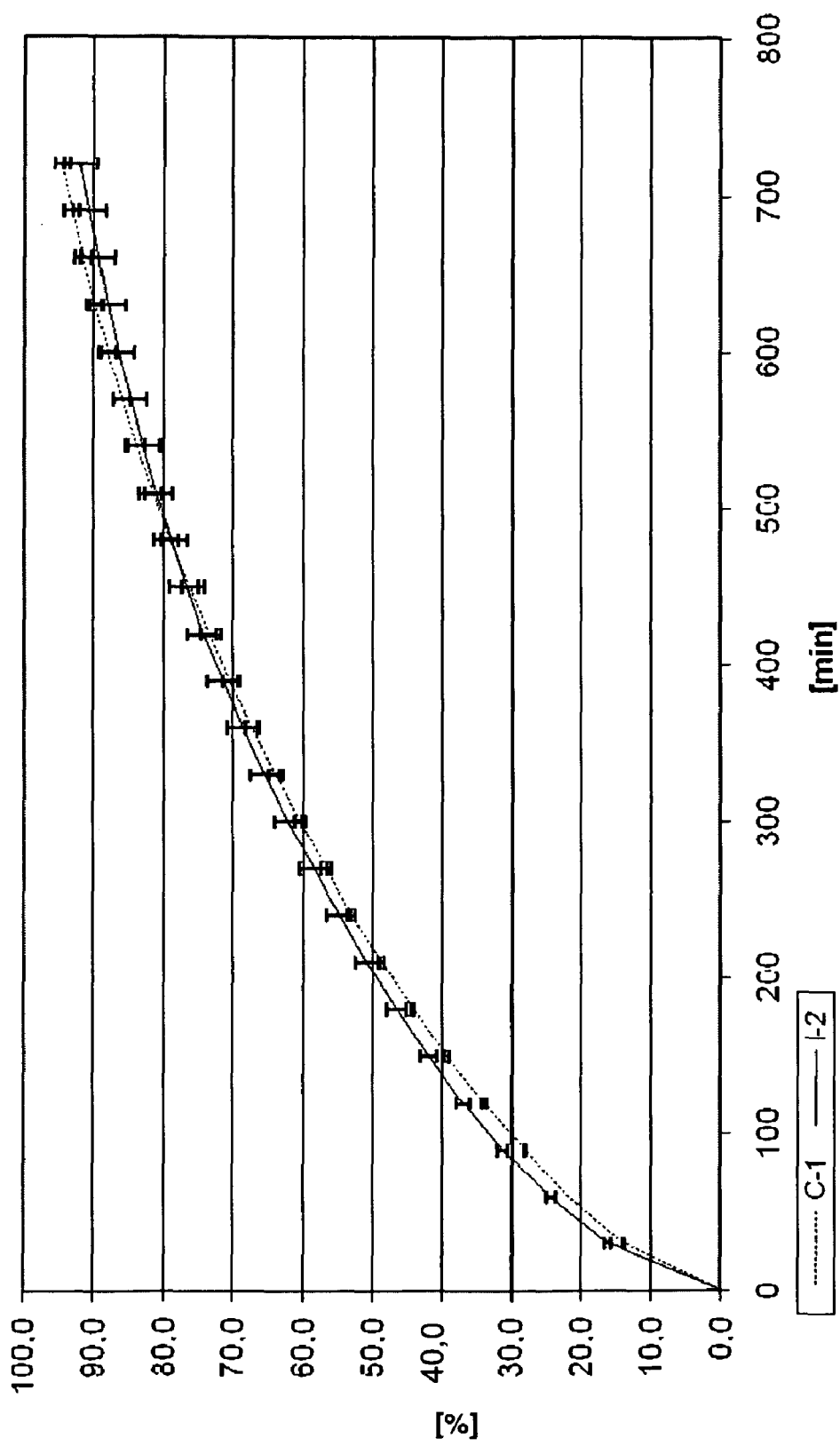
FIG. 21 shows the release profile of the tablet according to inventive example I-2 (H-shape) and of the tablet according to comparative example C-1 (oblong) immediately after manufacture.

FIG. 21 shows that immediately after manufacture the release profile of the tablet according to inventive example I-2 (H-shape) is comparable to the release profile of the tablet according to comparative example C-1 (oblong).

FIG. 22 shows that the release profile of the tablet according to inventive example I-1 (H-shape) is comparable to the release profile of the tablet according to inventive example I-2 (H-shape), i.e. that different batches provide reproducible results.

Figure 23:
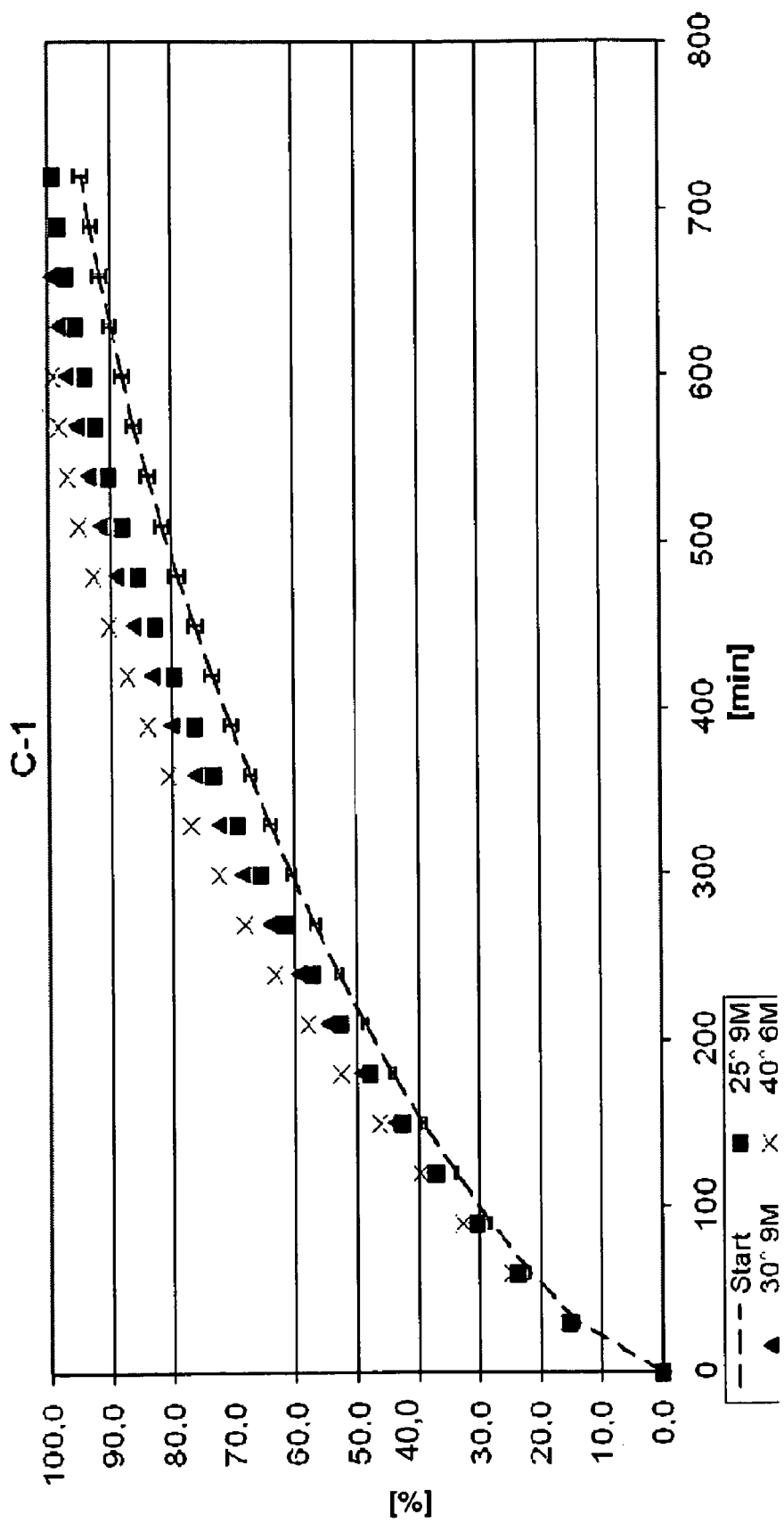
FIG. 23 shows the release profile of the tablet according to comparative example C-1 (oblong) before and after storage under various conditions (40° C., 6 months; 25° C., 9 months; and 30° C., 9 months, respectively).

FIG. 23 shows that the release profile of the tablet according to comparative example C-1 (oblong) changes upon storage (40° C., 6 months; 25° C. 9 months; and 30° C. 9 months, respectively).

Figure 24:
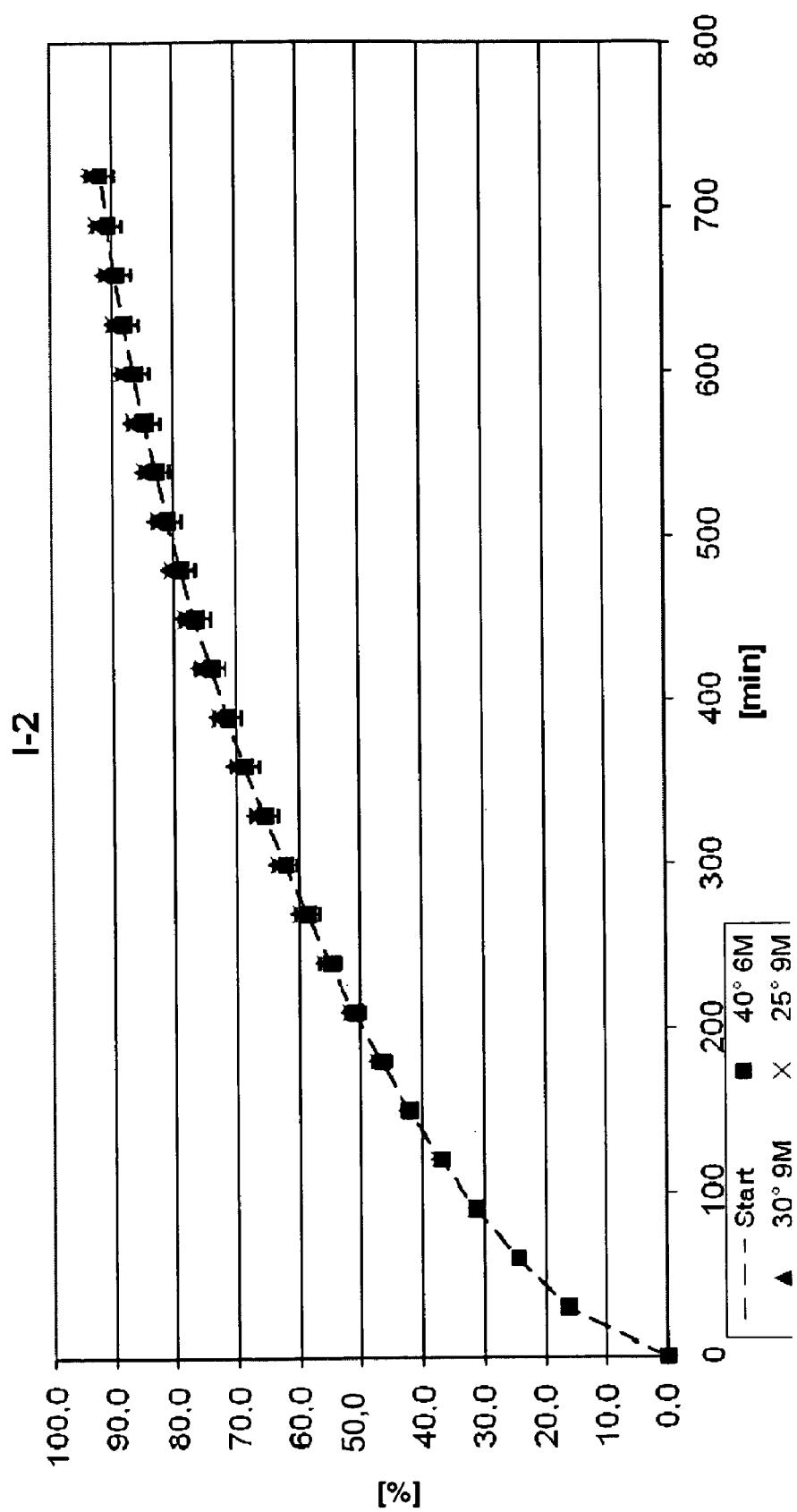
FIG. 24 shows that the release profile of the tablet according to inventive example I-2 (H-shape) before and after storage under various conditions (40° C., 6 months; 25° C., 9 months; and 30° C., 9 months, respectively).

FIG. 24 shows that the release profile of the tablet according to inventive example I-2 (H-shape) is stable, i.e. does not change upon storage (40° C., 6 months; 25° C. 9 months; and 30° C. 9 months, respectively).

These experimental findings demonstrate that the pharmaceutical dosage forms according to the invention have a storage stability in terms of the release profile that is better than the storage stability of comparative pharmaceutical dosage forms.

Example 4

In accordance with example 2, pharmaceutical dosage forms were manufactured from the following compositions:

| [mg] | C-2 | C-3 | C-4 | I-3 | I-4 |
|---|---|---|---|---|---|
| tapentadol HCl | 58.24 | 116.48 | 174.72 | 232.96 | 291.20 |
| PEO Mw 7 Mio g/mol | 225.16 | 187.12 | 166.83 | 260.39 | 245.00 |
| polyethylene glycole 6000 | 60.00 | 40.00 | 45.00 | 65.00 | 65.10 |
| HPMC 100,000 mPas | 56.00 | 56.00 | 63.00 | 91.00 | 98.00 |
| α-tocopherole | 0.60 | 0.40 | 0.45 | 0.65 | 0.70 |
| SUM | 400 | 400 | 450 | 650 | 700 |
| tablet format | oblong 7 × 17 mm | oblong 7 × 17 mm | oblong 7 × 17 mm | H-shape 9 × 21 mm | H-shape 9 × 21 mm |

Furthermore, two comparative H-shaped tablets (9×21 mm) containing 232.96 mg tapentadol HCl (C-5) and 291.20 mg tapentadol HCl (C-6) were manufactured without extrusion from conventional excipients not comprising polyalkylene oxide of high molecular weight.

The breaking strength of the pharmaceutical dosage forms was measured by means of a Sotax® HT100 at a constant speed of 120 mm/min. A tablet was regarded as failing the breaking strength test when during the measurement the force dropped below the threshold value of 25% of the maximum force that was observed during the measurement, regardless of whether the dosage form was fractured into separate pieces or not.

Figure 20C:
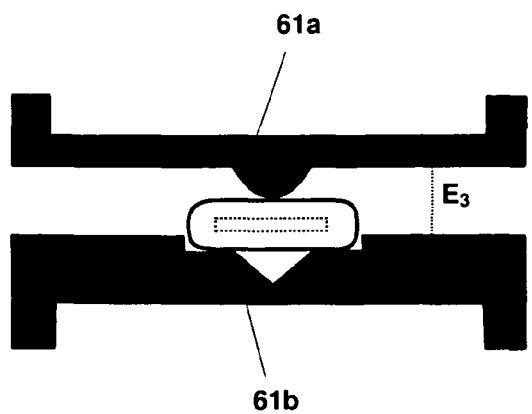
FIG. 20C) shows how the pharmaceutical dosage form should be placed between the two jaws (61a) and (61b) of the measuring device in order to measure the breaking strength in direction of extension $E_3$.

All values are given as mean of 10 measurements (n=10).
The results of the breaking strength measurements are summarized in the table here below:

|  | form | type of jaws | direction according to | breaking strength |
|---|---|---|---|---|
| C-2 | oblong | plain | FIG. 18B) | >500 N |
| C-3 | oblong | plain | FIG. 18B) | >500 N |
| C-4 | oblong | plain | FIG. 18B) | >500 N |
| C-5 | H-shape | plain | FIG. 18B) | 188 N |
| C-6 | H-shape | plain | FIG. 18B) | 188 N |
| I-3 | H-shape | plain | FIG. 18B) | 349 N |
| I-4 | H-shape | plain | FIG. 18B) | 399 N |
| I-3 | H-shape | embossment/indentation | FIG. 20A) | >500 N |
| I-4 | H-shape | embossment/indentation | FIG. 20A) | >500 N |
| I-3 | H-shape | embossment/indentation | FIG. 20C) | >500 N |
| I-4 | H-shape | embossment/indentation | FIG. 20C) | >500 N |

The above breaking strength data demonstrate that the dosage forms according to the invention I-3 and I-4 exhibit a breaking strength of more than 500 N ($B_1$) when measured in accordance with FIGS. 20A) and 20C) ($E_1$), even when equipping the tester jaws with embossment and indentation, whereas they exhibit a breaking strength of less than 500 N ($B_2$) when measured in accordance with FIG. 18B) ($E_2$).

Nonetheless, the breaking strength ($B_2$) of the dosage forms according to the invention I-3 and I-4 when measured in accordance with FIG. 18B) ($E_2$) is still much higher than that of H-shaped dosage forms that are manufactured from conventional excipients without extrusion (C-5 and C-6).

Still further, comparative oblong tablets having an increased breaking strength, such as described in WO2005/016314 or WO2005/016313 (C-2, C-3, and C-4), exhibit a breaking strength of more than 500 N when measured in accordance with FIG. 18B). Such oblong tablets exhibit a breaking strength of at least 500 N in each and every direction of extension and thus, are distinguished from the pharmaceutical dosage forms according to the invention.

Example 5

Tablets eq200 mg Tapentadol were prepared by extrusion (3.5 kg/h) in two different tablet shapes. The compositions were practically identical (minimal variation in α tocopherol), and had the same weight.

Composition of the tablets eq200 mg Tapentadol (in mg):

| tablets |  | 5.1 |  | 5.2 |  |
|---|---|---|---|---|---|
| Tapentadol HCL | 232.96 mg | 34.9% | 232.96 mg | 34.9% |
| PEO Mw 5 Mio | 300.38 mg | 45% | 300.38 mg | 45% |
| HPMC 100 000 | 66.75 mg | 10% | 66.76 mg | 10% |
| PEG | 66.58 mg | 9.975% | 66.76 mg | 10% |
| α tocopherol | 0.83 mg | 0.125% | 0.66 mg | 0.1% |
| tablet weight | 667.5 mg |  | 667.5 mg |  |

Percentage drug released for the Tapentadol eq200 mg TRF tested in dissolution at 50 rpm paddle speed, USP apparatus II, USP buffer pH 6.8:

| [%] | 5.1 standard shape average | 5.2 H0 shape average |
|---|---|---|
| 30 min | 10.8 | 14.9 |
| 120 min | 29.8 | 34.5 |
| 240 min | 44.3 | 51.3 |
| 600 min | 77.3 | 84.8 |

Example 6

Tablets eq250 mg Tapentadol were prepared by extrusion (3.5 kg/h) in different tablet shapes. The composition is shown in the next table.

Composition of the eq250 mg Tapentadol TRF tablets (in mg):

| Experiment | 6 | |
|---|---|---|
| Tapentadol HCL | 291.20 mg | 34.9% |
| PEO Mw 5 Mio | 375.47 mg | 45% |
| HPMC 100 000 | 83.44 mg | 10% |
| PEG | 83.44 mg | 10% |
| α tocopherol | 0.83 mg | 0.1% |
| tablet weight | 834.38 mg | |

Percentage drug released for the Tapentadol eq250 mg TRF tested in dissolution at 50 rpm paddle speed, USP apparatus II, USP buffer pH 6.8:

| [%] | standard shape (9 × 21 mm) average | H1-shape average |
|---|---|---|
| 30 min | 12.0 | 14.1 |
| 120 min | 29.3 | 32.2 |
| 240 min | 46.2 | 48.2 |
| 600 min | 78.7 | 79.3 |

A first set of comparative tablets was shaped by means of a conventional oblong plunger, 9×21 mm, and a second set of inventive tablets was shaped by means of an H-plunger (22.6*8.6H1, type CPS Batonett, $C_{7084}$-1, Elisabeth EPMO, France).

The invention claimed is:

1. A pharmaceutical dosage form with controlled release of a pharmacologically active compound (A) contained therein, the pharmaceutical dosage form having a first breaking strength ($B_1$) of at least 500 N in a first direction of extension ($E_1$) and having a second breaking strength ($B_2$) of less than 500 N in a second direction of extension ($E_2$).

2. A pharmaceutical dosage form according to claim 1, having a shape comprising a longitudinal axis and two opposite longitudinal edges, a transversal axis perpendicular to the longitudinal axis and two opposite transversal edges, a front side, an opposite back side and a circumferential rim between said front and back side, wherein the front side and/or the back side comprise a basis area and wherein the front side and/or the back side comprise at least one bulge which extends above said basis area, said at least one bulge being present at and/or adjacent to at least a section of one or both longitudinal edges and/or at and/or adjacent to at least a section of one or both transversal edges and/or between both longitudinal edges and both transversal edges.

3. The pharmaceutical dosage form according to claim 2, which is a tablet having an oblong shape.

4. The pharmaceutical dosage form according to claim 2, wherein the front side and the back side each comprise at least one bulge at least along a section at and/or adjacent to both longitudinal edges and/or at least along a section at and/or adjacent to both transversal edges.

5. The pharmaceutical dosage form according to claim 2, wherein said front side and said back side comprise an at least essentially continuous bulge at and/or adjacent to at least two thirds of both opposite longitudinal edges.

6. The pharmaceutical dosage form according to claim 2, wherein one or both longitudinal edges are essentially straight over at least a major part of their length and/or wherein one or both transversal edges are curved over a major part of their length.

7. The pharmaceutical dosage form according to claim 2, wherein the front side and/or the back side comprise an essentially circumferential bulge at and/or adjacent to the circumferential edge of the front side and/or the back side of said pharmaceutical dosage form.

8. The pharmaceutical dosage form according to claim 2, wherein said pharmaceutical dosage form has an oblong form, and in its oblong form comprises at and/or adjacent to major portions of both opposite longitudinal edges of the front side at least one bulge, or wherein said pharmaceutical dosage form in its oblong form comprises at least one bulge at and/or adjacent to major portions of both opposite longitudinal edges of both the front side and the back side of said pharmaceutical dosage form, or wherein said pharmaceutical dosage form comprises in its oblong form a circumferential bulge at and/or adjacent to the circumferential edge of the front side of said pharmaceutical dosage form, or wherein said pharmaceutical dosage form in its oblong form comprises a circumferential bulge at and/or adjacent to the circumferential edge of both the front side and the back side of said pharmaceutical dosage form.

9. The pharmaceutical dosage form according to claim 8, wherein said pharmaceutical dosage form in its oblong form comprises at major portions of both opposite longitudinal edges of the front side at least one bulge, or wherein said pharmaceutical dosage form in its oblong form comprises at least one bulge at major portions of both opposite longitudinal edges of both the front side and the back side of said pharmaceutical dosage form, or wherein said pharmaceutical dosage form comprises in its oblong form a circumferential bulge at the circumferential edge of the front side of said pharmaceutical dosage form, or wherein said pharmaceutical dosage form in its oblong form comprises a circumferential bulge at the circumferential edge of both the front side and the back side of said pharmaceutical dosage form.

10. The pharmaceutical dosage form according to claim 8, wherein said pharmaceutical dosage form in its oblong form comprises adjacent to major portions of both opposite longitudinal edges of the front side at least one bulge, or wherein said pharmaceutical dosage form in its oblong form comprises at least one bulge adjacent to major portions of both opposite longitudinal edges of both the front side and the back side of said pharmaceutical dosage form, or wherein said pharmaceutical dosage form in its oblong form comprises a circumferential bulge adjacent to the circumferential edge of the frontside of said pharmaceutical dosage form, or wherein said pharmaceutical dosage form in its oblong form comprises a circumferential bulge adjacent to the circumferential edge of both the front side and the back side of said pharmaceutical dosage form.

11. The pharmaceutical dosage form according to claim 8, wherein said pharmaceutical dosage form in its oblong form comprises a circumferential bulge adjacent to the circumferential edge of both the front side and the back side of said pharmaceutical dosage form.

12. The pharmaceutical dosage form according to claim 2, wherein the front side and/or the back side comprise, in addition to at least one bulge on the front side and/or the back side, at least one indentation.

13. The pharmaceutical dosage form according to claim 12, wherein the front and the back side comprise at least one indentation.

14. The pharmaceutical dosage form according to claim 13, wherein the indentation(s) in the front side and the back side are at least once at least partially off-set.

15. The pharmaceutical dosage form according to claim 13, wherein all the indentations of the front side and all the indentations of the back side are at least partially off-set.

16. The pharmaceutical dosage form according to claim 13, wherein at least one indentation of the front side and at least one indentation of the back side are positioned in a congruent manner.

17. The pharmaceutical dosage form according to claim 16, wherein all indentations of the front side and all indentations of the back side are positioned in a congruent manner.

18. The pharmaceutical dosage form according to claim 12, wherein the indentations have a cylindrical or cube-like or cuboid-like shape or the shape of a half-sphere.

19. The pharmaceutical dosage form according to claim 2, comprising one or more hydrophilic polymers.

20. The pharmaceutical dosage form according to claim 19, wherein the one or more hydrophilic polymers are hydroxypropyl methyl cellulose and/or hydroxypropyl cellulose.

21. The pharmaceutical dosage form according to claim 19, further comprising pregelatinized starch.

22. The pharmaceutical dosage form according to claim 2, wherein the length of the pharmaceutical dosage form does not exceed 30 mm.

23. The pharmaceutical dosage form according to claim 2, having an average thickness over the basis areas of the front and the back side of about at least 1 mm.

24. The pharmaceutical dosage form according to claim 2, wherein the bulge extends perpendicular from the basis area of the front side and/or from the basis area of the back side in average from about 0.5 mm to about 2 mm.

25. The pharmaceutical dosage form according claim 2, having a length in the range of about 5 mm to about 30 mm, a width in the range of about 5 mm to about 15 mm, and a thickness over the basis areas in the range of about 1 mm to about 6 mm.

26. The pharmaceutical dosage form according to claim 2, further comprising at least partially a coating.

27. The pharmaceutical dosage form according to claim 1, which is tamper-resistant and has a retarded release profile for pharmaceutical application as an oral dosage form, comprising at least one pharmaceutically active ingredient with potential for abuse, and having a shape comprising a longitudinal axis and two opposite longitudinal edges, a transversal axis perpendicular to the longitudinal axis and two opposite transversal edges, a front side, an opposite back side and a circumferential rim between said front and back side, wherein the front side and/or the back side comprise a basis area and wherein the front side and/or the back side comprise at least one bulge which extends above said basis area, said at least one bulge being present at and/or adjacent to at least a section of one or both longitudinal edges and/or at and/or adjacent to at least a section of one or both transversal edges and/or between both longitudinal edges and both transversal edges.

28. The pharmaceutical dosage form according to claim 27, which is a tablet having an oblong shape.

29. The pharmaceutical dosage form according to claim 27, wherein the front side and the back side each comprise at least one bulge at least along a section at and/or adjacent to both longitudinal edges and/or at least along a section at and/or adjacent to both transversal edges.

30. The pharmaceutical dosage form according to claim 27, wherein said front side and said back side comprise an at least essentially continuous bulge at and/or adjacent to at least two thirds of both opposite longitudinal edges.

31. The pharmaceutical dosage form according to claim 27, wherein one or both longitudinal edges are essentially straight over at least a major part of their length and/or wherein one or both transversal edges are curved over a major part of their length.

32. The pharmaceutical dosage form according to claim 27, wherein the front side and/or the back side comprise an essentially circumferential bulge at and/or adjacent to the circumferential edge of the front side and/or the back side of said pharmaceutical dosage form.

33. The pharmaceutical dosage form according to claim 27, wherein said pharmaceutical dosage form has an oblong form, and in its oblong form comprises at and/or adjacent to major portions of both opposite longitudinal edges of the front side at least one bulge, or wherein said pharmaceutical dosage form in its oblong form comprises at least one bulge at and/or adjacent to major portions of both opposite longitudinal edges of both the front side and the back side of said pharmaceutical dosage form, or wherein said pharmaceutical dosage form comprises in its oblong form a circumferential bulge at and/or adjacent to the circumferential edge of the front side of said pharmaceutical dosage form, or wherein said pharmaceutical dosage form in its oblong form comprises a circumferential bulge at and/or adjacent to the circumferential edge of both the front side and the back side of said pharmaceutical dosage form.

34. The pharmaceutical dosage form according to claim 33, wherein said pharmaceutical dosage form in its oblong form comprises at major portions of both opposite longitudinal edge of the front side at least one bulge, or wherein said pharmaceutical dosage form in its oblong form comprises at least one bulge at major portions of both opposite longitudinal edge of both the front side and the back side of said pharmaceutical dosage form, or wherein said pharmaceutical dosage form comprises in its oblong form a circumferential bulge at the circumferential edge of the front side of said pharmaceutical dosage form, or wherein said pharmaceutical dosage form in its oblong form comprises a circumferential bulge at the circumferential edge of both the front side and the back side of said pharmaceutical dosage form.

35. The pharmaceutical dosage form according to claim 33, wherein said pharmaceutical dosage form in its oblong form comprises adjacent to major portions of both opposite longitudinal edge of the front side at least one bulge, or wherein said pharmaceutical dosage form in its oblong form comprises at least one bulge adjacent to major portions of both opposite longitudinal edge of both the front side and the back side of said pharmaceutical dosage form, or wherein said pharmaceutical dosage form comprises in its oblong form a circumferential bulge adjacent to the circumferential edge of the front side of said pharmaceutical dosage form, or wherein said pharmaceutical dosage form in its oblong form comprises a circumferential bulge adjacent to the circumferential edge of both the front side and the back side of said pharmaceutical dosage form.

36. The pharmaceutical dosage form according to claim 33, wherein said pharmaceutical dosage form in its oblong form comprises a circumferential bulge adjacent to the circumferential edge of both the front side and the back side of said pharmaceutical dosage form.

37. The pharmaceutical dosage form according to claim 27, wherein the front side and/or the back side comprise, in addition to at least one bulge on the front side and/or the back side, at least one indentation.

38. The pharmaceutical dosage form according to claim 37, wherein the front and the back side comprise at least one indentation.

39. The pharmaceutical dosage form according to claim 38, wherein the indentation(s) in the front side and the back side are at least once at least partially off-set.

40. The pharmaceutical dosage form according to claim 38, wherein all the indentations of the front side and all the indentations of the back side are at least partially off-set.

41. The pharmaceutical dosage form according to claim 37, wherein at least one indentation of the front side and at least one indentation of the back side are positioned in a congruent manner.

42. The pharmaceutical dosage form according to claim 41, wherein all indentations of the front side and all indentations of the back side are positioned in a congruent manner.

43. The pharmaceutical dosage form according to claim 37, wherein the indentations have a cylindrical or cube-like or cuboid-like shape or the shape of a half-sphere.

44. The pharmaceutical dosage form according to claim 27, comprising a polyalkylene oxide.

45. The pharmaceutical dosage form according to claim 27, comprising at least one cellulose ether derivative.

46. The pharmaceutical dosage form according to claim 45, wherein the cellulose ether derivative is hydroxy propyl methyl cellulose.

47. The pharmaceutical dosage form according to claim 44, wherein the polyalkylene oxide is polyethylene oxide.

48. The pharmaceutical dosage form according to claim 47, wherein the polyethylene oxide has a molecular weight in the range of about 2,000,000 g mol$^{-1}$ to about 7,000,000 g mol$^{-1}$.

49. The pharmaceutical dosage form according to claim 27, wherein the pharmaceutical dosage form further comprises a polyalkylene glycol.

50. The pharmaceutical dosage form according to claim 49, wherein the polyalkylene glycol is polyethylene glycol.

51. The pharmaceutical dosage form according to claim 27, wherein the pharmaceutically active ingredient with potential for abuse is a pain-killing drug.

52. The pharmaceutical dosage form according to claim 51, wherein the pharmaceutically active ingredient is tapentadol.

53. The pharmaceutical dosage form according to claim 27, comprising at least one pharmaceutically active ingredient with potential for abuse; at least one polyalkylene oxide), at least one cellulose ether derivative; and at least one polyalkylene glycol; and optionally an additive.

54. The pharmaceutical dosage form according to claim 53, wherein the active ingredient with potential for abuse is present in an amount of at least 5 weight percent; poly(alkylene oxide) is present in an amount of at least 15 weight percent; cellulose ether derivative is present in an amount of at least 5 weight percent; and polyalkylene glycol, is present in an amount of at least 5 weight percent.

55. The pharmaceutical dosage form according to claim 27, wherein the length of the pharmaceutical dosage form does not exceed 30 mm.

56. The pharmaceutical dosage form according to claim 27, having an average thickness over the basis areas of the front and the back side of about at least 1 mm.

57. The pharmaceutical dosage form according to claim 27, wherein the bulge extends perpendicular from the basis area of the front side and/or from the basis area of the back side in average from about 0.5 mm to about 2 mm.

58. The pharmaceutical dosage form according to claim 27, having a length in the range of about 5 mm to about 30 mm, a width in the range of about 5 mm to about 15 mm, and a thickness over the basis areas in the range of about 1 mm to about 6 mm.

59. The pharmaceutical dosage form according to claim 27, wherein said pharmaceutical dosage form is a monolith.

60. The pharmaceutical dosage form according to claim 27, which has been prepared via compression using a die and a punch from a monolithic mass obtained by melt extrusion.

61. The pharmaceutical dosage form according to claim 59, wherein said pharmaceutical dosage form has been obtained by compressing a melt extruded monolithic mass which exhibits ambient temperature.

62. The pharmaceutical dosage form according to claim 61, wherein the extruded monolithic mass has been cut prior to compression.

63. The pharmaceutical dosage form according to claim 60, wherein melt extrusion has been conducted with a twin-screw extruder.

64. The pharmaceutical dosage form according to claim 27, further comprising at least partially a coating.

65. The pharmaceutical dosage form according to claim 1, wherein $E_1$ is orthogonal to $E_2$.

66. The pharmaceutical dosage form according to claim 1, which has a main direction of extension, wherein $E_2$ is the main direction of extension of the pharmaceutical dosage form.

67. The pharmaceutical dosage form according to claim 1, which provides fragments when exerting a force higher than $B_2$ in direction of extension $E_2$, said fragments in turn having a breaking strength of at least 500 N in any of their directions of extension.

68. The pharmaceutical dosage form according to claim 67, wherein the volume of each fragment is at least 5% of the volume of the pharmaceutical dosage form.

69. The pharmaceutical dosage form according to claim 1, which is deformed when exerting a force in direction of extension $E_2$ so that, when the amount of force reaches the breaking strength $B_2$, deformation causes tractive forces that lead to disruption of the dosage form.

70. The pharmaceutical dosage form according to claim 1, which has released under in vitro conditions
  after 0.5 h 1.0 to 35 wt.-%,
  after 1 h 5.0 to 45 wt.-%,
  after 2 h 10 to 60 wt.-%,
  after 4 h at least 15 wt.-%,
  after 6 h at least 20 wt.-%,
  after 8 h at least 25 wt.-% and
  after 12 h at least 30 wt.-%
  of the pharmacologically active compound (A) that was originally contained in the pharmaceutical dosage form.

71. The pharmaceutical dosage form according to claim 1, which is not radially symmetric about its principal direction of extension.

72. The pharmaceutical dosage form according to claim 1, which exhibits a maximum extension of the dosage form orthogonal to a main area of extension of the dosage form spaced from a centre of mass of the dosage form parallel to said main area of extension.

73. The pharmaceutical dosage form according to claim 1, wherein a portion of its surface is convex, and another portion of its surface is concave.

74. The pharmaceutical dosage form according to claim 1, which contains a polymer (C) having a weight average molecular weight of at least 100,000 g mol$^{-1}$.

75. The pharmaceutical dosage form according to claim 74, wherein the polymer (C) comprises a polyalkylene oxide.

76. The pharmaceutical dosage form according to claim 1, wherein
  a portion of the surface of the pharmaceutical dosage form is convex, another portion of its surface is concave; and
  the pharmacologically active compound (A) is a psychotropically acting substance; and
  the content of the pharmacologically active compound (A) is at least 0.5 wt. %, based on the total weight of the dosage form; and
  polymer (C) is an polyalkylene oxide having a weight average molecular weight of at least 200,000 g/mol; and
  the content of polymer (C) is at least 15 wt.-%, based on the total weight of the dosage form; and
  the pharmacologically active compound (A) is embedded in the polymer (C); and
  the pharmaceutical dosage form is adapted for oral administration once daily or twice daily; and
  the pharmaceutical dosage form is thermoformed.

77. A method of treating pain in a patient in need of such treatment, said method comprising administering to said patient an effective amount therefor of a pharmaceutical dosage form according to claim 2, wherein the pharmaceutically active ingredient is selected from the group consisting of analgesics.

78. A method of treating pain in a patient in need of such treatment, said method comprising administering to said patient an effective amount therefor of a pharmaceutical dosage form according to claim 27, wherein the pharmaceutically active ingredient with potential for abuse is selected from the group consisting of analgesics.

79. A method of treating pain in a patient in need of such treatment, said method comprising administering to said patient an effective amount therefor of a pharmaceutical dosage form according to claim 1, wherein the pharmacologically active compound (A) is selected from the group consisting of analgesics.

* * * * *

UNITED STATES PATENT AND TRADEMARK OFFICE
CERTIFICATE OF CORRECTION

PATENT NO. : 8,383,152 B2
APPLICATION NO. : 12/358415
DATED : February 26, 2013
INVENTOR(S) : Eugeen Marie Jozef Jans et al.

It is certified that error appears in the above-identified patent and that said Letters Patent is hereby corrected as shown below:

In The Specification

Column 9, line 23, "shows that the" -- should read -- shows the --.

Column 15, line 13, "remacemide)antitussive" -- should read -- remacemide); [new ¶] antitussive --.

Column 15, line 22, "propranolol)cardiac" -- should read -- propranolol); [new ¶] cardiac --.

Column 15, line 23, "aminone" -- should read -- amrinone --.

Column 15, line 31, "*cassia*" -- should read -- cassia --.

Column 15, line 41, "sulphasalazine) haemostatics" -- should read -- sulphasalazine); [new ¶] haemostatic --.

Column 15, line 44, "simvastatin) local anaesthetics" -- should read -- simvastatin); [new ¶] local anaesthetics --.

Column 16, line 64, "insulin" -- should read -- inulin --.

Column 21, line 57, "insulin" -- should read -- inulin --.

Column 30, line 46, "2.4±1.31" -- should read -- 2.4±1.3:1 --.

Column 30, line 61, "4.7±0.6:2.0±0.31" -- should read -- 4.7±0.6:2.0±0.3:1 --.

Column 32, line 30, "$C_2V$" -- should read -- $C_{2v}$ --.

Column 34, line 31, "$a=a_1=a_2+a_3$" -- should read -- $a=a_1+a_2+a_3$ --.

Column 34, line 35, "$C_3$" -- should read -- $c_3$ --.

Column 39, line 10, "S(56)" -- should read -- S(54b) --.

Column 44, line 33, "*Papaver somniferum*" -- should read -- Papaver somniferum --.

Column 47, line 21, "11-(3-" -- should read -- 1,1-(3- --.

Column 49, line 1, "[A1]" -- should read -- [A11] --.

Column 49, line 9, "[α]" -- should read -- [C] --.

Column 51, line 32, "*clostridium botulinum*" -- should read -- clostridium botulinum --.

Signed and Sealed this
Twenty-sixth Day of January, 2016

Michelle K. Lee
*Director of the United States Patent and Trademark Office*

Column 51, line 52, "diboterminalfa" -- should read -- dibotermin alfa --.

Column 52, line 23, "flecamide" -- should read -- flecainide --.

Column 52, line 34, 35, "Fosphenyloin" -- should read -- fosphenytoin --.

Column 54, line 31, "phenyloin" -- should read -- phenytoin --.

Column 55, line 30, "tocamide" -- should read -- tocainide --.

Column 61, line 4, "$M_wM_n$" -- should read -- $M_wM_\eta$ --.

Column 65, line 26, "*gallus*" -- should read -- gallus --.

Column 80, line 39, "Theological" -- should read -- rheological --.

Column 85, line 14, "$C_{7084}$-1" -- should read -- C-7084-1 --.

In The Claims

Column 89, line 28, "polyalkylene oxide)" -- should read -- poly(alkylene oxide) --.